United States Patent
Turovskiy

(10) Patent No.: US 9,066,713 B2
(45) Date of Patent: Jun. 30, 2015

(54) NEUROMODULATION CRYOTHERAPEUTIC DEVICES AND ASSOCIATED SYSTEMS AND METHODS

(75) Inventor: Roman Turovskiy, San Francisco, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 804 days.

(21) Appl. No.: 13/279,325

(22) Filed: Oct. 23, 2011

(65) Prior Publication Data
US 2012/0130359 A1    May 24, 2012

Related U.S. Application Data

(60) Provisional application No. 61/406,968, filed on Oct. 26, 2010, provisional application No. 61/528,091, filed on Aug. 26, 2011, provisional application No. 61/528,684, filed on Aug. 29, 2011, provisional application No. 61/546,510, filed on Oct. 12, 2011.

(51) Int. Cl.
*A61B 18/02* (2006.01)
*A61B 18/00* (2006.01)

(52) U.S. Cl.
CPC ......... *A61B 18/02* (2013.01); *A61B 2018/0022* (2013.01); *A61B 2018/00232* (2013.01); *A61B 2018/00261* (2013.01); *A61B 2018/00404* (2013.01); *A61B 2018/00434* (2013.01);
(Continued)

(58) Field of Classification Search
CPC ........... A61B 18/02; A61B 2018/0212; A61B 2018/0293; A61B 2018/0231
USPC ............................ 606/21, 22, 23, 25
See application file for complete search history.

(56) References Cited

U.S. PATENT DOCUMENTS

| | | |
|---|---|---|
| 3,125,096 A | 3/1964 | Antiles et al. |
| 3,298,371 A | 1/1967 | Lee |
| 3,901,241 A | 8/1975 | Allen, Jr. |

(Continued)

FOREIGN PATENT DOCUMENTS

| | | |
|---|---|---|
| DE | 4406451 | 9/1995 |
| EP | 0655225 | 5/1995 |

(Continued)

OTHER PUBLICATIONS

"2011 Edison Award Winners." Edison Awards: Honoring Innovations & Innovators, 2011, 6 pages, <http://www.edisonawards.com/BestNewProduct_2011.php>.

(Continued)

*Primary Examiner* — Christopher D Koharski
*Assistant Examiner* — Michael Carey

(57) ABSTRACT

Neuromodulation cryotherapeutic devices and associated systems and methods are disclosed herein. A cryotherapeutic device configured in accordance with a particular embodiment includes an elongated shaft and a cooling assembly at distal portion of the shaft. The shaft can be configured to locate the distal portion intravascularly at a treatment site within or otherwise proximate a renal artery. The cryotherapeutic device can further include a supply lumen configured to carry liquid refrigerant toward the cooling assembly. The cooling assembly can include an applicator in fluid communication with the supply lumen and configured to deliver cryotherapeutic cooling to nerves proximate the target site when in a deployed state.

32 Claims, 69 Drawing Sheets

(52) U.S. Cl.
CPC .................. *A61B2018/00511* (2013.01); *A61B 2018/0212* (2013.01)

(56) References Cited

U.S. PATENT DOCUMENTS

| | | |
|---|---|---|
| 3,924,628 A | 12/1975 | Droegemueller et al. |
| 4,018,227 A | 4/1977 | Wallach |
| 4,275,734 A | 6/1981 | Mitchiner |
| 4,602,624 A | 7/1986 | Naples et al. |
| 4,649,936 A | 3/1987 | Ungar et al. |
| 4,709,698 A | 12/1987 | Johnston et al. |
| 4,764,504 A | 8/1988 | Johnson et al. |
| 4,976,711 A | 12/1990 | Parins et al. |
| 5,108,390 A | 4/1992 | Potocky et al. |
| 5,190,539 A | 3/1993 | Fletcher et al. |
| 5,300,068 A | 4/1994 | Rosar et al. |
| 5,308,323 A | 5/1994 | Sogawa et al. |
| 5,334,181 A | 8/1994 | Rubinsky et al. |
| 5,342,301 A | 8/1994 | Saab |
| 5,358,514 A | 10/1994 | Schulman et al. |
| 5,368,591 A | 11/1994 | Lennox et al. |
| 5,383,856 A | 1/1995 | Bersin |
| 5,417,355 A | 5/1995 | Broussalian et al. |
| 5,423,744 A | 6/1995 | Gencheff et al. |
| 5,425,364 A | 6/1995 | Imran |
| 5,484,400 A | 1/1996 | Edwards et al. |
| 5,571,147 A | 11/1996 | Sluijter et al. |
| 5,588,964 A | 12/1996 | Imran et al. |
| 5,599,345 A | 2/1997 | Edwards et al. |
| 5,624,392 A | 4/1997 | Saab |
| 5,626,576 A | 5/1997 | Janssen |
| 5,672,174 A | 9/1997 | Gough et al. |
| 5,688,266 A | 11/1997 | Edwards et al. |
| 5,700,282 A | 12/1997 | Zabara |
| 5,707,400 A | 1/1998 | Terry, Jr. et al. |
| 5,741,248 A | 4/1998 | Stern et al. |
| 5,758,505 A | 6/1998 | Dobak, III et al. |
| 5,772,590 A | 6/1998 | Webster, Jr. |
| 5,807,391 A | 9/1998 | Wijkamp |
| 5,837,003 A | 11/1998 | Ginsburg |
| 5,860,970 A | 1/1999 | Goddard et al. |
| 5,865,787 A | 2/1999 | Shapland et al. |
| 5,868,735 A | 2/1999 | Lafontaine |
| 5,893,885 A | 4/1999 | Webster et al. |
| 5,902,299 A | 5/1999 | Jayaraman |
| 5,944,710 A | 8/1999 | Dev et al. |
| 5,954,719 A | 9/1999 | Chen et al. |
| 5,971,979 A | 10/1999 | Joye et al. |
| 5,983,141 A | 11/1999 | Sluijter et al. |
| 6,004,269 A | 12/1999 | Crowley et al. |
| 6,009,877 A | 1/2000 | Edwards |
| 6,012,457 A | 1/2000 | Lesh |
| 6,024,752 A | 2/2000 | Horn et al. |
| 6,066,134 A | 5/2000 | Eggers et al. |
| 6,099,524 A | 8/2000 | Lipson et al. |
| 6,117,101 A | 9/2000 | Diederich et al. |
| 6,135,999 A | 10/2000 | Fanton et al. |
| 6,149,620 A | 11/2000 | Baker et al. |
| 6,151,245 A | 11/2000 | Pio et al. |
| 6,161,048 A | 12/2000 | Sluijter et al. |
| 6,161,049 A | 12/2000 | Rudie et al. |
| 6,161,543 A | 12/2000 | Cox et al. |
| 6,164,283 A | 12/2000 | Lesh |
| 6,190,356 B1 | 2/2001 | Bersin |
| 6,219,577 B1 | 4/2001 | Brown, III et al. |
| 6,224,592 B1 | 5/2001 | Eggers et al. |
| 6,237,355 B1 | 5/2001 | Li |
| 6,241,722 B1 | 6/2001 | Dobak et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,283,959 B1 | 9/2001 | Lalonde et al. |
| 6,290,696 B1 | 9/2001 | Lafontaine |
| 6,292,695 B1 | 9/2001 | Webster, Jr. et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,355,029 B1 | 3/2002 | Joye et al. |
| 6,405,732 B1 | 6/2002 | Edwards et al. |
| 6,413,255 B1 | 7/2002 | Stern |
| 6,432,102 B2 | 8/2002 | Joye et al. |
| 6,451,045 B1 | 9/2002 | Walker et al. |
| 6,468,297 B1 | 10/2002 | Williams et al. |
| 6,488,679 B1 | 12/2002 | Swanson et al. |
| 6,496,737 B2 | 12/2002 | Rudie et al. |
| 6,497,703 B1 | 12/2002 | Korteling et al. |
| 6,506,189 B1 | 1/2003 | Rittman, III et al. |
| 6,514,226 B1 | 2/2003 | Levin et al. |
| 6,514,245 B1 | 2/2003 | Williams et al. |
| 6,517,533 B1 | 2/2003 | Swaminathan |
| 6,522,926 B1 | 2/2003 | Kieval et al. |
| 6,527,739 B1 | 3/2003 | Bigus et al. |
| 6,537,271 B1 | 3/2003 | Murray et al. |
| 6,540,734 B1 | 4/2003 | Chiu et al. |
| 6,542,781 B1 | 4/2003 | Koblish et al. |
| 6,551,309 B1 | 4/2003 | LePivert |
| 6,562,034 B2 | 5/2003 | Edwards et al. |
| 6,575,933 B1 | 6/2003 | Wittenberger et al. |
| 6,575,966 B2 | 6/2003 | Lane et al. |
| 6,602,247 B2 | 8/2003 | Lalonde |
| 6,610,083 B2 | 8/2003 | Keller et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,648,879 B2 | 11/2003 | Joye et al. |
| 6,666,858 B2 | 12/2003 | Lafontaine |
| 6,685,648 B2 | 2/2004 | Flaherty et al. |
| 6,711,444 B2 | 3/2004 | Koblish |
| 6,736,835 B2 | 5/2004 | Pellegrino et al. |
| 6,755,823 B2 | 6/2004 | Lalonde |
| 6,786,901 B2 | 9/2004 | Joye et al. |
| 6,824,543 B2 | 11/2004 | Lentz |
| 6,845,267 B2 | 1/2005 | Harrison et al. |
| 6,850,801 B2 | 2/2005 | Kieval et al. |
| 6,875,209 B2 | 4/2005 | Zvuloni et al. |
| 6,885,888 B2 | 4/2005 | Rezai |
| 6,893,436 B2 | 5/2005 | Woodard et al. |
| 6,905,510 B2 | 6/2005 | Saab |
| 6,908,462 B2 | 6/2005 | Joye et al. |
| 6,923,808 B2 | 8/2005 | Taimisto |
| 6,939,346 B2 | 9/2005 | Kannenberg et al. |
| 6,981,382 B2 | 1/2006 | Lentz et al. |
| 7,060,062 B2 | 6/2006 | Joye et al. |
| 7,081,112 B2 | 7/2006 | Joye et al. |
| 7,081,115 B2 | 7/2006 | Taimisto |
| 7,149,574 B2 | 12/2006 | Yun et al. |
| 7,156,840 B2 | 1/2007 | Lentz et al. |
| 7,162,303 B2 | 1/2007 | Levin et al. |
| 7,220,257 B1 | 5/2007 | Lafontaine |
| 7,221,979 B2 | 5/2007 | Zhou et al. |
| 7,306,590 B2 | 12/2007 | Swanson |
| 7,357,797 B2 | 4/2008 | Ryba |
| 7,381,200 B2 | 6/2008 | Katoh et al. |
| 7,390,894 B2 | 6/2008 | Weinshilboum et al. |
| 7,604,631 B2 | 10/2009 | Reynolds |
| 7,617,005 B2 | 11/2009 | Demarais et al. |
| 7,641,679 B2 | 1/2010 | Joye et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,758,571 B2 | 7/2010 | Saadat |
| 7,778,703 B2 | 8/2010 | Gross et al. |
| 7,785,289 B2 | 8/2010 | Rios et al. |
| 7,861,725 B2 | 1/2011 | Swanson |
| 7,972,327 B2 | 7/2011 | Eberl et al. |
| 8,088,125 B2 | 1/2012 | Lafontaine |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |

(56) References Cited

U.S. PATENT DOCUMENTS

| | | |
|---|---|---|
| 8,298,217 B2 | 10/2012 | Lane et al. |
| 8,473,067 B2 | 6/2013 | Hastings et al. |
| 8,475,441 B2 | 7/2013 | Babkin et al. |
| 8,480,664 B2 | 7/2013 | Watson et al. |
| 8,663,211 B2 | 3/2014 | Fourkas et al. |
| 8,740,895 B2 | 6/2014 | Mayse et al. |
| 8,777,943 B2 | 7/2014 | Mayse et al. |
| 2002/0007180 A1 | 1/2002 | Wittenberger et al. |
| 2002/0026182 A1 | 2/2002 | Joye et al. |
| 2002/0045893 A1 | 4/2002 | Lane et al. |
| 2002/0120258 A1 | 8/2002 | Lalonde |
| 2002/0165532 A1 | 11/2002 | Hill et al. |
| 2002/0183682 A1 | 12/2002 | Darvish et al. |
| 2003/0036752 A1 | 2/2003 | Joye et al. |
| 2003/0050681 A1 | 3/2003 | Pianca et al. |
| 2003/0060762 A1 | 3/2003 | Zvuloni et al. |
| 2003/0060858 A1 | 3/2003 | Kieval et al. |
| 2003/0088240 A1* | 5/2003 | Saadat ............................ 606/21 |
| 2003/0125790 A1 | 7/2003 | Fastovsky et al. |
| 2003/0181897 A1 | 9/2003 | Thomas et al. |
| 2003/0199863 A1 | 10/2003 | Swanson et al. |
| 2003/0216792 A1 | 11/2003 | Levin et al. |
| 2004/0010289 A1 | 1/2004 | Biggs et al. |
| 2004/0024392 A1 | 2/2004 | Lewis et al. |
| 2004/0034344 A1 | 2/2004 | Ryba |
| 2004/0215186 A1 | 10/2004 | Cornelius et al. |
| 2004/0254528 A1 | 12/2004 | Adams et al. |
| 2005/0080409 A1 | 4/2005 | Young et al. |
| 2005/0187579 A1 | 8/2005 | Danek et al. |
| 2005/0228460 A1 | 10/2005 | Levin et al. |
| 2005/0240117 A1 | 10/2005 | Zvuloni et al. |
| 2006/0030843 A1* | 2/2006 | Lane et al. ....................... 606/21 |
| 2006/0084962 A1 | 4/2006 | Joye et al. |
| 2006/0095029 A1 | 5/2006 | Young et al. |
| 2006/0100618 A1 | 5/2006 | Chan et al. |
| 2006/0206150 A1 | 9/2006 | Demarais et al. |
| 2006/0212027 A1 | 9/2006 | Marrouche et al. |
| 2006/0247611 A1 | 11/2006 | Abboud et al. |
| 2006/0271111 A1 | 11/2006 | Demarais et al. |
| 2007/0129720 A1 | 6/2007 | Demarais et al. |
| 2007/0185445 A1* | 8/2007 | Nahon et al. ................ 604/96.01 |
| 2007/0265687 A1 | 11/2007 | Deem et al. |
| 2007/0299433 A1 | 12/2007 | Williams et al. |
| 2008/0009851 A1 | 1/2008 | Wittenberger et al. |
| 2008/0208182 A1 | 8/2008 | Lafontaine et al. |
| 2008/0300584 A1 | 12/2008 | Lentz et al. |
| 2008/0306475 A1 | 12/2008 | Lentz et al. |
| 2008/0312644 A1 | 12/2008 | Fourkas et al. |
| 2008/0319513 A1 | 12/2008 | Pu et al. |
| 2009/0036948 A1 | 2/2009 | Levin et al. |
| 2009/0182316 A1 | 7/2009 | Bencini |
| 2009/0182317 A1 | 7/2009 | Bencini |
| 2009/0209949 A1 | 8/2009 | Ingle et al. |
| 2009/0281532 A1 | 11/2009 | Reddy |
| 2009/0281533 A1 | 11/2009 | Ingle et al. |
| 2009/0287202 A1 | 11/2009 | Ingle et al. |
| 2009/0299355 A1 | 12/2009 | Bencini et al. |
| 2010/0049184 A1 | 2/2010 | George et al. |
| 2010/0069900 A1 | 3/2010 | Shirley et al. |
| 2010/0100087 A1 | 4/2010 | Mazzone et al. |
| 2010/0106148 A1 | 4/2010 | Joye et al. |
| 2010/0114269 A1 | 5/2010 | Wittenberger et al. |
| 2010/0125266 A1 | 5/2010 | Deem et al. |
| 2010/0130970 A1 | 5/2010 | Williams et al. |
| 2010/0137860 A1 | 6/2010 | Demarais et al. |
| 2010/0137952 A1 | 6/2010 | Demarais et al. |
| 2010/0179526 A1 | 7/2010 | Lawrence |
| 2010/0179527 A1 | 7/2010 | Watson et al. |
| 2010/0191112 A1 | 7/2010 | Demarais et al. |
| 2010/0191231 A1 | 7/2010 | Heberer |
| 2010/0198203 A1 | 8/2010 | Kuck et al. |
| 2010/0222851 A1 | 9/2010 | Deem et al. |
| 2010/0222854 A1 | 9/2010 | Demarais et al. |
| 2010/0234838 A1 | 9/2010 | Watson |
| 2010/0249766 A1 | 9/2010 | Saadat |
| 2010/0256621 A1 | 10/2010 | Babkin et al. |
| 2010/0280507 A1 | 11/2010 | Babkin et al. |
| 2011/0152855 A1 | 6/2011 | Mayse et al. |
| 2011/0263921 A1 | 10/2011 | Vrba et al. |
| 2011/0270238 A1 | 11/2011 | Rizq et al. |
| 2011/0282272 A1 | 11/2011 | Lafontaine |
| 2012/0029509 A1* | 2/2012 | Smith ............................. 606/41 |
| 2012/0029511 A1 | 2/2012 | Smith et al. |
| 2012/0089047 A1 | 4/2012 | Ryba et al. |
| 2012/0123261 A1 | 5/2012 | Jenson et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136417 A1 | 5/2012 | Buckley et al. |
| 2012/0136418 A1 | 5/2012 | Buckley et al. |
| 2012/0143097 A1 | 6/2012 | Pike, Jr. |
| 2012/0143294 A1 | 6/2012 | Clark et al. |
| 2012/0150267 A1 | 6/2012 | Buckley et al. |
| 2012/0158104 A1 | 6/2012 | Huynh et al. |
| 2012/0172837 A1 | 7/2012 | Demarais et al. |
| 2012/0253336 A1 | 10/2012 | Littrup et al. |
| 2013/0090650 A1 | 4/2013 | Jenson et al. |
| 2013/0123770 A1 | 5/2013 | Smith |
| 2013/0184696 A1 | 7/2013 | Fourkas et al. |
| 2013/0345688 A1 | 12/2013 | Babkin et al. |
| 2014/0046313 A1 | 2/2014 | Pederson et al. |
| 2014/0066914 A1 | 3/2014 | Lafontaine |

FOREIGN PATENT DOCUMENTS

| | | |
|---|---|---|
| EP | 0955012 | 11/1999 |
| EP | 1129670 | 9/2001 |
| EP | 1164963 | 1/2002 |
| EP | 1389477 | 2/2004 |
| EP | 1502553 | 2/2005 |
| EP | 1559362 | 8/2005 |
| EP | 2558016 | 2/2013 |
| EP | 2598070 | 6/2013 |
| EP | 2598071 | 6/2013 |
| EP | 2608837 | 7/2013 |
| GB | 228367 | 2/1925 |
| GB | 1422535 | 1/1976 |
| GB | 2283678 | 5/1995 |
| GB | 2289414 | 11/1995 |
| SU | 718099 | 2/1980 |
| SU | 1153901 | 5/1985 |
| SU | 1329781 | 8/1987 |
| SU | 1378835 | 3/1988 |
| SU | 1771725 | 6/1990 |
| WO | WO-9525472 | 9/1995 |
| WO | WO-9725011 | 7/1997 |
| WO | WO-9736548 | 10/1997 |
| WO | WO-99/00060 | 1/1999 |
| WO | WO-9905979 | 2/1999 |
| WO | WO-9927862 | 6/1999 |
| WO | WO-0054684 | 9/2000 |
| WO | WO-0122897 | 4/2001 |
| WO | WO-0164145 | 9/2001 |
| WO | WO-0170114 | 9/2001 |
| WO | WO-0200128 | 1/2002 |
| WO | WO-0200128 A2 | 1/2002 |
| WO | WO-0204042 | 1/2002 |
| WO | WO-0204042 A2 | 1/2002 |
| WO | WO-0207625 | 1/2002 |
| WO | WO-0207625 A2 | 1/2002 |
| WO | WO-0207628 | 1/2002 |
| WO | WO-0213710 | 2/2002 |
| WO | WO-02058576 | 8/2002 |
| WO | WO-03020334 | 3/2003 |
| WO | WO-03020334 A2 | 3/2003 |
| WO | WO-03061496 | 7/2003 |
| WO | WO-2005030072 | 4/2005 |
| WO | WO-2005038357 | 4/2005 |
| WO | WO-2005041748 | 5/2005 |
| WO | WO-2005110528 | 11/2005 |

(56) References Cited

FOREIGN PATENT DOCUMENTS

| | | |
|---|---|---|
| WO | WO-2006041881 | 4/2006 |
| WO | WO-2006096272 | 9/2006 |
| WO | WO-2006124177 | 11/2006 |
| WO | WO-2007008954 | 1/2007 |
| WO | WO-2008131037 | 10/2008 |
| WO | WO-2011056684 | 5/2011 |
| WO | WO-2011082278 | 7/2011 |
| WO | WO-2011082279 | 7/2011 |
| WO | WO-2012016135 | 2/2012 |
| WO | WO-2012016137 | 2/2012 |
| WO | WO 2012019156 | 2/2012 |
| WO | WO-2012058153 | 5/2012 |
| WO | WO-2012058156 | 5/2012 |
| WO | WO-2012058158 | 5/2012 |
| WO | WO-2012058159 | 5/2012 |
| WO | WO-2012058160 | 5/2012 |
| WO | WO-2012058161 | 5/2012 |
| WO | WO-2012058163 | 5/2012 |
| WO | WO-2012058165 | 5/2012 |
| WO | WO-2012058167 | 5/2012 |
| WO | WO-2012058430 | 5/2012 |
| WO | WO-2013074683 | 5/2013 |
| WO | WO-2013106859 | 7/2013 |

OTHER PUBLICATIONS

"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.

"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.

"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.

"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.

"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.

"Iberis—Renal Sympathetic Denervation System: Turning innovation into quality care." [Brochure], Terumo Europe N.V., 2013, Europe, 3 pages.

"Neurotech Reports Announces Winners of Gold Electrode Awards." Neurotech business report, 2009. 1 page. <http://www.neurotechreports.com/pages/goldelectrodes09.html>.

"Quick. Consistent. Controlled. OneShot renal Denervation System" [Brochure], Covidien: positive results for life, 2013, (n.l.), 4 pages.

"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.

"The Edison AwardsTM" Edison Awards: Honoring Innovations & Innovators, 2013, 2 pages, <http://www.edisonawards.com/Awards.php>.

"The Future of Renal denervation for the Treatment of Resistant Hypertension." St. Jude Medical, Inc., 2012, 12 pages.

"Vessix Renal Denervation System: So Advanced It's Simple." [Brochure], Boston Scientific: Advancing science for life, 2013, 6 pages.

Asbell, Penny, "Conductive Keratoplasty for the Correction of Hyperopia." Tr Am Ophth Soc, 2001, vol. 99, 10 pages.

Badoer, Emilio, "Cardiac afferents play the dominant role in renal nerve inhibition elicited by volume expansion in the rabbit." Am J Physiol Regul Integr Comp Physiol, vol. 274, 1998, 7 pages.

Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.

Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.

Bohm, Michael et al., "Rationale and design of a large registry on renal denervation: the Global Symplicity registry." EuroIntervention, vol. 9, 2013, 9 pages.

Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.

Davis, Mark et al., "Effectiveness of Renal Denervation Therapy for Resistant Hypertension." Journal of the American College of Cardiology, vol. 62, No. 3, 2013, 11 pages.

Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.

Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.

Hering, Dagmara et al., "Chronic kidney disease: role of sympathetic nervous system activation and potential benefits of renal denervation." EuroIntervention, vol. 9, 2013, 9 pages.

Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.

Kaiser, Chris, AHA Lists Year's Big Advances in CV Research, medpage Today, Dec. 18, 2012, 4 pages, <http://www.medpagetoday.com/Cardiology/PCI/36509>.

Linz, Dominik et al., "Renal denervation suppresses ventricular arrhythmias during acute ventricular ischemia in pigs." Heart Rhythm, vol. 0, No. 0, 2013, 6 pages.

Mabin, Tom et al., "First experience with endovascular ultrasound renal denervation for the treatment of resistant hypertension." EuroIntervention, vol. 8, 2012, 5 pages.

Mahfoud, Felix et al., "Ambulatory Blood Pressure Changes after Renal Sympathetic Denervation in Patients with Resistant Hypertension." Circulation, 2013, 25 pages.

Mahfoud, Felix et al., "Expert consensus document from the European Society of Cardiology on catheter-based renal denervation." European Heart Journal, 2013, 9 pages.

Mahfoud, Felix et al., "Renal Hemodynamics and Renal Function After Catheter-Based Renal Sympathetic Denervation in Patients With Resistant Hypertension." Hypertension, 2012, 6 pages.

Ormiston, John et al., "First-in-human use of the OneShotTM renal denervation system from Covidien." EuroIntervention, vol. 8, 2013, 4 pages.

Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.

Pedersen, Amanda, "TCT 2012: Renal denervation device makers play show and tell." Medical Device Daily, Oct. 26, 2012, 2 pages,

(56) References Cited

OTHER PUBLICATIONS

<http://www.medicaldevicedaily.com/servlet/com.accumedia.web.Dispatcher?next=bioWorldHeadlines_article&forceid=80880>.
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Stouffer, G. A. et al., "Catheter-based renal denervation in the treatment of resistant hypertension." Journal of Molecular and Cellular Cardiology, vol. 62, 2013, 6 pages.
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
European Search Report for European Application No. 13159256, Date Mailed: Oct. 17, 2013, 6 pages.
510K Summary of CryoGen Cryosurgery System, filed with FDA Jul. 3, 1997—approved Oct. 1, 1997, 1997, 5 pages.
CO2/Gas Composite Regulator, Sep. 6, 2011, 2 pages. <http://www.genuineinnovations.com/composite-regulator.html>.
CryoGen SS&E: HerOption Uterine Cryoblatin Therapy System, filed with FDA Aug. 15, 2000—approved Apr. 20, 2001, 1999, 84 pages.
Lura Harrison, Ph.D. et al., "Cryosurgical Ablation of the A-V Node-His Bundle—A New Method for Producing A-V Block," Circulation, vol. 55, 1977 pp. 463-470.
Medical Grade Gas Dispenser, Sep. 6, 2011, 1 page, <http://www.abd-inc.com/Frame-904990-page1namepage904990.html?refresh=1205442262133>.
Sesia G. et al., "The use of nitrous oxide as a freezing agent in cryosurgery of the prostate," International Surgery [Int Surg], vol. 53, 1970, pp. 82-90.
Special Order Only Thermal Dilution Injector, Obsolete Product, Sep. 6, 2011, 1 page, <http://www.abd-inc.com/Frame-904990-page1namepage904990.html?refresh=1205442262133>.
Torre, Douglas, MD, "Alternate Cryogens for Cryosurgery," J. Derm. Surgery, Jun. 1975, pp. 56-58.
Vo Voïtynatyna SV, "Cryocatheter-tourniquet," Meditsinskaia Tekhnika [Med Tekh], vol. 6, 1976, pp. 47-48.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter," Journal of the American College of Cardiology, 1999; 33; pp. 972-984.
Blessing, Erwin et al., Cardiac Ablation and Renal Denervation Systems Have Distinct Purposes and Different Technical Requirements, JACC Cardiovascular Interventions, vol. 6, No. 3, 2013.
ClinicalTrials.gov, Renal Denervation in Patients with uncontrolled Hypertension in Chinese (2011), www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Sdentific's Maestro 30000 Cardiac Ablation System, Version of Oct. 17, 2005 , (4 pages).
Schneider, Peter A., "Endovascular Skills—Guidewire and Catheter Skills for Endovascular Surgery," Second Edition Revised and Expanded, 10 pages, (2003).
Kandarpa, Krishna et al., "Handbook of Interventional Radiologic Procedures", Third Edition, pp. 194-210 (2002).
ThermoCool Irrigated Catheter and Intergrated Ablation System, Biosense Webster (2006).
Mount Sinai School of Medicine clinical trial for Impact of Renal Sympathetic Denervation of Chronic Hypertension, Mar. 2013, http://clinicaltrials.gov/ct2/show/NCT01628198.
Opposition to European Patent No. EP2092957, Granted Jan. 5, 2011, Date of Opposition Oct. 5, 2011, 26 pages.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2011, 25 pages.
Oz, Mehmet, Pressure Relief, TIME, Jan. 9, 2012, 2 pages. <www.time.come/time/printout/0,8816,2103278,00.html>.
Prochnau, Dirk et al., Catheter-based renal denervation for drug-resistant hypertension by using a standard eiectrophysiology catheter; Euro Intervention 2012, vol. 7, pp. 1077-1080.
Purerfellner, Helmut et al., Pulmonary Vein Stenosis Following Catheter Ablation of Atrial Fibrillation, Curr. Opin. Cardio. 20 :484-490, 2005.
Papademetriou, Vasilios, Renal Sympathetic Denervation for the Treatment of Difficult-to-Control or Resistant Hypertension, Int. Journal of Hypertension, 2011, 8 pages.
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Purerfellner, Helmut et al., Incidence, Management, and Outcome in Significant Pulmonary Vein Stenosis Complicating Ablation for Atrial Fibrillation, Am, J. Cardiol , 93, Jun. 1, 2004, 4 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
Allen, E.V., Sympathectomy for essential hypertension, Circulation, 1952, 6:131-140.
Bello-Reuss, E. et al., "Effects of Acute Unilaterai Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hemaluria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiologicai Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.

(56) References Cited

OTHER PUBLICATIONS

Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principie Cohort Study," Lancet 2009; 373:1275-81.
Krum, et al., "Renal Sympathetic-Nerve Ablation for Uncontrolled Hypertension." New England Journal of Med, Aug. 2009, 361;9.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011:108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 169, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial", Lancet, Dec. 4, 2010, vol. 376, pp. 1903-1909.
USRDS United States Renal Data System 2003 Annual Data Reort.
Valente, John F. et al., "Laparoscopic Renal Denervation for Intractable ADPKD-Related Pain", Nephrol Dial Transplant (2001) 16:160.
Wagner, C.D. et al., "Very Low Frequency Oscillations in Arterial Blood Pressure After Autonomic Blockade in Conscious Dogs," Feb. 5, 1997, Am J Physiol Regul lntegr Comp Physiol 1997, vol. 272, 1997 the American Physiological Society, pp. 2034-2039.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
Benito, F., et al. "Radiofrequency catheter ablation of accessory pathways in infants." Heart, 78:160-162 (1997).
Dibona, G.F. "Sympathetic nervous system and kidney in hypertension." Nephrol and Hypertension, 11: 197-200 (2002).
Dibona, G.F., et al. "Neural control of renal function." Physiol Rev, 77:75-197 (1997).
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; Mailed on Feb. 5, 2013, 61 pages.
Gelfand, M., et al., "Treatment of renal failure and hypertension." U.S. Appl. No. 60/442.970, 2003.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." *Am. J. Roentgenol*,174: 1592-1594 (2000).
Han, Y.-M, et al., "Renal artery eboiization with diluted hot contrast medium: An experimental study." J Vasc Interv Radiol, 12: 862-868 (2001).
Hanson, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response." *American Medical Association White Paper* (1988).
Huang et al., "Renal denervation prevents and reverses hyperinsulinemia-induced hypertension in rats." Hypertension 32 (1998) pp. 249-254.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Lustgarten, D.L.,et al., "Cryothermal ablation: Mechanism of tissue injury and current experience in the treatment of tachyarrhythmias." Progr Cardiovasc Dis, 41:481-498 (1999).
Millard, F. C., et al, "Renal Embolization for ablation of function in renal failure and hypertension." Postgraduate Medical Journal, 65, 729-734, (1989).
Medical-Dictionary.com, Definition of "Animal Model," http://medical-dictionary.com (search "Animal Model"), 2005.
Medtronic, Inc., Annual Report (Form 10-K) (Jun. 28, 2011).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), http://www.medtronic.com/rdn/mediakit/RDN%20FAQ.pdf.
Schauerte, P., et al. "Catheter ablation of cardiac autonomic nerves for prevention of vagal atrial fibrillation." Circulation, 102:2774-2780 (2000).
Smithwick et al., "Splanchnicectomy for essential hypertension." J. Am. Med, Assn. 152:16 (1953), pp. 1501-1504.
Solis-Herruzo et al., "Effects of lumbar sympathetic block on kidney function in cirrhotic patients with hepatorenal syndrome," J. Hepatol. 5 (1987), pp. 167-173.
Stella, A.., et al., "Effects of reversible renal denervation on haemodynamic and excretory functions on the ipsilateral and contralateral kidney in the cat." Hypertension, 4:181-188 (1986).
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites," PACE, 21:2517-2521 (1998).
Valente, J.F. "Laparoscopic renal denervation for intractable ADPKD-related pain," Nephrol Dial Transplant, 16: 160 (2001).
Weinstock, M., et al., "Renal denervation prevents sodium retention and hypertension in salt sensitive rabbits with genetic baroreflex impairment," Clinical Science, 90:287-293 (1996).
Wilcox, Josiah N., Scientific Basis Behind Renal Denervation for the Control of Hypertension, ICI 2012, Dec. 5-6, 2012. 38 pages.
International Search Report and Written Opinion dated Feb. 23, 2012, International Application No. PCT/US2011/057490, 14 pages.

(56) References Cited

OTHER PUBLICATIONS

Beale et al., "Minimally Invasive Treatment for Varicose Veins: A Review of Endovenous Laser Treatment and Radiofrequency Ablation". Lower Extremity Wounds 3(4), 2004, 10 pages.
International Search Report and Written Opinion for International App. No. PCT/US2011/057511, mailed Mar. 16, 2012, 16 pages.
International Search Report and Written Opinion for International Application No. PCT/US2011/046845, mailed Dec. 16, 2011, 16 pages.
International Search Report and Written Opinion for International Application No. PCT/US2011/057483, mailed Feb. 20, 2012, 11 pages.
International Search Report and Written Opinion for International Application No. PCT/US2011/057497, mailed Feb. 6, 2012, 12 pages.
International Search Report and Written Opinion for International Application No. PCT/US2011/057502, mailed Apr. 13, 2012, 14 pages.
International Search report and Written Opinion for International Application No. PCT/US2011/057504, mailed Feb. 14, 2012, 12 pages.
International Search Report and Written Opinion for International Application No. PCT/US2011/057508, Mailed Dec. 28, 2011, 12 pages.
International Search Report and Written Opinion for International Application No. PCT/US2011/057514, mailed Apr. 12, 2012, 15 pages.
International Search Report and Written Opinion for International Application No. PCT/US2011/057523, mailed Mar. 9, 2012, 15 pages.
International Search Report and Written Opinion for International Application No. PCT/US2012/063411 mailed Jun. 13, 2013, 13 pages.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios, "Renal Denervation and Symplicity HTN-3: "Dubium Sapientiae Initium" (Doubt Is the Beginning of Wisdom)", Circulation Research, 2014; 115: 211-214.

* cited by examiner

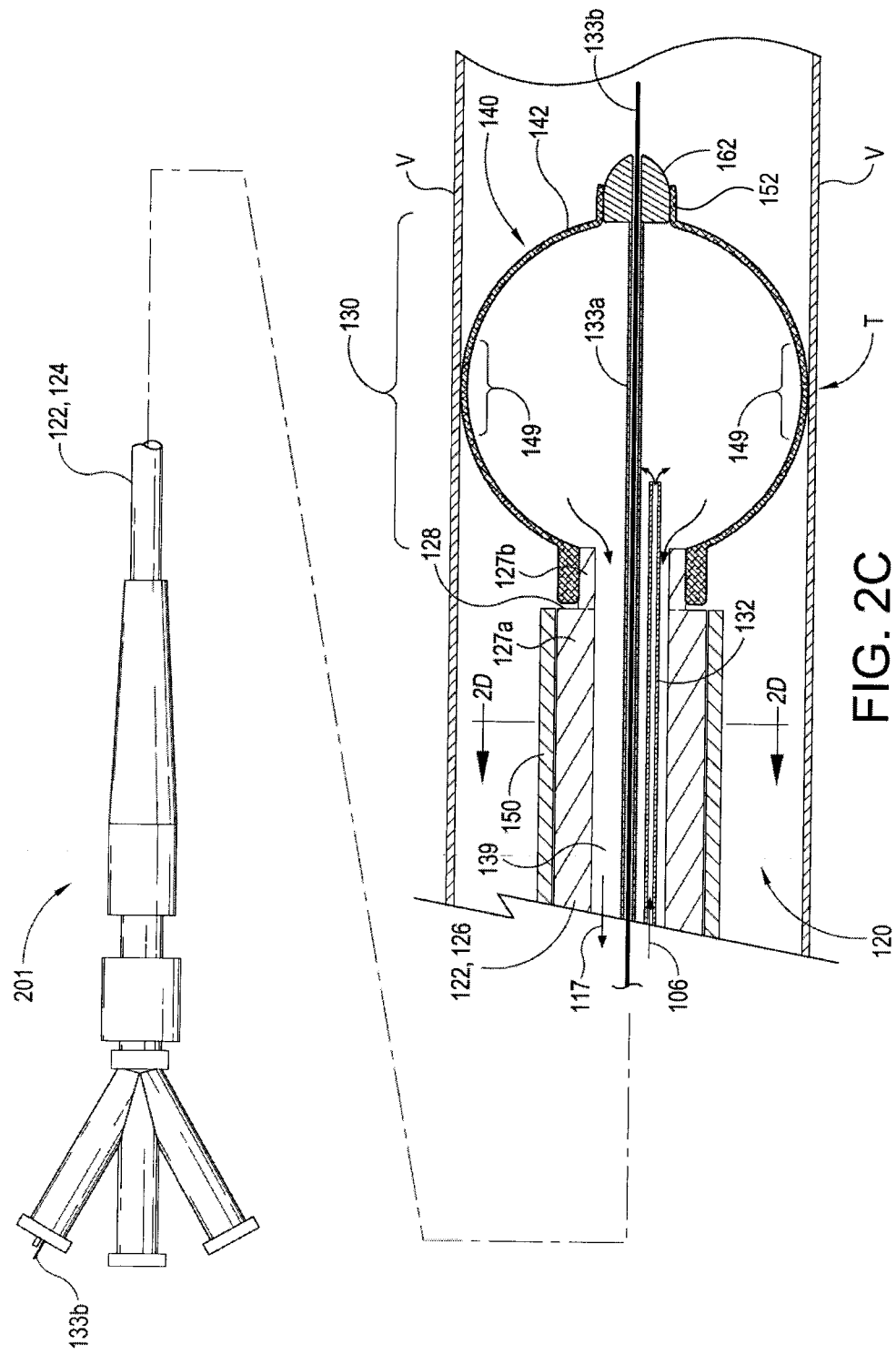

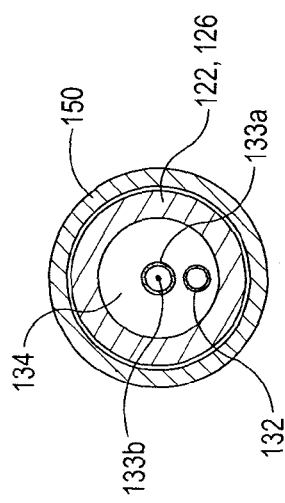
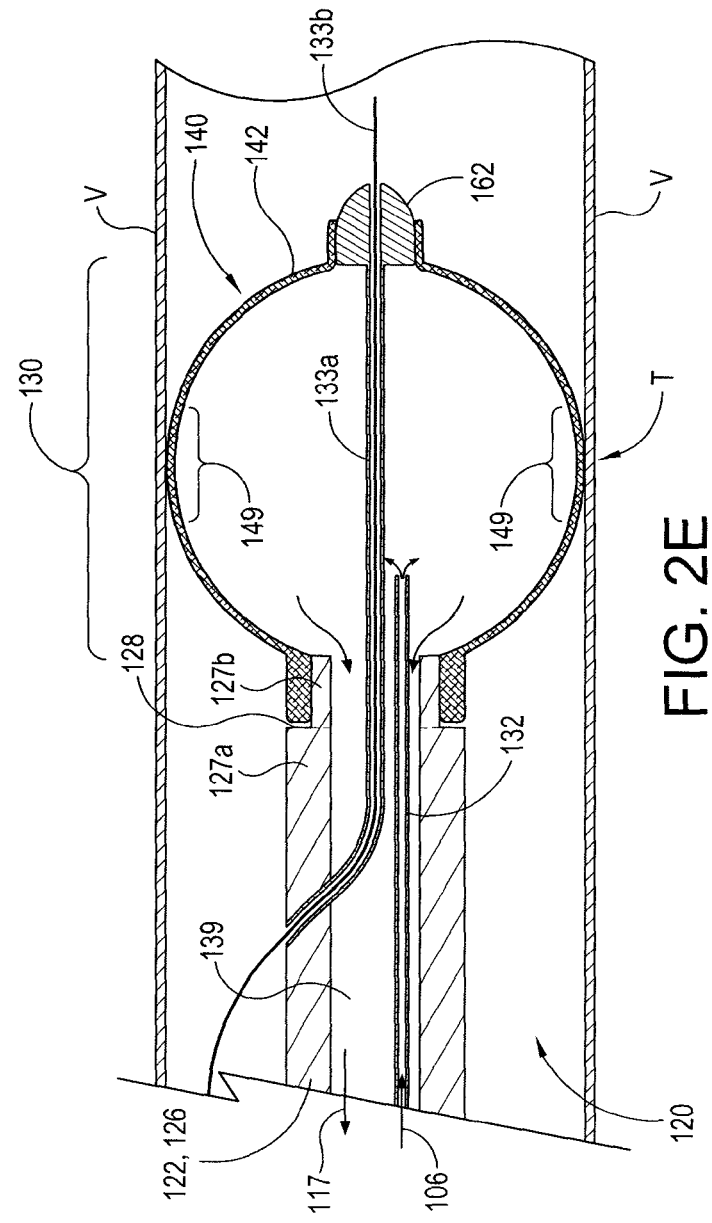

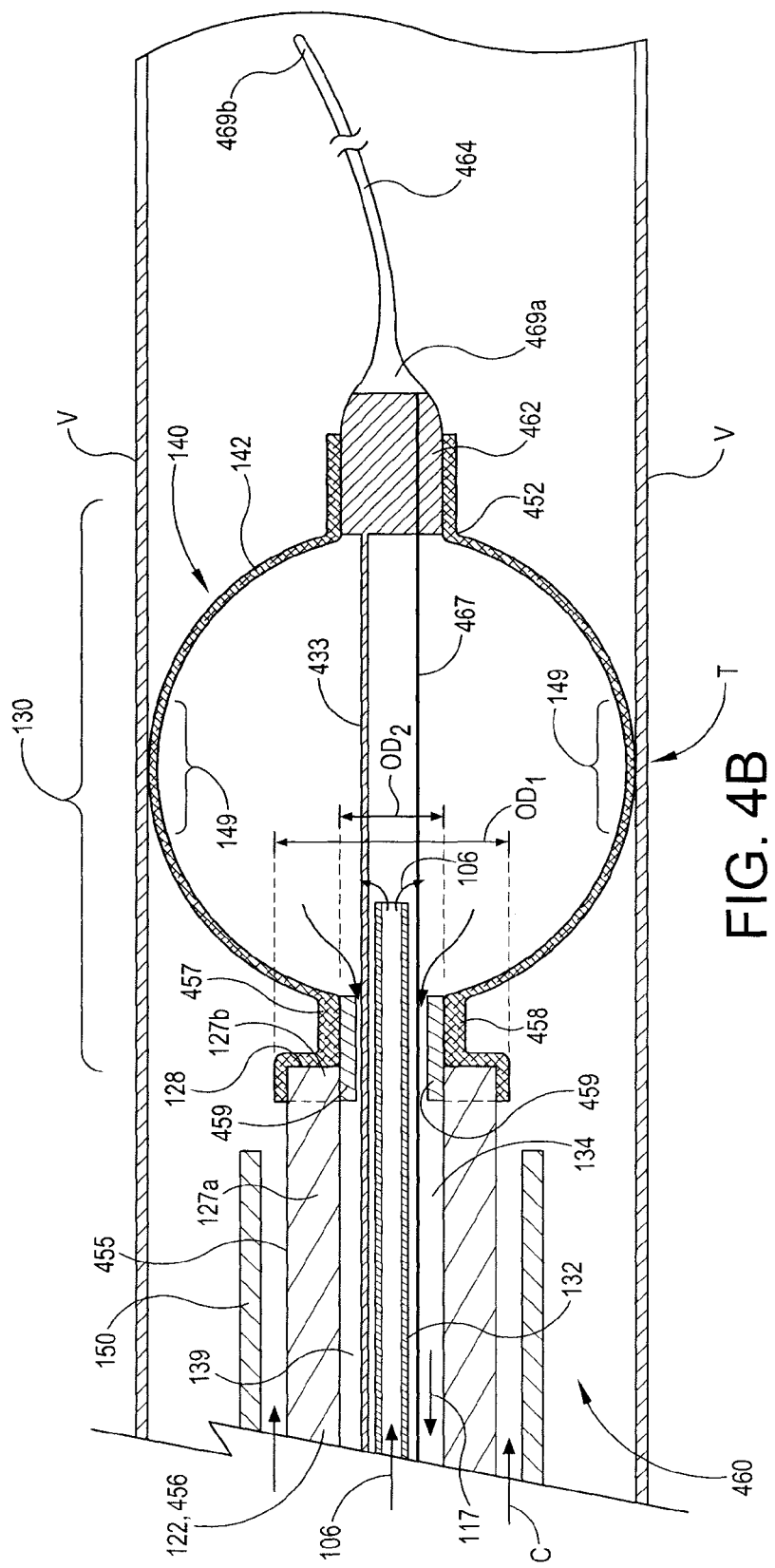

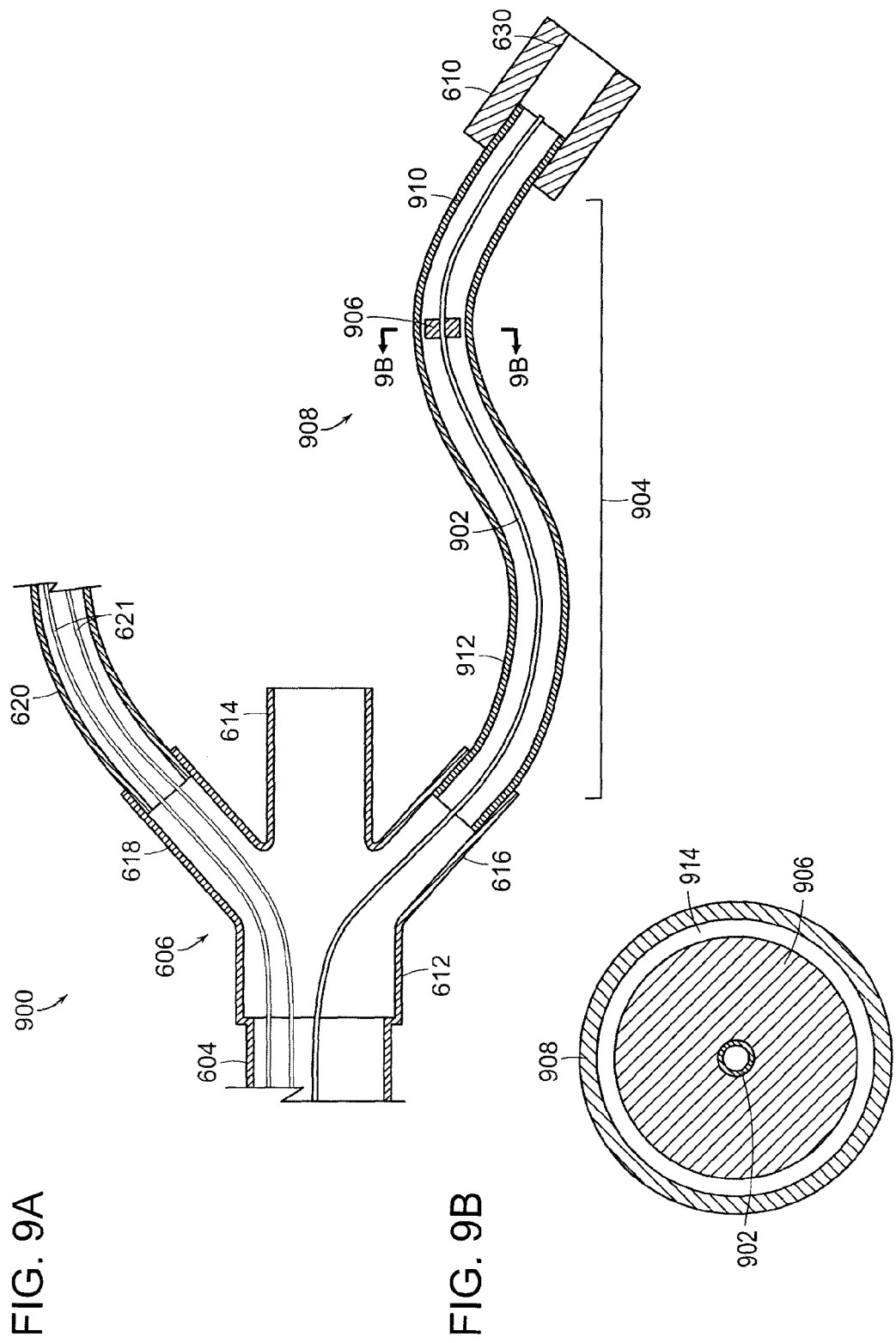

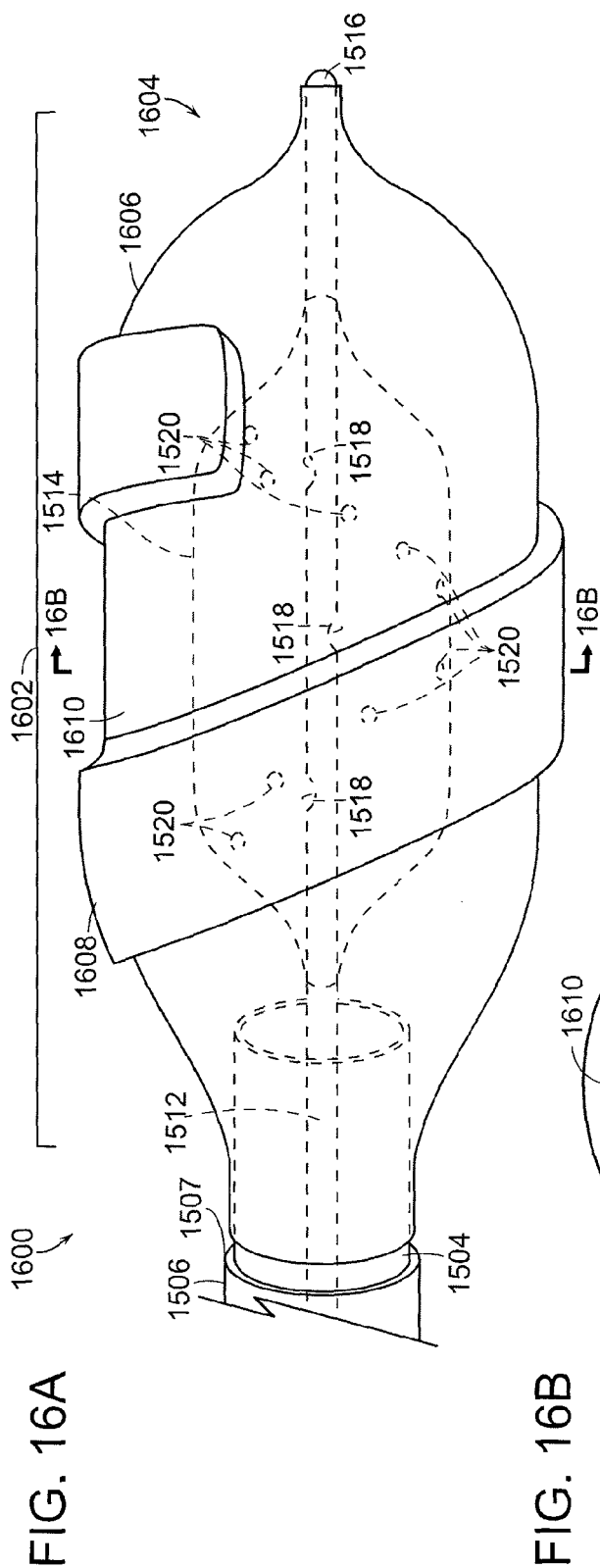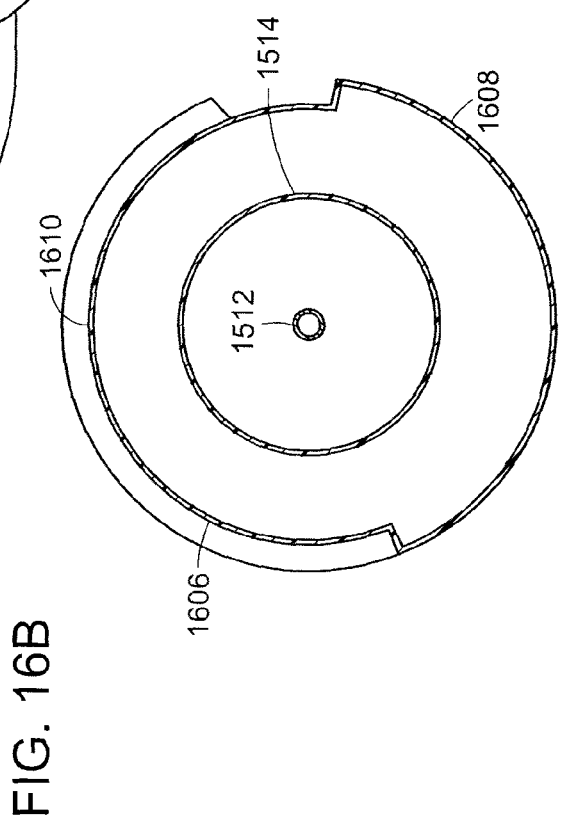
FIG. 16A
FIG. 16B

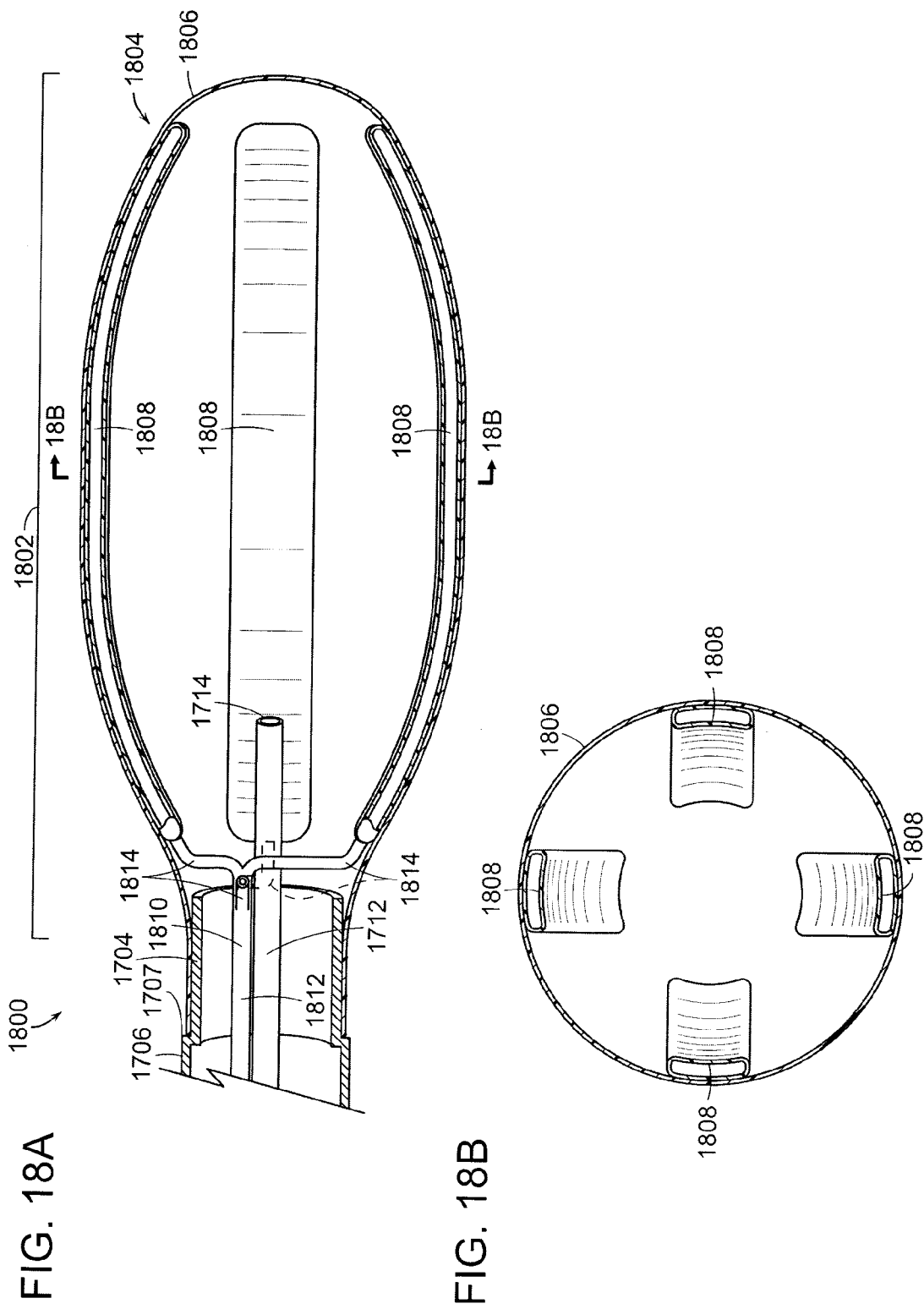

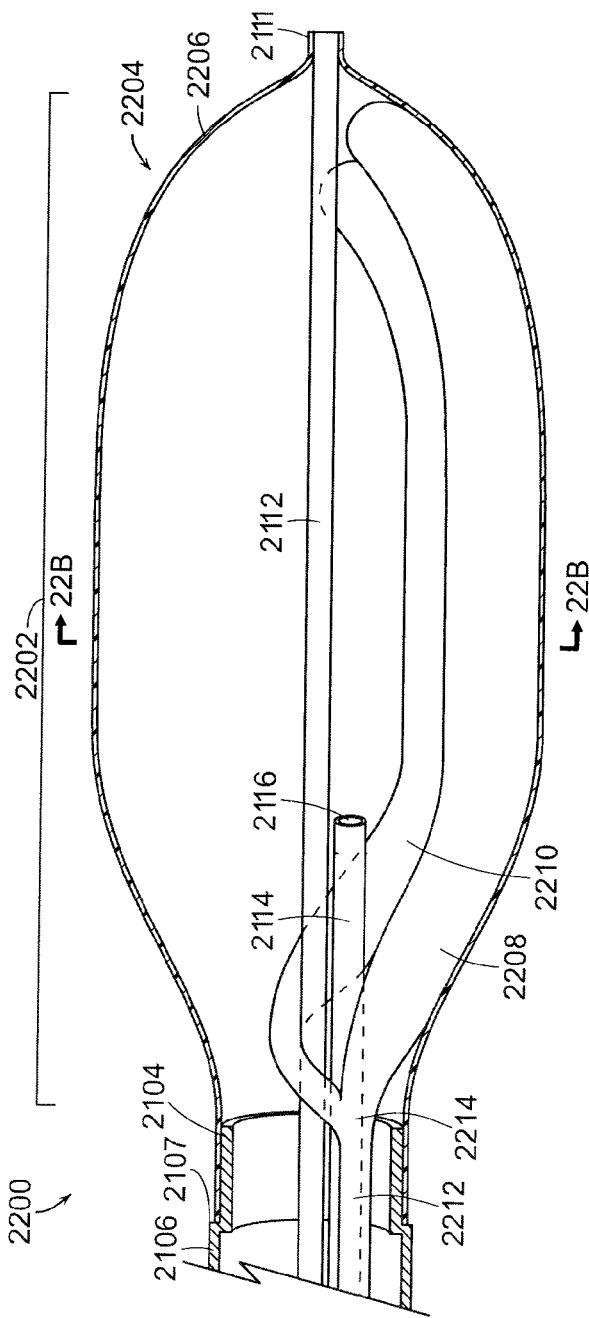

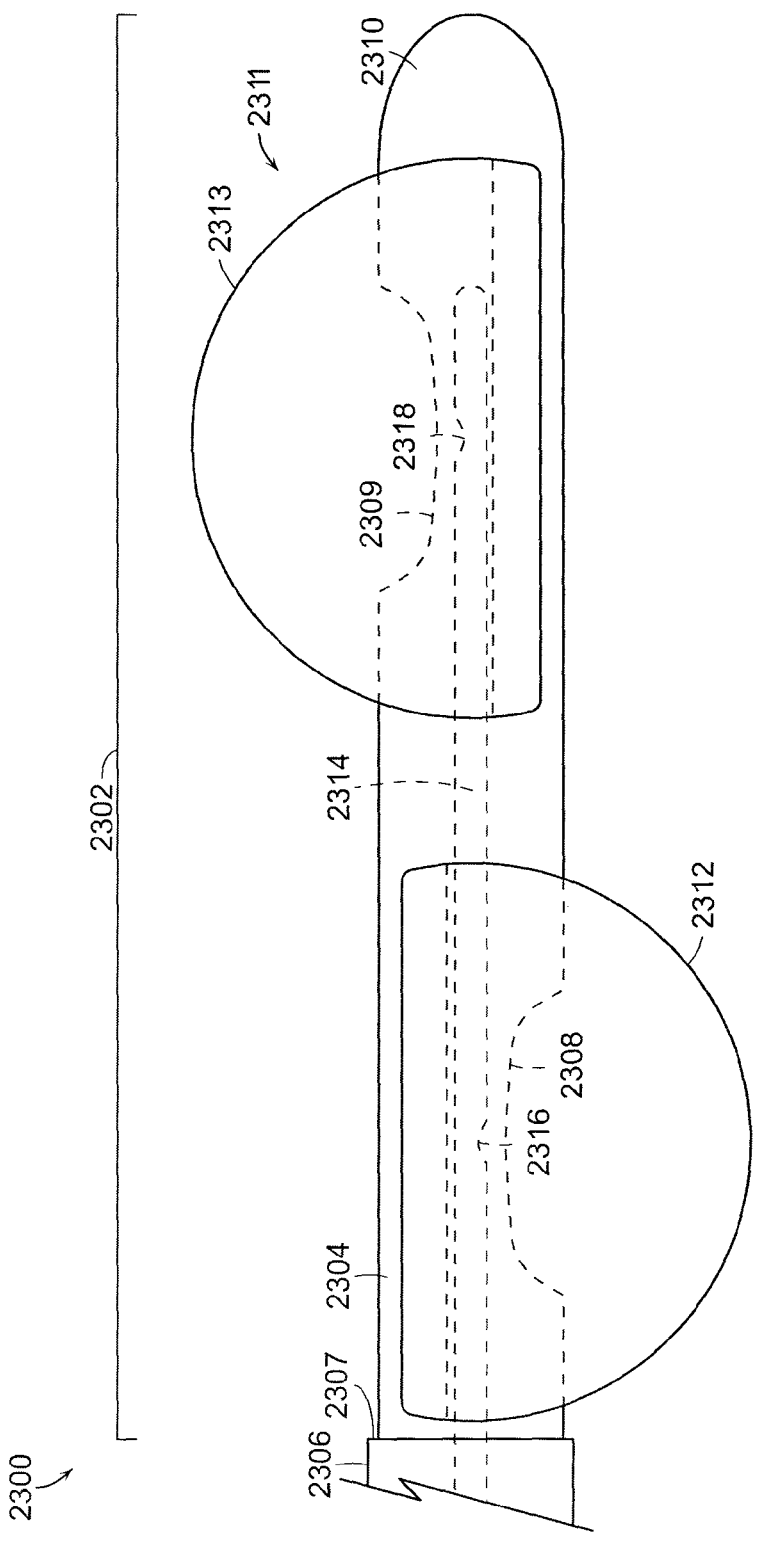

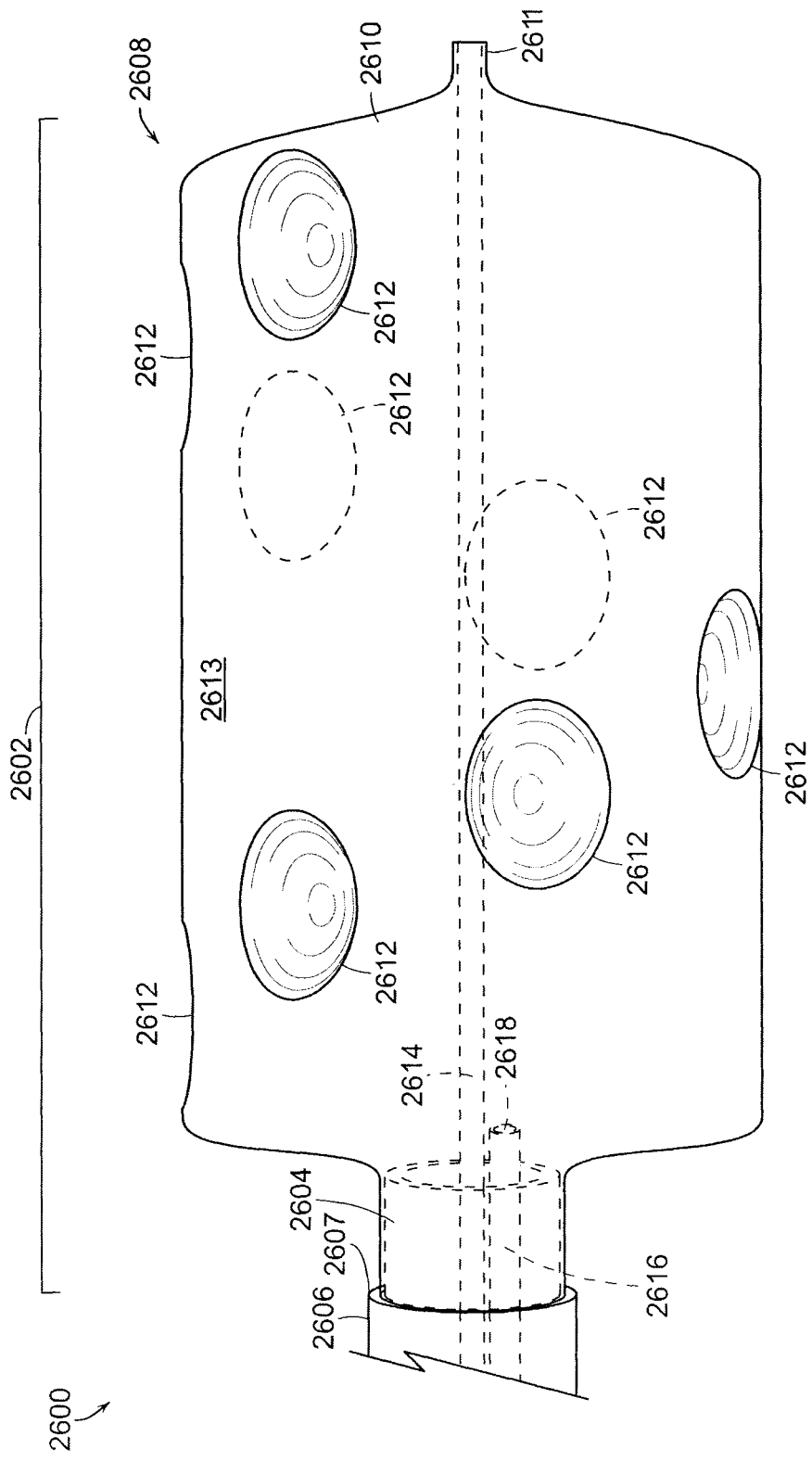

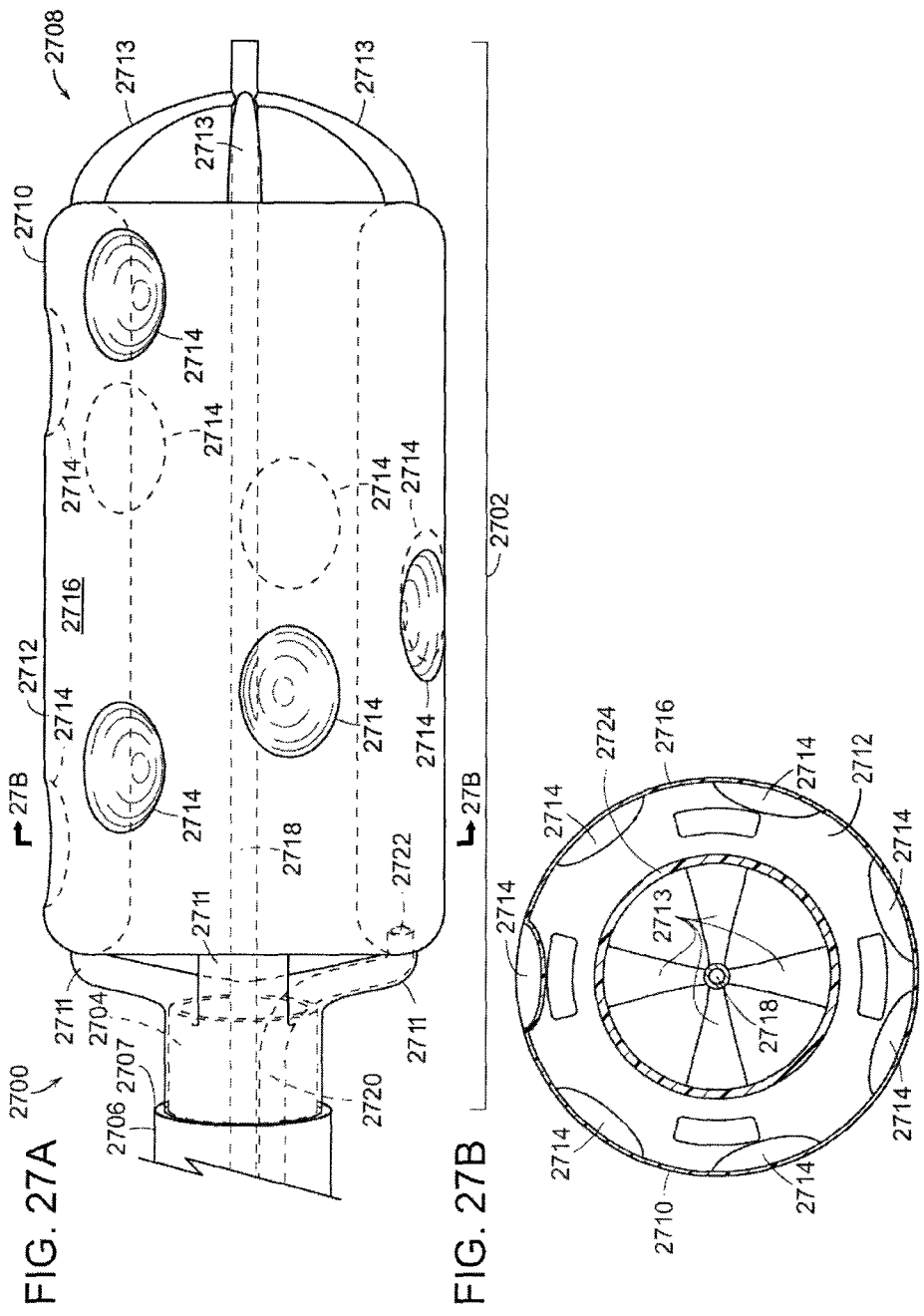

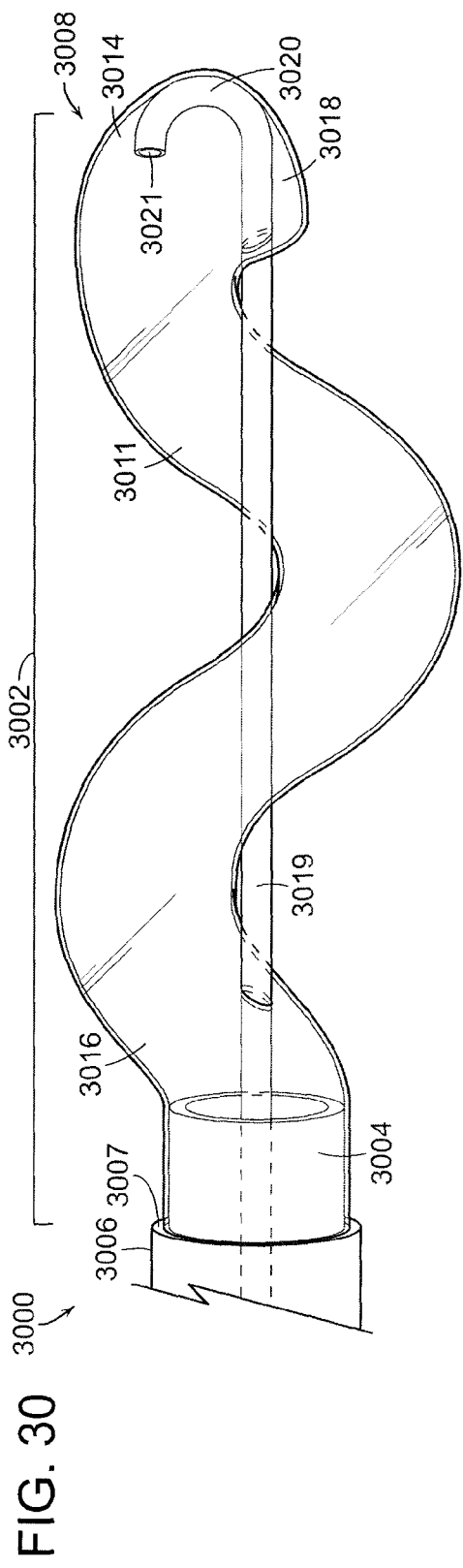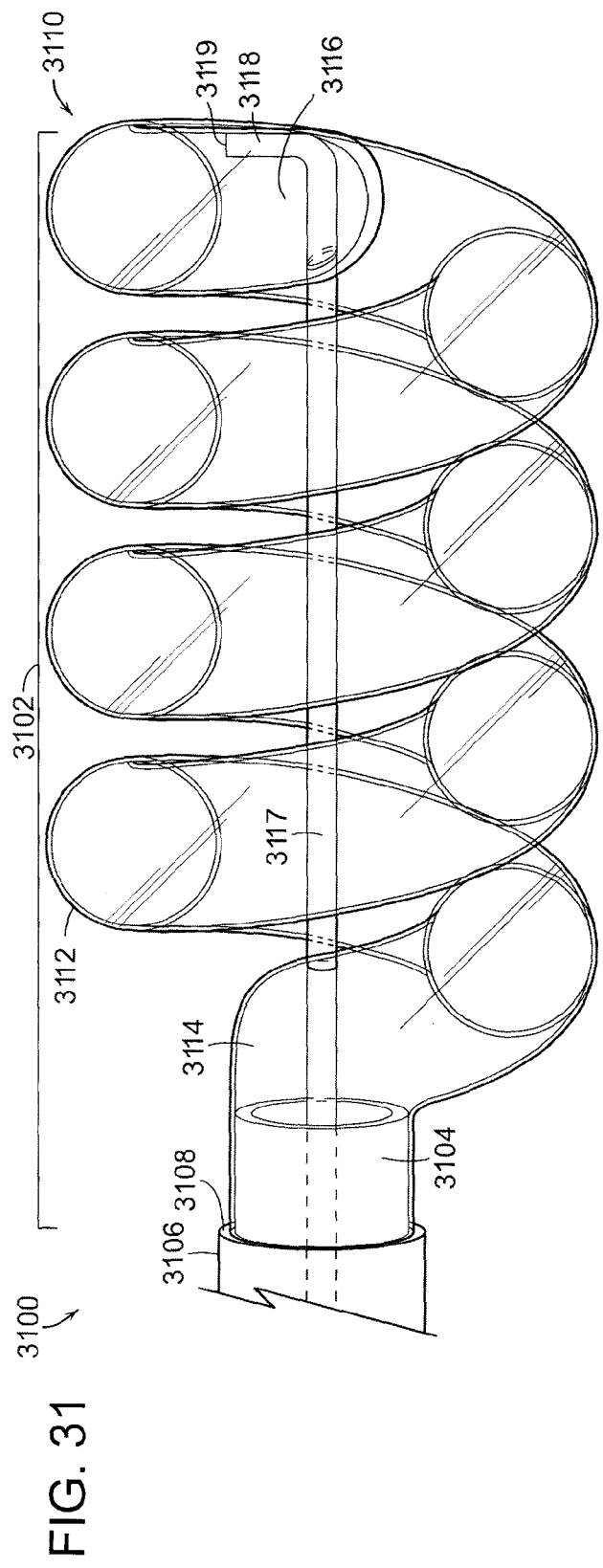

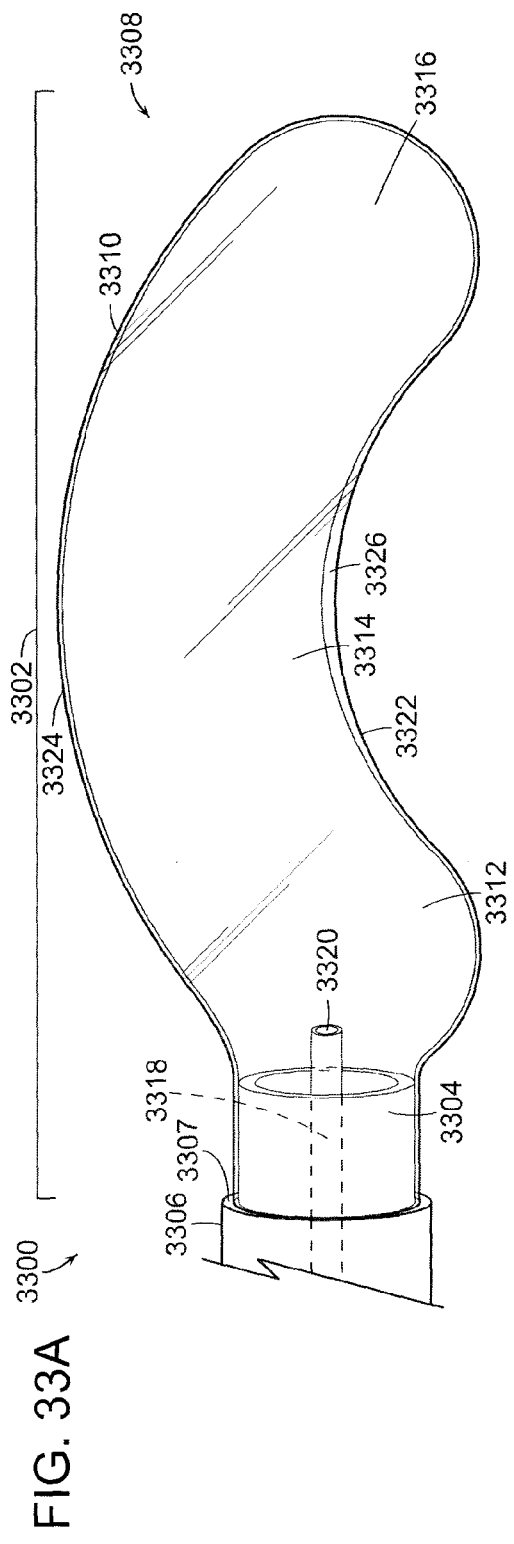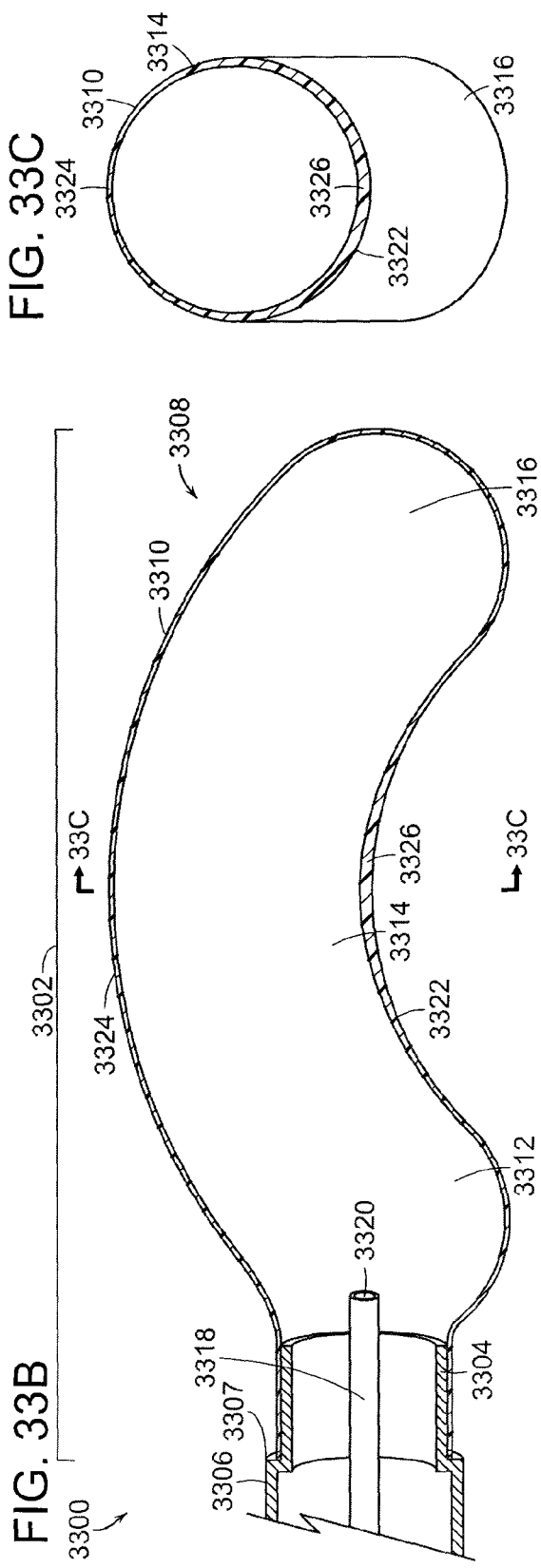

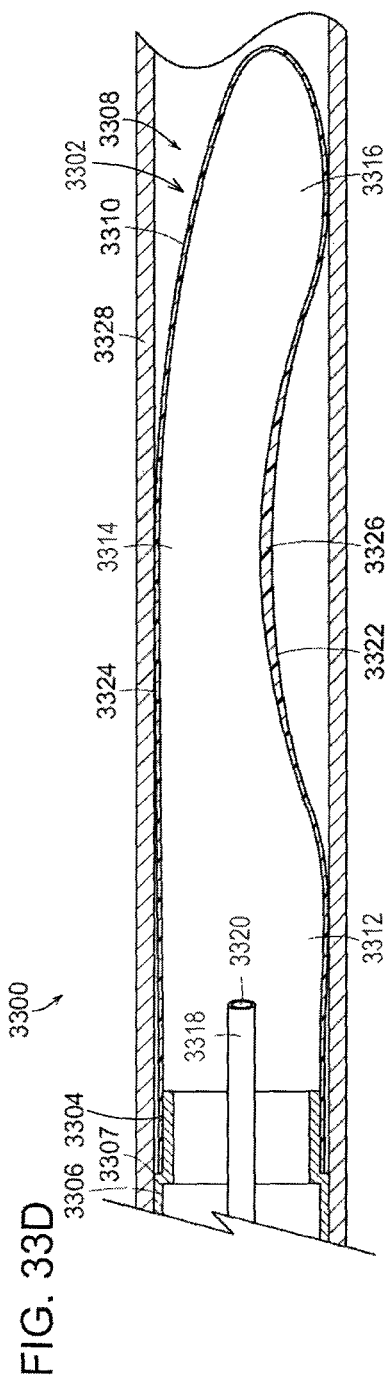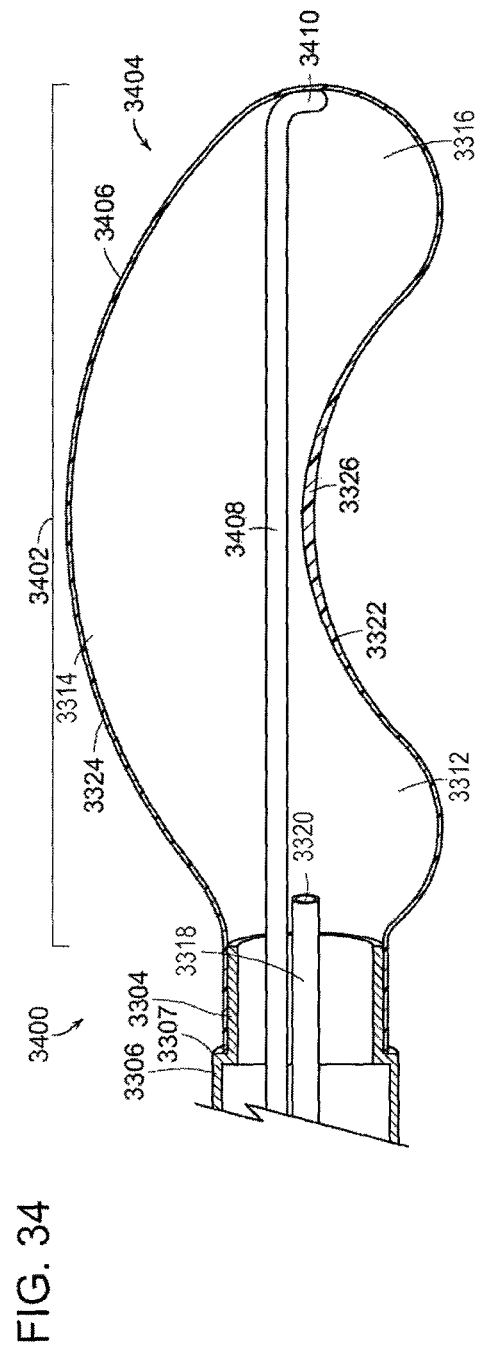

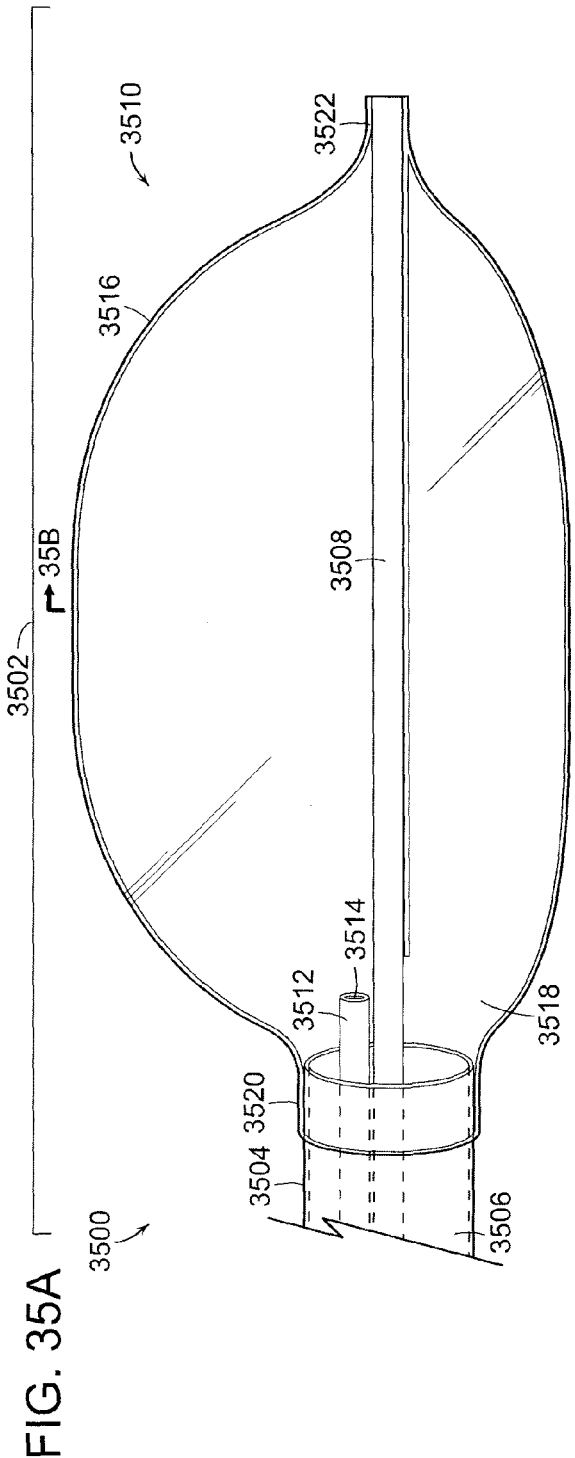
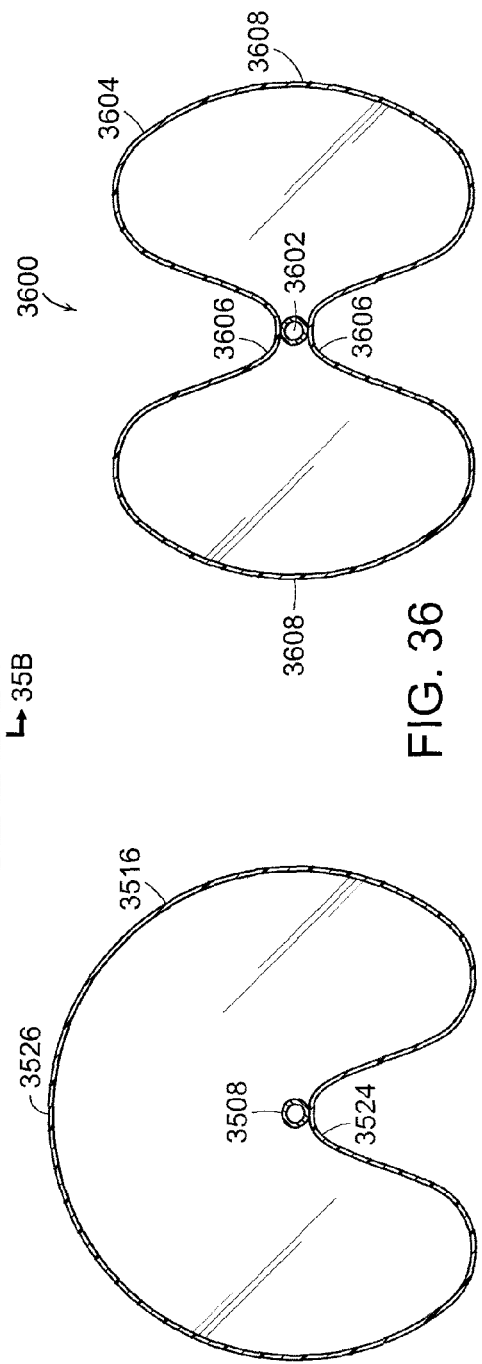
FIG. 35A
FIG. 35B
FIG. 36

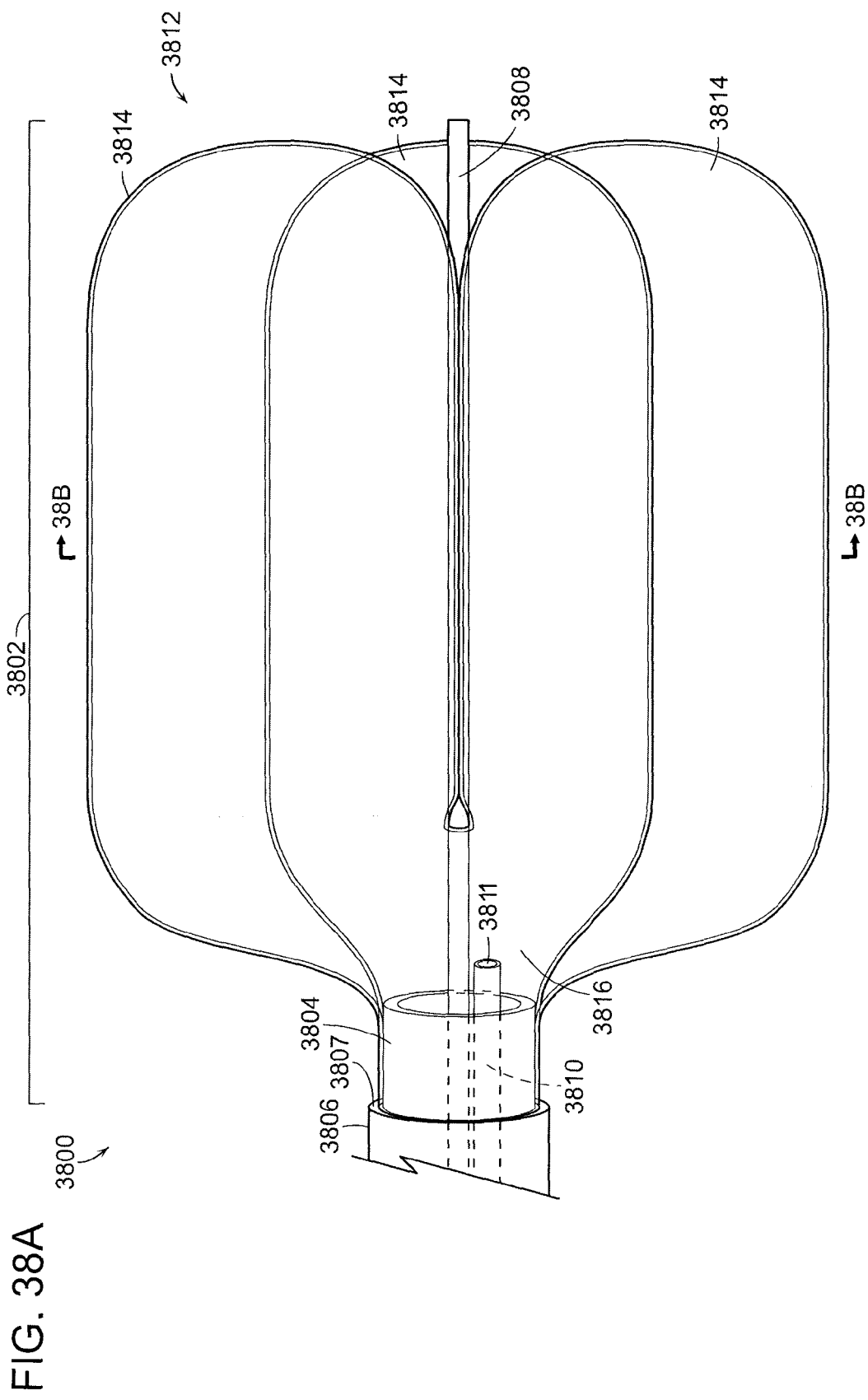

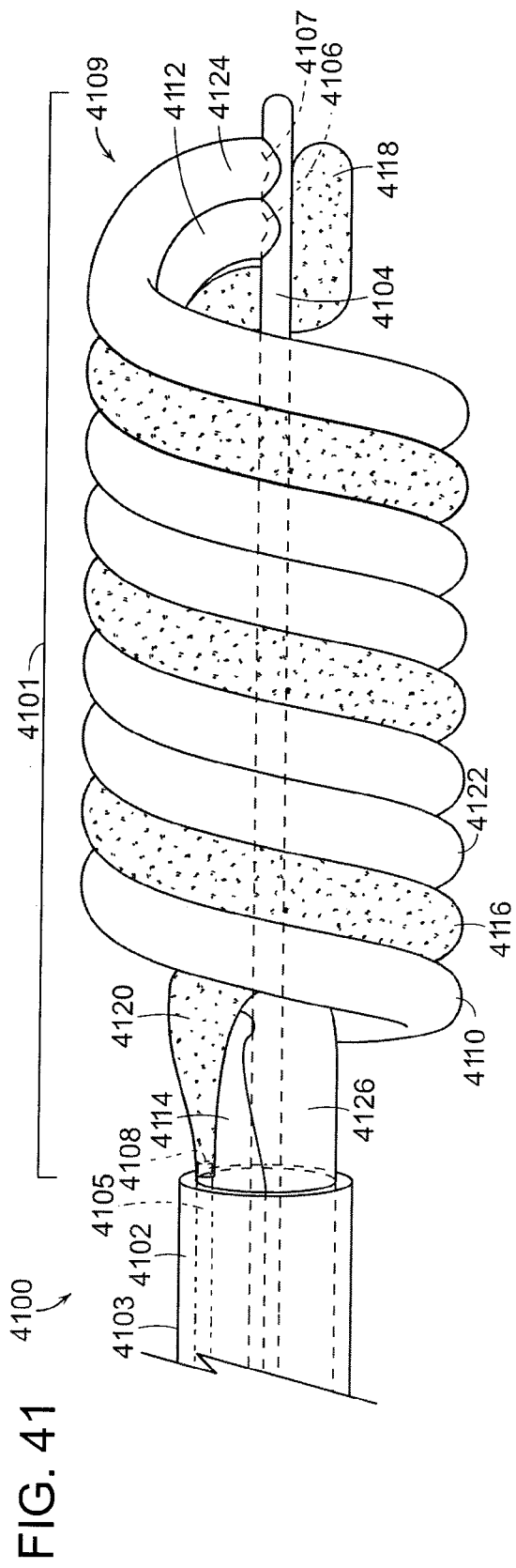
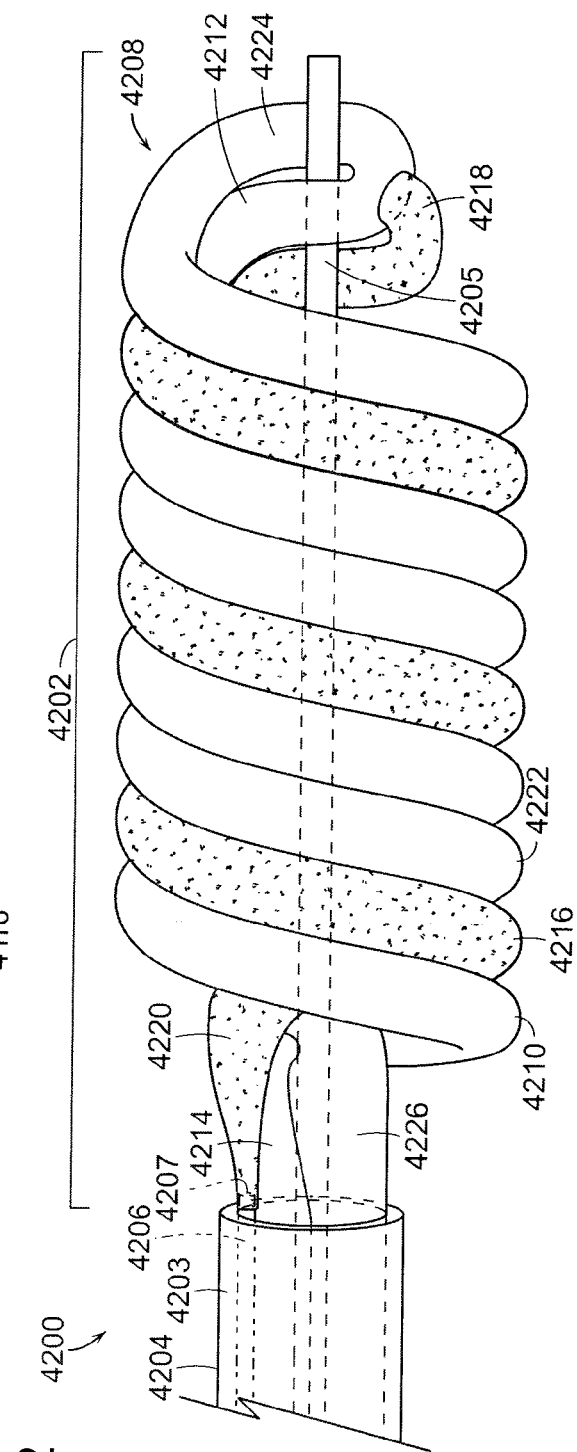
FIG. 41
FIG. 42

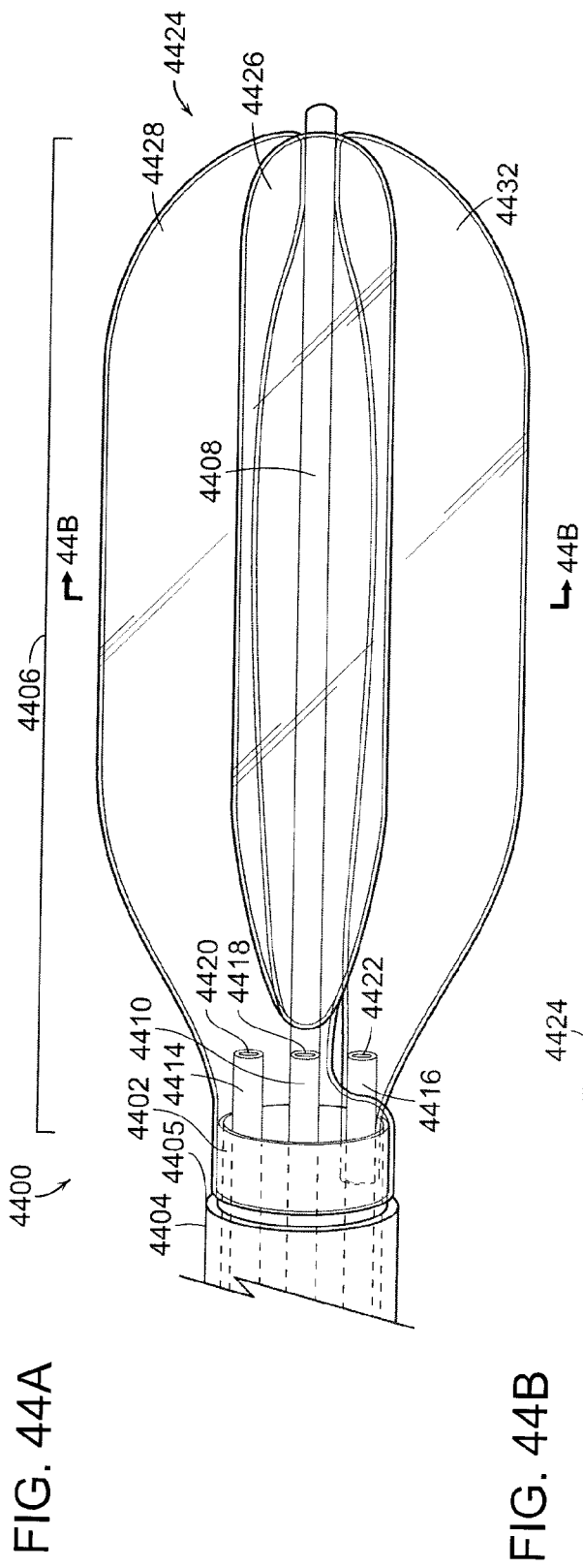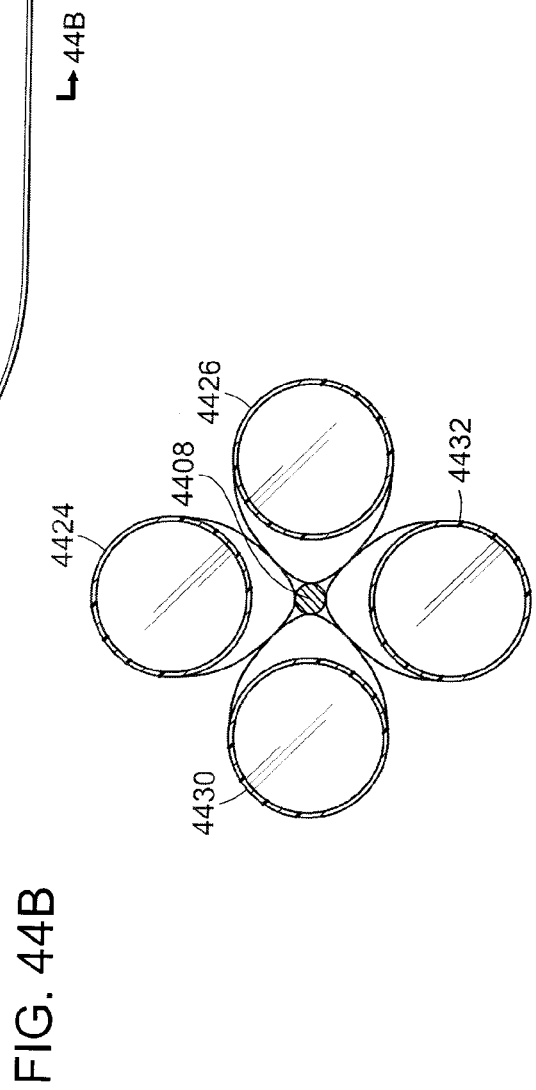
FIG. 44A
FIG. 44B

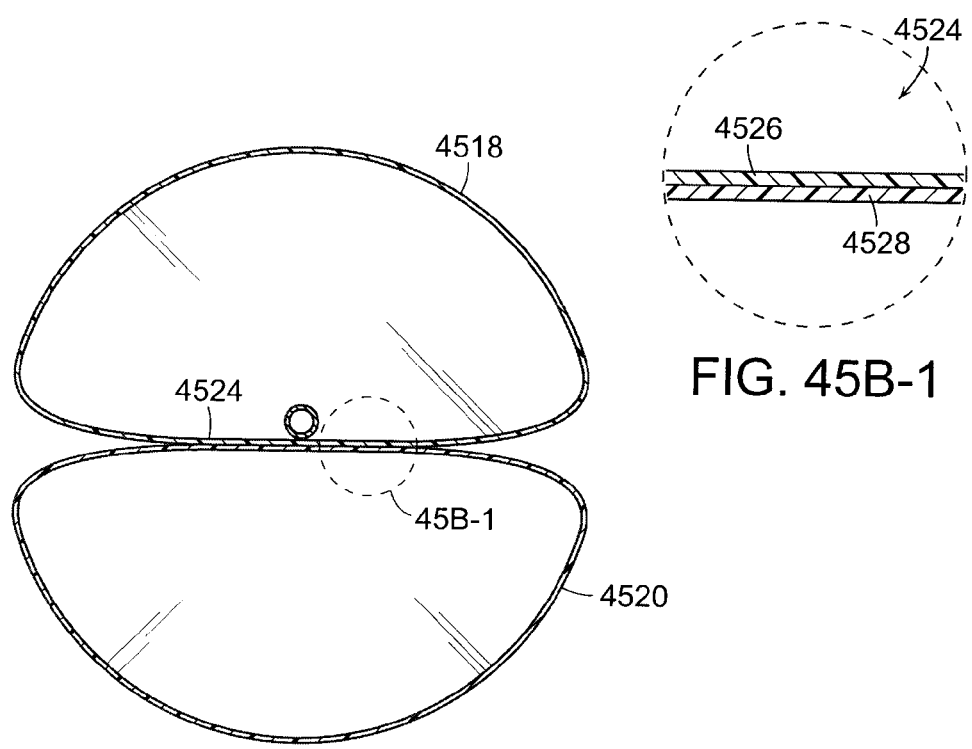
FIG. 45B-1
FIG. 45B
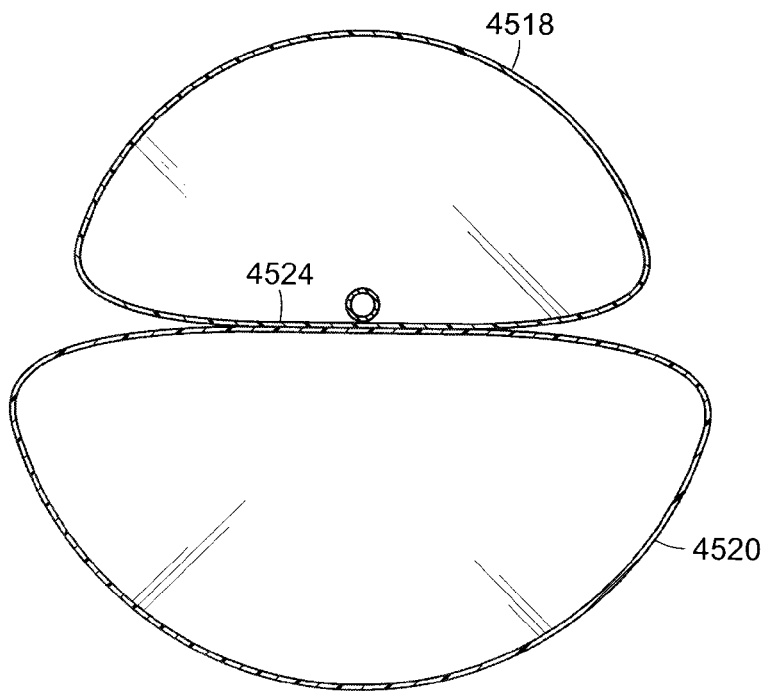
FIG. 45C

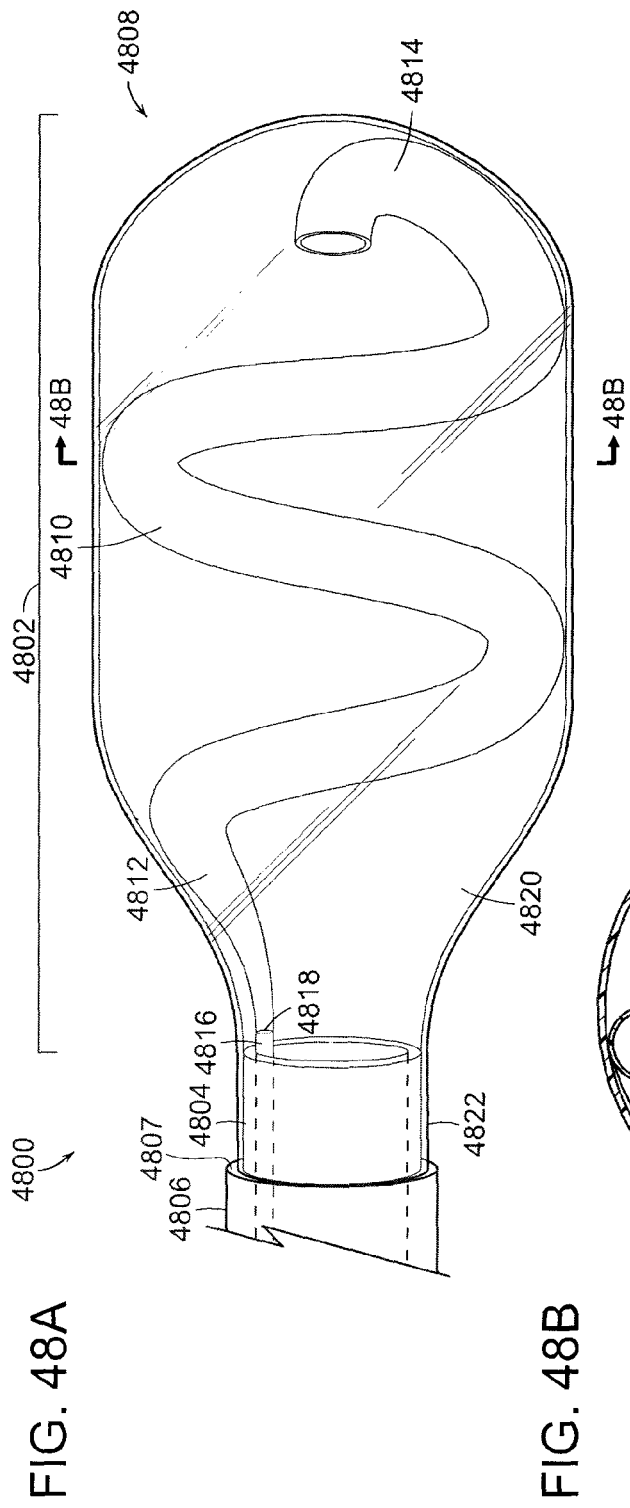
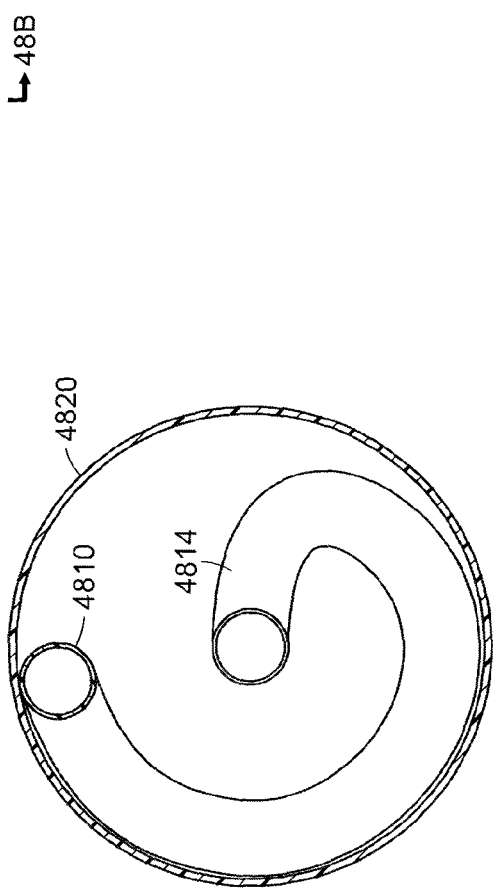
FIG. 48A
FIG. 48B

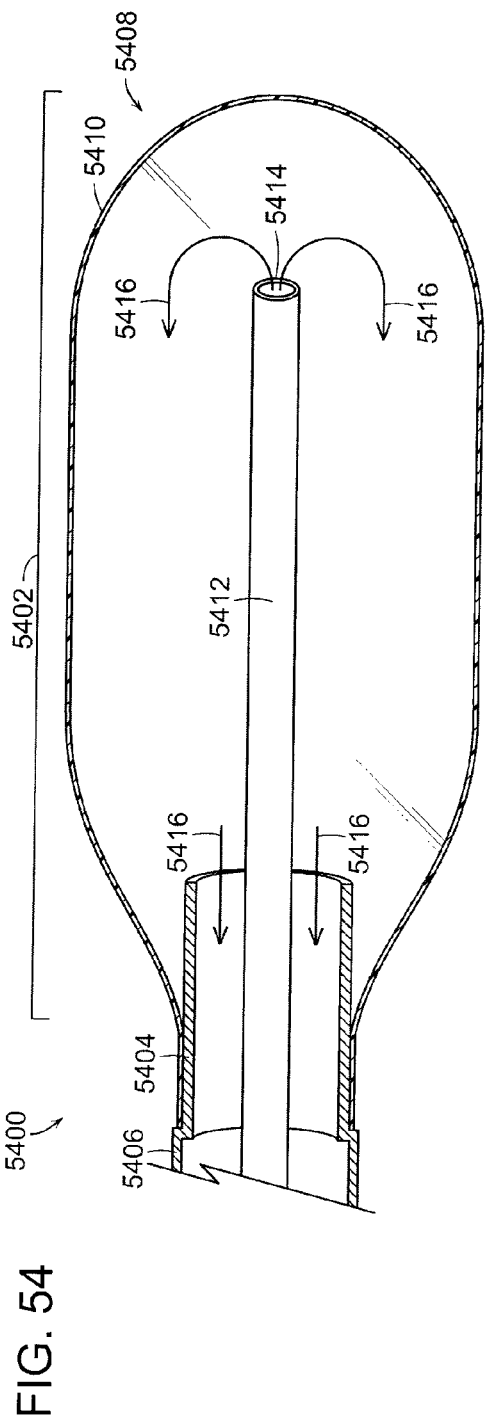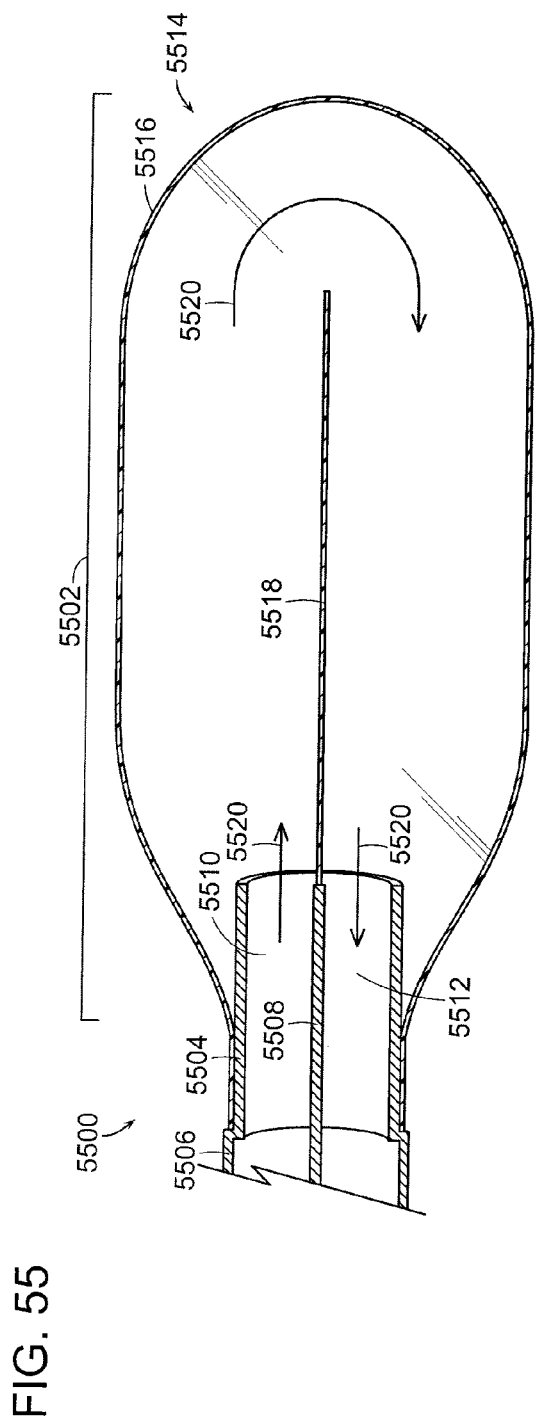

*Arterial Vasculature*

*Venous Vasculature*

NEUROMODULATION CRYOTHERAPEUTIC DEVICES AND ASSOCIATED SYSTEMS AND METHODS

CROSS-REFERENCE TO RELATED APPLICATION(S)

This application claims the benefit of the following pending applications:

(a) U.S. Provisional Application No. 61/406,968, filed Oct. 26, 2010;
(b) U.S. Provisional Application No. 61/528,091, filed Aug. 26, 2011;
(c) U.S. Provisional Application No. 61/528,684, filed Aug. 29, 2011; and
(d) U.S. Provisional Application No. 61/546,510, filed Oct. 12, 2011.

All of the foregoing applications are incorporated herein by reference in their entireties. Further, components and features of embodiments disclosed in the applications incorporated by reference may be combined with various components and features disclosed and claimed in the present application.

RELATED APPLICATIONS INCORPORATED BY REFERENCE

U.S. Provisional Application No. 61/545,052, filed Oct. 7, 2011, U.S. patent application Ser. No. 13/204,504, (filed Aug. 5, 2011, and published as U.S. 2012/0089047), PCT International Application No. PCT/US2011/46845 (filed Aug. 5, 2011 and published as WO2012/019156), and U.S. Provisional Application No. 61/371,110 (filed Aug. 5, 2010), are related to the present application. The foregoing applications are incorporated herein by reference in their entireties. As such, components and features of embodiments disclosed in the applications incorporated by reference may be combined with various components and features disclosed and claimed in the present application.

TECHNICAL FIELD

The present technology relates generally to cryotherapeutic devices. In particular, several embodiments are directed to cryotherapeutic devices for intravascular neuromodulation and associated systems and methods.

BACKGROUND

The sympathetic nervous system (SNS) is a primarily involuntary bodily control system typically associated with stress responses. Fibers of the SNS innervate tissue in almost every organ system of the human body and can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (such as heart failure), and progressive renal disease. For example, radiotracer dilution has demonstrated increased renal norepinephrine (NE) spillover rates in patients with essential hypertension.

Cardio-renal sympathetic nerve hyperactivity can be particularly pronounced in patients with heart failure. For example, an exaggerated NE overflow from the heart and kidneys to plasma is often found in these patients. Heightened SNS activation commonly characterizes both chronic and end stage renal disease. In patients with end stage renal disease, NE plasma levels above the median have been demonstrated to be predictive for cardiovascular diseases and several causes of death. This is also true for patients suffering from diabetic or contrast nephropathy. Evidence suggests that sensory afferent signals originating from diseased kidneys are major contributors to initiating and sustaining elevated central sympathetic outflow.

Sympathetic nerves to the kidneys terminate in the blood vessels, the juxtaglomerular apparatus, and the renal tubules. Stimulation of the renal sympathetic nerves can cause increased renin release, increased sodium ($Na^+$) reabsorption, and a reduction of renal blood flow. These neural regulation components of renal function are considerably stimulated in disease states characterized by heightened sympathetic tone and likely contribute to increased blood pressure in hypertensive patients. The reduction of renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others. Accordingly, there is a strong public-health need for alternative treatment strategies.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent.

FIGS. 2C and 2D are enlarged side and end cross-sectional views of a cooling assembly configured in accordance with another embodiment of the present technology.

FIG. 2E is an enlarged cross-sectional view of proximal and distal portions of a cryotherapeutic device configured in accordance with yet another embodiment of the present technology.

FIGS. 4A and 4B are enlarged cross-sectional views of cryotherapeutic devices having stepped distal end portions configured in accordance with embodiments of the present technology.

FIG. 9A is a cross-sectional view illustrating a pre-cooling assembly having a flow separator configured in accordance with another embodiment of the present technology.

FIG. 9B is a cross-sectional view illustrating the pre-cooling assembly of FIG. 9A.

FIG. 16A is a cross-sectional view illustrating a cooling assembly having an inner balloon with inner-balloon orifices and an outer balloon with a raised helical portion configured in accordance with an embodiment of the present technology.

FIG. 16B is a cross-sectional view illustrating the cooling assembly of FIG. 16A.

FIG. 18A is a cross-sectional view illustrating a cooling assembly having elongated, thermally-insulative members configured in accordance with another embodiment of the present technology.

FIG. 18B is a cross-sectional view illustrating the cooling assembly of FIG. 18A.

FIG. 22A is a cross-sectional view illustrating a cooling assembly having elongated, thermally-insulative members movable within a balloon configured in accordance with an embodiment of the present technology.

FIG. 22B is a cross-sectional view illustrating the cooling assembly of FIG. 22A.

FIG. 23A is a profile view illustrating a cooling assembly having multiple partially-circumferential balloons configured in accordance with an embodiment of the present technology.

FIG. 26 is a profile view illustrating a cooling assembly having spaced apart recesses configured in accordance with an embodiment of the present technology.

FIG. 27A is a profile view illustrating a cooling assembly having spaced apart recesses configured in accordance with another embodiment of the present technology.

FIG. 27B is a cross-sectional view illustrating the cooling assembly of FIG. 27A.

FIG. 30 is a profile view illustrating a cooling assembly having a helical balloon wrapped around a supply lumen configured in accordance with an embodiment of the present technology.

FIG. 31 is a profile view illustrating a cooling assembly having a helical balloon wrapped around a supply lumen configured in accordance with another embodiment of the present technology.

FIG. 33A is a profile view illustrating a cooling assembly having a balloon curved along its length configured in accordance with an embodiment of the present technology.

FIGS. 33B and 33C are cross-sectional views illustrating the cooling assembly of FIG. 33A.

FIG. 33D is a cross-sectional view illustrating the cooling assembly of FIG. 33A in a delivery state within a delivery sheath.

FIG. 34 is a cross-sectional view illustrating a cooling assembly having a balloon curved along its length configured in accordance with another embodiment of the present technology.

FIG. 35A is a profile view illustrating a cooling assembly having a balloon having a constrained longitudinal portion configured in accordance with an embodiment of the present technology.

FIG. 35B is a cross-sectional view illustrating the cooling assembly of FIG. 35A.

FIG. 36 is a cross-sectional view illustrating a cooling assembly having a balloon having a constrained longitudinal portion configured in accordance with another embodiment of the present technology.

FIG. 38A is a profile view illustrating a cooling assembly having multiple elongated balloons configured in accordance with an embodiment of the present technology.

FIG. 41 is a profile view illustrating a cooling assembly having multiple helical balloons configured in accordance with an embodiment of the present technology.

FIG. 42 is a profile view illustrating a cooling assembly having multiple helical balloons configured in accordance with another embodiment of the present technology.

FIG. 44A is a profile view illustrating a cooling assembly having multiple elongated balloons attached to a shaping member configured in accordance with another embodiment of the present technology.

FIG. 44B is a cross-sectional view illustrating the cooling assembly of FIG. 44A.

FIG. 45B is a cross-sectional view illustrating the cooling assembly of FIG. 45A expanded to a first cross-sectional dimension.

FIG. 45B-1 is an enlarged cross-sectional view illustrating a partition shown in FIG. 45B.

FIG. 45C is a cross-sectional view illustrating the cooling assembly of FIG. 45A expanded to a second cross-sectional dimension, larger than the first cross-sectional dimension.

FIG. 46-1 is an enlarged cross-sectional view illustrating a partition shown in FIG. 46.

FIG. 48A is a profile view illustrating a cooling assembly having a helical primary balloon within a secondary balloon configured in accordance with an embodiment of the present technology.

FIG. 48B is a cross-sectional view illustrating the cooling assembly of FIG. 48A.

FIG. 54 is a cross-sectional view illustrating a cooling assembly that can be well-suited for circulation of refrigerant without phase change configured in accordance with an embodiment of the present technology.

FIG. 55 is a cross-sectional view illustrating a cooling assembly that can be well-suited for circulation of refrigerant without phase change configured in accordance with another embodiment of the present technology.

DETAILED DESCRIPTION

Figure 1:
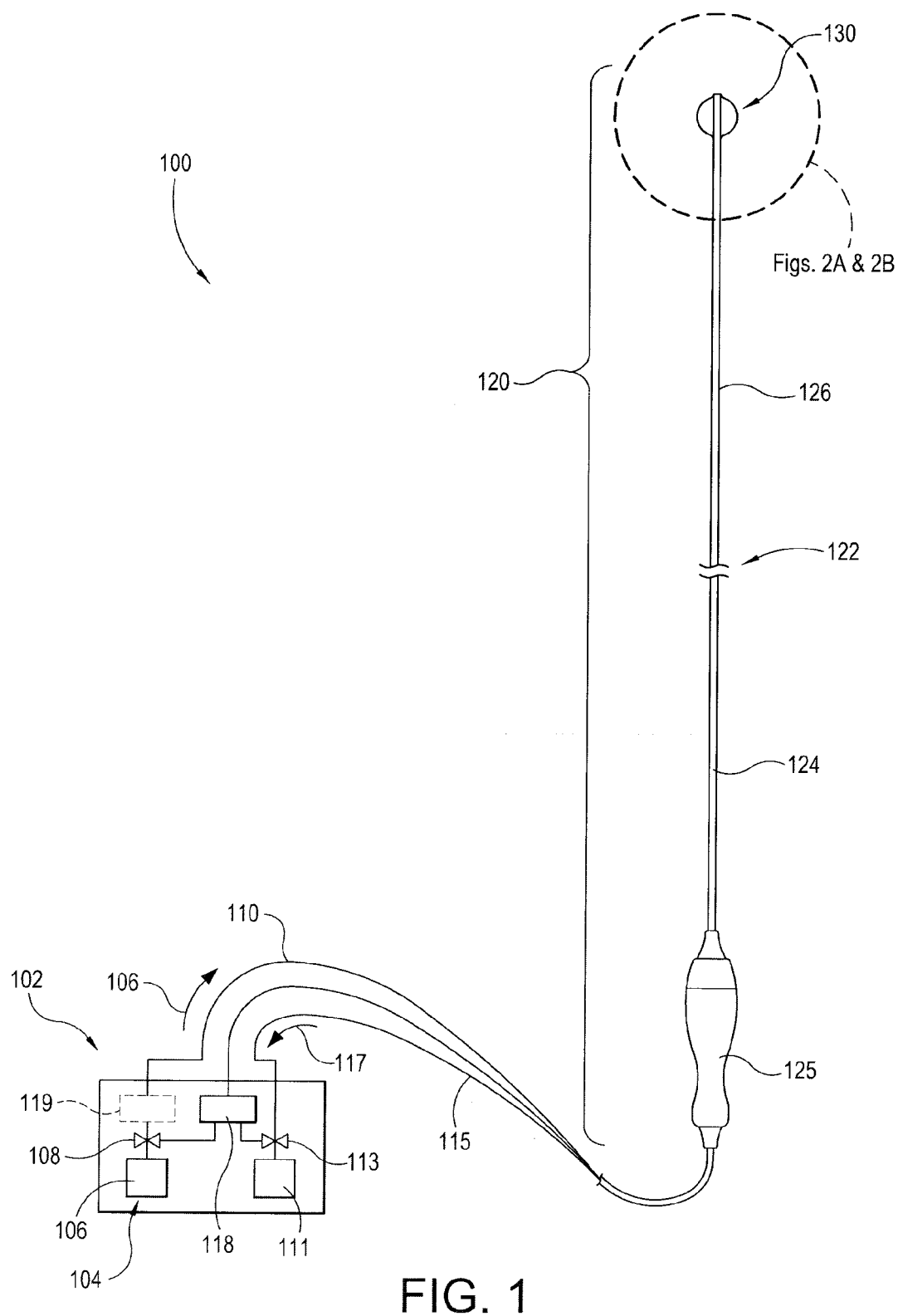
FIG. 1 illustrates a cryotherapeutic system in accordance with an embodiment of the present technology.

Specific details of several embodiments of the technology are described below with reference to FIGS. 1-59B. Although many of the embodiments are described below with respect to devices, systems, and methods for intravascular modulation of renal nerves using cryotherapeutic approaches, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-59B.

With regard to the terms "distal" and "proximal" within this description, unless otherwise specified, the terms can reference a relative position of the portions of a cryotherapeutic device and/or an associated delivery device with reference to an operator and/or a location in the vasculature. For example, proximal can refer to a position closer to the operator of the device or an incision into the vasculature, and distal can refer to a position that is more distant from the operator of the device or further from the incision along the vasculature.

Renal Neuromodulation

Renal neuromodulation is the partial or complete incapacitation or other effective disruption of nerves innervating the kidneys. In particular, renal neuromodulation comprises inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks). Renal neuromodulation is expected to efficaciously treat several clinical conditions characterized by increased overall sympathetic activity, and in particular conditions associated with central sympathetic overstimulation such as hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, and sudden death. The reduction of afferent neural signals contributes to the systemic reduction of sympathetic tone/drive, and renal neuromodulation is expected to be useful in treating several conditions associated with systemic sympathetic overactivity or hyperactivity. Renal neuromodulation can potentially benefit a variety of organs and bodily structures innervated by sympathetic nerves. For example, a reduction in central sympathetic drive may reduce insulin resistance that afflicts patients with metabolic syndrome and Type II diabetics. Additionally, osteoporosis can be sympathetically activated and might benefit from the downregulation of sympathetic drive that accompanies renal neuromodulation. A more detailed description of pertinent patient anatomy and physiology is provided below.

Various techniques can be used to partially or completely incapacitate neural pathways, such as those innervating the kidneys. Cryotherapy, for example, includes cooling tissue at a target site in a manner that modulates neural function. The mechanisms of cryotherapeutic tissue damage include, for example, direct cell injury (e.g., necrosis), vascular injury (e.g., starving the cell from nutrients by damaging supplying blood vessels), and sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Several embodiments of the present technology include cooling a structure at or near an inner surface of a renal artery wall such that proximate (e.g., adjacent) tissue is effectively cooled to a depth where sympathetic renal nerves reside. For example, the cooling structure is cooled to the extent that it causes therapeutically effective, cryogenic renal-nerve modulation. Sufficiently cooling at least a portion of a sympathetic renal nerve is expected to slow or potentially block conduction of neural signals to produce a prolonged or permanent reduction in renal sympathetic activity.

Cryotherapy has certain characteristics that can be beneficial for intravascular renal neuromodulation. For example, rapidly cooling tissue provides an analgesic effect such that cryotherapies may be less painful than ablating tissue at high temperatures. Cryotherapies may thus require less analgesic medication to maintain patient comfort during a procedure compared to heat ablation procedures. Additionally, reducing pain mitigates patient movement and thereby increases operator success and reduces procedural complications. Cryotherapy also typically does not cause significant collagen tightening, and thus cryotherapy is not typically associated with vessel stenosis.

Cryotherapies generally operate at temperatures that cause cryotherapeutic applicators to adhere to moist tissue. This can be beneficial because it promotes stable, consistent, and continued contact during treatment. The typical conditions of treatment can make this an attractive feature because, for example, a patient can move during treatment, a catheter associated with an applicator can move, and/or respiration can cause the kidneys to rise and fall and thereby move the renal arteries. In addition, blood flow is pulsatile and causes the renal arteries to pulse. Adhesion associated with cryotherapeutic cooling also can be advantageous when treating short renal arteries in which stable intravascular positioning can be more difficult to achieve.

Selected Embodiments of Renal Cryogenic Systems

FIG. 1 illustrates a cryotherapeutic system 100 configured in accordance with several embodiments of the present technology. The cryotherapeutic system 100 can include a console 102 and a cryotherapeutic device 120. In the embodiment shown in FIG. 1, the console 102 includes a supply container 104, a refrigerant 106 in the supply container 104, and a supply control valve 108 in fluid communication with the supply container 104. The supply container 104 can be a single-use cartridge or a larger container that contains a sufficient volume of refrigerant 106 to perform multiple procedures. The larger supply containers, for example, can be refillable cylinders. The supply container 104 is configured to retain the refrigerant 106 at a desired pressure. For example, in one embodiment, liquid $N_2O$ is contained in the supply container 104 at a pressure of 750 psi or greater so it is in at least a substantially liquid state at ambient temperatures. In other embodiments, the refrigerant 106 can include carbon dioxide, a hydrofluorocarbon ("HFC"; e.g., Freon®, R-410A, etc.), and/or other suitable compressed or condensed refrigerants that can be retained in the supply container 104 at a sufficiently high pressure to maintain the refrigerant 106 in at least a substantially liquid state at ambient temperatures (e.g., approximately 210 psi for R-410A).

The supply control valve 108 is coupled to a supply line 110 configured to transport the refrigerant 106 to the cryotherapeutic device 120. The supply control valve 108 can be operated manually or automatically. The console 102 can optionally include a pump 111, such as a vacuum pump or a DC power pump, and/or a backpressure control valve 113 coupled to an exhaust line 115 configured to receive exhausted refrigerant 117 from the cryotherapeutic device 120. The pump 111 can reduce the backpressure of evaporated refrigerant and, in conjunction with the supply flow rate, increase refrigeration power. In other embodiments, the expanded refrigerant 117 can exhaust to ambient pressure.

The console 102 can further include an optional controller 118 that operates the supply control valve 108 and the backpressure control valve 113. The controller 118, for example, can be a processor or dedicated circuitry that implements a computerized algorithm for executing a procedure automatically. The console 102 may also include an optional user interface that receives user input and/or provides information to the user and/or circuitry for monitoring optional sensors (e.g., pressure or temperature) if present in the cryotherapeutic device 120. In one embodiment, the controller 118 operates the backpressure control valve 113 to control the amount of vacuum applied to the exhausted refrigerant 117 returning from the cryotherapeutic device 120. This modulates the backpressure of the evaporated refrigerant to control the temperature in the cryotherapeutic device 120. In another embodiment, the supply control valve 108 and/or the backpressure control valve 113 can be used to increase the backpressure of exhausted refrigerant 117. Increasing the backpressure of exhausted refrigerant 117 could increase the boiling point of the refrigerant. For example, in the case of $N_2O$, a slight increase in backpressure from 1 atm to about 2 atm would raise the boiling point from about −88° C. to about −75° C.; an increase in backpressure to 3 atm would raise the boiling point to about −65° C.

In certain embodiments, the cryotherapeutic system 100 may also precool the refrigerant 106 to provide greater refrigeration power in the refrigerant 106 by the time it reaches the cooling system. The system 100, for example, can include a precooler 119 (shown in dashed lines) in the console 102. In other embodiments, the system 100 can include a precooler along the supply line 110, at a handle at a proximal region of the system 100, or elsewhere coupled to the cryotherapeutic device 120.

The cryotherapeutic device 120 includes a shaft 122 that has a proximal portion 124, a handle 125 at a proximal region of the proximal portion 124, and a distal portion 126 extending distally relative to the proximal portion 124. The cryotherapeutic device 120 can further include a cooling assembly 130 at the distal portion 126 of the shaft 122. The shaft 122 is configured to locate the distal portion 126 intravascularly at a treatment site proximate (e.g., in or near) a renal artery or renal ostium, and the cooling assembly 130 is configured to provide therapeutically-effective cryogenic renal-nerve modulation.

Figure 2A:
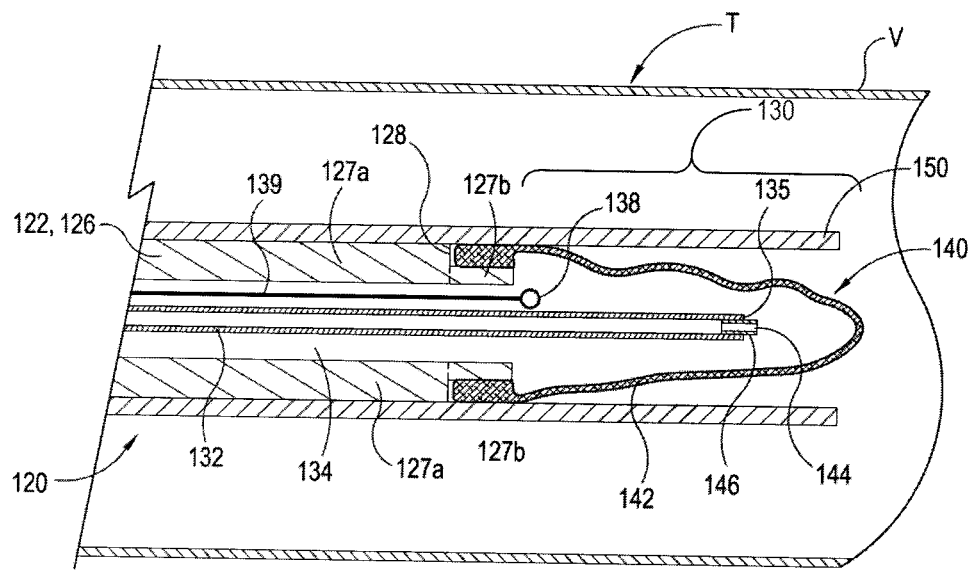
FIG. 2A is an enlarged cross-sectional view illustrating an embodiment of a distal portion of a shaft and a cooling assembly in a delivery state (e.g., low-profile or collapsed configuration) in accordance with an embodiment of the present technology.
Figure 2B:
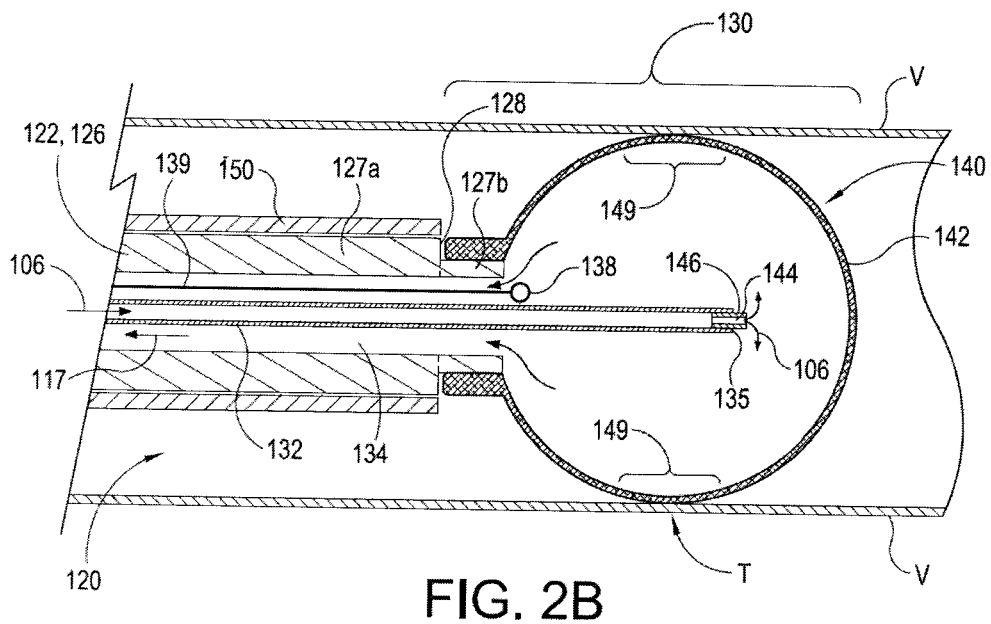
FIG. 2B is an enlarged cross-sectional view of the cooling assembly of FIG. 2A in a deployed stated (e.g., expanded configuration).

FIG. 2A is an enlarged cross-sectional view illustrating an embodiment of the distal portion 126 of the shaft 122 and the cooling assembly 130 in a delivery state (e.g., low-profile or collapsed configuration), and FIG. 2B is an enlarged cross-sectional view of the cooling assembly 130 in a deployed stated (e.g., expanded configuration). In the embodiment shown in FIG. 2A, the distal portion 126 of the shaft 122 can include a first zone 127a and a second zone 127b (separated by broken lines) recessed inwardly relative to the first zone 127a. The first zone 127a can be demarcated from the second zone 127b by a step 128, such as a rabbet (e.g., an annular or other circumferential groove configured to be fitted with another member). The first zone 127a can accordingly have a first outer dimension or first cross-sectional dimension (e.g., area or diameter), and the second zone 127b can have a second outer dimension or second cross-sectional dimension less than the first dimension. The shaft 122 can be sized to fit within a sheath 150 of 8 Fr or smaller (e.g., a 6 Fr guide sheath) to accommodate small renal arteries.

The cryotherapeutic device 120 can also include a supply tube or lumen 132 and an exhaust tube or lumen 134 along at least a portion of the shaft 122. The supply lumen 132 can be a small tube configured to retain the refrigerant in a liquid state at a high pressure. The inner diameter of the supply lumen 132 is selected such that at least a portion of the refrigerant reaching the cooling assembly 130 is in a liquid state at a distal end 135 of the supply lumen 132. The exhaust lumen 134 can be an outer tube, and the supply lumen 132 can extend within the exhaust lumen 134 along at least the distal portion 126 of the shaft. As described in further detail below, several embodiments of the cryotherapeutic device 120 can further include one or more sensors 138, such as a temperature sensor or pressure sensor, coupled to the controller 118 (FIG. 1) by a lead 139. In several embodiments, the cryotherapeutic system 100 can be configured to verify the proper calibration of the sensors 138 before a cryotherapeutic treatment. For example, the cryotherapeutic system 100 can automatically compare a measured temperature from a temperature sensor with room temperature as the cryotherapeutic system 100 initiates a power up cycle to check that the temperature sensor is functioning properly.

The embodiment of the cooling assembly 130 shown in FIGS. 2A and 2B can have an applicator 140 including a balloon 142 or other type of expandable member that defines an expansion chamber configured to fully occlude a renal artery or renal ostium. The balloon 142 can be relatively short (e.g., 10 mm or less) to accommodate the length and tortuosity of a renal artery (e.g., between 4-6 cm) and can have a diameter in an expanded configuration large enough to contact a significant portion of the inner circumference of the renal artery (e.g., between 3-10 mm in diameter). In other embodiments described below, balloons can be configured to only partially occlude a renal artery or renal ostium. The balloon 142 can comprise a compliant material, a non-compliant material, and/or a combination of compliant and non-compliant materials. In various embodiments, for example, the balloon 142 can be made from polyurethane and/or other compliant or semi-compliant materials that can expand and conform to vessel walls to fully occlude vessels of varying sizes (e.g., vessels having an inner diameter from approximately 3 mm to approximately 10 mm, or in specific applications approximately 4 mm to approximately 8 mm). In other embodiments, the balloon 142 can be made from nylon and/or other non-compliant materials and sized to accommodate vessels within a certain size range. For example, a non-compliant nylon balloon can be sized to accommodate vessels having an inner diameter between approximately 3 mm and 6 mm, and a larger non-compliant nylon balloon can be sized to accommodate vessels having an inner diameter between approximately 7 mm and 10 mm.

In the embodiment illustrated in FIGS. 2A and 2B, the distal portion of the balloon 142 is not connected to a support member (e.g., the supply lumen 132 and/or other support), and can therefore be dip molded and/or otherwise formed to have a continuous distal portion. The continuous distal portion of the balloon 142 provides a gentle surface with which to contact vessel walls so as to avoid tearing, puncturing, and/or otherwise damaging vessel walls. Additionally, the cooling assembly 130 shown in FIG. 2B can have a shorter overall length than a distally connected balloon, which may facilitate positioning the cooling assembly 130 in relatively short vessels (e.g., a renal artery having a length of 6 cm or less).

The cooling assembly 130 can further include an orifice 144 in fluid communication with the expansion chamber. In one embodiment, the orifice 144 can be defined by a distal end of a capillary tube 146 inserted into the distal end 135 of the supply lumen 132. Alternatively, the opening at the distal end 135 of the supply lumen 132 can define an orifice. The capillary tube 146 and/or the orifice 144 can have a diameter less than that of the supply lumen 132 to impede the flow of refrigerant proximate the expansion chamber, thereby increasing the pressure drop of the refrigerant 106 entering the expansion chamber and concentrating the refrigeration power at the cooling assembly 130. In other embodiments, the supply lumen 132 may have a substantially constant inner diameter (e.g., 0.008 inch (0.203 mm), 0.009 inch (0.023 mm), 0.010 inch (0.254 mm), etc.) such that the orifice 144 has a diameter at least equal to that of the supply lumen 132. The cryotherapeutic device 120 can then further include additional hardware (e.g., valves, flow and pressure gauges, etc.) and/or software in the handle 125 (FIG. 1) and/or in the console 102 (FIG. 1) to control the refrigerant 106 through the supply lumen 132 and focus the refrigeration power toward the distal end portion 126 of the shaft 122.

The orifice 144 can be sized relative to the area and/or length of the exhaust lumen 134 at the distal portion 126 of the shaft 122 to provide a sufficient flow rate of refrigerant, produce a sufficient pressure drop in the expansion chamber, and allow for sufficient venting of the exhausted refrigerant 117 through the exhaust lumen 134. In one embodiment, the orifice 144 can have a diameter of approximately 0.003 inch (0.076 mm) or more, such as about 0.004 inch (0.101 mm) to about 0.009 inch (0.229 mm). In various embodiments, the inner diameter and/or cross-sectional area of the exhaust lumen 132 and the diameter and/or cross-sectional area of the orifice 144 can have a ratio between approximately 4:1 and 10:1. For example, the exhaust lumen 132 can have an inner diameter between approximately 0.030 inch (0.762 mm) and approximately 0.050 inch (1.27 mm), and the orifice 144 can have a diameter of approximately 0.003 inch (0.0762 mm) to approximately 0.008 inch (0.203 mm; e.g., 0.004 inch (0.101 mm)). In other embodiments, the exhaust lumen 134 and the orifice 144 can have other suitable dimensions. In further embodiments, the shaft 122 may include additional lumens or devices extending there through (e.g., pressure sensing lumens, additional fluid passageways, etc.) and the ratio of the cross-sectional dimension of the exhaust lumen 132 to the total cross-sectional dimension occupied by the supply lumen and/or other members within the shaft 122 can be approximately 4:1 and 10:1.

The flow rate of the refrigerant 106 can also be manipulated by changing the lengths of the supply lumen 132 and the capillary tube 146 relative to one another. For example, in certain embodiments, the capillary tube 146 can be at most ⅓ the length of the supply lumen 132. In various embodiments, the capillary tube 146 can have a length between 2 inches (5.08 cm) and 30 inches (76.2 cm) and the supply lumen 132 can be sized accordingly. In other embodiments, the capillary tube 146 can be shorter or longer relative to the supply lumen 132 and/or the capillary tube 146 can be omitted.

The cooling assembly 130 is passed intravascularly to a target site T in a vessel V while in the delivery configuration shown in FIG. 2A. Referring to FIG. 2B, the cooling assembly 130 and the sheath 150 are then moved relative to each other such that the cooling assembly 130 extends distally beyond the sheath 150. For example, the sheath 150 can be pulled proximally and/or the cooling assembly 130 can be pushed distally. In operation, the refrigerant 106 passes through the supply lumen 132, through the orifice 144, and into the expansion chamber defined by the balloon 142. As the refrigerant 106 passes through the orifice 144, it expands into a gaseous phase, thereby inflating the balloon and causing a significant temperature drop in the expansion chamber. The portion of the applicator 140 contacting the tissue at the target T can be a heat-transfer region 149 or heat-transfer zone that, together with the refrigerant 106 in the expansion chamber, causes therapeutically-effective, cryogenic renal-nerve modulation. Exhausted refrigerant 117 passes in a proximal direction through the exhaust lumen 134. In various embodiments, the length of shaft 122 can be minimized to decrease the losses (e.g., friction losses) of the refrigerant flowing through the supply lumen 132 and through the exhaust lumen 134, thereby enhancing the refrigeration potential and the efficiency of the cooling assembly 130. The additional friction losses that may be caused by longer exhaust lumens, for example, may inhibit venting of the exhausted refrigerant 117, and thereby increase the pressure and temperature within the balloon 142. Accordingly, the shaft 122 can be configured to have a total overall length of less than 90 cm (e.g., 80 cm to 85 cm, 70 cm to 80 cm, etc.). In other embodiments, the shaft 122 can be longer and/or include additional features to enhance the refrigeration power at the cooling assembly 130.

The embodiment of the cooling assembly 130 illustrated in FIGS. 2A and 2B fully occludes the vessel V and produces a full-circumferential treatment at the target site T (i.e., a continuous cooled region extending completely around the inner circumference of the vessel V in a plane that is perpendicular or otherwise transverse relative to a longitudinal direction of the vessel V at the target T). Fully occluding the vessel V limits blood flow from heating the heat-transfer region 149 such that the cooling power of the refrigerant can be more efficiently applied to the target T. Although occlusion of the renal blood vessel for an excessive period of time can potentially cause ischemia of a kidney, it has been found that renal blood flow can be fully occluded for a period of time sufficient to complete cryotherapy at the target T (e.g., 2-5 minutes). The controller 118 (FIG. 1) can be programmed to limit the duration of refrigerant flow (e.g., 2-5 minutes) by using an electronic or mechanical timer to control a valve. Alternatively, a timer can be incorporated into the handle 125 (FIG. 1) or other portion of the cryotherapeutic device 120. If present, the sensor 138 may provide feedback to the controller 118 to regulate or control the system 100. In some embodiments, it may be desirable for the control algorithm to be fully automated, but in other embodiments the delivered therapy may utilize user input. In further embodiments, the duration of refrigerant flow can be limited by the volume of the refrigerant in the supply container 104. As described in greater detail below, in other embodiments, the cooling assembly 130 can be configured to partially occlude blood flow.

In various embodiments, the sensor 138 can be a thermocouple positioned on an outer surface of the balloon 142 and configured to provide a real-time temperature reading of the external temperature of the balloon 142. As such, the cryotherapeutic system 100 can be regulated via the controller 118 (e.g., using a software control loop) such that it ramps the cooling power output up and down based on the difference between the real-time external balloon temperature and a predetermined treatment temperature (e.g., −40° C., −60° C., etc.). For example, the cooling power output can be regulated by switching valves (e.g., the supply control valve 108 and/or the backpressure control valve 113) on and off at various stages of a cryotherapeutic treatment in response to measured temperatures. In other embodiments, the cooling power output can be modulated using proportional control wherein the delivery pressure of the refrigerant 106 and/or the flow rate of the vacuum pump 111 can be varied in response to the measured external balloon temperature. Accordingly, the external thermocouple allows the cryotherapeutic system 100 to compensate for variables that affect cooling at the target site T, such as variations in artery diameter, blood flow through the artery, and/or blood flow through other vessels in the vicinity of the renal artery.

FIGS. 2C-2E are enlarged cross-sectional views illustrating the distal portion 126 of the cryotherapeutic device 120 configured in accordance with other embodiments of the present technology. Referring to FIG. 2C, a distal portion 152 of the balloon 142 can be connected to a distal connector 162 via thermal bonding, adhesives, and/or other suitable attachment mechanisms. The distal connector 162 can have a curved, bullet-like tip as shown in FIG. 2C or can be otherwise configured to provide an atraumatic tip for navigation through the vasculature.

The cryotherapeutic device 120 further includes a guide wire lumen 133a through which a guide wire 133b can be received to guide the distal portion 126 of the shaft 122 through the vasculature. In the embodiment illustrated in FIG. 2C, the guide wire lumen 133a extends completely through the shaft 122 from the proximal opening of the shaft 122 at an adaptor 201 (e.g., at the handle 125 shown in FIG. 1) to beyond the distal opening of the shaft 122 in an over-the-wire (OTW) configuration, whereas in the embodiment illustrated in FIG. 2E, the guide wire lumen 133a extends through only a portion of the shaft 122 in a rapid exchange (RX) configuration. Although the proximal end of the guide wire lumen 133a is shown in FIG. 2E extending through the sidewall of the shaft 122 at the distal portion 126, in other embodiments, the proximal end of the guide wire lumen 133a can be accessible anywhere between the proximal and distal ends of the shaft 122. The guide wire lumen 133a shown in FIGS. 2C-2E, or variations thereof, may be included in various embodiments described herein to facilitate navigation through the vasculature. Suitable OTW and RX guide wire configurations are disclosed in U.S. Pat. No. 545,134, filed Oct. 27, 1994, U.S. Pat. No. 5,782,760, filed May 23, 1995, U.S. Patent Publication No. 2003/0040769, filed Aug. 23, 2001, and U.S. Patent Publication No. 2008/0171979, filed Oct. 17, 2006, each of which is incorporated herein by reference in its entirety.

Figure 3A:
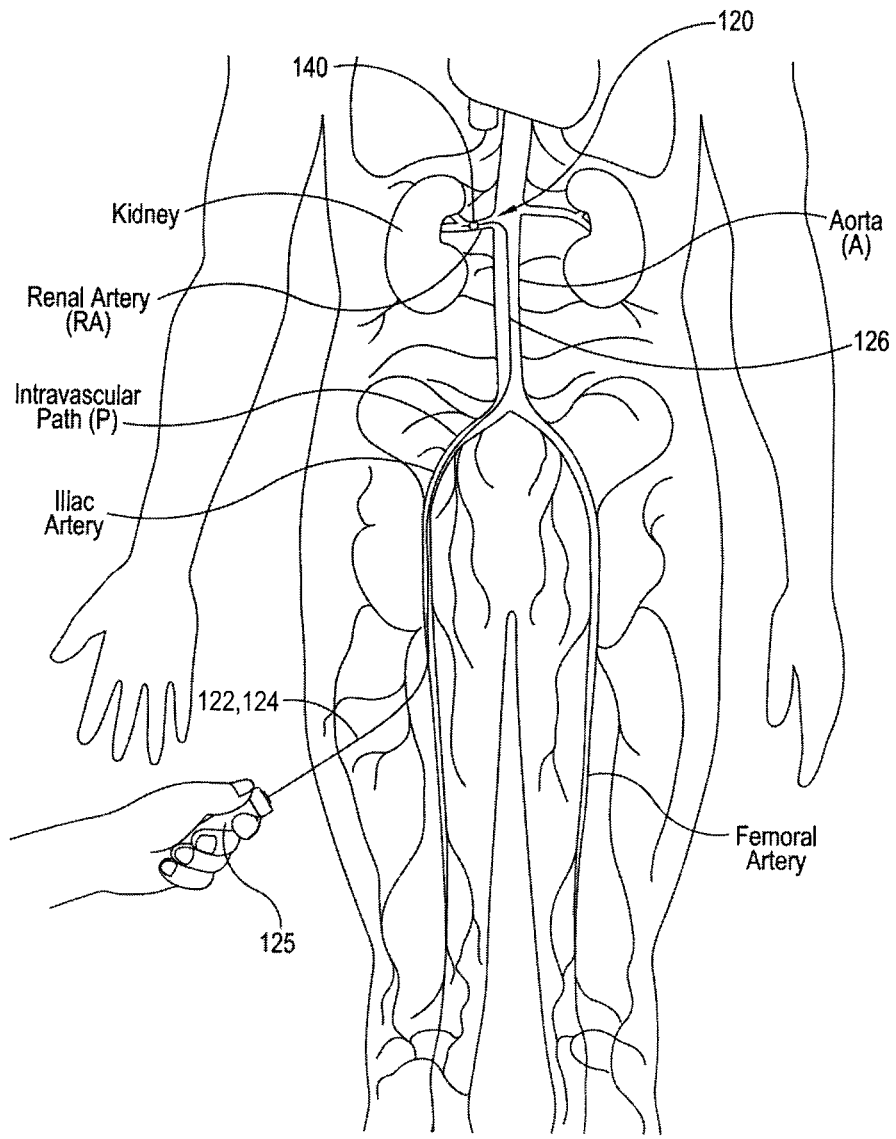
FIG. 3A illustrates cryogenically modulating renal nerves with a cryotherapeutic system in accordance with an embodiment of the technology.

FIG. 3A illustrates cryogenically modulating renal nerves with an embodiment of the system 100. The cryotherapeutic device 120 provides access to the renal plexus through an intravascular path P that leads to a respective renal artery RA. As illustrated, a section of the proximal portion 124 of the shaft 122 is exposed externally of the patient. By manipulating the proximal portion 124 of the shaft 122 from outside the intravascular path P, the caregiver may advance the shaft 122 through the tortuous intravascular path P (e.g., via the femoral artery or a radial artery) and remotely manipulate the distal portion 126 (e.g., with an actuator in the handle 125). For example, the shaft 122 may further include one or more pull-wires or other guidance devices to direct the distal portion 126 through the vasculature. Image guidance, e.g., CT, radiographic, IVUS, OCT or another suitable guidance modality, or combinations thereof, may be used to aid the caregiver's manipulation. After the cooling applicator 140 is adequately positioned in the renal artery RA or at the renal ostium, it can be expanded or otherwise deployed using the console 102 (FIG. 1), the handle 125 (FIG. 1), and/or another means until the applicator 140 contacts the inner wall of the renal artery RA. The purposeful application of cooling power from the applicator 140 is then applied to tissue to induce one or more desired neuromodulating effects on localized regions of the renal artery and adjacent regions of the renal plexus, which lay intimately within, adjacent to, or in close proximity to the adventitia of the renal artery. The purposeful application of the neuromodulating effects may achieve neuromodulation along all or a portion of the renal plexus.

The neuromodulating effects are generally a function of, at least in part, the temperature of the applicator 140, contact between the applicator 140 and vessel wall, dwell time of the applicator 140 while cooling, number of cooling cycles (e.g., one or more cooling cycles separated by a warming period), and blood flow through the vessel. Desired cooling effects may include cooling the applicator such that the temperatures of target neural fibers are below a desired threshold to achieve cryo alteration or ablation. For example, the refrigerant gas in the applicator 140 can be cooled to a temperature of about −88° C. to about −60° C., or in other embodiments the gas in the applicator 140 can have a temperature of about −80° C. to about −40° C.

In various embodiments, neuromodulating effects can occur within 100 seconds (e.g., 90 seconds, 75 seconds, 60 seconds, 30 seconds, etc.) of applying the cooled applicator 140 to the renal artery RA or renal ostium in one or more cooling cycles. In one embodiment, the process can include two cooling cycles separated by a warming period, but in other embodiments the process can have more than two cooling cycles separated by warming periods. The cooling cycles can have the same duration or different durations, such as approximately 10 seconds to approximately 90 seconds each. The duration(s) of the warming periods can be sufficient to partially or completely thaw frozen matter at the cooling interface. In several embodiments, the duration(s) of the warming periods can be from about 5 seconds to about 90 seconds. Individual warming periods between cooling cycles may last for the same amount of time or for different amounts of time. The durations of the cooling and warming cycles can be predetermined and programmed into an algorithm, or the system can include an automatic control algorithm using a feedback loop based on the pressure and/or temperature within and/or on the external surface of the balloon. For example, the control algorithm can terminate a warming cycle and initiate a cooling cycle by assessing when the frozen matter has sufficiently thawed based on the pressure and/or temperature measurements. Depending upon the number and length of cooling cycles, the total procedure time from the deployment of the cooling assembly 130 (e.g., as shown in FIG. 2B) to retraction of the cooling assembly to the delivery state (e.g., as shown in FIG. 2A) can be less than five minutes (e.g., less than 3 minutes). When both renal arteries RA are treated, the total procedure time from the time of deployment of the cooling assembly 130 in the first renal artery RA, to repositioning, deployment, and retraction of the cooling assembly 130 in the second renal artery RA can be less than 12 minutes (e.g., 10 minutes, 6 minutes, etc.). In certain embodiments, the procedure time can be decreased by locating the applicator 140 around a full circumference of the renal artery RA (e.g., along the same plane or along parallel planes spaced laterally apart) and performing neuromodulation in a single application. In other embodiments, the applicator 140 can be applied to less than a full circumference of the renal artery RA and/or in more than one application.

Figure 3B:
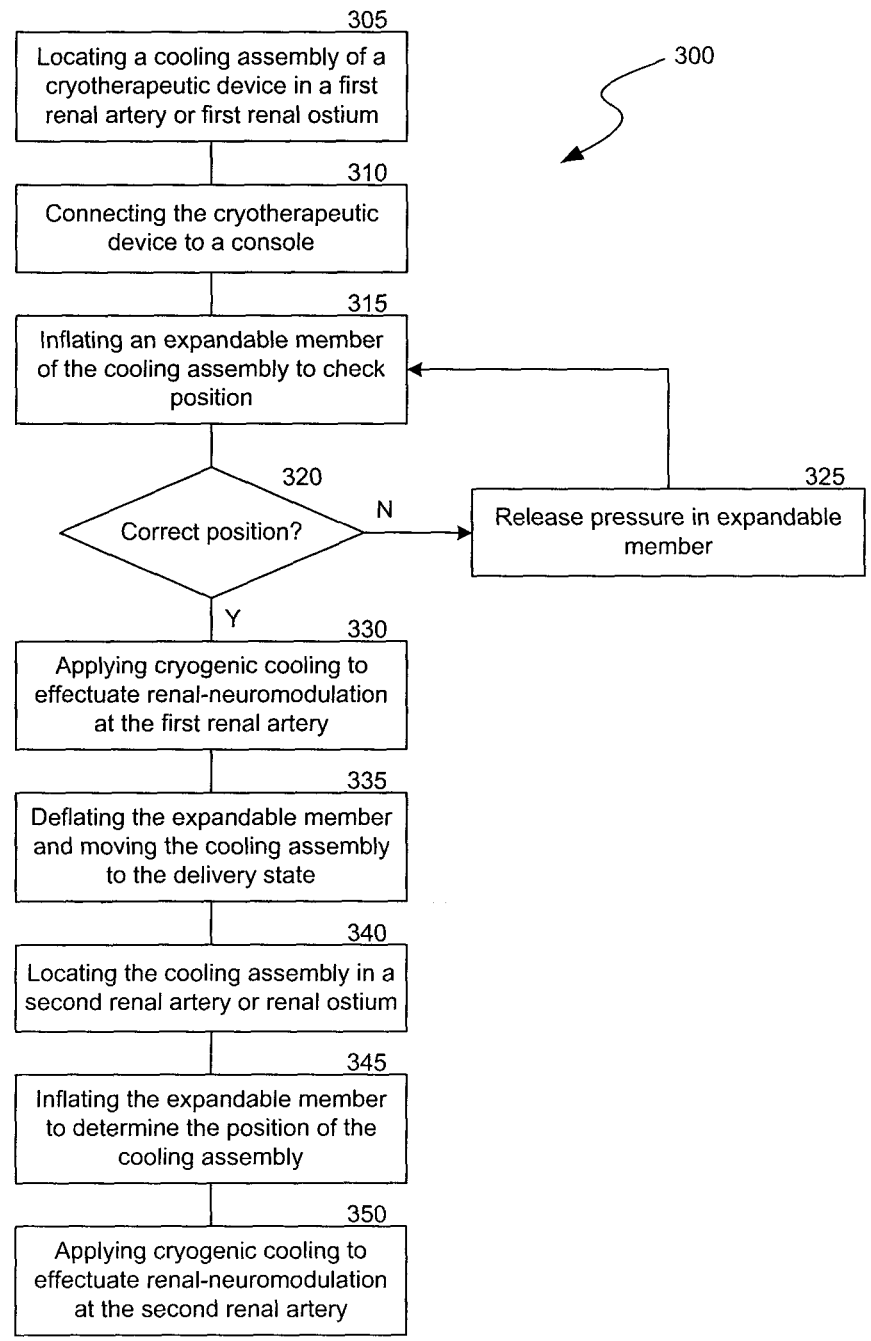
FIG. 3B is a block diagram illustrating a method of cryogenically modulating renal nerves in accordance with any embodiment of the present technology.

FIG. 3B is a block diagram illustrating a method 300 of cryogenically modulating renal nerves using the system 100 described above with reference to FIGS. 1-3A or another suitable system in accordance with an embodiment of the present technology described below. Referring to FIGS. 1-3B together, the method 300 can include intravascularly locating the cooling assembly 130 in the delivery state (e.g., as shown in FIG. 2A) in a renal artery or renal ostium (block 305). The cryotherapeutic device 120 and/or portions thereof (e.g., the cooling assembly 130) can be inserted into a guide catheter (e.g., the sheath 150 shown in FIGS. 2A-2C) to facilitate intravascular delivery of the cooling assembly 130. In certain embodiments, for example, the cryotherapeutic device 120 can be configured to fit within an 8 Fr guide catheter or smaller (e.g., 7 Fr, 6 Fr, etc.) to access small peripheral vessels. As described above, an OTW or RX guide wire can also be used to manipulate and enhance control of the shaft 122 and the cooling assembly 130.

The method 300 can further include connecting the cryotherapeutic device 120 to the console 102 (block 310), and partially or fully inflating an expandable member of the cooling assembly 130 (e.g., the balloon 142) to determine whether the cooling assembly 130 is in the correct position at the target site (blocks 315 and 320). The expandable member can be inflated via the supply lumen 132 with refrigerant from the supply container 104 at the console 102 and/or with other suitable fluids (e.g., air) from a secondary fluid supply reservoir in fluid communication the expandable member. If the cooling assembly 130 is not in the desired location, at least some of the pressure in the expandable member can be released (block 325). In certain embodiments, for example, the expandable member can be fully deflated by disconnecting the cryotherapeutic device 120 from the console 102 and using a syringe to manually deflate the expandable member via a proximal end portion of the shaft 122. In other embodiments, the cryotherapeutic device 120 can remain attached to the console 102, and a syringe can be connected along the length of the shaft 122 (e.g., a stopcock syringe) to deflate the expandable member. In further embodiments, the controller 118 at the console 102 can include algorithms for partially or fully deflating the expandable member. In still further embodiments, the cooling assembly 130 can be positioned at the target site using radiopaque markers and/or markings.

Once the cooling assembly 130 is properly located within the first renal artery or ostium thereof, the console 102 can be manipulated to initiate cooling at the cooling assembly 130 that modulates the renal nerves to cause partial or full denervation of the kidney (block 330). Cryogenic cooling can be applied for one or more cycles (e.g., for 30 second increments, 60 second increments, 90 second increments, etc.) in one or more locations along the circumference and/or length of the first renal artery or first renal ostium. In one particular embodiment, for example, two 90 second cycles may be used. In various embodiments, the expandable member can remain fully or partially inflated to maintain the position of the cooling assembly 130 at the target site between cooling cycles.

After renal-neuromodulation at the first renal artery, the method 300 can further include deflating the expandable member and retracting the cooling assembly 130 into the delivery state (block 335). The expandable member can be deflated manually by detaching the cryotherapeutic device 120 from the console 102 and connecting a syringe or other suitable evacuation device to the proximal end of the shaft 122. In other embodiments, a syringe can be connected along the length of the shaft 122 without detaching the cryotherapeutic device 120 from the console 102, or the expandable member can be deflated automatically (e.g., via the controller 118). In certain embodiments, the cooling assembly 130 can be withdrawn back into the guide catheter after the expandable member is deflated. Optionally, the cooling assembly 130 can be removed from the guide catheter during repositioning and temporarily stored in a sterile location (e.g., in a saline solution).

The cooling assembly 130 can then be located in a second renal artery or second renal ostium (block 340), and the expandable member can be expanded to confirm the position of the cooling assembly 130 (block 345). In selected embodiments, a contrast material can be delivered distally beyond the cooling assembly 130 and fluoroscopy and/or other suitable imaging techniques can be used to locate the second renal artery. If necessary, the used supply container 104 in the console 102 can be refilled or removed and replaced with a new supply container (e.g., a disposable refrigerant cartridge) to provide sufficient refrigerant for renal-neuromodulation at the second renal artery or second renal ostium. In embodiments where the console 102 was detached from the cryotherapeutic device 120 during repositioning of the cooling assembly 130, the console 102 can be reconnected to the cryotherapeutic device 120 such that the method 300 continues by applying cryogenic cooling to effectuate renal-neuromodulation at the second renal artery or second renal ostium (block 350).

In other embodiments, various steps in the method 300 can be modified, omitted, and/or additional steps may be added. For example, the console 102 can be turned on and loaded with the supply container 104 outside the sterile field in which the cryotherapy occurs, and positioned in a sterile bag or housing such that it can be brought into the sterile field. If the supply container 104 must be reloaded or refilled during cryotherapy, the console 102 can be removed from the sterile field, reloaded, and placed back into the sterile field (e.g., in a sterile bag or housing). In other embodiments, the empty supply container 104 can be removed from the console 102 and deposited within a sterile bag or housing surrounding the console 102, and a new supply container can be attached to the console 102 within the sterile bag or housing such that the console 102 does not leave the sterile field during treatment. In further embodiments, the console 102 can remain outside the sterile field and operated remotely.

Figure 4A:
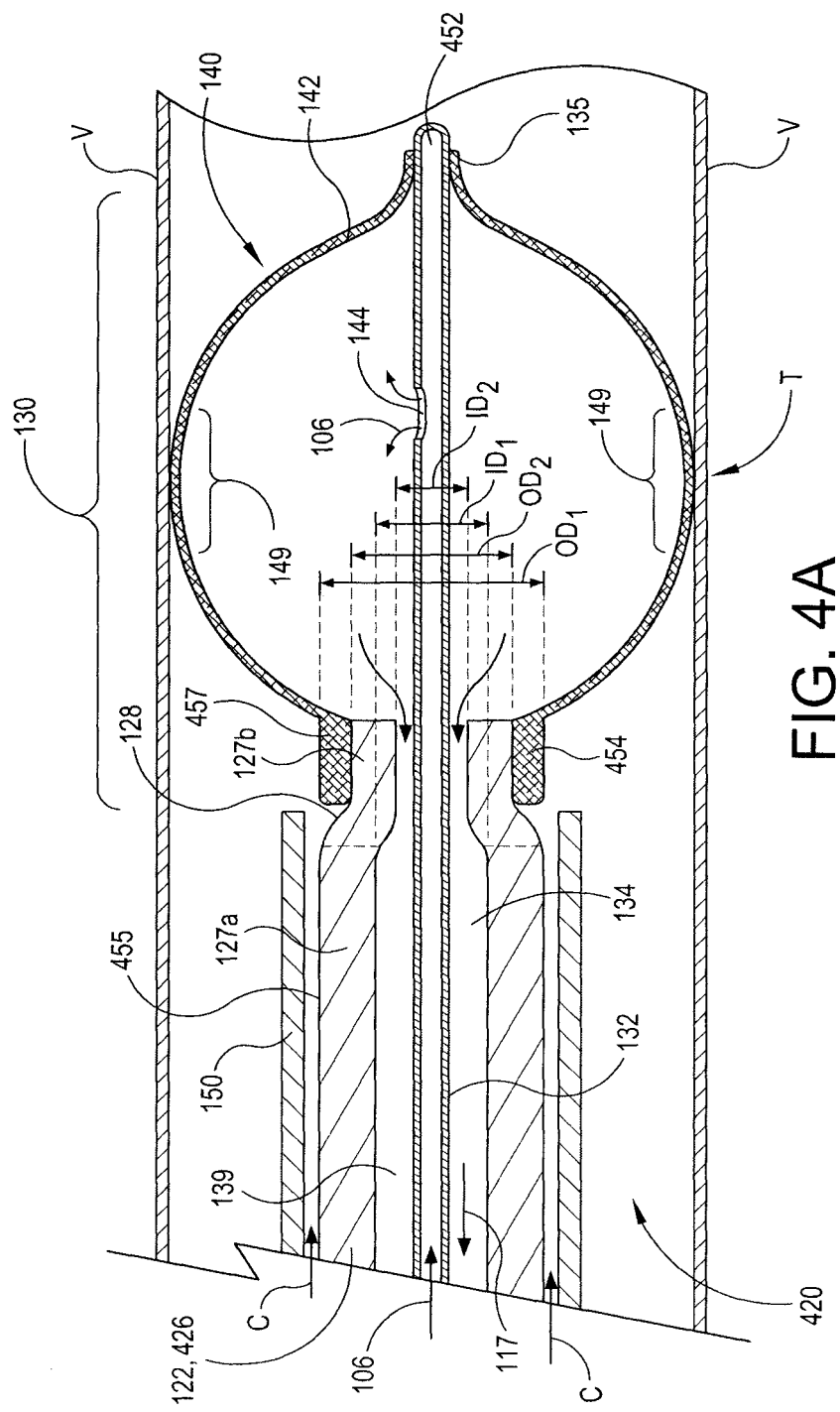

FIG. 4A is an enlarged cross-sectional view of a distal portion 426 of a cryotherapeutic device 420 configured in accordance with another embodiment of the present technology. The cryotherapeutic device 420 includes features generally similar to the features of the cryotherapeutic device 120 described above with reference to FIGS. 1-3B. For example, the cryotherapeutic device 420 includes the elongated shaft 122, the supply and exhaust lumens 132 and 134 extending along at least a portion of the shaft 122, and the cooling assembly 130 at the distal portion 426 of the shaft 102. The cooling assembly 130 includes an expandable member, such as the balloon 142 or other suitable expandable member, that defines at least a portion of the expansion chamber and receives the refrigerant 106 in an at least substantially gas phase via the orifice 144.

In the illustrated embodiment, the distal end 135 of the supply lumen 132 is coupled to a distal portion 452 of the balloon 142 to provide additional support and/or control for the cooling assembly 130, and the orifice 144 is an opening positioned along the length of the supply lumen 132 (e.g., rather than at the distal end 135 of the supply lumen 132 or at the end of a capillary tube). The supply lumen 132 and the distal portion 452 of the balloon 142 can be attached together using adhesives (e.g., thermal bonds), fasteners, and/or other suitable attachment mechanisms known in the art. In other embodiments, the supply lumen 132 can terminate at or in the expansion chamber, and/or the cryotherapeutic device 420 can further include a support member (not shown) that extends from the shaft 122 to at least the distal portion 452 of the balloon 142.

As shown in FIG. 4A, the cryotherapeutic device 420 can further include a connector 454 at the proximal portion of the balloon 142 that can be attached over the distal portion 426 of the shaft 122 and thereby couple the balloon 142 to the shaft 122. The connector 454 can be defined by a proximal portion of the balloon 142 (e.g., the neck of the balloon 142) that is integral with the expandable portion as shown in FIG. 4A, or the connector 454 can be a separate and distinct component from the balloon 142, such as a collar or other suitable retainer. The connector 454 can be attached to the distal portion 426 of the shaft 122 using thermal bonds, adhesives, interlocking surfaces (e.g., threads), friction fit, snap fit, suction, and/or other suitable attachment mechanisms, or the connector 454 can be formed integrally with the distal portion 426.

In the illustrated embodiment, the connector 454 is positioned proximate the step 128 over the second zone 127b of the distal portion 426 of the shaft 122. As shown in FIG. 4A, the first zone 127a of the distal portion 426 can have a first outer cross-sectional dimension or diameter $OD_1$ and the second zone 127b distal to the step 128 can have a second outer cross-sectional dimension or diameter $OD_2$ less than the first outer cross-sectional dimension $OD_1$. The reduction in the outer dimension of the distal portion 426 at the step 128 forms an inward recess relative to the first zone 127a in which at least a portion of the connector 454 and the proximal region of the expandable portion of the balloon 142 can sit, and thereby reduces the profile of the distal portion 426 of the shaft 122. In certain embodiments, the step 128 can be dimensioned such that an outer surface 455 of the first zone 127a is at least substantially flush with an outer surface 457 of the connector 454. Accordingly, the outer diameter $OD_2$ of the second zone 127b can be equivalent to the outer diameter $OD_1$ of the first zone 127a less twice the thickness of the connector 454. In other embodiments, the outer diameter $OD_2$ of the second zone 127b can be greater than or less than twice the thickness of the connector 454.

In selected embodiments, the connector 454 is non-expandable such that it remains within the recess and/or substantially flush with the outer surface 455 of the first zone 127a when the cooling assembly 130 moves to the deployed state (e.g., as shown in FIG. 4A). In other embodiments, the connector 454 may be expandable and increase in cross-sectional area as the cooling assembly 130 moves to the deployed state.

In the embodiment shown in FIG. 4A, the cross-sectional area of the exhaust lumen (e.g., defined by the inner surface(s) of the shaft 122) also decreases at the transition between the first zone 127a and the second zone 127b such that the distal portion 426 of the shaft 122 has a first inner cross-sectional dimension or diameter $ID_1$ at the first zone 127a and a lesser second inner cross-sectional dimension or diameter $ID_2$ at the second zone 127b. To avoid a build up of pressure in the expansion chamber that may be caused by insufficient venting through the necked-down exhaust lumen 134, the second zone 127b can be positioned only at the distal-most end of the shaft 122 proximate the expansion chamber where the density of the exhausted refrigerant 117 is the highest. For example, the second zone 127b can have a length of less than 4 cm (e.g., 2 cm, 1 cm, etc.). The exhausted refrigerant 117 also vents adequately through the smaller inner diameter $ID_2$ of the second zone 127b without undue restriction because the length of the second zone 127b along the longitudinal axis of the shaft 122 can be relatively short. For example, the length of the second zone 127b can be minimized to sufficiently accommodate the connector 454. Accordingly, the smaller exhaust lumen 134 at the second zone 127b can transport primarily high density exhausted refrigerant 117 and can expel the exhausted refrigerant 117 into the larger exhaust lumen 134 at the first zone 127a as the exhausted refrigerant 117 decreases in density, thereby facilitating adequate venting through the smaller second inner diameter $ID_2$ of the second zone 127b.

In operation, the inwardly recessed second zone 127b can reduce the profile of the distal portion 426 of the shaft 122 and/or provide a substantially smooth transition from the shaft 122 to the connector 454 without jeopardizing the venting characteristics of the exhaust lumen 134. The low-profile distal portion 426 of the shaft 122 can also facilitate the delivery of a fluidic contrast material between the shaft 122 and the sheath 150 from the proximal portion 124 (FIG. 1) of the shaft 122 to the distal portion 426 and around the cooling assembly 130 in the delivery state (e.g., as shown in FIG. 2A) to image and locate (e.g., using fluoroscopy) a target in the vasculature. As shown in FIG. 4A, for example, the recessed second zone 127b provides one or more passageways or channels C around the distal portion 426 of the shaft 122 that are large enough to deliver contrast material distally beyond the cooling assembly 130 without being blocked by a protruding connector or balloon. In certain embodiments, a sufficient channel C for the contrast material can be formed when the difference between the first outer diameter $OD_1$ and the second outer diameter $OD_2$ of the corresponding first and second zones 127a and 127b is less than 0.01 inch (0.254 mm). In other embodiments, the difference between the outer dimensions $OD_1$ and $OD_2$ of the first and second zones 127a and 127b may be greater or smaller. When used during renal-neuromodulation, a first renal artery can be located by delivering contrast material distally beyond the cooling assembly 130 in the delivery state via the channel C. After renal-neuromodulation at the first renal artery, the cooling assembly 130 can be retracted back from the deployed state to the delivery state wherein additional contrast material can be delivered distally beyond the cooling assembly 130 via the channel C to locate a second renal artery.

In other embodiments, the distal portion 426 of the shaft 122 does not include the stepped-down exhaust lumen 134 shown in FIG. 4A and, instead, may have a substantially uniform cross-sectional dimension. Such an exhaust lumen may relatively easily accommodate a guide wire lumen (e.g., as shown in FIGS. 2C-2E) through which a guide wire can be extended to locate the cooling assembly 130 at the target site T in the vessel V. In this embodiment, contrast material for imaging target sites (e.g., two renal arteries) can be delivered distally via the guide wire lumen after the guide wire has been retracted.

FIG. 4B is an enlarged cross-sectional view of a distal portion 456 of a cryotherapeutic device 460 configured in accordance with another embodiment of the present technology. The cryotherapeutic device 460 includes features generally similar to the features of the cryotherapeutic device 420 described above with reference to FIG. 4A. For example, the distal portion 456 of the shaft 122 has the step 128 that demarcates the first zone 127a from the smaller second zone 127b. However, in the embodiment shown in FIG. 4B, the second zone 127b is defined by a separate tube 459 that protrudes from the shaft 122. The tube 459 decreases the cross-sectional area of the exhaust lumen 134 at the second zone 127b similar to the inwardly stepped portion of the shaft 122 shown in FIG. 4A.

As shown in FIG. 4B, the cryotherapeutic device 460 can further include a proximal connector 458 that attaches the balloon 142 to the distal portion 456 of the shaft 122. Unlike the connector 456 of FIG. 4A that sits substantially within the recess formed by the step 128, the proximal connector 458 shown in FIG. 4B extends over the second zone 127b onto the outer surface 455 of the first zone 127a. By extending the proximal connector 456 over the first zone 127a, a larger surface area is made available for attaching the balloon 142 to the distal portion 456 of the shaft 122. Accordingly, the length of the second zone 127b can be reduced to facilitate adequate venting of the refrigerant 117 through the necked-down exhaust lumen 134 (e.g., as shown in FIGS. 4A and 4B).

In certain embodiments, the proximal connector 458 is non-expandable such that it maintains a substantially low profile against the outer surface 455 of the first zone 127a in both the deployed and delivery states. This can reduce or prevent the proximal connector 458 from catching on the sheath 150 as it is retracted from the deployed to the delivery configuration. In other embodiments, at least a portion of the proximal connector 458 can be expandable, but configured to maintain the low profile of the distal portion 456 while the cooling assembly 130 is in the delivery state. Accordingly, the cryotherapeutic device 460 with the extended proximal connector 458 can provide a substantially low profile for intravascularly delivering the cooling assembly 130 at a target site within a small, peripheral vessel (e.g., a renal artery) and/or can provide one or more channels C through which a fluidic contrast material can be delivered distally beyond the cooling assembly 130.

As further shown in FIG. 4B, the cryotherapeutic device 460 also includes a distal connector 462 that retains the distal portion 452 of the balloon 142 and a support member 433 extending through the balloon 142 that braces the balloon 142 in both the delivery and deployed states. The distal connector 462 can also be attached to (e.g., by thermal bonding) or formed integrally with an atraumatic tip 464 that extends distally therefrom. The atraumatic tip 464 can extend approximately 0.5 cm to 5 cm (e.g., approximately 1-2 cm) from the distal connector 462 and have an outer diameter between approximately 0.010 inch (0.254 mm) to approximately 0.050 inch (1.27 mm). In one embodiment, for example, the atraumatic tip 464 can have a length of approximately 2 cm and an outer diameter of at least 0.035 inch (0.889 mm; e.g., 0.038 inch (0.965 mm)). In other embodiments, the atraumatic tip 464 can have other suitable lengths and/or outer diameters. The atraumatic tip 464 can serve as a fixed guide to facilitate navigation through the vasculature. In several embodiments, the angle and/or rotational orientation of the atraumatic tip 464 can be adjusted by a control wire 467 (e.g., a pull-wire) that extends through at least a portion of the shaft 122. A user can manipulate the control wire 467 to torsionally deflect or otherwise move the atraumatic tip 464 to steer the distal portion 456 of the shaft 122 to the target site T. In other embodiments, the atraumatic tip 464 can be defined by a distal end portion of a guide wire (e.g., the guide wire 133b shown in FIG. 2C) that extends through the shaft 122 and beyond the distal connector 462.

The atraumatic tip 464 can be made from substantially smooth and flexible materials or structures such that it can gently contact and deflect off of vessel walls as the cryotherapeutic device 460 navigates the vasculature, and therefore avoids perforation and/or other trauma to the vessels through which it navigates. For example, the atraumatic tip 464 can be made from a flexible coil (e.g., a platinum coil) over a core or wire (e.g., a stainless steel wire). In various embodiments, the wire can be configured to gradually taper from a proximal portion 469a of the atraumatic tip 464 to a distal portion 469b of the atraumatic tip 464. A tapered wire, for example, can be generally round at the proximal portion 469a having an outer diameter between approximately 0.005 inch (0.127 mm) and 0.015 inch (0.381 mm; e.g., 0.009 inch (0.229 mm)) and can flatten toward the distal portion 469b to a thickness between approximately 0.001 inch (0.025 mm) and approximately 0.005 inch (0.127 mm; e.g., 0.003 inch (0.076 mm)). In selected embodiments, the wire is substantially flat by about ⅓ to ½ of the length of the atraumatic tip 464 from the proximal terminus. In other embodiments, the atraumatic tip 464 can have a tapered or non-tapered generally circular cross-section throughout. In several embodiments, at least a portion of the atraumatic tip 464 (e.g., a coil wrapped around the wire) can be made from platinum and/or other radiopaque materials (e.g., a platinum/iridium alloy) that can facilitate navigation of the cryotherapeutic device 460 through the vasculature using imaging techniques known in the art. In certain aspects of the technology, the balloon 142 can also include radiopaque markers and/or radiopaque markings (e.g., made with radiopaque ink) at both its proximal and distal end portions to further facilitate navigation and deployment. In other embodiments, the atraumatic tip 464 can be made from other deflectable and gentle materials and structures, such as a polymer material (e.g., Pebax® polymer, nylon, etc.), a polymer material over a metallic wire (e.g., a stainless steel wire), and/or other suitable materials.

In the embodiment illustrated in FIG. 4B, the atraumatic tip 464 is shaped and/or otherwise formed into a curve or angled portion. When the atraumatic tip 464 is made from a shapeable material (e.g., stainless steel, platinum, etc.), the atraumatic tip 464 can be formed and/or reformed into the desired curvature. In other embodiments, the atraumatic tip 464 can be pre-formed from a non-shapeable material such that it has a non-adjustable, set curve. The curve in the atraumatic tip 464 can further aid in navigation of the vasculature. For example, the curve can aid in keeping the cooling assembly 130 within a desired vessel (e.g., a renal artery) and avoiding side branches thereof.

Pressure Monitoring in Cryotherapeutic Systems

Figure 5A:
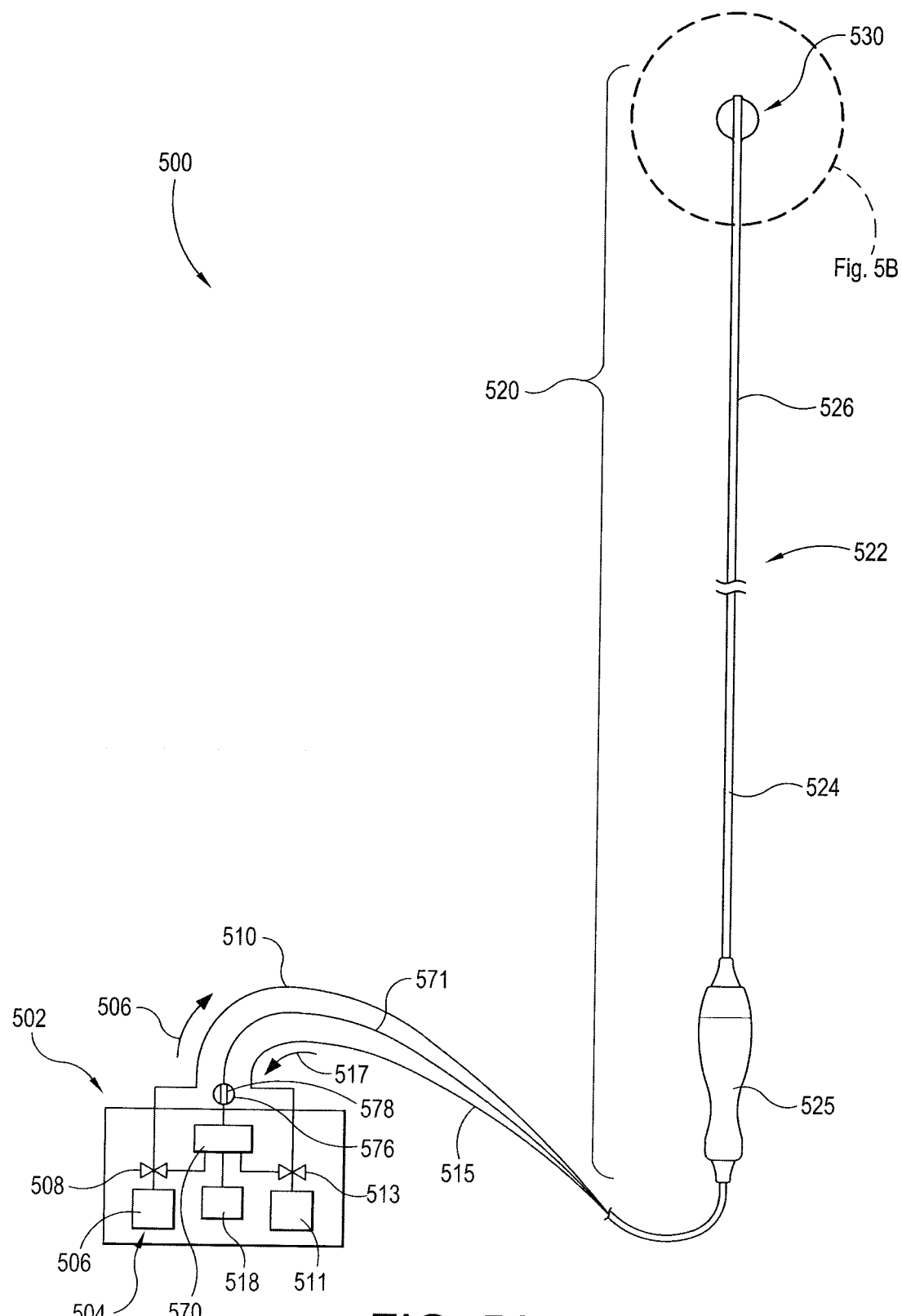
FIG. 5A is a partially schematic view of a cryotherapeutic system configured in accordance with another embodiment of the present technology.
Figure 5B:
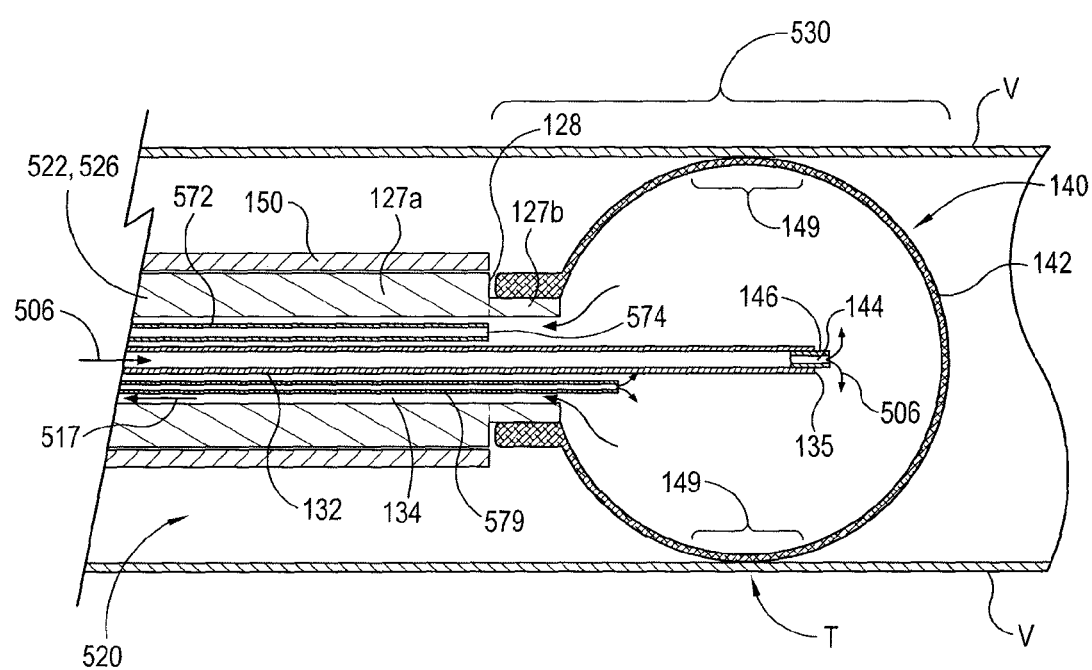
FIG. 5B is an enlarged cross-sectional view of a distal portion of a shaft and a cooling assembly in a deployed state in accordance with an embodiment of the present technology.

FIG. 5A is a partially schematic view of a cryotherapeutic system 500 configured in accordance with another embodiment of the present technology, and FIG. 5B is an enlarged cross-sectional view of a distal end portion of the system 500 of FIG. 5A. The cryotherapeutic system 500 can include features generally similar to the features of the cryotherapeutic system 100 described above with reference to FIGS. 1-3B. Referring to FIG. 5A, for example, the cryotherapeutic system 500 can include a cryotherapeutic device 520 and a console 502. The console 502 can include a refrigerant supply container 504 and a supply control valve 508 that are coupled to a supply line 510 configured to transport the refrigerant 506 to the cryotherapeutic device 520. The console 502 can also optionally include a pump 511 and/or a backpressure control valve 513 that are coupled to an exhaust line 515 configured to receive evaporated refrigerant 517 from the cryotherapeutic device 520. A controller 518 can be operably coupled to the supply control valve 508 and/or the backpressure control valve 513 to regulate refrigerant flow through the cryotherapeutic device 520. In the illustrated embodiment, the cryotherapeutic device 520 includes a shaft 522, a handle 525 at a proximal region of a proximal portion 524 of the shaft 522, and a distal portion 526 having a cooling assembly 530 at a distal end region of a distal portion 526 of the shaft 522.

As further shown in FIG. 5A, the console 502 can also include a pressure transducer or sensor 570 (e.g., a PX209-100G5V pressure transducer made by Omega Engineering of Stamford, Conn.) coupled to a pressure line 571 to monitor pressure within a portion of the cooling assembly 530 (e.g., an expansion chamber) during cryotherapy. In various embodiments, the pressure sensor 570 can be coupled to the controller 518 to serve as a feedback mechanism that controls the supply control valve 508 and/or the backpressure control valve 513, and thereby regulates refrigerant flow to and/or from the cooling assembly 530 in response to a pressure sensed at the cooling assembly 530. For example, the pressure sensor 570 can be configured to indicate a pressure above a predetermined threshold (e.g., within a range of a burst pressure of the expansion chamber). In response, the controller 518 can decrease or terminate refrigerant flow by at least partially closing the supply control valve 508 and/or increasing refrigerant flow from the cooling assembly 530 by decreasing the backpressure in the exhaust line 515 (e.g., using the vacuum pump 511). In other embodiments, the pressure sensor 570 can be coupled directly to the supply control valve 508 and/or the backpressure control valve 513 to automatically regulate the valves 508 and 513 on and/or off in response to a sensed pressure. In several embodiments, the cryotherapeutic system 500 can be configured to verify that the pressure sensor 570 is calibrated properly before cryotherapy. For example, the system 500 can automatically check the functionality of the pressure sensor 570 as the system 500 powers on by comparing a pressure reading from the pressure sensor 570 with the ambient pressure.

Referring now to FIG. 5B, the distal region of the cryotherapeutic device 520 can include features generally similar to the features of the cryotherapeutic device 120 described above with reference to FIGS. 2A-2E. For example, the cryotherapeutic device 520 includes the supply lumen 132 coupled to the supply line 510 (FIG. 5A), the exhaust lumen 134 coupled to the exhaust line 515 (FIG. 5A), and the applicator 140 including the balloon 142 or other type of expandable member that defines the expansion chamber.

As shown in FIG. 5B, the cryotherapeutic device 520 can further include a pressure monitoring lumen 572 coupled to the pressure sensor 570 (FIG. 5A) via the pressure line 571 (FIG. 5A). The pressure monitoring lumen 572 can extend through the shaft 522 and have a distal opening 574 in fluid communication with the expansion chamber (e.g., defined by the balloon 142). The dimensions (e.g., cross-sectional area, inner diameter, and/or outer diameter) of the pressure monitoring lumen 572 can be large enough to sense a pressure reading within the expansion chamber with substantial accuracy, but small enough to reduce or prevent interference with the outflow of refrigerant through the exhaust lumen 134. For example, the supply lumen 132 and the pressure monitoring lumen 572 together can have a first cross-sectional dimension (e.g., a first cross-sectional area) and the exhaust lumen 134 can have a second cross-sectional dimension (e.g., a second cross-sectional area) such that the ratio of the second cross-sectional dimension to the first cross-sectional dimension is between 4:1 and 10:1. In certain embodiments, the pressure monitoring lumen 572 can have an inner diameter of no more than 0.03 inch (0.762 mm; e.g., 0.015 inch (0.381 mm), 0.010 inch (0.762 mm), etc.) and an outer diameter of no more than 0.060 inch (1.52 mm; e.g., 0.02 inch (0.508 mm), 0.015 inch (0.381 mm), etc.), and the exhaust lumen 134 can be sized accordingly. In the embodiment illustrated in FIG. 5B, the pressure monitoring lumen 572 terminates in the shaft 522 before the outer diameter necks down at the second zone 127b of the distal portion 520. This configuration may be used in embodiments where the inner diameter of the shaft 522 necks down (e.g., as shown in FIGS. 4A and 4B) so as not to restrict the venting of the expanded refrigerant 517 at the smaller second zone 127b. In other embodiments, the opening 574 of the pressure monitoring lumen 572 can be at or in the balloon 542.

The pressure monitoring lumen 572 can also have a length sufficient to intravascularly locate the opening 574 along with the cooling assembly 530 at the target site T (e.g., a renal artery or renal ostium via a femoral artery or a radial artery). For example, the pressure monitoring lumen 572 can have a length equivalent to the full length of the shaft 522 (e.g., at least 48 inches (122 cm)). In other embodiments, the pressure monitoring lumen 572 can have other suitable different lengths and/or dimensions. For example, the pressure monitoring lumen 572 can have a first length and the pressure line 571 attached thereto can have a second length (e.g., 48 inches (122 cm), 30 inches (76 cm), 12 inches (30 cm), etc.) to extend the pressure monitoring lumen 572 to the pressure sensor 570, thereby allowing the console 502 to be positioned in a desired location (e.g., on a table) during cryotherapeutic treatments.

During cryotherapeutic treatments, the pressure monitoring lumen 572 and the pressure sensor 570 (FIG. 5A) may be configured to provide a signal indicating a change in pressure within the expansion chamber. For example, the pressure sensor 570 can be configured to indicate a threshold pressure below the rupture pressure of the balloon 142 to reduce the likelihood that the balloon 142 bursts during cryotherapy. The balloon 142 may have a burst pressure dependent at least in part on the material from which the balloon 142 is made. Compliant materials (e.g., polyurethane), for example, typically have lower burst pressures (e.g., 80 psi, 100 psi, 200 psi, etc.) than non-compliant materials (e.g., nylon) that can have burst pressures of 300 psi or higher. The pressure sensor 570 can be configured to monitor a threshold pressure, which may be equal to a pressure value below the burst pressure that provides an adequate response time to react to the change in pressure before the balloon 142 ruptures. In other embodiments, the pressure sensor 570 can be configured to indicate when the balloon 142 operates outside its desired operating pressure (e.g., 20-60 psi).

The time delay between the pressure at the opening 574 of the pressure monitoring lumen 572 at the expansion chamber and the pressure reading at the pressure sensor 570 may depend on the volume of the pressure monitoring lumen 572. As such, the pressure monitoring lumen 572 can have a volume that has a response time sufficient to adequately respond to the change in pressure in the expansion chamber (e.g., before rupture of the balloon 142). In certain embodiments, for example, the pressure sensor 570 has a response time of less than 1.5 seconds, such as a response time of less than 1 second, 0.2 second, 0.1 second, or 15 milliseconds. To enhance the accuracy of the pressure reading and decrease the response time of the pressure sensor 570, the length of the pressure monitoring lumen 572 can be shortened and significant increases in volume in the pressure monitoring lumen 572 before connecting to the pressure sensor 570 can be reduced. For example, the pressure monitoring lumen 572 can be coupled to the pressure line 571 at the proximal portion 524 (FIG. 5A) of the shaft 522 (e.g., at the handle 525), and the pressure line 571 can have a cross-sectional area similar to that of the pressure monitoring lumen 572. In other embodiments, the pressure monitoring lumen 572 can be coupled to the pressure sensor 570 at the handle 525 (e.g., omitting the pressure line 571) to shorten the total length of the pressure tube to the pressure sensor 570, and electrical wires can be coupled to the pressure sensor 570 to carry a signal to the console 502.

Referring to FIGS. 5A and 5B together, in certain embodiments, the pressure line 571 and/or the pressure monitoring lumen 572 can be coupled to the pressure sensor 570 using a fitting or adaptor 576 (e.g., a quick connect adapter). In the embodiment illustrated in FIG. 5A, for example, the adaptor 576 includes an internal reservoir or channel 578 that fluidly connects the pressure line 571 with the pressure sensor 570. The channel 578 can have a substantially small volume so as not to disrupt the pressure differential from the pressure line 571 to the pressure sensor 570 and enhance the accuracy of the pressure measurement. For example, in one embodiment, the channel 578 has an internal volume of no more than 0.1 cc. In other embodiments, the channel 578 can have a larger internal volume. In further embodiments, the adaptor 576 can couple the pressure monitoring lumen 572 to the pressure line 571 at the handle 525 or other position proximate the proximal portion 524 of the shaft 522. The adaptor 576, therefore, allows the pressure monitoring lumen 572 and/or the pressure line 571 to be detached from the pressure transducer 570 after a cryotherapeutic treatment such that the pressure monitoring lumen 572 can be discarded and the pressure transducer 570 can be stored (e.g., along with the handle 525 and/or the console 502) for subsequent cryotherapy treatments without disrupting the accuracy of the pressure reading at the pressure sensor 570.

Referring back to FIG. 5B, in various other embodiments, the cryotherapeutic device 520 can further include an additional gas supply lumen 579 coupled to the supply container 504 (FIG. 5A) or other gas supply reservoir to deliver additional gas to the expansion chamber and thereby modulate the temperature of the applicator 140. For example, the gas supply lumen 579 can deliver the refrigerant 506 (e.g., nitrous oxide) and/or other pressurized or non-pressurized gas (e.g., air) into the balloon 142 before or during delivery of the refrigerant 506 via the orifice 144 to increase the pressure within the balloon 142 (e.g., from approximately 5 psi to approximately 60 psi). The additional gas in the balloon 142 decreases the pressure drop of the refrigerant 506 in the expansion chamber, and thereby increases the temperature within the balloon 142. As such, the gas supply lumen 579 can be used to initiate, restrict, and/or suspend the inflow of additional gas to the expansion chamber (e.g., using a valve) and regulate the temperature of the balloon 142 without requiring complex components in the console 502 (e.g., a pressure regulator, a sub-cooler, etc.) to change the pressure drop within the balloon 142. Additionally, when the gas supply lumen 579 is coupled to a separate gas reservoir (e.g., an air supply), the gas supply lumen 579 can be used to deliver a gas into the balloon 142 before delivering the refrigerant 506 into the balloon 142 to monitor the position of the applicator 140 at the target site T.

In further embodiments, a pressure regulator (not shown; e.g., a pressure relief valve) can be added to the exhaust lumen 134 to trap the evaporated refrigerant 517 from exiting the balloon 142 and/or in the exhaust lumen 134 until the pressure within the balloon 142 is at a predetermined value (e.g., as sensed using the pressure monitoring lumen 572). In still further embodiments, the cryotherapeutic device 520 can include both a pressure regulator for the exhaust lumen 134 and the gas supply lumen 579 such that the pressure within the balloon 142 can be modulated during cryotherapeutic treatment.

Pre-Cooling in Cryotherapeutic Systems

In cryogenic renal nerve modulation, the volume of refrigerant available for cooling can be limited. Accordingly, it can be useful to increase the cooling capacity of a refrigerant. Pre-cooling the refrigerant before expanding the refrigerant in a cooling assembly is one example of a process that can increase the cooling capacity of a refrigerant. Even when cooling occurs primarily through phase change, using colder refrigerant before the phase change can increase the amount of cooling. Moreover, if a supply tube is in thermal communication with an exhaust tube, decreasing the temperature of refrigerant in the supply tube can cool refrigerant exhaust in the exhaust tube, which can reduce back pressure in an associated cooling assembly and thereby further increase cooling at the associated cooling assembly. Pre-cooling can reduce the volume of refrigerant needed for cryogenic renal nerve modulation, which can allow smaller and more flexible shafts to be used within the vasculature. Pre-cooling also can mitigate reductions in cooling capacity associated with other components of a cryotherapeutic system, such as thermally-insulative members within an applicator and in-line solenoid valves that release heat during operation.

Pressurized refrigerant used in cryogenic renal nerve modulation typically is supplied outside the vasculature at room temperature (e.g., from a room-temperature dewar). As the pressurized refrigerant travels along a supply tube within the vasculature, it can increase in temperature via heat transfer with warm blood and tissue. For example, as pressurized refrigerant supplied at about room temperature (e.g., about 23° C.) passes through the vasculature at body temperature (e.g., about 37° C.), the temperature of the pressurized refrigerant can increase to about 25° C. to 37° C. before reaching a cooling assembly. Cryotherapeutic devices configured in accordance with several embodiments of the present technology can include a pre-cooling assembly configured to cool pressurized refrigerant before the pressurized refrigerant expands in an associated cooling assembly. For example, pressurized refrigerant can be cooled to have a temperature just before expansion in an associated cooling assembly that is less than body temperature (e.g., less than about 20° C. or less than about 10° C.). Such pre-cooling assemblies can be configured to be outside the vasculature and/or to utilize the same refrigerant supply as an associated cooling assembly. In several embodiments configured in accordance with the present technology, pre-cooling can be useful to maintain refrigerant in liquid form until it reaches a cooling assembly where cryogenic cooling is desired. For example, evaporation associated with warming of refrigerant passing through portions of a cryotherapeutic device proximal to a cooling assembly can be reduced. In this section, the terms "proximal" and "distal" can reference a position relative to a pressurized refrigerant source. For example, proximal can refer to a position closer to a pressurized refrigerant source, and distal can refer to a position farther from a pressurized refrigerant source.

Figure 6A:
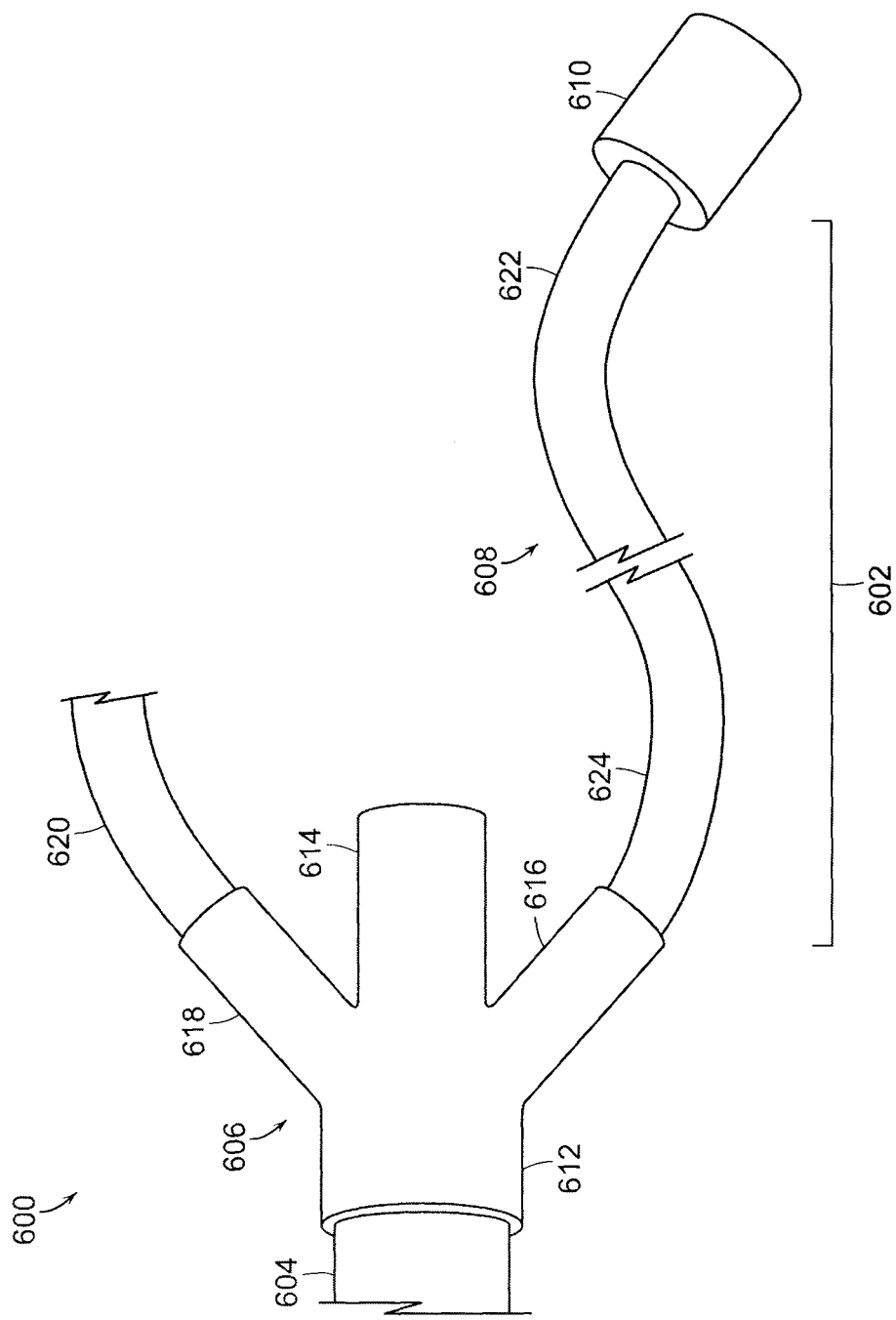
FIG. 6A is a plan view illustrating a pre-cooling assembly configured in accordance with an embodiment of the present technology.
Figure 6B:
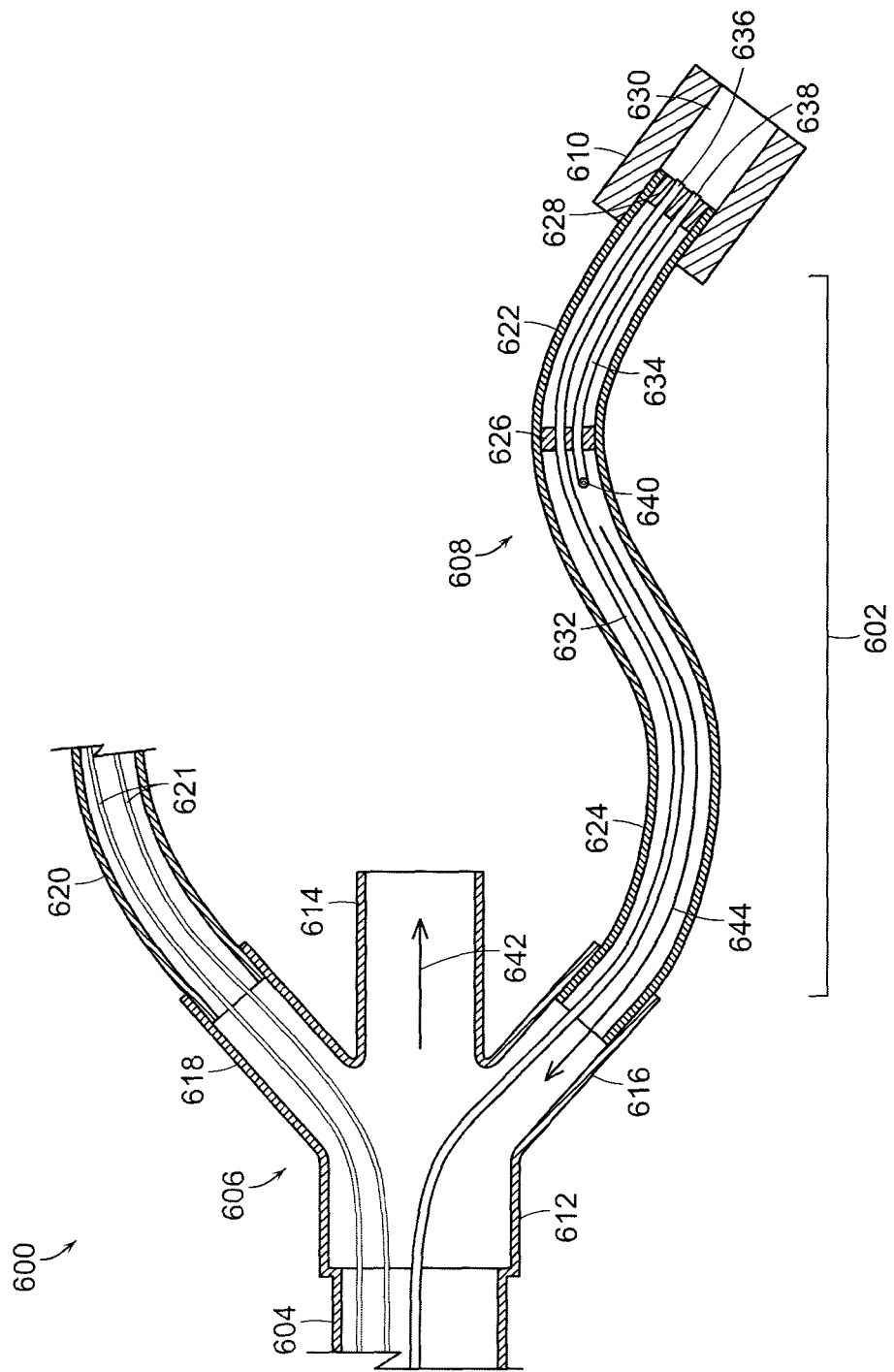
FIG. 6B is a cross-sectional view illustrating the pre-cooling assembly of FIG. 6A.

FIGS. 6A-6B illustrate a portion of a cryotherapeutic device 600 including a pre-cooling assembly 602, an elongated shaft 604 defining an exhaust passage, and a hub 606 between the pre-cooling assembly and the shaft. The pre-cooling assembly 602 includes a flexible tubular member 608 extending between the hub 606 and an adapter 610 configured to connect to a pressurized-refrigerant source (not shown). The hub 606 can include a primary connector 612 attached to the shaft 604, an exhaust portal 614 venting to the atmosphere, a first branch 616 attached to the tubular member 608, and a second branch 618 attached to a control-wire conduit 620. In several embodiments, the hub 606 can include one or more additional branches, such as a branch including a tube fluidly connected to a proximal syringe adapter (e.g., a proximal syringe adapter including a diaphragm configured to be punctured with a needle of a syringe). Such a structure can be useful, for example, to introduce contrast agent in the vicinity of a cooling assembly within the vasculature and/or to introduce filler material into a filler lumen of a cooling assembly within the vasculature. Filler materials are discussed in greater detail below.

With reference again to FIGS. 6A-6B, two control wires 621 (FIG. 6B) can extend from the control-wire conduit 620, through the hub 606, and into the shaft 604. The hub 606 can define a generally straight primary-exhaust flow path from the shaft 604 to the atmosphere through the exhaust portal 614. The tubular member 608 includes a tubular proximal portion 622 at the adapter 610 and a tubular distal portion 624 at the first branch 616. As most clearly shown in FIG. 6B, the tubular proximal portion 622 can include a first plug 626 and a second plug 628, and the adapter 610 can include an opening 630 proximate the second plug 628. The adapter 610 can include a variety of suitable structures for connection to a pressurized-refrigerant source, such as a threaded fitting, a compression fitting, or a barbed fitting.

In the embodiment shown in FIG. 6B, the device 600 includes a primary-supply tube 632 defining a primary-supply lumen, and the pre-cooling assembly 602 includes a pre-cooling supply tube 634 defining a pre-cooling supply lumen. The primary-supply tube 632 and the pre-cooling supply tube 634 can include a primary-supply proximal opening 636 and a pre-cooling supply proximal opening 638, respectively, at the second plug 628. The primary-supply proximal opening 636 and the pre-cooling supply proximal opening 638 fluidly connect the primary-supply tube 632 and the pre-cooling supply tube 634, respectively, to a passage defined by the opening 630. From the second plug 628, the primary-supply tube 632 and the pre-cooling supply tube 634 extend through the tubular proximal portion 622 and through the first plug 626. The tubular distal portion 624 defines a pre-cooling expansion chamber extending from the first plug 626 to the primary exhaust flow path. The pre-cooling supply tube 634 extends slightly past the first plug 626 and terminates at a pre-cooling distal opening 640 within the pre-cooling expansion chamber. The pre-cooling expansion chamber is accordingly in fluid connection with a flow of refrigerant through the pre-cooling supply tube 634 such that a pre-cooling exhaust flow path extends from the pre-cooling distal opening 640 to the primary exhaust flow path. The primary-supply tube 632 extends through the pre-cooling expansion chamber, through the hub 606 and into the shaft 604. The portion of the primary-supply tube 632 extending from primary-supply proximal opening 636 to the shaft is a first portion of the primary-supply tube 632. A second portion (not shown) of the primary-supply tube 632 is proximate a cooling assembly (not shown) configured to be within the vasculature.

Expanding pressurized refrigerant into the pre-cooling expansion chamber from the pre-cooling supply tube 634 can cool the pre-cooling expansion chamber and thereby cool the primary-supply tube 632 and liquid refrigerant within the primary-supply tube. If pre-cooling is performed distant from an entry point into the vasculature (e.g., if pressurized refrigerant is cooled in a console before being transported to an entry point into the vasculature), heat from the atmosphere can cause undesirable warming of the pre-cooled pressurized refrigerant. Positioning the pre-cooling expansion chamber proximate the hub can reduce such undesirable warming. A pre-cooling assembly configured in accordance with several embodiments of the present technology can have a length sufficient to allow heat-transfer between expanded refrigerant within a pre-cooling expansion chamber and pressurized refrigerant within a portion of a primary-supply tube within the pre-cooling expansion chamber. For example, a pre-cooling chamber configured in accordance with several embodiments of the present technology can have a length greater than about 10 cm, such as greater than about 15 cm, or greater than about 25 cm. A pre-cooling chamber configured in accordance with several embodiments of the present technology has a length from about 20 cm to about 30 cm.

After cooling the primary-supply tube 632, refrigerant from the pre-cooling expansion chamber can join a flow of refrigerant from the exhaust passage and vent out the exhaust portal 614 to the atmosphere. FIG. 6B shows a first arrow 642 indicating a flow direction of refrigerant through the exhaust portal 614 and a second arrow 644 indicating a flow direction of refrigerant through the pre-cooling expansion chamber. The flow direction of refrigerant through the exhaust portal 614 is generally aligned with the exhaust passage. In contrast, the flow direction of refrigerant through the pre-cooling expansion chamber is not aligned with the exhaust passage or the flow direction of refrigerant through the exhaust portal 614.

Figure 7:
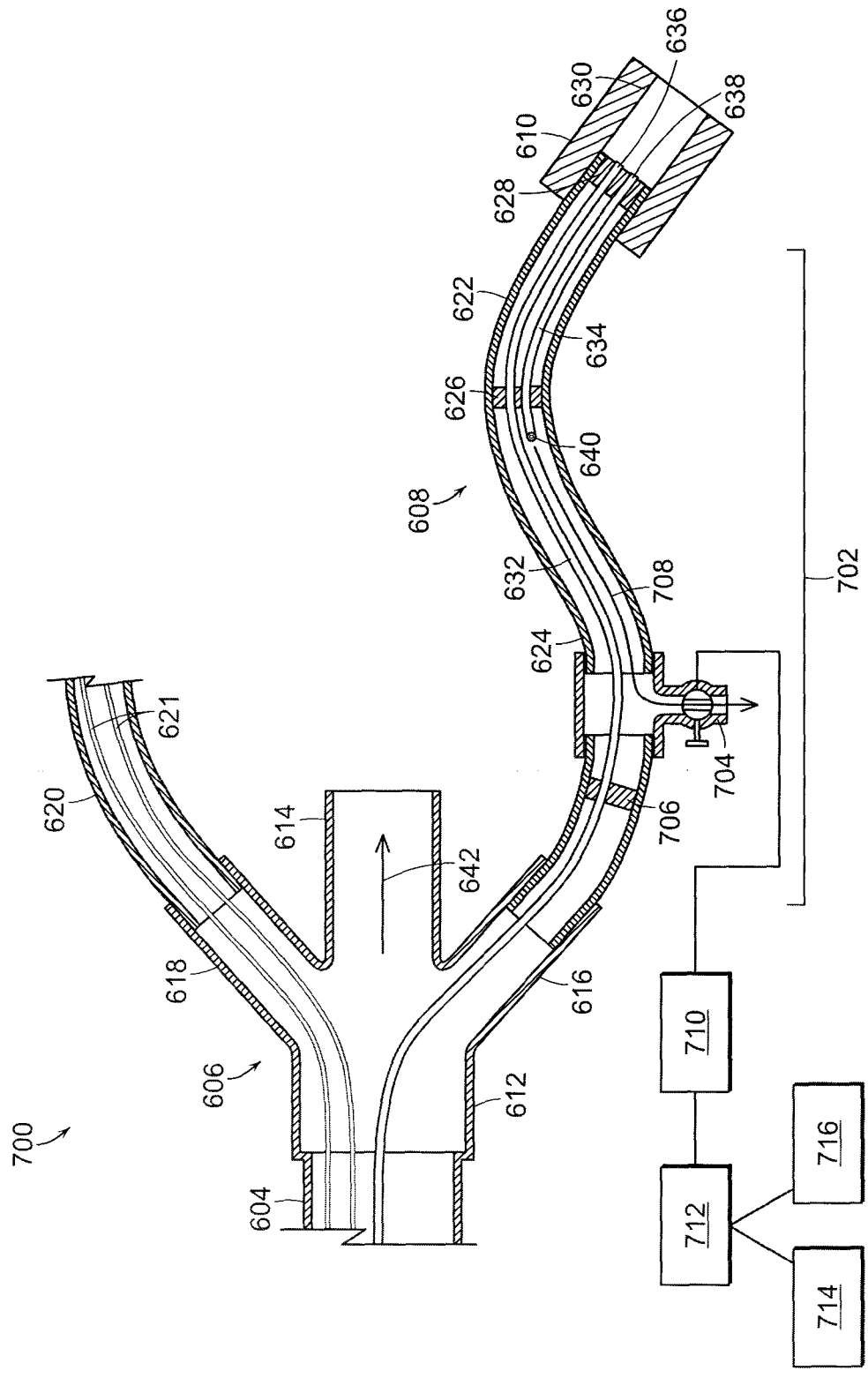
FIG. 7 is a cross-sectional view illustrating a pre-cooling assembly having a valve configured in accordance with an embodiment of the present technology.

FIG. 7 illustrates a portion of a cryotherapeutic device 700 similar to the cryotherapeutic device 600 of FIGS. 6A-6B, except that the device 700 has a pre-cooling expansion chamber fluidly separate from the exhaust passage. The cryotherapeutic device 700, for example, includes a pre-cooling assembly 702 including a valve 704 and a third plug 706 fluidly separating the pre-cooling expansion chamber from internal portions of the shaft 604 and the hub 606. The primary-supply tube 632 extends through the third plug 706 and into the shaft 604.

An arrow 708 indicates a flow direction of refrigerant through the pre-cooling expansion chamber when the valve 704 is open. When the valve 704 is closed, pressure within the pre-cooling expansion chamber can increase until it equilibrates with the pre-cooling supply tube 634, thereby causing flow through the pre-cooling supply tube to stop. In this way, opening and closing the valve 704 can turn pre-cooling on or off. Partially opening the valve 704 can regulate pressure within the pre-cooling expansion chamber and thereby regulate refrigerant flow through the pre-cooling supply tube 634 and an associated pre-cooling temperature. For example, an actuator 710 can be operably connected to the valve 704 and be configured to receive a signal from a processor 712. The processor 712 can be configured to receive a signal from a user interface 714 and/or a sensor 716 to direct the actuator 710 to open or close the valve fully or incrementally. The sensor 716, for example, can be a temperature sensor of an associated cooling assembly. In one embodiment, the temperature sensor can send a signal to the processor 712 causing the valve 704 to (a) open and pre-cooling to increase if a detected temperature of the cooling assembly or tissue proximate the cooling assembly is higher than a desired value, or to (b) close and pre-cooling to decrease if a detected temperature of the cooling assembly or tissue proximate the cooling assembly is lower than a desired value.

Figures 8A, 8B:
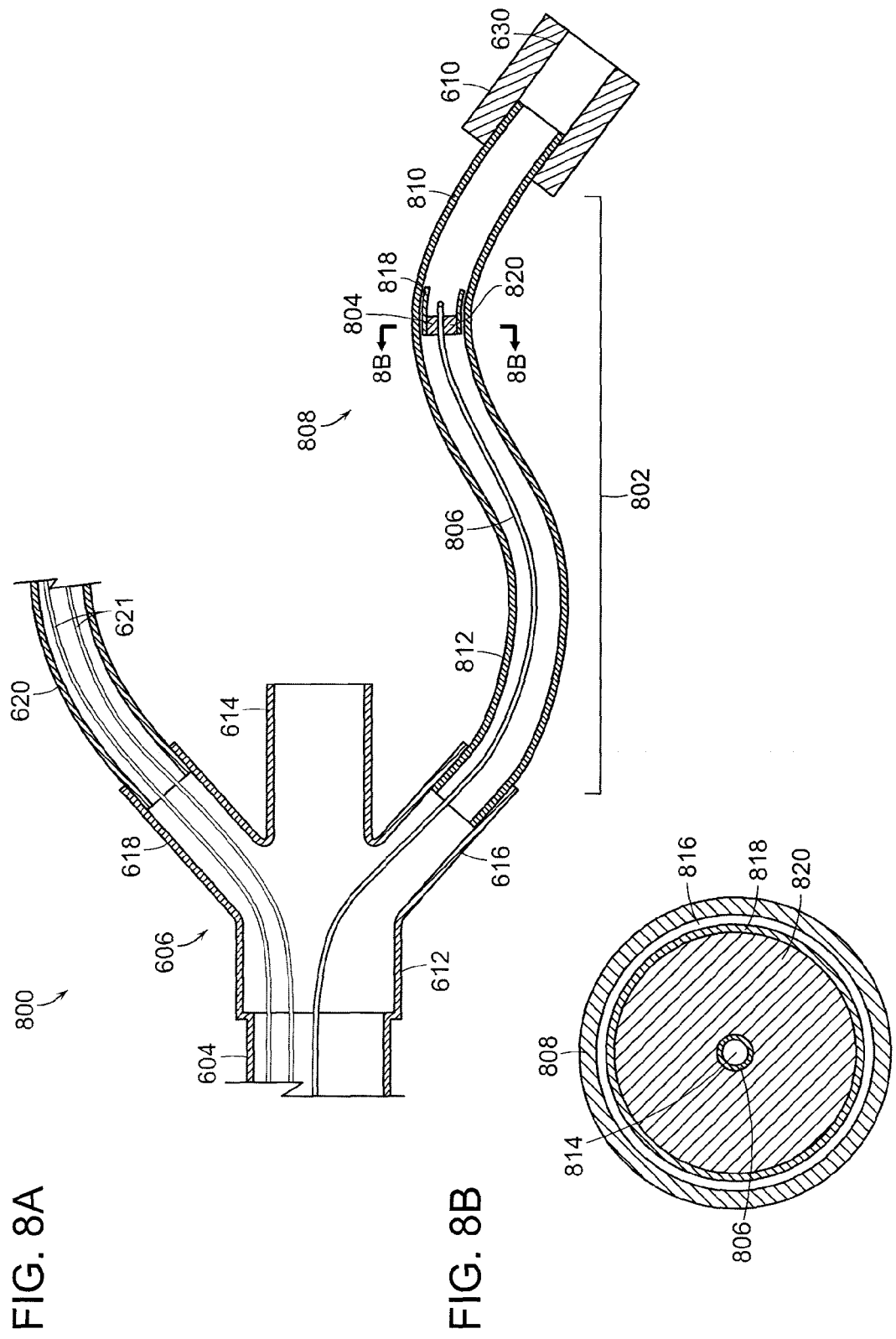
FIG. 8A is a cross-sectional view illustrating a pre-cooling assembly having a flow separator configured in accordance with an embodiment of the present technology.
FIG. 8B is a cross-sectional view illustrating the pre-cooling assembly of FIG. 8A.

FIGS. 8A-8B illustrate a portion of a cryotherapeutic device 800 with a pre-cooler 802 configured in accordance with another embodiment of the present technology. Accessing an internal portion of the tubular member 608 to form the first plug 626 of the pre-cooling assembly 602 (FIGS. 6A-6B)

can be challenging. Instead of the first plug 626 and the pre-cooling supply tube 634 (FIG. 6B), the pre-cooler 802 can include a flow separator attached to a primary-supply tube. For example, the pre-cooler 802 can include a flow separator 804 attached to a primary-supply tube 806 and a container 808 having a container proximal portion 810 and a container distal portion 812. In this embodiment, the flow separator 804 divides the container 802 into the container proximal portion 810 and the container distal portion 812. The container proximal portion 810 defines a proximal chamber or a combined supply lumen between the opening 630 and the flow separator 804 and the container distal portion 812 defines a pre-cooling expansion chamber. As most clearly shown in FIG. 8B, the flow separator 804 defines a primary passage 814 fluidly connected to the primary-supply tube 806 and a pre-cooling passage 816 along a periphery of the flow separator 804.

Referring still to FIG. 8B, the pre-cooling passage 816 is sized to cause a pressure drop sufficient to expand refrigerant and cool the pre-cooling expansion chamber. The flow separator 804 includes a tubular segment 818 and a flow-separator plug 820. The flow-separator plug 820 is positioned between an outer surface of the primary-supply tube 806 and an inner surface of the container 808. The tubular segment 818 can be selected to have an outer cross-sectional dimension (e.g., diameter) slightly smaller than an inner cross-sectional dimension (e.g., diameter) of the container 808. The flow-separator plug 820 can include, for example, an adhesive material configured to bond to the outer surface of the primary-supply tube 806 and the inner surface of the container 808.

In one embodiment, the flow separator 804 floats in the container 808 (i.e., it is not fixed within the container 808) such that the pre-cooling passage 816 is an annular space between the flow separator 804 and an inner surface of the container 808. In other embodiments, flow separators can have different configurations. For example, a flow separator can be fixed to the container and a pre-cooling passage can extend through the flow separator around only a portion of the periphery of the flow separator, such as a curved portion. In still other embodiments, the flow separator can be attached to the container around generally its entire circumference and the flow separator can include an opening spaced inwardly apart from the periphery of the flow separator. For example, a flow separator can include an internal opening configured to expand refrigerant into the pre-cooling expansion chamber.

FIGS. 9A-9B illustrate a portion of a cryotherapeutic device 900 similar to the cryotherapeutic device 800 of FIGS. 8A-8B, except having different flow-separator and primary-supply tube configurations. The cryotherapeutic device 900 includes a primary supply tube 902 and a pre-cooler 904 including a flow separator 906 attached to the primary-supply tube 902. The pre-cooler 904 can also include a container 908 having a container proximal portion 910 and a container distal portion 912 on opposite sides of the flow separator 906. In this embodiment, the flow separator 906 does not include a tubular segment and can be constructed, for example, from a cylindrical block of material (e.g., rubber, polymer, metal, or another material) having a hole through which the primary-supply tube 902 can be threaded or otherwise attached. As most clearly shown in FIG. 9B, the flow separator 906 can define a pre-cooling passage 914 along a periphery of the flow separator 906. The primary-supply tube 902 can extend through the flow separator 906 and can be attached to an inner surface of the container proximal portion 910 proximate the opening 630. Attaching the primary-supply tube 906 to an accessible portion of the container proximal portion 910 can be useful to prevent undesirable longitudinal movement of the flow separator 906 and the primary-supply tube 902 when the proximal chamber is at high pressure.

Figure 10:
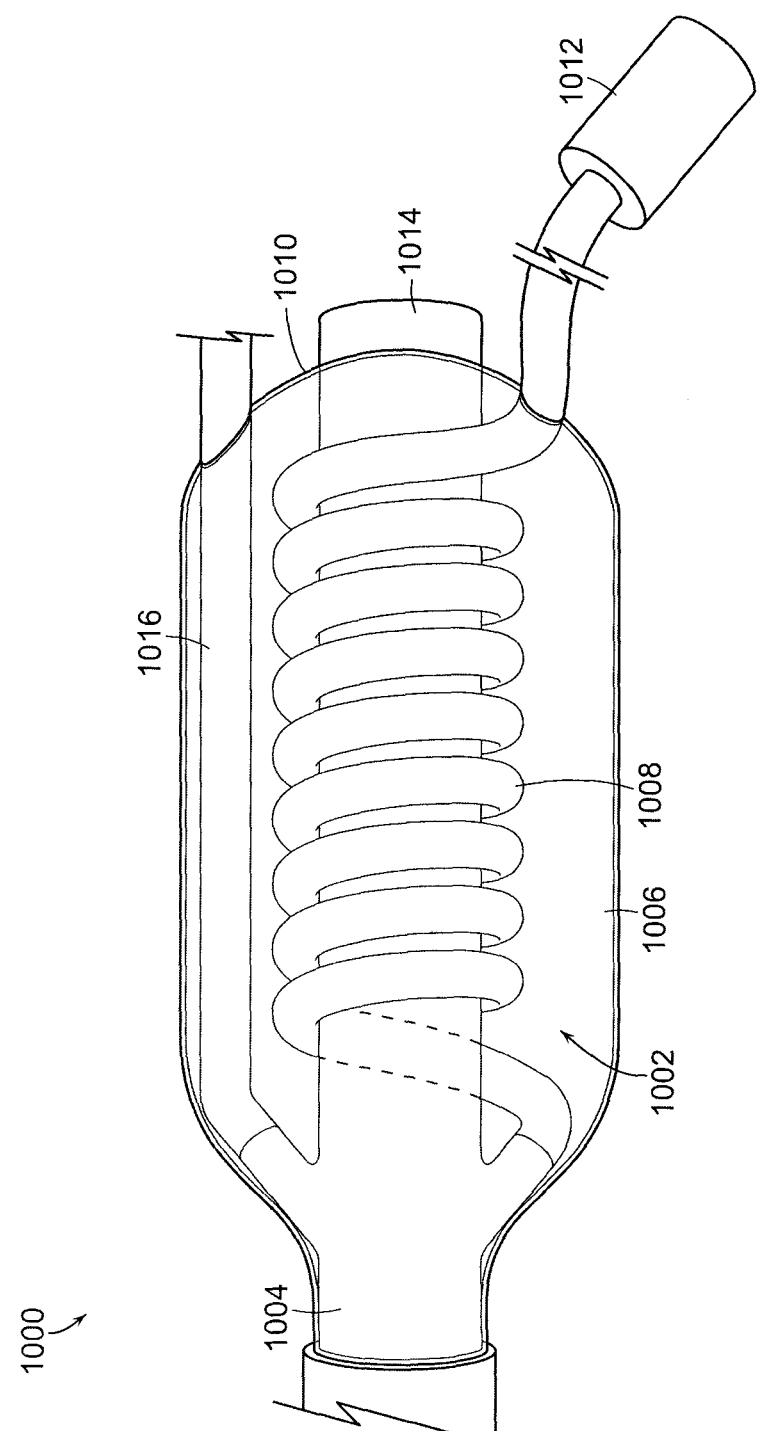
FIG. 10 is a partially schematic view illustrating a tubular member of a pre-cooling assembly coiled around an exhaust portal within a handle configured in accordance with an embodiment of the present technology.

A pre-cooling assembly configured in accordance with several embodiments of the present technology can be arranged in a compact configuration. For example, at least a portion of such a pre-cooling assembly can be within a handle of a cryotherapeutic device. FIG. 10 illustrates a portion of a cryotherapeutic device 1000 including a pre-cooling assembly 1002 and a hub 1004 within a handle 1006. The pre-cooling assembly 1002 includes a flexible tubular member 1008 extending from the hub 1004, through a bottom portion 1010 of the handle 1008, and to an adapter 1012 configured to connect to a pressurized-refrigerant source (not shown). The hub 1004 can include an elongated exhaust portal 1014 extending through the bottom portion 1010, and a control-wire conduit 1016 can extend from the hub 1004 through the bottom portion 1010. In one embodiment, the tubular member 1008 is coiled around the exhaust portal 1014. The handle 1006 also can be insulated to prevent heat loss to the atmosphere and improve pre-cooling efficiency.

Figure 11:
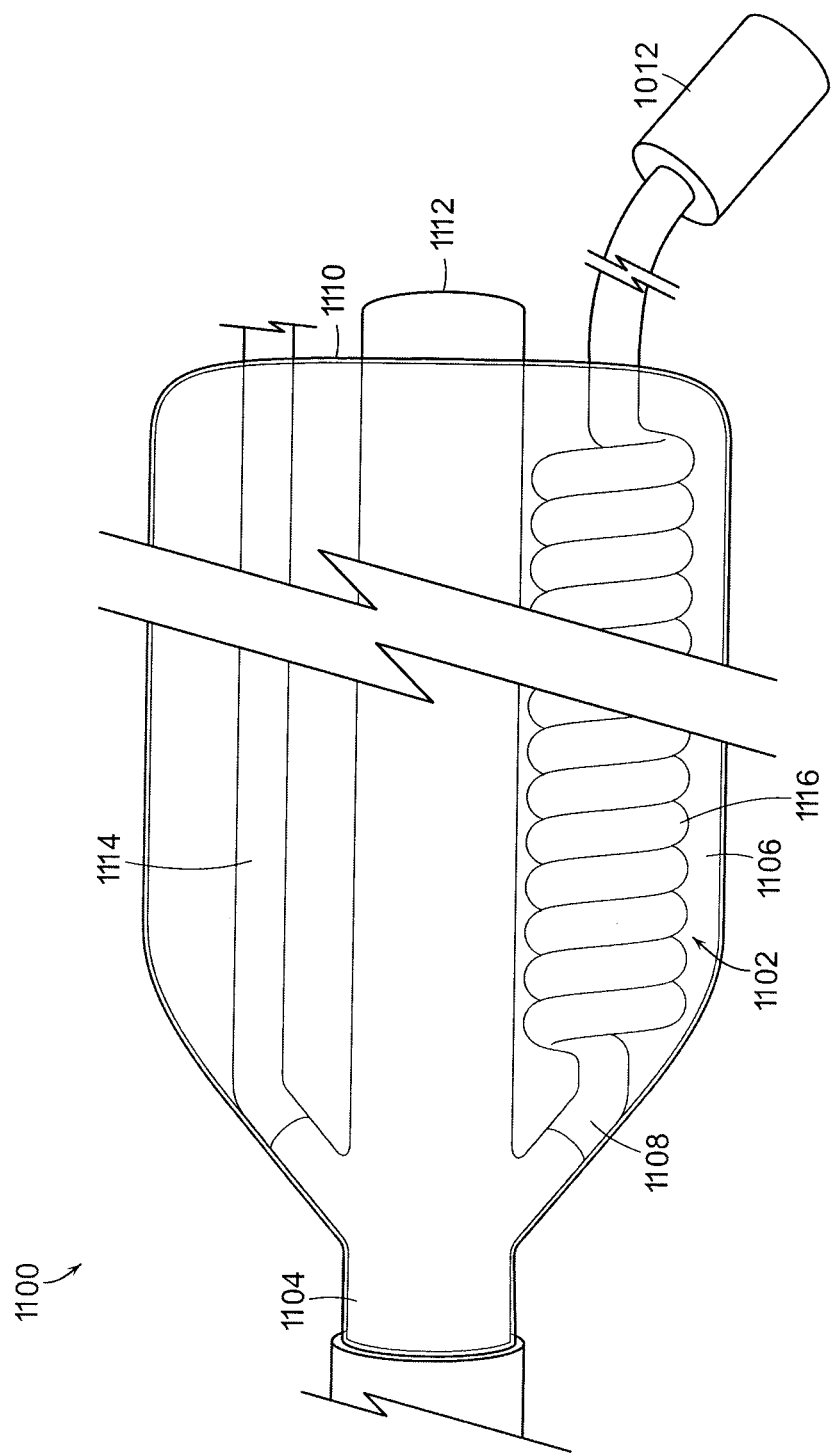
FIG. 11 is a partially schematic view illustrating a tubular member of a pre-cooling assembly coiled near an exhaust portal within a handle configured in accordance with an embodiment of the present technology.

FIG. 11 illustrates a portion of a cryotherapeutic device 1100 having an alternative configuration within and around a handle. The cryotherapeutic device 1100 includes a pre-cooling assembly 1102 and a hub 1104 within a handle 1106. The pre-cooling assembly 1102 includes a flexible tubular member 1108 extending from the hub 1104 and through a bottom portion 1110 of the handle 1106. The hub 1104 can include an elongated exhaust portal 1112 extending through the bottom portion 1110, and a control-wire conduit 1114 can extend from the hub 1104 through the bottom portion 1110. In one embodiment, the tubular member 1108 includes a helical portion 1116 spaced apart from the exhaust portal 1112. The handle 1106 also can be insulated to prevent heat loss to the atmosphere and improve pre-cooling efficiency.

Cryotherapeutic-Device Components

Having in mind the foregoing discussion of cryotherapeutic devices configured in accordance with several embodiments of the present technology, a variety of different cooling assemblies, occlusion members, and other cryotherapeutic-device components are described below with reference to FIGS. 12-55. It will be appreciated that the cryotherapeutic-device components described below and/or specific features of the cryotherapeutic-device components described below can be used with the cryotherapeutic system 100 shown in FIG. 1, used in a standalone or self-contained handheld device, or used with another suitable system. For ease of reference, throughout this disclosure identical reference numbers are used to identify similar or analogous components or features, but the use of the same reference number does not imply that the parts should be construed to be identical. Indeed, in many examples described herein, the identically-numbered parts are distinct in structure and/or function.

Several embodiments of cryotherapeutic-device components described below can be configured to facilitate one or more treatment objectives related to cryogenic renal-nerve modulation. For example, several embodiments of applicators described below are configured to apply cryogenic cooling in a desirable localized or overall treatment pattern. A desirable localized treatment pattern can include, for example, partially-circumferential cooling at one or more longitudinal segments of a renal artery or a renal ostium. A desirable overall treatment pattern can include a combination of localized treatment patterns at a treatment site. For example, a desirable overall treatment pattern can be a partially-circumferential or a fully-circumferential treatment pattern in a plane perpendicular to a renal artery or a renal ostium. To facilitate a desirable localized or overall treatment pattern, an applicator configured in accordance with several embodiments of the present technology can have more than one heat-transfer portion, such as a primary heat-transfer portion and a secondary heat-transfer portion. When a cooling assembly including such an applicator is operating in a deployed state, a primary heat-transfer portion of the applicator can have a heat-transfer rate sufficient to cause therapeutically-effective, cryogenic renal-nerve modulation. A secondary heat-transfer portion of the applicator can have a lower heat-transfer rate during operation, such as a heat-transfer rate insufficient to cause therapeutically-effective, cryogenic renal-nerve modulation. The positioning of the primary and secondary heat-transfer portions can correspond to a desirable localized or overall treatment pattern.

Several embodiments of applicators described below include features configured to affect the positioning of primary and secondary heat-transfer portions. Such features can include, for example, features related to (a) differential convective heat-transfer within an applicator, (b) differential conductive heat-transfer through an applicator, and/or (c) differential contact or spacing between an applicator and a renal artery or a renal ostium at a treatment site. Features related to differential convective heat transfer can include, for example, refrigerant supply tubes and orifices configured to selectively direct expansion of refrigerant toward different portions of an applicator. Features related to differential conductive heat transfer through an applicator can include, for example, additional balloons (e.g., non-cooling balloons and balloons having low levels of cooling), differential composition (e.g., low thermal conductivity and high thermal conductivity materials), differential thicknesses (e.g., balloon-wall thicknesses), and thermally-insulative structures (e.g., elongated, thermally-insulative members within balloons or attached to balloon walls). Features related to differential contact or spacing between an applicator and a renal artery or a renal ostium can include, for example, additional balloons, and characteristics of complex balloons, such as shape (e.g., helical, curved, longitudinally-asymmetrical, and radially-asymmetrical), surface differentiation (e.g., recesses, groves, protrusions, and projections), and differential expansion (e.g., partially-constrained expansion).

Several embodiments of applicators described below are also configured to facilitate sizing, such as delivery at a reduced (e.g., low-profile) cross-sectional dimension and deployment at a cross-sectional dimension suitable for providing therapeutically-effective treatment to renal arteries and/or renal ostiums having different sizes. For example, several embodiments of applicators described below include a balloon that is at least partially collapsed when an associated cooling assembly is in a delivery state and at least partially expanded when an associated cooling assembly is in a deployed state. Features related to sizing can include, for example, balloon composition (e.g., compliant and non-compliant materials), additional balloons, and characteristics of complex balloons, such as shape (e.g., compliant and non-compliant shapes). Non-compliant materials (e.g., polyethylene terephthalate) can have compliance (e.g., elasticity), for example, from about 0% to about 30%. Compliant materials (e.g., polyurethane and other thermoplastic elastomers) can have compliance, for example, from about 30% to about 500%. Non-compliant materials typically have greater strength (e.g., higher pressure ratings) than compliant materials. Several embodiments of applicators described below can be configured to facilitate a desirable level of occlusion of a renal artery and/or a renal ostium. For example, several embodiments of applicators described below are configured to be partially occlusive, such as to apply therapeutically-effective cooling for renal nerve modulation at a treatment site without preventing blood flow through the treatment site. Features related to partial occlusion include, for example, characteristics of complex balloons, such as shape (e.g., helical, curved, longitudinally-asymmetrical, and radially-asymmetrical) and differential expansion (e.g., partially-constrained expansion). Full occlusion, such as complete or near-complete blockage of blood-flow through a renal artery or a renal ostium can be desirable with regard to certain treatments. Features related to full occlusion can include, for example, any suitable feature related to sizing. As described below, cryotherapeutic devices configured in accordance with several embodiments of the present technology can include an occlusion member, such as an expandable member of a cooling assembly (e.g., a balloon defining an expansion chamber) or a separate occlusion member (e.g., proximal to a cooling assembly). An occlusion member can be combined with any suitable applicator described herein to provide occlusion in conjunction with features associated with the applicator.

Cooling assemblies configured in accordance with the present technology can include structures that take advantage of frozen and/or liquid blood proximate an applicator to facilitate one or more treatment objectives related to cryogenic renal-nerve modulation. Frozen and/or liquid blood proximate an applicator can affect factors such as heat transfer, sizing, and occlusion. For example, several embodiments can be configured to freeze blood around an applicator to cause full or partial occlusion. In some cases, therapeutically-effective cooling can occur through a layer of frozen blood (e.g. a layer of frozen blood having a thickness less than about 0.8 mm, 1 mm, or 1.2 mm). A balloon can be configured such that frozen blood having a thickness through which therapeutically-effective cooling can occur is formed between a primary heat-transfer portion of the balloon and a renal artery or a renal ostium. This layer, for example, can facilitate sizing or a desired level of occlusion. Moreover, a balloon can be configured such that frozen blood having a thickness through which therapeutically-effective cooling cannot occur (e.g., a thickness greater than about 0.8 mm, 1 mm, or 1.2 mm) is formed between a secondary heat-transfer portion and a renal artery or a renal ostium. Such balloons can include, for example, recessed and non-recessed portions and other suitable structures as described in greater detail below.

Convective Heat Transfer

FIGS. 12-16B illustrate several embodiments of cryotherapeutic devices that can use differential convective heat-transfer to affect a treatment. Features related to convective heat transfer within an applicator can facilitate one or more treatment objectives of cryogenic renal-nerve modulation, such as a desirable localized or overall treatment pattern. Such features can include, for example, refrigerant supply tubes and orifices configured to selectively direct expansion of refrigerant toward different portions of an applicator.

Figures 12, 13:
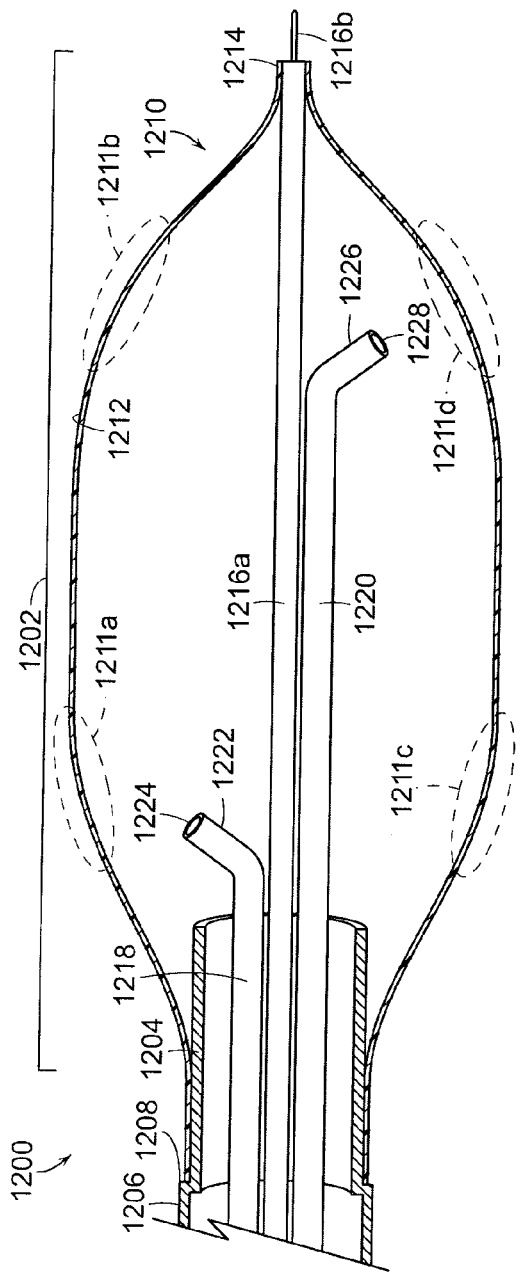
FIG. 12 is a cross-sectional view illustrating a cooling assembly having supply tubes with angled distal portions configured in accordance with an embodiment of the present technology.
FIG. 13 is a cross-sectional view illustrating a cooling assembly having a supply tube with a helical portion wrapped around an exhaust passage configured in accordance with an embodiment of the present technology.

FIG. 12 illustrates a portion of a cryotherapeutic device 1200 including a cooling assembly 1202 at a distal portion 1204 of an elongated shaft 1206 defining an exhaust passage. As described above, the distal portion 1204 can have a step 1208 and the cooling assembly 1202 can include an applicator 1210 having a plurality of heat transfer portions (individually identified as 1211a-d). The applicator 1210 also can have a balloon 1212 with a distal neck 1214, and the balloon 1212 can define an expansion chamber configured to generate and deliver cryogenic cooling. The device 1200 can further include an elongated guide member 1216a, a first supply tube 1218 defining a first supply lumen, and a second supply tube 1220 defining a second supply lumen. The guide member 1216a can define a guide-wire lumen shaped to receive a guide wire 1216b, as described in greater detail above. Guide members described with respect to other cryotherapeutic-device components described herein can be similarly configured, although for clarity of illustration, associated guide wires typically are not shown. In the illustrated embodiment, the guide member 1216a has a straight end and extends to the distal neck 1214. Alternatively, the guide member 1216a can include a rounded end and/or an end that extends beyond the distal neck 1214. Similarly, in other cryotherapeutic-device components described herein, illustrated ends of guide members and/or supply tubes that exit distal portions of balloons can have various suitable shapes (e.g., atraumatic shapes) and can extend varying distances relative to distal necks of balloons.

The first supply tube 1218 can include a first angled distal portion 1222, and the cooling assembly 1202 can include a first orifice 1224 at the end of the first angled distal portion 1222. Similarly, the second supply tube 1220 can include a second angled distal portion 1226, and the cooling assembly can include a second orifice 1228 at the end of the second angled distal portion. The first and second angled distal portions 1222, 1226 of the illustrated embodiment are longitudinally and radially spaced apart along and about the length of the cooling assembly 1202. In several other embodiments, the first and second angled distal portions 1222, 1226 have the same longitudinal and/or radial position, or another configuration. When the cooling assembly 1202 is in a deployed state, refrigerant can flow through the first and second supply tubes 1218, 1220, flow through the first and second angled distal portions 1222, 1226, respectively, and flow out the first and second orifices 1224, 1228, respectively. The first and second angled distal portions 1222, 1226 can direct expanded refrigerant toward the heat-transfer portions 1211a and 1211d, respectively. As a result, when refrigerant flows out of the first and second orifices 1224, 1228, the heat-transfer portions 1211a and 1211d can have higher overall and particularly convective heat-transfer rates relative to other heat-transfer portions of the applicator 1210. This variation in heat-transfer rate can correspond to a desired cooling pattern, such as a partially-circumferential cooling pattern at some or all longitudinal segments of the applicator 1210. The difference in heat-transfer rate can vary depending on a distance from the heat-transfer portions 1211a and 1211d. A functionally significant difference in heat-transfer rate can separate the heat-transfer portion 1211a from the heat-transfer portion 1211c, which is generally circumferentially opposite to the heat-transfer portion 1211a. Similarly, a functionally significant difference in heat-transfer rate can separate the heat-transfer portion 1211d from the heat-transfer portion 1211b, which is generally circumferentially opposite to the heat-transfer portion 1211d. In several embodiments, the heat-transfer portions 1211a and 1211d have heat-transfer rates sufficient to cause therapeutically-effective renal nerve modulation, while the heat-transfer portions 1211b and 1211c have heat-transfer rates insufficient to cause therapeutically-effective renal nerve modulation.

The first and second supply tubes 1218, 1220 can be configured, for example, to direct expansion of refrigerant at angles about 45° offset from the length of the applicator 1210 or the length of the cooling assembly 1202. In several other embodiments, one or more supply tubes are configured to direct refrigerant at an angle from about 15° to about 90° relative to a length of an applicator or a cooling assembly, such as from about 30° to about 45°, or from about 30° to about 40°. Additionally, the first supply tube 1218 can be at a different angle than the second supply tube 1220. The longitudinal distance between a first orifice 1224 and a second orifice 1228 of a cooling assembly configured in accordance with several embodiments of the present technology can be, for example, from about 1 mm to about 20 mm, such as from about 2 mm to about 15 mm, or from about 3 mm to about 10 mm.

Cooling assemblies configured in accordance with several embodiments of the present technology can alternatively include a supply tube or lumen having a curved and/or helical portion. FIG. 13 illustrates a portion of a cryotherapeutic device 1300 including a cooling assembly 1302 at a distal portion 1304 of an elongated shaft 1306 defining an exhaust passage open at the end of the distal portion 1304. The distal portion 1304 can have a step 1307 and the cooling assembly 1302 can include an applicator 1308 having a first heat-transfer portion 1309 and a second heat-transfer portion 1310. The first and second heat-transfer portions 1309, 1310 are elongated and radially spaced apart around the length of the cooling assembly 1302. The applicator 1308 also can have a balloon 1311 that can define an expansion chamber configured to generate and deliver cryogenic cooling. The device 1300 can further include an elongated guide member 1312 and a supply tube 1313 extending along the length of the shaft 1306. Within the balloon 1311, the supply tube 1313 can include a helical portion 1314 that exits the distal portion 1304 and wraps around the distal portion 1304 (e.g., the distal portion 1304 can define a central axis of the helical portion 1314). The cooling assembly 1302 can include a plurality of orifices (individually identified as 1316a-e) laterally spaced apart along the helical portion 1314. In the illustrated embodiment, if the helical portion 1314 were straightened, the orifices 1316a-e would be generally radially aligned. In this embodiment, the shape of the helical portion 1314 causes the orifices 1316a-e to point in different radial directions. In other embodiments, the helical portion 1314 can have a different number and/or orientation of orifices 1316a-e.

The helical portion 1314 locates the orifices 1316a-e closer to the balloon 1311 than they would be if the supply tube 1312 were straight. This can cause refrigerant exiting the orifices 1316a-e to contact the balloon 1311 at higher velocities and increase the amount of convective cooling at corresponding heat-transfer portions of the balloon 1311. This can also provide more control of the size and spacing of where refrigerant first contacts the balloon 1311. Cooling assemblies configured in accordance with several embodiments of the present technology can include orifices spaced apart greater than about 0.01 mm (e.g., greater than about 0.1 mm, greater than about 0.5 mm, or greater than about 1 mm) from central longitudinal axes of cooling assemblies when the cooling assemblies are in a deployed state. For example, orifices in several embodiments can be between about 0.01 mm and about 4 mm or between about 0.1 mm and about 2 mm from central longitudinal axes of cooling assemblies when the cooling assemblies are in a deployed state. Similarly, cooling assemblies configured in accordance with several embodiments of the present technology can include orifices spaced apart by less than about 4 mm (e.g., less than about 2 mm, less than about 1 mm, or less than about 0.5 mm) from balloons when the cooling assemblies are in a deployed state. For example, orifices in several embodiments can be between about 0.1 mm and about 4 mm or between about 0.5 mm and about 2 mm apart from balloons when the cooling assemblies are in a deployed state. Furthermore, cooling assemblies configured in accordance with several embodiments of the present technology can include an orifice positioned such that a distance from a central longitudinal axis of a cooling assembly to the orifice is not less than about 20% (e.g., not less than about 25%, 40%, or 60%) of a distance from the central longitudinal axis to an inner surface of a balloon in a plane at the orifice and perpendicular to the central longitudinal axis.

In the illustrated embodiment, the orifices 1316a, 1316c, 1316e point generally toward an upper half of the balloon 1311, while the orifices 1316b, 1316d point generally toward a lower half of the balloon 1311. When the cooling assembly 1302 is in a deployed state, refrigerant flow through orifices 1316a, 1316c, 1316e produces the first heat-transfer portion 1309, while refrigerant flow through orifices 1316b, 1316d produces the second heat-transfer portion 1310. As a result of the refrigerant flow, the first and second heat-transfer portions 1309, 1310 can have higher overall and particularly convective heat-transfer rates relative to other heat-transfer portions of the applicator 1308. This variation in heat-transfer rate can correspond to a desired cooling pattern, such as a partially-circumferential cooling pattern at some or all longitudinal segments of the applicator 1308. In several embodiments, the first and second heat-transfer portions 1309, 1310 have heat-transfer rates sufficient to cause therapeutically-effective renal nerve modulation, while portions of the applicator 1308 between the first and second heat-transfer portions 1309, 1310 have heat-transfer rates insufficient to cause therapeutically-effective renal nerve modulation.

Figure 14:
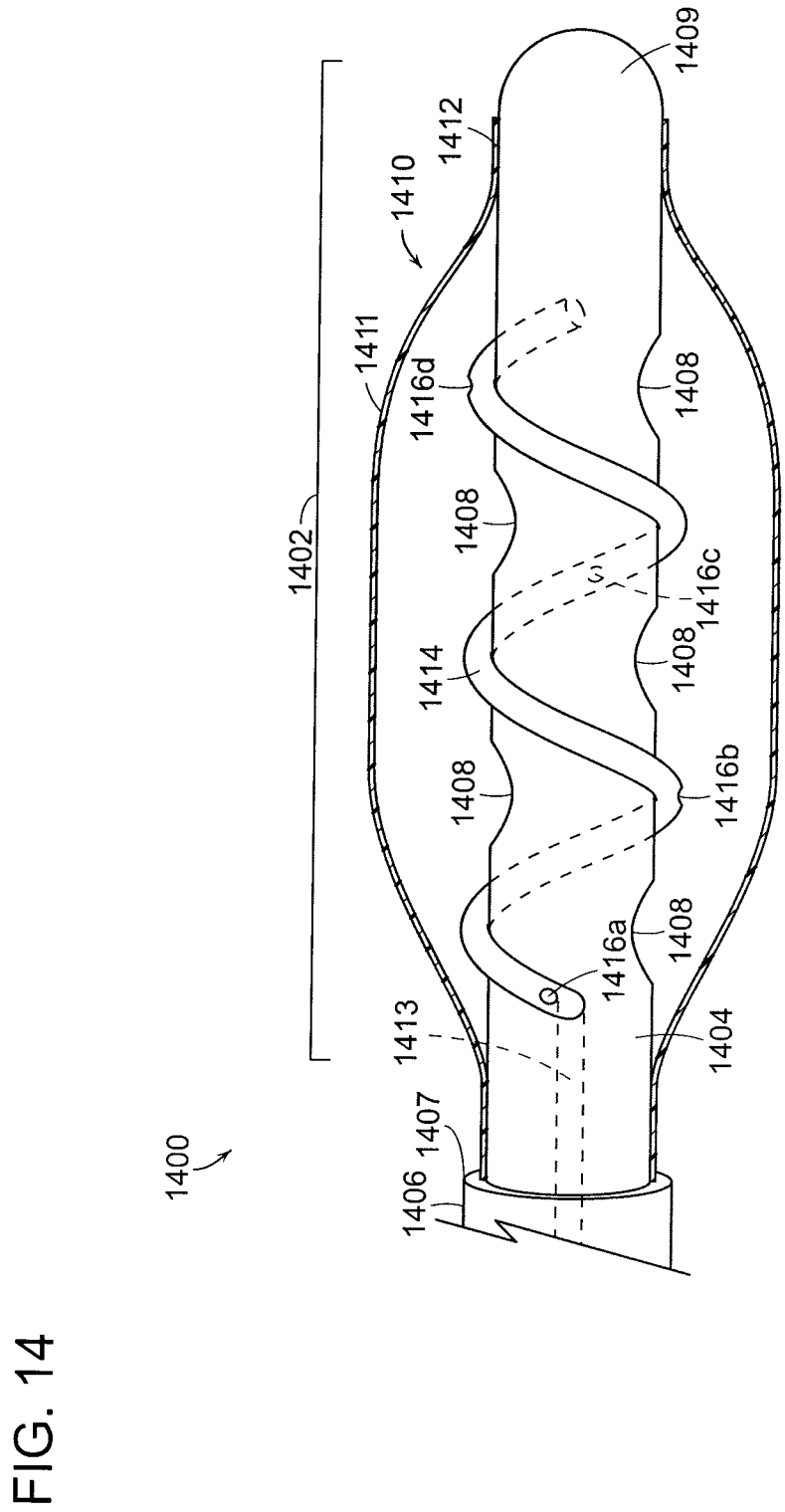
FIG. 14 is a cross-sectional view illustrating a cooling assembly having a supply tube with a helical portion wrapped around an exhaust passage configured in accordance with another embodiment of the present technology.

FIG. 14 illustrates a portion of a cryotherapeutic device 1400 that differs from the device 1300 of FIG. 13 primarily with respect to an exhaust configuration. The device 1400 includes a cooling assembly 1402 at a distal portion 1404 of an elongated shaft 1406 defining an exhaust passage. The distal portion 1404 can have a step 1407, a plurality of exhaust openings 1408, and a rounded end 1409. The cooling assembly 1402 can include an applicator 1410 with a balloon 1411 having a distal neck 1412 and the balloon 1411 can define an expansion chamber configured to generate and deliver cryogenic cooling. The device 1400 can further include a supply tube 1413 extending along the length of the shaft 1406 and into the balloon 1411. Within the balloon 1411, the supply tube 1413 can include a helical portion 1414 that exits the distal portion 1404 and wraps around the distal portion 1404 (e.g., the distal portion 1404 can define a central axis of the helical portion 1414). The helical coils of the helical portion 1414 can be located between the exhaust openings 1408. The cooling assembly 1402 can include a plurality of orifices (individually identified as 1416a-d) laterally spaced apart along the helical portion 1414. In the illustrated embodiment, the distal portion 1404 is sufficiently narrow to allow the helical portion 1414 to wrap around the distal portion 1404 generally without extending beyond the diameter of the shaft 1406 proximal to the distal portion 1404. Accordingly, the cooling assembly 1402 in a delivery state can be configured to fit within a delivery sheath sized according to the shaft 1406. The plurality of exhaust openings 1408 can promote exhaust flow and mitigate any flow restriction associated with the sizing of the distal portion 1404. Thus, as discussed above, the relatively high density of expanded refrigerant entering the exhaust passage can allow the distal portion 1404 to be sized down without necessarily causing an unsuitable increase in back pressure.

Similar to the orifices 1316a-e of the device 1300 of FIG. 13, the orifices 1416a-d in the illustrated embodiment are laterally spaced apart along the helical portion 1414. However, unlike the orifices 1316a-d of the device 1300 of FIG. 13, the orifices 1416a-d in the illustrated embodiment are configured to direct refrigerant flow in different radial directions around the length of the cooling assembly 1402. Specifically, the orifices 1416a-d are configured to direct refrigerant flow in directions radially spaced apart by increments of about 90°. The orifices 1416a-d are sized to cause corresponding heat-transfer portions having circumferential arcs greater than about 90°. As a result, the projected circumference of the heat-transfer portions corresponding to the orifices 1416a-d is generally fully circumferential, while being partially circumferential in particular longitudinal segments of the cooling assembly 1402.

Figures 15A, 15B:
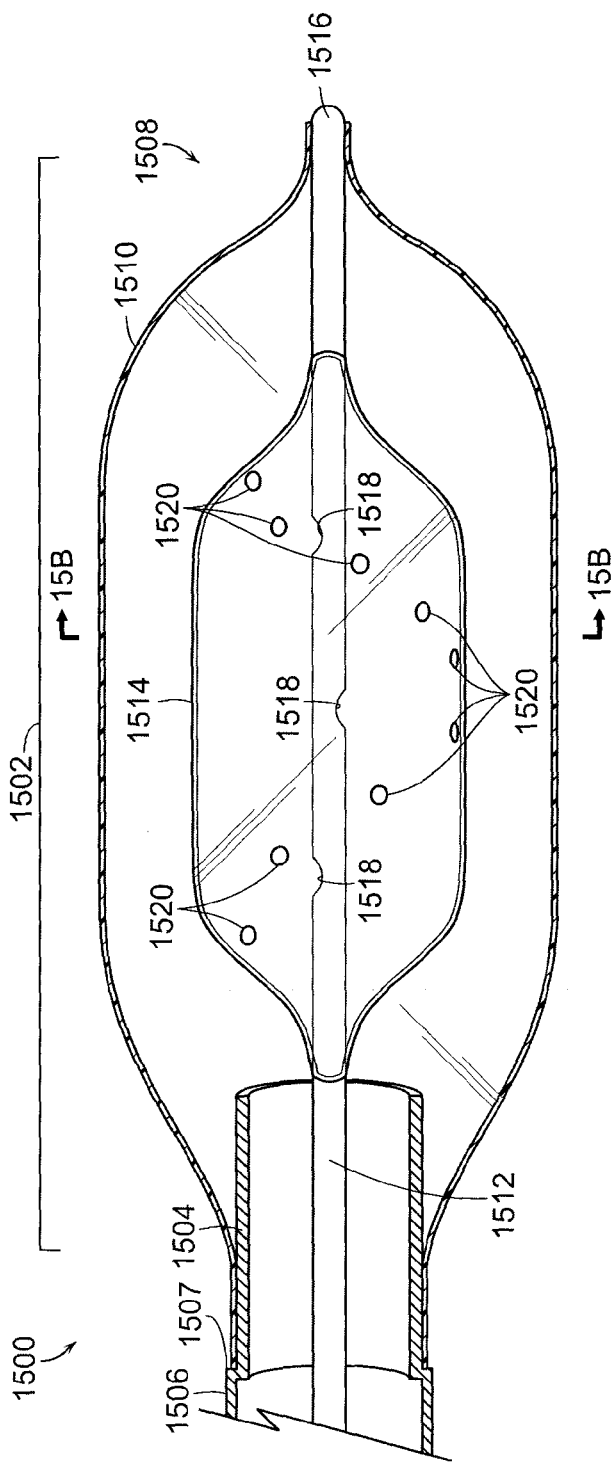
FIG. 15A is a cross-sectional view illustrating a cooling assembly having an inner balloon with inner-balloon orifices configured in accordance with an embodiment of the present technology.
FIG. 15B is a cross-sectional view illustrating the cooling assembly of FIG. 15A.

As discussed above with reference to FIG. 13, locating primary refrigerant expansion areas closer to a balloon can facilitate convective heat transfer. FIGS. 15A-15B illustrate a portion of a cryotherapeutic device 1500 that also can be configured to locate primary refrigerant expansion areas closer to a balloon. The device 1500 includes a cooling assembly 1502 at a distal portion 1504 of an elongated shaft 1506 defining an exhaust passage. The distal portion 1504 can have a step 1507, and the cooling assembly 1502 can include an applicator 1508 with an outer balloon 1510 that can define an expansion chamber configured to generate and deliver cryogenic cooling. The device 1500 can further include a supply tube 1512 and an inner balloon 1514. The supply tube 1512 has a rounded end 1516 and can extend along the length of the shaft 1506 and through a distal portion of the outer balloon 1510. The inner balloon 1514 extends around a portion of the supply tube 1512 within the outer balloon 1510. In several other embodiments configured in accordance with the present technology, a supply tube 1512 terminates within an inner distributor, such as the inner balloon 1514, and/or the device can include a guide member that can extend through the inner balloon 1514 and through the distal portion of the outer balloon 1510. With reference again to the embodiment of the device 1500 shown in FIGS. 15A-15B, the portion of the supply tube 1512 within the inner balloon 1514 can include supply-tube orifices 1518. The cooling assembly 1502 can include inner-balloon orifices 1520 distributed in a helical arrangement or other suitable arrangement on the inner balloon 1514. The inner-balloon orifices 1520 can be, for example, laser-cut holes in the inner balloon 1514. When the cooling assembly 1502 is in a delivery state, the outer balloon 1510 and the inner balloon 1514 can be at least partially collapsed to fit within a delivery sheath.

When the cooling assembly 1502 is in a deployed state, refrigerant can flow from the supply tube 1512, through the supply-tube orifices 1518, and into the inner balloon 1514. The supply-tube orifices 1518 can be large enough to allow refrigerant to enter the inner balloon 1514 without liquid-to-gas phase change of a significant portion of liquid refrigerant (e.g., a majority of liquid refrigerant). For example, in the deployed state, a refrigerant absolute vapor pressure within the inner balloon 1514 outside the supply tube 1512 can be from about 40% to about 100% of a refrigerant absolute vapor pressure within the portion of the supply tube within the inner balloon 1514, such as from about 20% to about 100%, or from about 33% to about 100%. A first free-passage area equal to the total free-passage area of the inner-balloon orifices 1520 can be less than a second free-passage area equal to the total free-passage area of the supply-tube orifices 1518. The size and/or number of inner-balloon orifices 1520 can be selected to control the first free-passage area. Similarly, the size and/or number of supply-tube orifices 1518 can be selected to control the second free-passage area. From the inner balloon 1514, refrigerant can expand through the inner-balloon orifices 1520 to cool one or more corresponding heat-transfer portions of the applicator 1508. In particular, the inner-balloon orifices 1520 can be configured to cool a generally helical heat-transfer portion.

FIGS. 16A-16B illustrate a cryotherapeutic device 1600 that differs from the cooling assembly 1500 of FIG. 15A with respect to an outer-balloon shape. The device 1600 includes a cooling assembly 1602 including an applicator 1604 with an outer balloon 1606 having a raised helical portion 1608 and a recessed portion 1610. The inner surface of the raised helical portion 1608 can be configured to receive expanded refrigerant from the inner-balloon orifices 1520, and the shape of the inner surface of the raised helical portion 1608 can help to localize increased convective cooling at the raised helical portion 1608. The recessed portion 1610 is generally configured not to contact a renal artery or a renal ostium. Localizing increased convective cooling to the raised helical portion 1606 can promote cooling efficiency as well as cooling-location selectivity. The raised helical portion 1608 can correspond to a heat-transfer portion having a higher heat-transfer rate than other heat-transfer portions of the applicator 1604, such as a heat-transfer portion corresponding to the recessed portion 1610. For example, during operation, the raised helical portion 1608 can correspond to a heat-transfer portion having a heat-transfer rate sufficient to cause therapeutically-effective renal nerve modulation, while another heat-transfer portion of the applicator (e.g., a heat-transfer portion corresponding to the recessed portion 1610) has a heat-transfer rate insufficient to cause therapeutically-effective renal nerve modulation.

Conductive Heat Transfer

FIGS. 17A-22B illustrate several embodiments of cryotherapeutic devices that can use differential conductive heat-transfer to affect a treatment. Features related to conductive heat transfer through an applicator can facilitate one or more treatment objectives of cryogenic renal-nerve modulation, such as a desirable localized or overall treatment pattern. In several embodiments, the devices control conduction using thermally-insulative members. Features related to differential conductive heat transfer through an applicator can include, for example, additional balloons (e.g., non-cooling balloons and balloons having low levels of cooling), differential composition (e.g., low thermal conductivity and high thermal conductivity materials), differential thicknesses (e.g., balloon-wall thicknesses), and thermally-insulative structures (e.g., elongated, thermally-insulative members within balloons or attached to balloon walls).

Figure 17A:
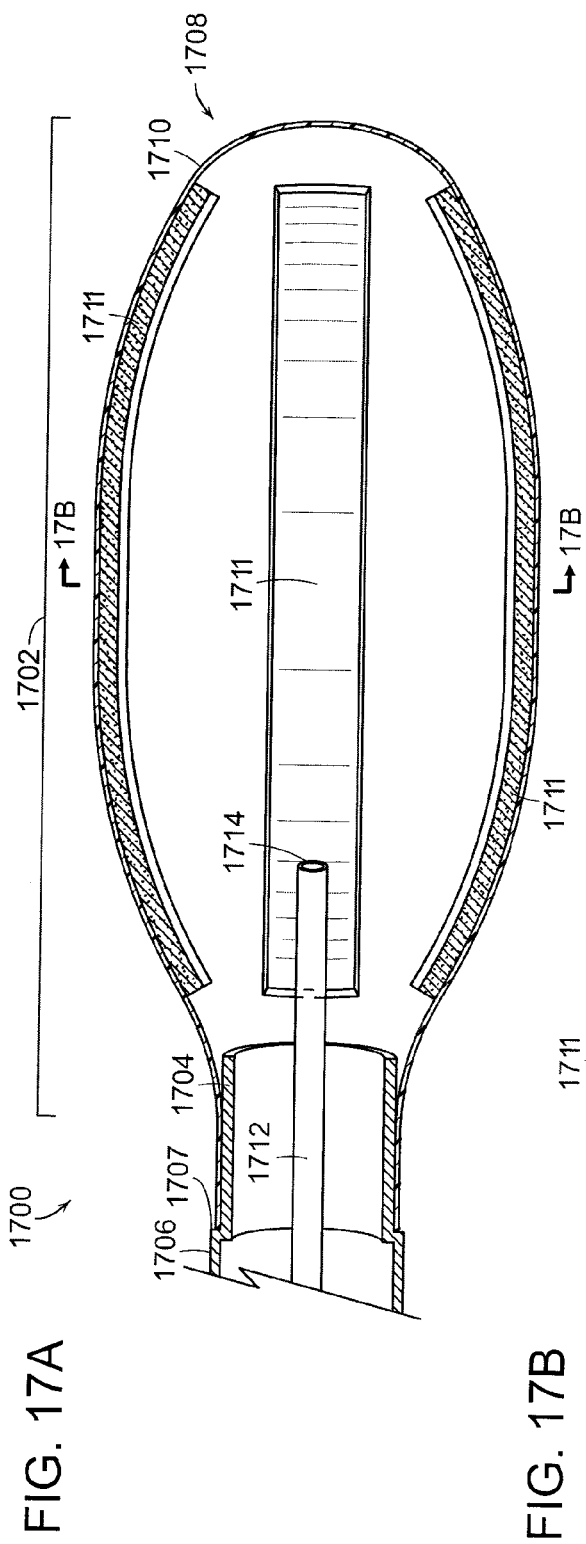
FIG. 17A is a cross-sectional view illustrating a cooling assembly having elongated, thermally-insulative members configured in accordance with an embodiment of the present technology.
Figure 17B:
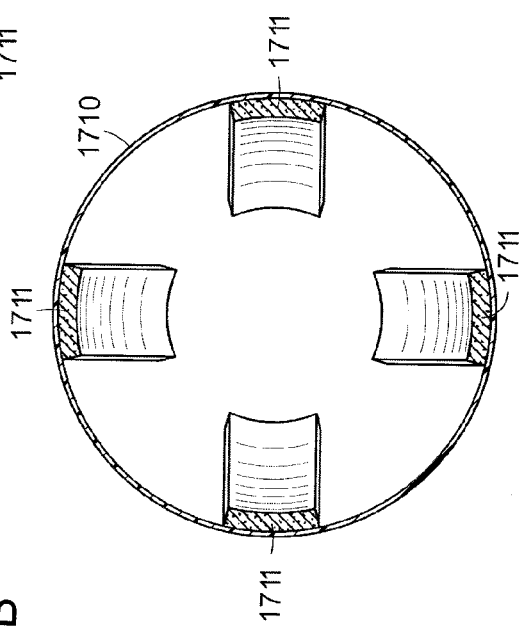
FIG. 17B is a cross-sectional view illustrating the cooling assembly of FIG. 17A.

FIGS. 17A-17B illustrate a portion of a cryotherapeutic device 1700 including a cooling assembly 1702 at a distal portion 1704 of an elongated shaft 1706 defining an exhaust passage. The distal portion 1704 can have a step 1707, and the cooling assembly 1702 can include an applicator 1708 having a balloon 1710 configured to contact a renal artery or a renal ostium. The applicator 1708 can further include a plurality of elongated, thermally-insulative members 1711 with lengths generally parallel to the length of the cooling assembly 1702 and radially spaced apart around the circumference of the cooling assembly 1702. The balloon 1710 can define an expansion chamber configured to generate and deliver cryogenic cooling. The device 1700 can further include a supply tube 1712 extending along the length of the shaft 1706 and into the balloon 1710, and the cooling assembly 1702 can include an orifice 1714 at the end of the supply tube 1712. During operation when the cooling assembly 1702 is in a deployed state, the thermally-insulative members 1711 can reduce conductive cooling through adjacent portions of the balloon 1710. For example, portions of the balloon 1710 between the thermally-insulative members 1711 can have heat-transfer rates sufficient to cause therapeutically-effective renal nerve modulation, while portions of the balloon at the thermally-insulative members 1711 can have lower heat-transfer rates, such as heat-transfer rates insufficient to cause therapeutically-effective renal nerve modulation. The thermally-insulative members 1711 can be elongated and generally continuous along the length of portions of the applicator 1708. Accordingly, heat-transfer portions corresponding to portions of the balloon 1710 between the thermally-insulative members 1711 can be generally non-circumferential at longitudinal segments of the cooling assembly 1702.

The thermally-insulative members 1711 can include a primary material having a thermal conductivity lower than or equal to a thermal conductivity of a primary material of the balloon 1710. In several embodiments, the thermally-insulative members 1711 have different compositions than the balloon 1710 and are attached to an inner surface of the balloon 1710. Several other embodiments can include thermally-insulative members 1711 that are compositionally similar to (e.g., the same as) or different than the balloon 1710. Suitable primary materials for a thermally-insulative member configured in accordance with several embodiments of the present technology include thermally-insulative polymer foams (e.g., polyurethane foams). In several embodiments, a thermally-insulative member 1711 can be integrally formed with a balloon 1710 or attached to a balloon 1710.

FIGS. 18A-18B illustrate a portion of a cryotherapeutic device 1800 similar to the device 1700 of FIGS. 17A-17B except with regard to a configuration of thermally-insulative members. Thermally-insulative members configured in accordance with several embodiments of the present technology can have different insulative properties in the delivery state than in deployed state. For example, a thermally-insulative member can be configured to be filled with a filler material in the deployed state. The device 1800 includes a cooling assembly 1802 having an applicator 1804 with a balloon 1806 that can define an expansion chamber configured to generate and deliver cryogenic cooling. The applicator 1804 also includes a plurality of thermally-insulative members 1808. The device 1800 can further include a filler tube 1810, and the thermally-insulative members 1808 can be configured to be filled in the deployed state via the filler tube 1810. In the illustrate embodiment, the filler tube 1810 includes a main portion 1812 and four branches 1814, in which the branches fluidly connect the main portion with one of the thermally-insulative members 1808. The thermally-insulative members 1808 and the filler tube 1810 are fluidly separate from the expansion chamber within the balloon 1806.

The filler tube 1810 has a proximal portion (not shown) configured to receive filler material from a filler-material source (not shown) from outside the vasculature. The filler tube 1810 and the thermally-insulative members 1808 can be configured to be fully, mostly, or partially collapsed in the delivery state. This can be useful to allow the introduction of fluidic filler material in the delivery state without the need to vent displaced gas. Several other embodiments can include a filler tube that is generally not collapsible and a thermally-insulative member configured to receive displaced gas or liquid from such a filler tube. A proximal portion of a filler tube configured in accordance with several embodiments of the present technology can be fluidly connected to a filler port, such as a filler port including syringe adapter, such as a syringe adapter including a diaphragm configured to be punctured with a needle of a syringe containing filler material. Such a filler port can be configured, for example, to reduce (e.g., prevent) passage of air before, during, and/or after passage of filler material. However, in several embodiments, air can be a suitable filler material. Other components of cryotherapeutic devices configured in accordance with several embodiments of the present technology including a filler tube (including such embodiments described herein) can be similarly configured. Suitable filler materials for use with cryotherapeutic devices configured in accordance with several embodiments of the present technology include liquids (e.g., saline), gases (e.g., air), biologically inert materials, and radiopaque materials (e.g., contrast agents).

Although four thermally-insulative members are shown in FIGS. 17A-18B, cooling assemblies configured in accordance with several embodiments of the present technology can include any suitable number of thermally-insulative members, such as at least one or more thermally-insulative members. Additionally, thermally-insulative members configured in accordance with several embodiments of the present technology can be generally separate elements or portions of a single element and can have a variety of suitable shapes.

Figure 19A:
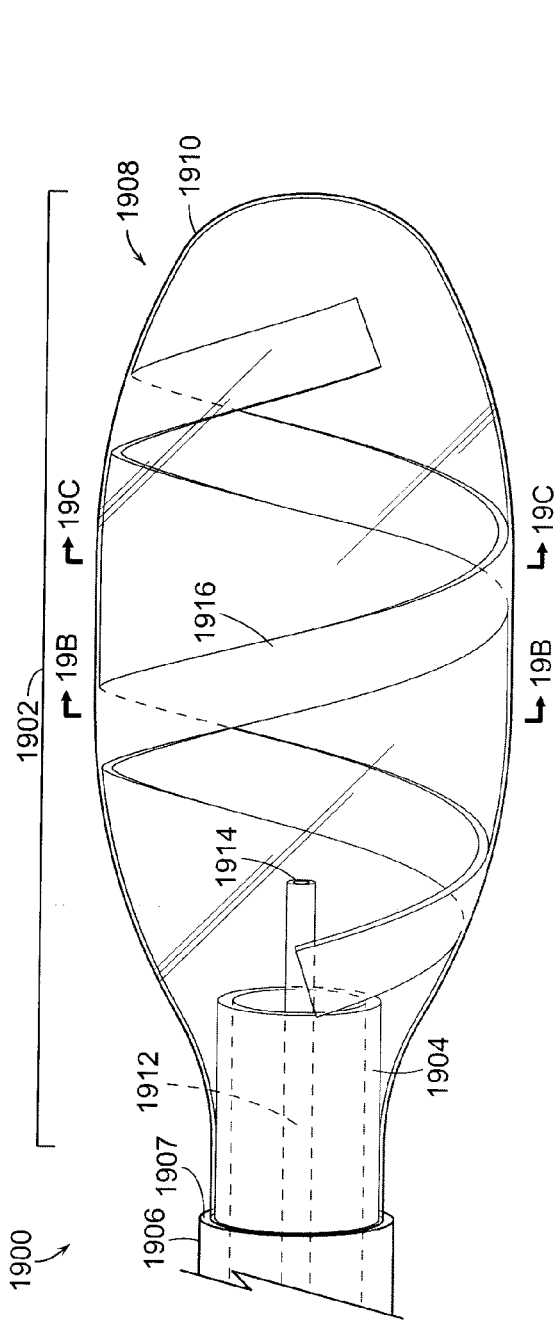
FIG. 19A is a profile view illustrating a cooling assembly having a helical thermally-insulative member configured in accordance with an embodiment of the present technology.
Figure 19C:
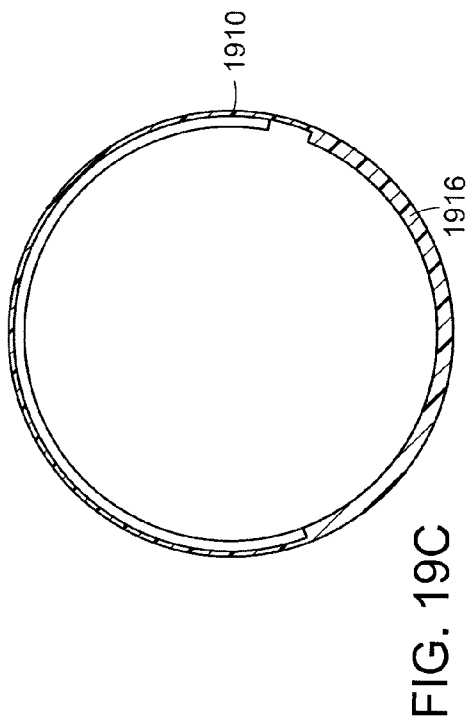
FIGS. 19B and 19C are cross-sectional views illustrating the cooling assembly of FIG. 19A.
Figure 19B:
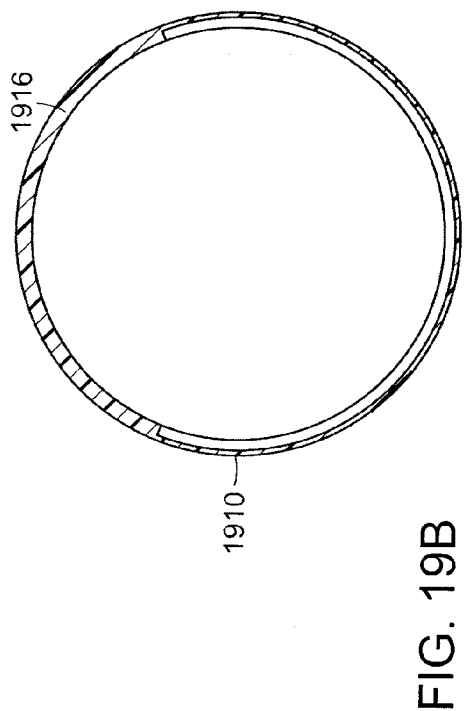

FIGS. 19A-19C illustrate a portion of a cryotherapeutic device 1900. Referring to FIG. 19A, the device 1900 can include a cooling assembly 1902 at a distal portion 1904 of an elongated shaft 1906 defining an exhaust passage. The distal portion 1904 can have a step 1907, and the cooling assembly 1902 can include an applicator 1908 with a balloon 1910 that can define an expansion chamber configured to generate and deliver cryogenic cooling. The device 1900 can further include a supply tube 1912 extending along the length of the shaft 1906 and into the balloon 1910, and the cooling assembly 1902 can include an orifice 1914 at an end of the supply tube 1912. The device 1900 can further include a helical thermally-insulative member 1916 that can be, for example, a thicker portion of the balloon 1910 with the extra thickness at an inner surface of the balloon 1910 (i.e., an outer surface of the balloon 1910 can be generally smooth or otherwise even at the helical thermally-insulative member 1916 and around the helical thermally-insulative member 1916). During operation when the cooling assembly 1902 is in a deployed state, the helical thermally-insulative member 1916 can correspond to a heat-transfer portion of the applicator 1908 having a lower heat-transfer rate than other portions of the applicator 1908. For example, a heat-transfer rate of a portion of the applicator 1908 apart from the helical thermally-insulative member 1916 can be sufficient to cause therapeutically-effective renal nerve modulation during operation, while a heat-transfer rate of a portion of the applicator 1908 at the helical thermally-insulative member 1916 can be insufficient to cause therapeutically-effective renal nerve modulation. FIGS. 19B and 19C are cross-sectional views of the applicator 1908 at different longitudinal positions. As shown in FIGS. 19B and 19C, the circumferential position of the helical thermally-insulative member 1916 changes along the length of the cooling assembly 1902 such that the portion of the balloon 1910 apart from the helical thermally-insulative member 1916 is generally non-circumferential in longitudinal segments along the length of the cooling assembly 1902.

Figure 20A:
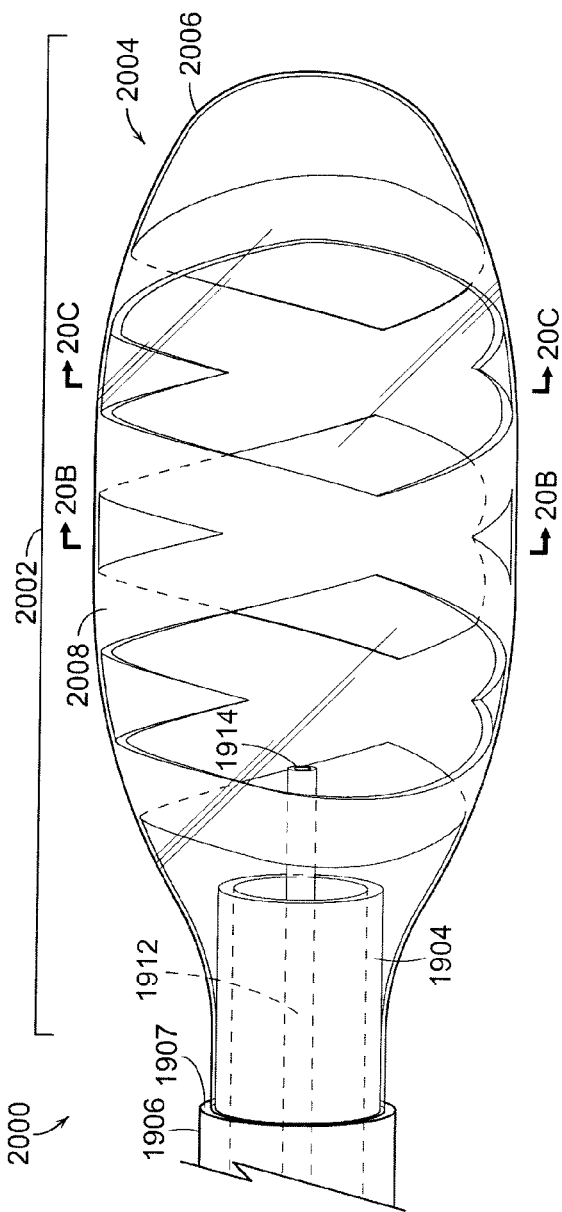
FIG. 20A is a profile view illustrating a cooling assembly having a thermally-insulative member resembling an intertwined double helix configured in accordance with an embodiment of the present technology.
Figure 20C:
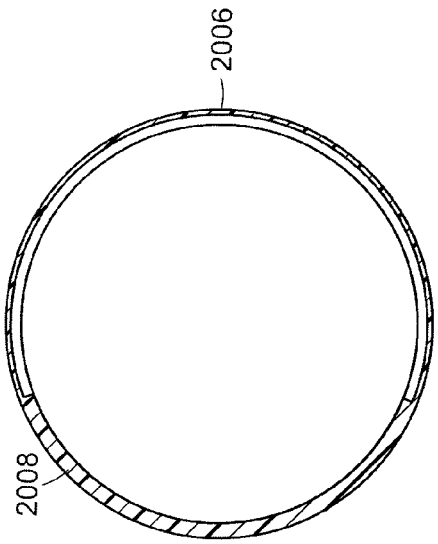
FIGS. 20B and 20C are cross-sectional views illustrating the cooling assembly of FIG. 20A.
Figure 20B:
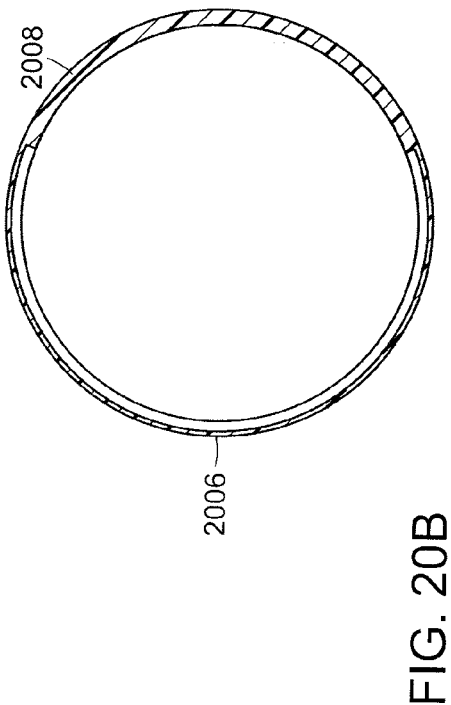

FIGS. 20A-20C illustrate a portion of a cryotherapeutic device 2000 similar to the device 1900 of FIGS. 19A-19C except with regard to a thermally-insulative member shape. Referring to FIG. 20A, the device 2000 includes a cooling assembly 2002 having an applicator 2004 with a balloon 2006 that can define an expansion chamber configured to generate and deliver cryogenic cooling. The applicator 2004 also includes a thermally-insulative member 2008 generally resembling an intertwined double helix (e.g., an intertwined right-handed helix and left-handed helix). A heat-transfer portion of the applicator 2004 at the thermally-insulative member 2008 generally isolates heat-transfer portions of the applicator 2004 apart from the thermally-insulative member 2008. The thermally-insulative member 2008 can be configured to collapse and/or expand with the balloon 2006 when the cooling assembly 2002 moves between the delivery state and the deployed state. For example, if the balloon 2006 is generally flexible and non-compliant, the thermally-insulative member 2008 can be either generally flexible and compliant or non-compliant. If the balloon 2006 is generally compliant, the thermally-insulative member 2008 can be generally compliant so as to compliantly expand and contract in conjunction with the balloon 2006. The thermally insulative members 1716, 1808 shown in FIGS. 17A-18B, and the helical thermally-insulative member 1916 shown in FIGS. 19A-19B, can be similarly configured relative to the corresponding balloons 1710, 1806, 1910. In several embodiments of the present technology, a thermally-insulative member has a modulus of elasticity between about 50% and about 150% of a modulus of elasticity of a corresponding balloon, such as between about 20% and about 140%, or between about 33% and about 130%.

Figure 21A:
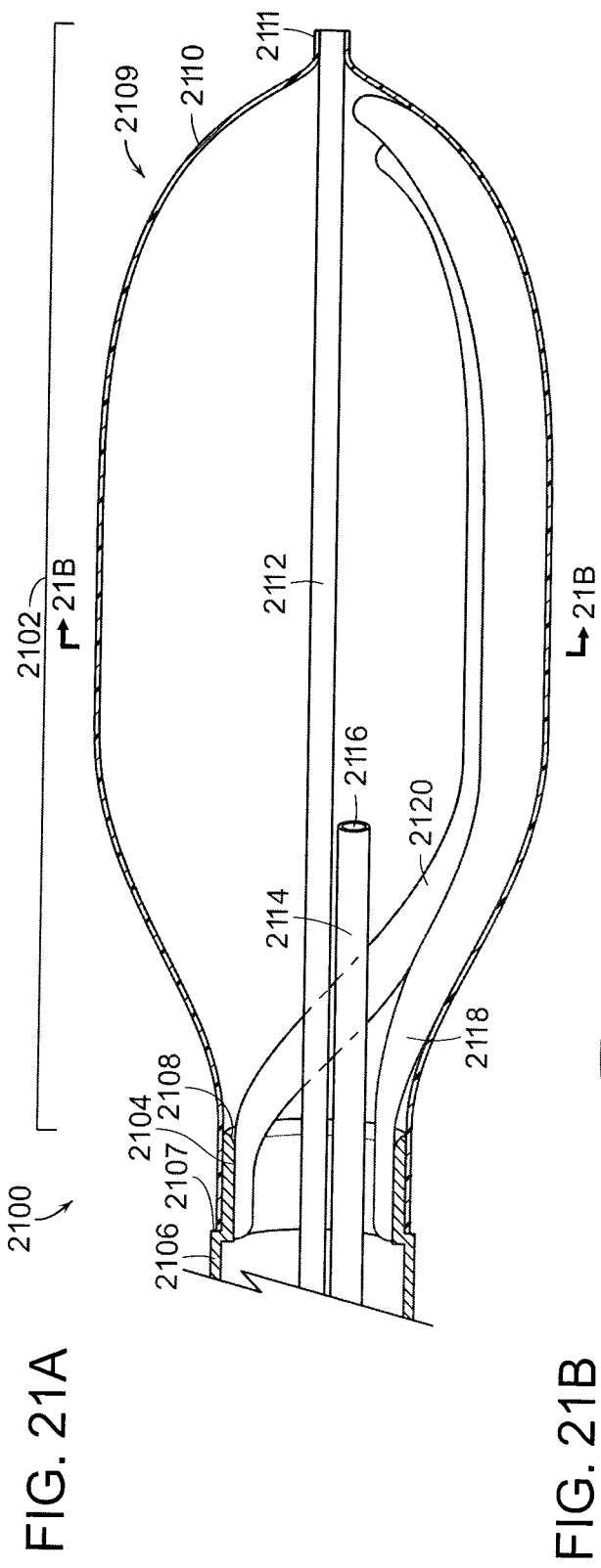
FIG. 21A is a cross-sectional view illustrating a cooling assembly having elongated, thermally-insulative members movable within a balloon configured in accordance with another embodiment of the present technology.
Figure 21B:
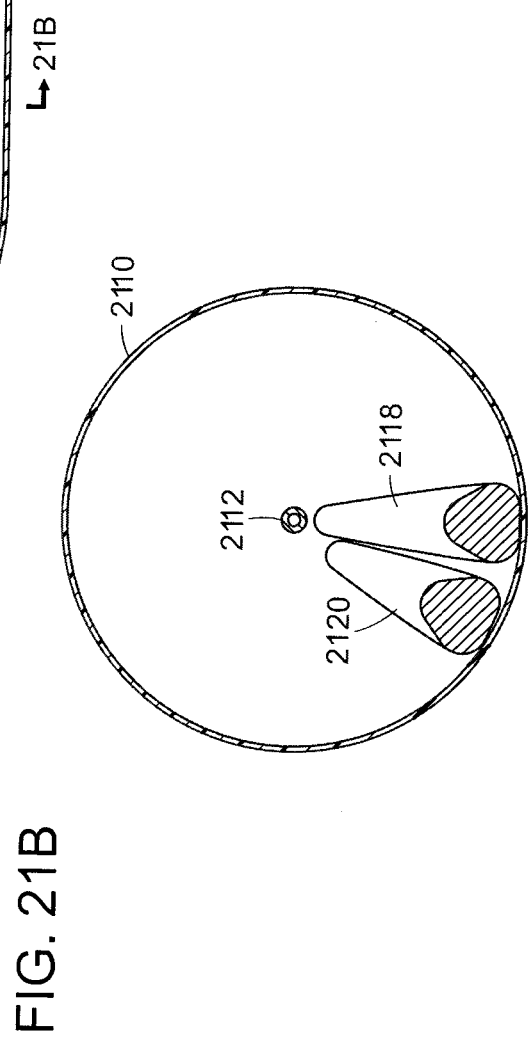
FIG. 21B is a cross-sectional view illustrating the cooling assembly of FIG. 21A.
Figure 21C:
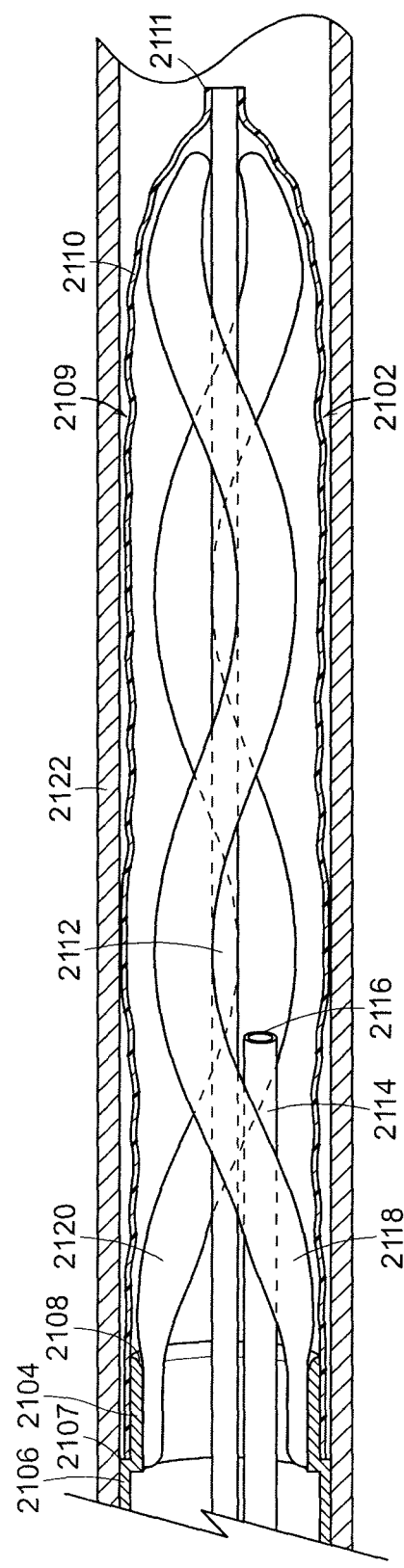
FIG. 21C is a cross-sectional view illustrating the cooling assembly of FIG. 21A in a delivery state within a delivery sheath.

Thermally-insulative members configured in accordance with additional embodiments of the present technology can be fully or partially attached to a corresponding balloon, or in other embodiments, the thermally-insulative members are not attached to the balloon. When a thermally-insulative member is only partially attached or not attached to a corresponding balloon, expansion and/or contraction of the corresponding balloon can be relatively independent of the thermally-insulative member. FIGS. 21A-21C illustrate a portion of a cryotherapeutic device 2100 including a cooling assembly 2102 at a distal portion 2104 of an elongated shaft 2106 defining an exhaust passage. The distal portion 2104 can have a step 2107 and a rounded lip 2108. The cooling assembly 2102 can include an applicator 2109 with a balloon 2110 having a distal neck 2111 and the balloon 2110 can define an expansion chamber configured to generate and deliver cryogenic cooling. The device 2100 can further include an elongated guide member 2112 and a supply tube 2114 extending along a length of the shaft 2106 and into the balloon 2110. The cooling assembly 2102 can include an orifice 2116 at the end of the supply tube. In the illustrated embodiment, the guide member 2112 extends through to the distal neck 2111. The applicator 2109 further includes a first elongated, thermally-insulative member 2118 and a second elongated, thermally-insulative member 2120. The first and second elongated, thermally-insulative members 2118, 2120 are not attached to the balloon 2110. Instead, the first and second elongated, thermally-insulative members 2118, 2120 are attached to an inner surface of the distal portion 2104.

When the cooling assembly 2102 is in a deployed state, the first and second thermally-insulative members 2118, 2120 can be movable relative to the balloon 2110 in response to gravity. The first and second thermally-insulative members 2118, 2120 can move over the rounded lip 2108 as they settle within the balloon. As shown in FIG. 21A, the first and second thermally-insulative members 2118, 2120 can settle along a lower portion of the balloon 2110. As shown in FIG. 21B, the first and second thermally-insulative members 2118, 2120 have cross-sectional areas resembling rounded triangles. In other embodiments, a similar thermally-insulative member can have a different cross-sectional area. A rounded triangular cross-sectional area can be particularly useful to increase a contact area between a side of a generally unattached thermally-insulative member and an inner surface of a balloon while preventing multiple generally unattached thermally-insulative members from overlapping. With reference to FIG. 21C, the device 2100 is shown in the delivery state within a delivery sheath 2122. As shown in FIG. 21C, the first and second thermally-insulative members 2118, 2120 can collapse with the balloon 2110 in the delivery state.

FIGS. 22A-22B illustrate a portion of a cryotherapeutic device 2200 similar to the device 2100 of FIGS. 21A-21C except with regard to a configuration of thermally-insulative members. The device 2200 includes a cooling assembly 2202 having an applicator 2204 with a balloon 2206 that can define an expansion chamber configured to generate and deliver cryogenic cooling. The applicator 2204 also includes a first elongated, thermally-insulative member 2208 and a second thermally-insulative member 2210. The device 2200 can further include a filler tube 2212 and the first and second thermally-insulative members 2208, 2210 can be configured to be filled in the deployed state via the filler tube 2212. The filler tube 2212 can include a hub 2214 where it branches into the first and second thermally-insulative members 2208, 2210. As discussed above with reference to the thermally-insulative members 1808 of the device 1800 shown in FIGS. 18A-18B, the first and second thermally-insulative members 2208, 2210 and the filler tube 2212 can be fluidly separate from the balloon 2206. The filler tube 2212 can have a proximal portion (not shown) configured to receive filler material from outside the vasculature. The filler tube 2212 and the first and second thermally-insulative members 2208, 2210 can be configured to be fully, mostly, or partially collapsed when the cooling assembly 2202 is in a delivery state.

A cooling assembly configured in accordance with several embodiments of the present technology can include one or more thermally-insulative members having a variety of suitable shapes to cause different patterns of heat-transfer portions around an applicator. A pattern can be selected, for example, so that a generally uninterrupted heat-transfer portion at a thermally-insulative member can be large enough to sufficiently localize cooling therapeutically-effective for renal nerve modulation (e.g., such that cooling therapeutically-effective for renal nerve modulation generally does not bridge across a heat-transfer portion at a thermally-insulative member). In addition or instead, a pattern can be selected, for example, so that a heat-transfer portion spaced apart from a thermally-insulative member is large enough to allow therapeutically-effective cooling for renal nerve modulation. Heat transfer is proportional to area, so if a heat-transfer portion spaced apart from a thermally-insulative member is too small, the total heat transfer through that part of the heat transfer portion can be inadequate to cause therapeutically-effective cooling for renal nerve modulation.

Complex Balloons

FIGS. 23A-37 illustrate several embodiments of cryotherapeutic devices that include complex balloons which can facilitate one or more treatment objectives related to cryogenic renal-nerve modulation, such as a desirable localized or overall treatment pattern, sizing, and partial occlusion. Complex balloons can have a variety of suitable characteristics, such as shape (e.g., helical, curved, longitudinally-asymmetrical, and radially-asymmetrical), surface differentiation (e.g., recesses, groves, protrusions, and projections), and differential expansion (e.g., partially-constrained expansion).

Figure 23B:
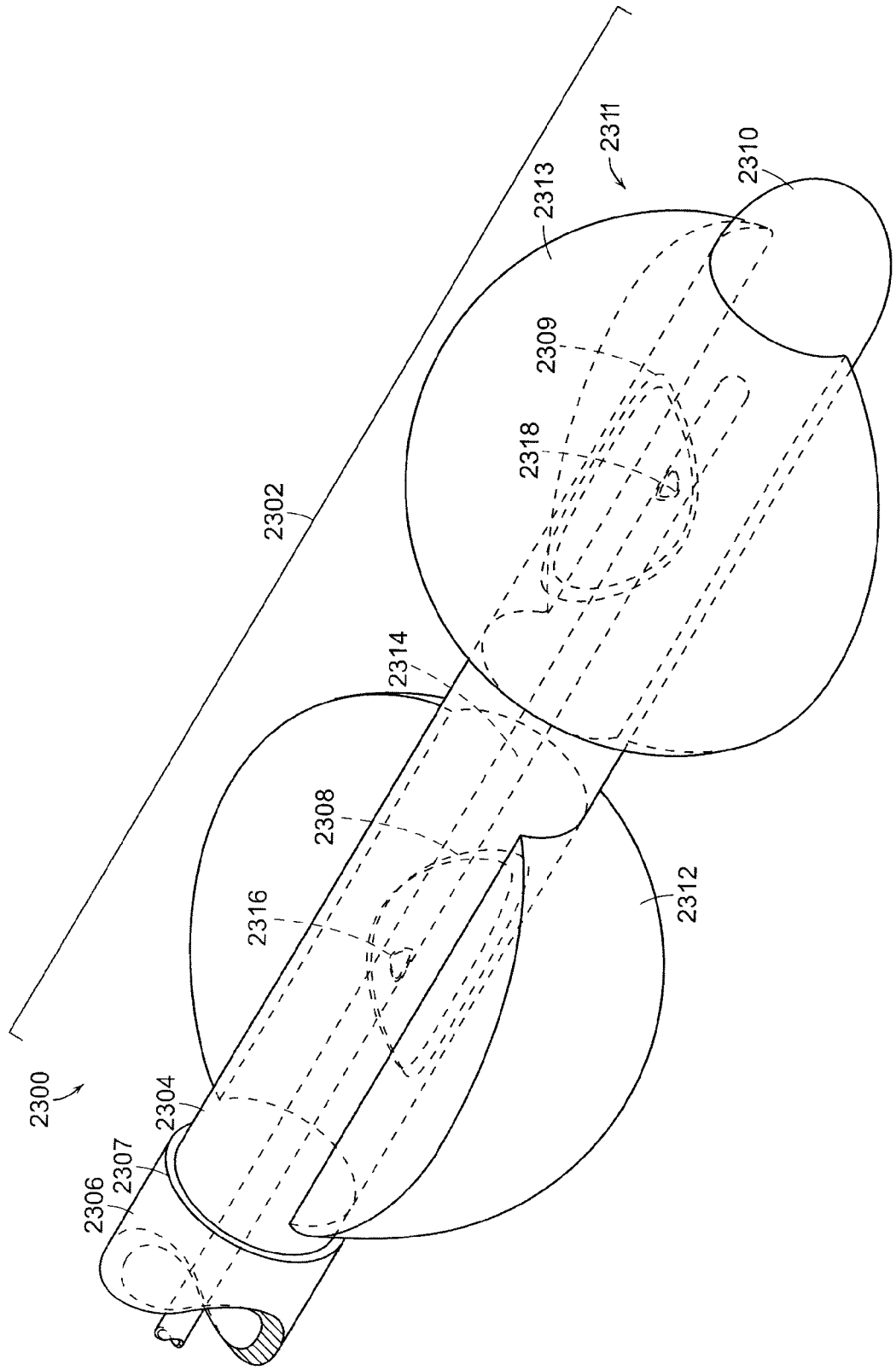
FIG. 23B is an isometric view illustrating the cooling assembly of FIG. 23A.

FIGS. 23A-23B illustrate a portion of a cryotherapeutic device 2300 including a cooling assembly 2302 at a distal portion 2304 of an elongated shaft 2306 defining an exhaust passage. The distal portion 2304 can have a step 2307, a first exhaust port 2308, a second exhaust port 2309, and a rounded end 2310. The cooling assembly 2302 can include an applicator 2311 having a first balloon 2312 that defines a first expansion chamber and a second balloon 2313 that defines a second expansion chamber. The first balloon 2312 and the second balloon 2313 are fluidly connected to the exhaust passage through the first exhaust port 2308 and the second exhaust port 2309, respectively. The device 2300 can further include a supply tube 2314 extending along a length of the shaft 2306, and the cooling assembly 2302 can further include a first orifice 2316 and a second orifice 2318. The first orifice 2316 is aligned with the first exhaust port 2308 such that refrigerant expands through the first exhaust port 2308 and into the first balloon 2312, and the second orifice 2318 is aligned with the second exhaust port 2309 such that refrigerant expands through the second exhaust port 2309 and into the second balloon 2313.

The first and second balloons 2312, 2313 are spaced apart along the length of the cooling assembly 2302 and configured to expand laterally across different partially-circumferential arcs along the length of the cooling assembly 2302. When the cooling assembly 2302 is in a deployed state, the first balloon 2312 can be configured to contact a first partially-circumferential portion of an inner surface of a renal artery or a renal ostium, and the second balloon 2313 can be configured to contact a second partially-circumferential portion of the inner surface of the renal artery or the renal ostium. The first and second partially-circumferential portions can have a fully-circumferential combined projection in a plane perpendicular to a length of the renal artery or the renal ostium. Accordingly, when a treatment calls for partially-circumferential cooling at longitudinal segments and a fully-circumferential overall cooling pattern, the cooling assembly 2302 can be configured to facilitate such a treatment without repositioning the cooling assembly 2302 during the treatment.

When the first and second balloons 2312, 2313 are both in the deployed state, they can urge each other toward generally opposite sides of an inner surface of a renal artery or a renal ostium. For example, the distal portion 2304 can transfer forces between the first and second balloons 2312, 2313 while a portion of the shaft 2306 proximal to the distal portion holds the distal portion generally parallel to a length of a renal artery or a renal ostium. During this and other operation, the cooling assembly 2302 can be configured to be non-occlusive (i.e., to less than fully occlude a renal artery or a renal ostium). For example, the cooling assembly 2302 can be configured to allow a percentage of normal blood flow through a renal artery or a renal ostium (e.g., at least about 1%, at least about 10%, or at least about 25% of normal blood flow).

Figure 24A:
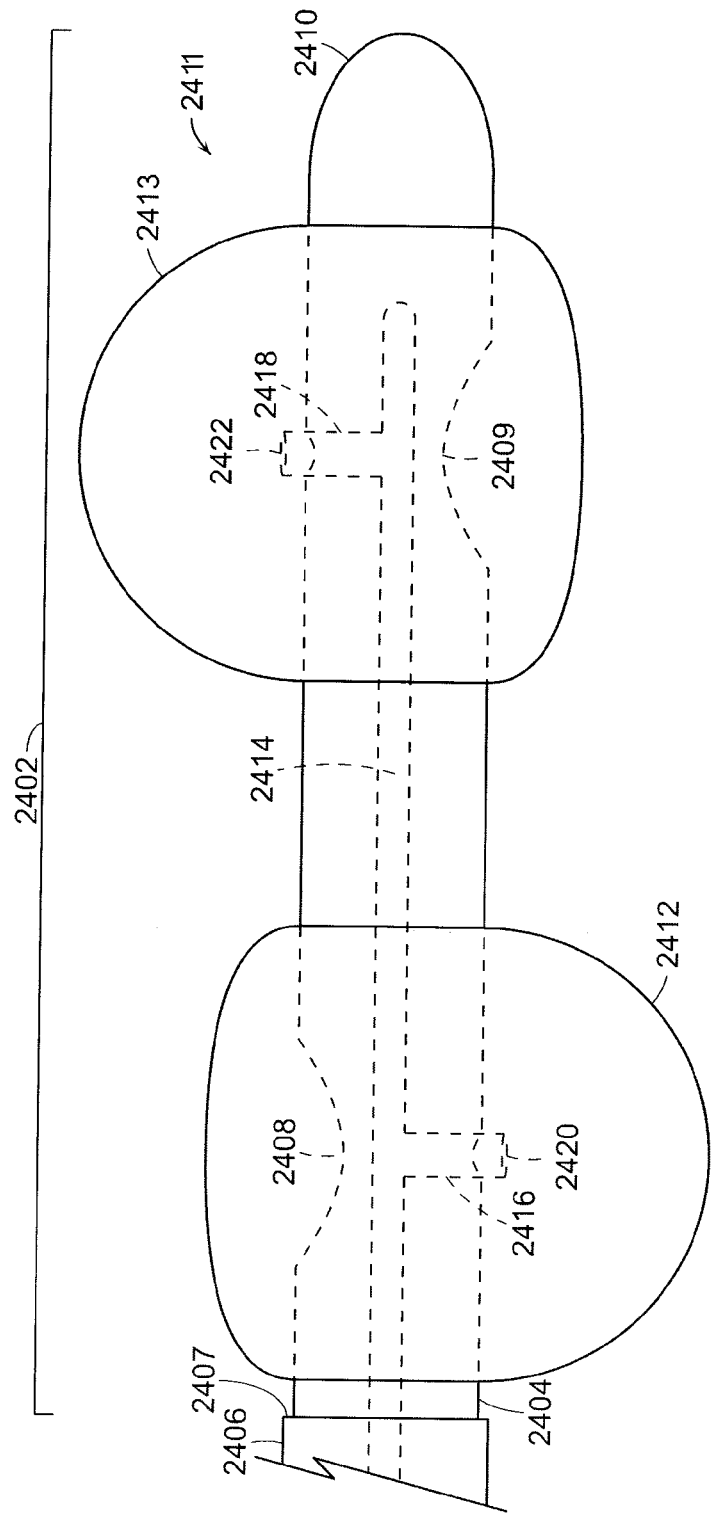
FIG. 24A is a profile view illustrating a cooling assembly having multiple partially-circumferential balloons configured in accordance with another embodiment of the present technology.
Figure 24B:
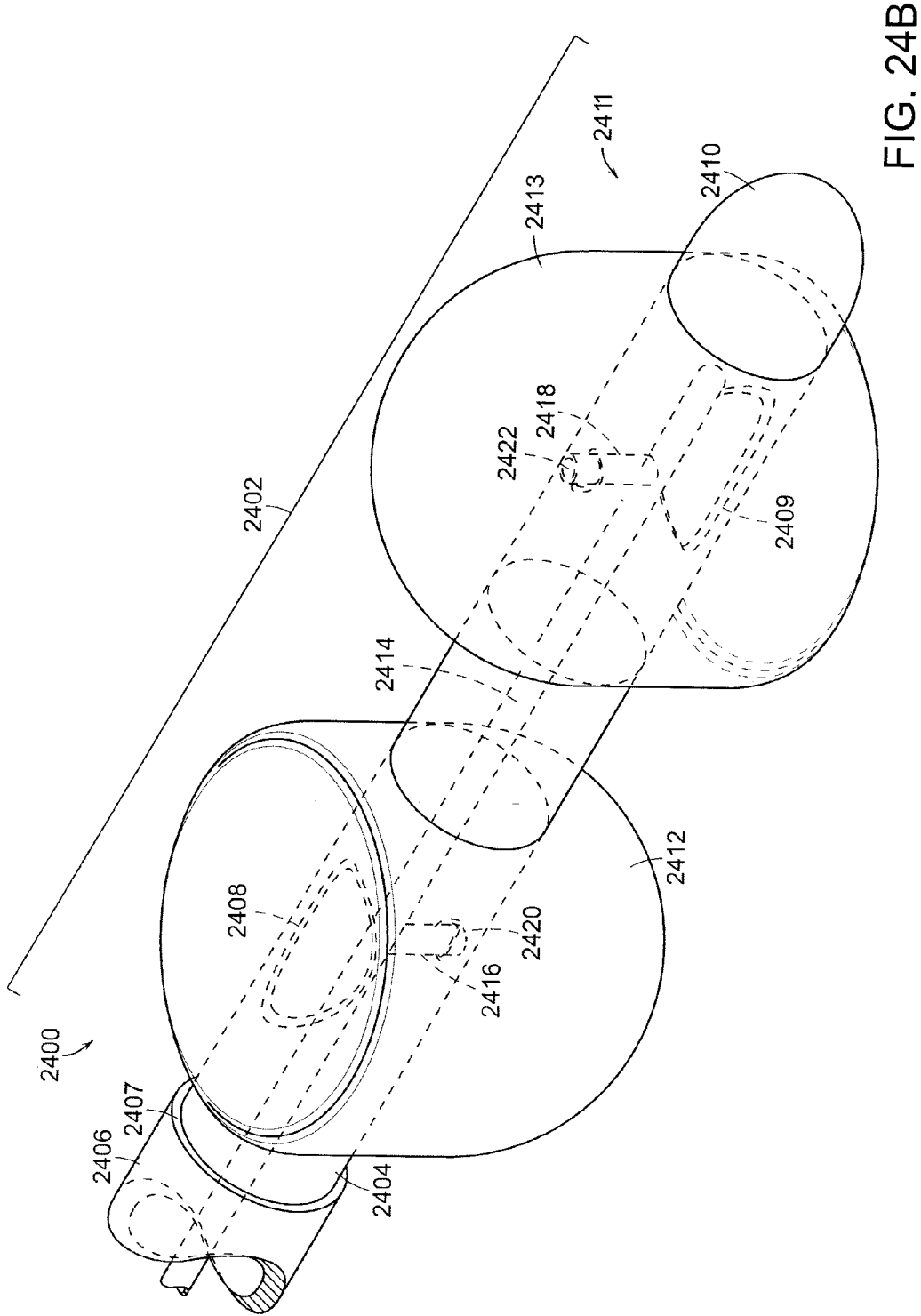
FIG. 24B is an isometric view illustrating the cooling assembly of FIG. 24A.

FIGS. 24A-24B illustrate a portion of a cryotherapeutic device 2400 that differs from the device 2300 of FIGS. 23A-23B primarily with respect to an exhaust configuration. The device 2400 includes a cooling assembly 2402 at a distal portion 2404 of an elongated shaft 2406 defining an exhaust passage. The distal portion 2404 can have a step 2407, a first exhaust port 2408, a second exhaust port 2409, and a rounded end 2410. The cooling assembly 2402 can include an applicator 2411 having a first balloon 2412 that defines a first expansion chamber and a second balloon 2413 that defines a second expansion chamber. The first balloon 2412 and the second balloon 2413 are fluidly connected to the exhaust passage through the first exhaust port 2408 and the second exhaust port 2409, respectively. The device 2400 can further include a supply tube 2414 extending along a length of the shaft 2406 and having a first lateral branch 2416 and a second lateral branch 2418. The cooling assembly 2402 can further include a first orifice 2420 at the end of the first lateral branch 2416 open to the first balloon 2412 and a second orifice 2422 at the end of the second lateral branch 2418 open to the second balloon 2413. Unlike the device 2300 shown in FIGS. 23A-23B, the device 2400 includes refrigerant supply and refrigerant exhaust at circumferentially opposite sides of the distal portion 2404 for the first and second balloons 2412, 2413. The first and second balloons 2412, 2413 extend around fully-circumferential longitudinal segments of the distal portion 2404, but are attached to the distal portion 2404 and shaped so as to expand asymmetrically about the distal portion 2404.

Cooling assemblies configured in accordance with several embodiments of the present technology can include a different number of partially-circumferential balloons from the cooling assemblies 2302, 2402 shown in FIGS. 23A-24B. For example, in several embodiments, the cooling assembly 2302 can include the first balloon 2312 or the second balloon 2313 rather than both. Similarly, the cooling assembly 2402 can include the first balloon 2412 or the second balloon 2413 rather than both. The cooling assemblies 2302, 2402 shown in FIGS. 23A-24B also can include a greater number of balloons, such as three or four balloons longitudinally and radially spaced apart. Furthermore, the sizes of the balloons can vary. For example, in several embodiments, the first and second balloons 2312, 2313 of the cooling assembly 2302 or the first and second balloons 2412, 2413 of the cooling assembly 2402 are configured to provide a partially-circumferential overall cooling pattern.

Figure 25:
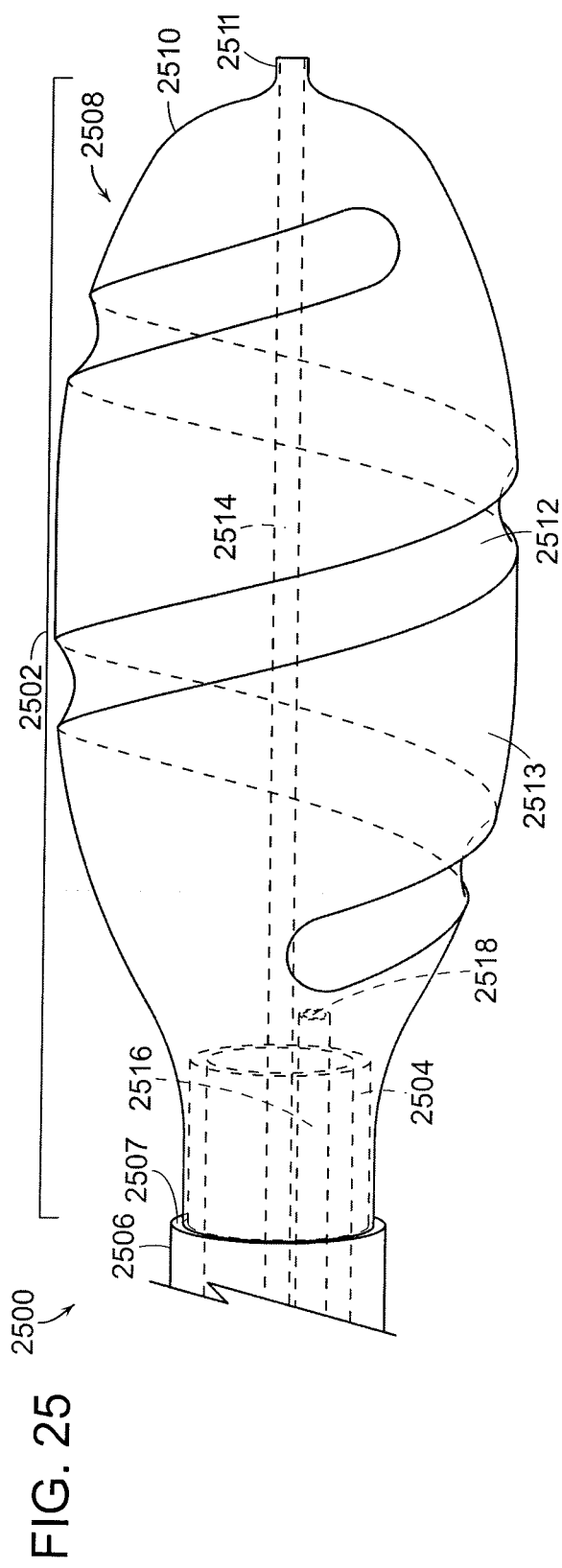
FIG. 25 is a profile view illustrating a cooling assembly having a helical recess configured in accordance with an embodiment of the present technology.

Cooling assemblies configured in accordance with several embodiments of the present technology can include applicators with balloons having a variety of suitable surface characteristics, such as surface characteristics configured to facilitate partially-circumferential cooling at longitudinal segments alone or in combination with a fully-circumferential overall cooling pattern. FIG. 25 illustrates a portion of a cryotherapeutic device 2500 including a cooling assembly 2502 at a distal portion 2504 of an elongated shaft 2506 defining an exhaust passage. The distal portion 2504 can have a step 2507, and the cooling assembly 2502 can include an applicator 2508 with a balloon 2510 that defines an expansion chamber and has a distal neck 2511, a helical recess 2512, and a non-recessed portion 2513. The device 2500 can further include an elongated guide member 2514 that extends through the distal neck 2511, as well as a supply tube 2516 that extends along the length of the shaft 2506 and into the balloon 2510. The cooling assembly 2502 can further include an orifice 2518 at the distal end of the supply tube 2516. When the cooling assembly 2502 is in a delivery state, the helical recess 2512 can correspond to a heat-transfer portion of the applicator 2508 having a lower heat-transfer rate than portions of the applicator 2508 spaced apart from the helical recess 2512.

The space between the helical recess 2512 and an inner surface of a renal artery or a renal ostium at a treatment site can thermally insulate portions of the renal artery or the renal ostium closest to the helical recess 2512 from a cryogenic temperature within the balloon 2510. For example, frozen or liquid blood within this space can provide thermal insulation. The depth of the helical recess 2512 relative to the non-recessed portion 2513 can be, for example, a depth corresponding to a thickness of material (e.g., liquid or frozen blood) sufficient to thermally insulate a portion of a renal artery or a renal ostium from cryogenic cooling within the balloon 2510. For example, the depth can be between about 0.2 mm and about 2 mm, such as between about 0.3 mm and about 1.5 mm. Recessed portions of balloons in several other embodiments of cryotherapeutic-device components described herein can have similar depths relative to non-recessed portions of the balloons.

FIG. 26 illustrates a portion of another embodiment of a cryotherapeutic device 2600 including a cooling assembly 2602 at a distal portion 2604 of an elongated shaft 2606 defining an exhaust passage. The distal portion 2604 can have a step 2607, and the cooling assembly 2602 can include an applicator 2608 with a balloon 2610 that defines an expansion chamber and has a distal neck 2611, a plurality of recesses 2612, and a non-recessed portion 2613. The recesses 2612 can be arranged in a helical pattern around the circumference of the balloon 2610. The cooling assembly 2602 can further include an elongated guide member 2614 that extends through the distal neck 2611. The device 2600 can also include a supply tube 2616 that extends along the length of the shaft 2606 and into the balloon 2610. The cooling assembly 2602 can further include an orifice 2618 at the distal end of the supply tube 2616. When the cooling assembly 2602 is in a deployed state, the recesses 2612 and the non-recessed portion 2613 can function similarly to the helical recess 2512 and the non-recessed portion 2513 of the device 2500 shown in FIG. 25.

Figure 27C:
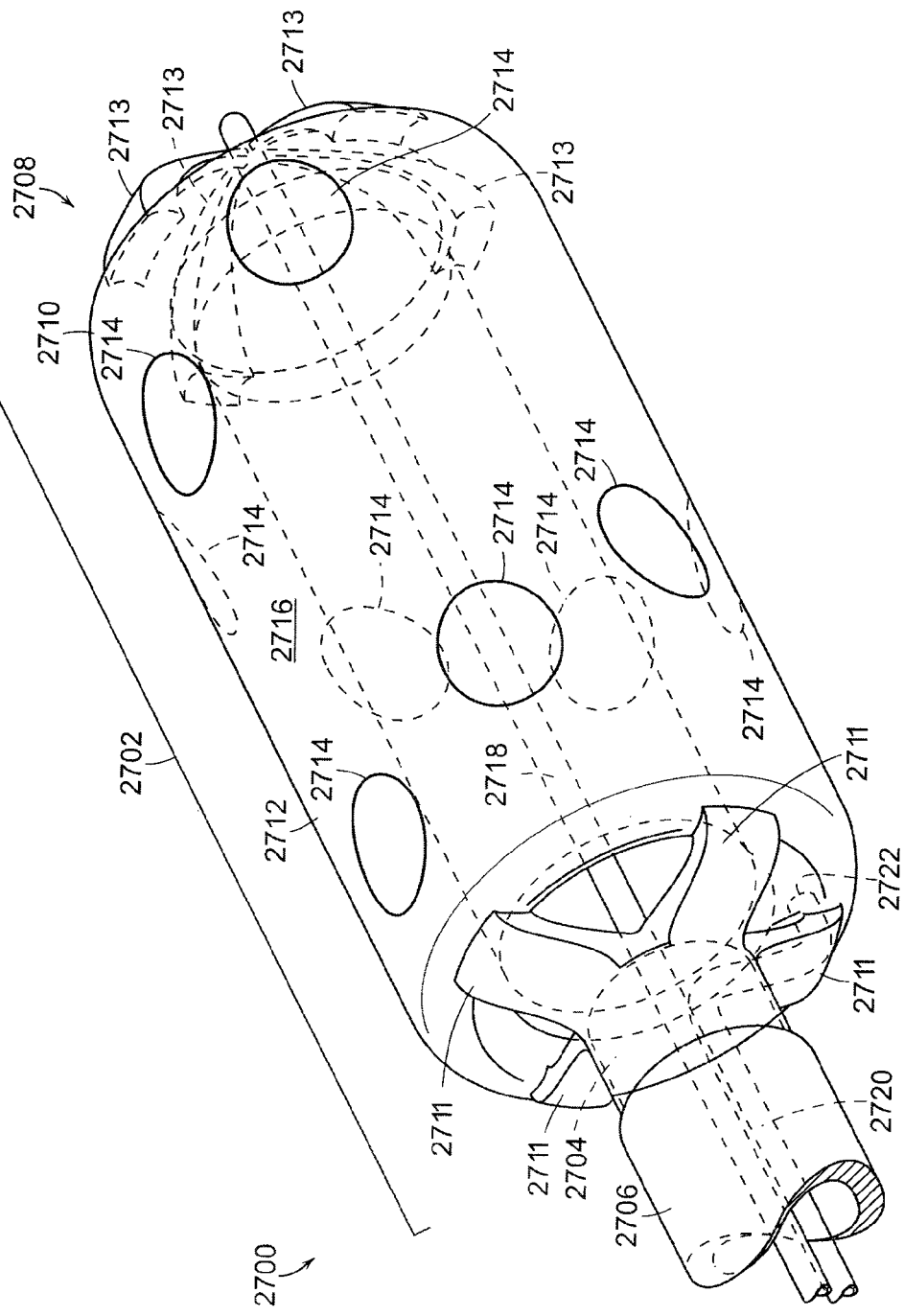
FIG. 27C is an isometric view illustrating the cooling assembly of FIG. 27A.

FIGS. 27A-27C illustrate a portion of a cryotherapeutic device 2700 similar to the device 2600 of FIG. 26, but the device 2700 is configured to be less occlusive within a renal artery or a renal ostium than the device 2600 of FIG. 26. The device 2700 includes a cooling assembly 2702 at a distal portion 2704 of an elongated shaft 2706 defining an exhaust passage. The distal portion 2704 can have a step 2707, and the cooling assembly 2702 can include an applicator 2708 with a balloon 2710 that defines an expansion chamber and has proximal branches 2711, a tubular main portion 2712, distal branches 2713, a plurality of recesses 2714, and a non-recessed portion 2716. The plurality of recesses 2714 can be arranged in a helical pattern around the circumference of the balloon 2710. When the cooling assembly 2702 is in a deployed state, the recesses 2714 and the non-recessed portion 2716 can function similarly to the recesses 2612 and the non-recessed portion 2613 of the device 2600 shown in FIG. 26. The proximal branches 2711 can be configured to fluidly connect the tubular main portion 2712 to the exhaust passage. The device 2700 can further include an elongated guide member 2718 that can extend along the length of the shaft 2706 and attach to the distal branches 2713, as well as a supply tube 2720 that extends along the length of the shaft 2706, through one of the proximal branches 2711, and into the tubular main portion 2712. The proximal branches 2711 and the distal branches 2713 can be configured to space apart the tubular main portion 2712 from the guide member 2718. The cooling assembly 2702 can further include an orifice 2722 at the distal end of the supply tube 2720.

When the cooling assembly 2702 is in a deployed state, the cooling assembly 2702 can define a flow path (e.g., a blood flow path) between an outside surface of the guide member 2718 and the balloon 2710. The flow path can extend, for example, around the proximal branches 2711, through the tubular main portion 2712 (e.g., between the guide member 2718 and an inner surface of the tubular main portion 2712), and around the distal branches 2713. As shown in FIG. 27B, the tubular main portion 2712 can include a thermally-insulative inner portion 2724 around the flow path. The thermally-insulative inner portion 2724 can be configured to at least partially insulate fluid in the flow path from cryogenic cooling within the tubular main portion 2712. In the illustrated embodiment, the thermally-insulative inner portion 2724 can be a portion of the balloon 2710 having a greater thickness than other portions of the balloon 2710. In several other embodiments, the thermally-insulative inner portion 2724 has a different composition from other portions of the balloon 2710 and/or includes one or more separate thermally-insulative structures. Alternatively, the balloon 2710 can include a tubular main portion 2712 with an inner portion that is not more thermally insulative than other portions of the balloon 2710.

Figure 28:
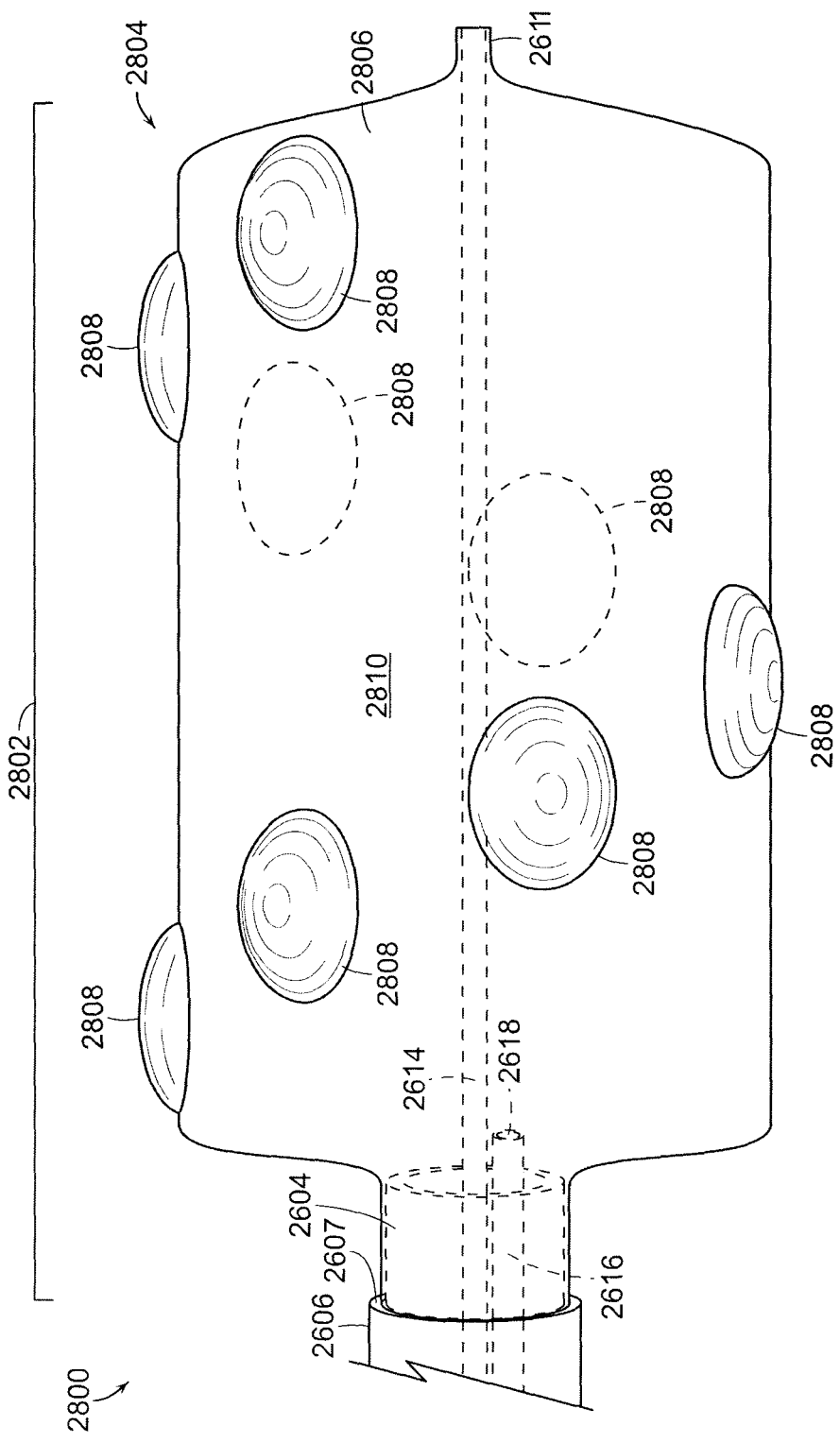
FIG. 28 is a profile view illustrating a cooling assembly having spaced apart protrusions configured in accordance with an embodiment of the present technology.

FIG. 28 illustrates a portion of a cryotherapeutic device 2800 similar to the device 2600 of FIG. 26 except with regard to a configuration of recessed and non-recessed portions. The device 2800 includes a cooling assembly 2802 having an applicator 2804 with a balloon 2806 that can define an expansion chamber. The balloon 2806 includes a plurality of protrusions 2808 and a non-protruding portion 2810. The protrusions 2808 can be arranged in a helical pattern or other suitable pattern around the circumference of the balloon 2806. When the cooling assembly 2802 is in a delivery state, the non-protruding portion 2810 can correspond to a heat-transfer portion of the applicator 2804 having a lower heat-transfer rate than portions of the applicator at the protrusions 2808. The space between the non-protruding portion 2810 and an inner surface of a renal artery or a renal ostium at a treatment site can thermally insulate portions of the renal artery or the renal ostium closest to the non-protruding portion from cryogenic temperatures within the balloon 2806. For example, frozen or liquid blood within this space can provide thermally insulation.

Figure 29:
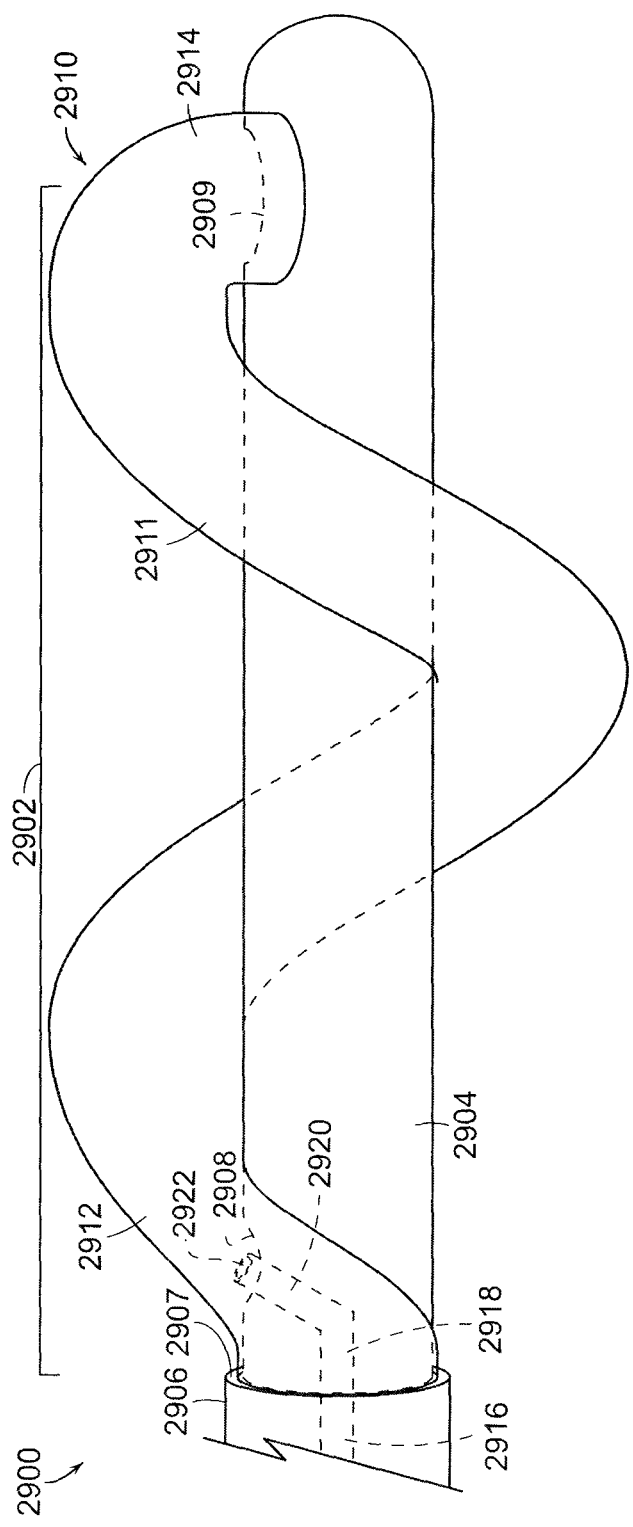
FIG. 29 is a profile view illustrating a cooling assembly having a helical balloon wrapped around an exhaust passage configured in accordance with an embodiment of the present technology.

Balloons having different shapes can facilitate certain treatment objectives related to cryogenic renal-nerve modulation. For example, helical shapes can facilitate a desirable localized or overall treatment pattern. FIG. 29 illustrates a portion of a cryotherapeutic device 2900 including a cooling assembly 2902 at a distal portion 2904 of an elongated shaft 2906 defining an exhaust passage. The distal portion 2904 can have a step 2907, an exit hole 2908, and an exhaust port 2909. The cooling assembly 2902 can include an applicator 2910 with a helical balloon 2911 that defines an expansion chamber and has a balloon proximal portion 2912 and a balloon distal portion 2914. The balloon proximal portion 2912 has minor fluid connection with the exhaust passage through the exit hole 2908. The balloon distal portion 2914 is attached to the outside surface of the distal portion 2904 around the exhaust opening 2909, thereby fluidly connecting the helical balloon 2911 to the exhaust passage. The helical balloon 2911 is wrapped around the distal portion 2904 (e.g., the distal portion 2904 can define a central axis of the helical balloon 2911). The device 2900 can further include a supply tube 2916 defining a supply lumen and having a main portion 2918 extending along the length of the shaft 2906 and an angled distal portion 2920 exiting the shaft 2906 through the exit hole 2908. The cooling assembly 2902 also can include an orifice 2922 at the distal end of the angled distal portion 2920. The supply tube 2916 and the orifice 2922 can be configured to direct expansion of refrigerant into the balloon proximal portion 2912 in a direction generally corresponding to a longitudinal orientation of the balloon proximal portion 2912. When the cooling assembly 2902 is in a deployed state, refrigerant can flow from the balloon proximal portion 2912 to the balloon distal portion 2914 and then proximally along the exhaust passage. Upon reaching the balloon distal portion 2914, the refrigerant can have exhausted some, most, or all of its capacity for cryogenic cooling.

FIG. 30 illustrates a portion of a cryotherapeutic device 3000 that differs from the device 2900 of FIG. 29 primarily with respect to a refrigerant flow direction. The device 3000 includes a cooling assembly 3002 at a distal portion 3004 of an elongated shaft 3006 defining an exhaust passage. The distal portion 3004 can have a step 3007, and the cooling assembly 3002 can include an applicator 3008 having a helical balloon 3014 that defines an expansion chamber and has a balloon proximal portion 3016 and a balloon distal portion 3018. The balloon proximal portion 3016 can be attached to an outside surface of the distal portion 3004 proximate a distal end of the distal portion 3004, thereby fluidly connecting the helical balloon 3014 to the exhaust passage. The device 3000 can further include a supply tube 3019 having a curved distal portion 3020. The helical balloon 3014 can be wrapped around the supply tube 3019 (e.g., the supply tube 3019 can define a central axis of the helical balloon 3014). The supply tube 3019 can extend along the length of the shaft 3006, out of the shaft, out of the balloon proximal portion 3016, along a central axis of the helical balloon 3014, and into the balloon distal portion 3018. The balloon distal portion 3016 can be sealed around the supply tube 3019 and at least partially attached to the curved distal portion 3020. The cooling assembly 3002 can further include an orifice 3021 fluidly connecting the supply tube 3019 to the balloon distal portion 3018. The supply tube 3019 and the orifice 3021 can be configured to direct expansion of refrigerant into the balloon distal portion 3018 in a direction generally corresponding to a longitudinal orientation of the balloon distal portion 3018. When the cooling assembly 3002 is in a deployed state, refrigerant can flow from the balloon distal portion 3018 to the balloon proximal portion 3016 and then proximally along the exhaust passage.

FIG. 31 illustrates a portion of a cryotherapeutic device 3100 similar to the device 3000 of FIG. 30 except with regard to a helical balloon shape. The device 3100 includes a cooling assembly 3102 at a distal portion 3104 of an elongated shaft 3106 defining an exhaust passage. The distal portion 3104 can have a step 3108, and the cooling assembly 3102 can include an applicator 3110 having a helical balloon 3112 that defines an expansion chamber and has a balloon proximal portion 3114 and a balloon distal portion 3116. The balloon proximal portion 3114 can be attached to an outside surface of the distal portion 3104 proximate a distal end of the distal portion 3104, thereby fluidly connecting the helical balloon 3112 to the exhaust passage. The device 3100 can further include a supply tube 3117 having an angled distal portion 3118 The helical balloon 3112 can be wrapped around the supply tube 3117 but also radially spaced apart from the supply tube 3117. The supply tube 3117 can extend along the length of the shaft 3106, out of the shaft 3106, out of the balloon proximal portion 3114, along a central axis of the helical balloon 3112, and into the balloon distal portion 3116. The balloon distal portion 3116 can be sealed around the supply tube 3117. The cooling assembly can further include an orifice 3119 fluidly connecting the supply tube 3117 to the balloon distal portion 3116. When the cooling assembly 3102 is in a deployed state, refrigerant can flow from the balloon distal portion 3116 to the balloon proximal portion 3114 and then proximally along the exhaust passage. The wide helical diameter of the helical balloon 3112 can facilitate partial occlusion. For example, when the cooling assembly 3102 is in the deployed state, the cooling assembly 3102 can define a flow path (e.g., a blood flow path) between an outside surface of the supply tube 3117 and the helical balloon 3112.

Figure 32A:
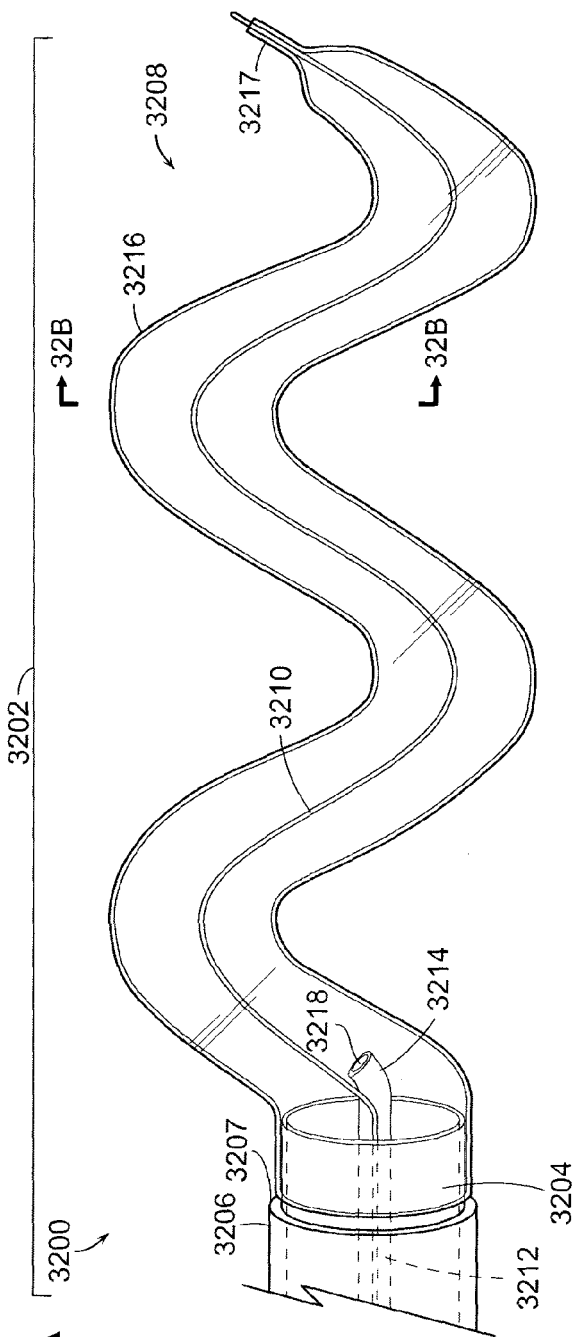
FIG. 32A is a profile view illustrating a cooling assembly having a shaping member with a shape memory configured in accordance with an embodiment of the present technology.
Figure 32B:
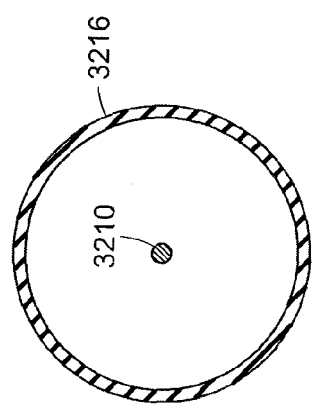
FIG. 32B is a cross-sectional view illustrating the cooling assembly of FIG. 32A.

FIGS. 32A-32B illustrate a portion of a cryotherapeutic device 3200 that can have a complex shape corresponding to a shaping member, such as a shaping member having a shape memory. As discussed above, balloons in cryotherapeutic devices configured in accordance with several embodiments of the present technology can move from being at least partially collapsed when a corresponding cooling assembly is in a delivery state, to being at least partially expanded when the cooling assembly is in a deployed state. When expanded in the deployed state, complex balloons can have pre-defined shapes (e.g., integral shapes molded or otherwise incorporated into the balloon) or shapes corresponding to separate shaping structures. The cryotherapeutic device 3200 shown in FIGS. 32A-32B includes a cooling assembly 3202 at a distal portion 3204 of an elongated shaft 3206 defining an exhaust passage. The distal portion 3204 can have a step 3207, and the cooling assembly 3202 can include an applicator 3208. The device 3200 can further include an elongated shaping member 3210 and a supply tube 3212 having an angled distal portion 3214. The applicator 3208 can include a balloon 3216 with a distal seal 3217. The balloon 3216 can extend around the elongated shaping member 3210 and can define an expansion chamber. The distal seal 3217 can be a flattened portion of the balloon 3216 at which walls of the balloon 3216 are sealed together (e.g., thermally and/or with adhesive). Balloons configured in accordance with several other embodiments of the present technology can have another type of closed distal end. As discussed above, balloons can be closed around structures, such as guide members and/or supply tubes. Balloons also can be closed around plugs. Furthermore, balloons can have integral closed distal ends. For example, balloons can be molded (e.g., dip molded) with integral closed distal ends.

The shaping member 3210 can be configured to have a generally linear configuration when the cooling assembly 3202 is in a delivery state and a curvilinear configuration when the cooling assembly 3202 is in a deployed state. The cooling assembly 3202 can also include an orifice 3218 at the distal end of the angled distal portion 3214. The supply tube 3212 and the orifice 3218 can be configured to direct expansion of refrigerant into the balloon 3216 in a direction generally corresponding to a longitudinal orientation of the balloon 3216 proximate the orifice 3218. As shown in FIG. 32A, the balloon 3216 has a shape in the deployed state at least partially corresponding to the curvilinear configuration of the shaping member 3210. The illustrated curvilinear configuration is generally helical, but also could be another shape, such as a serpentine shape. The shaping member 3210 can have a shape memory (e.g., a one-way shape memory or a two-way shape memory) and can include a shape-memory material, such as a nickel-titanium alloy (e.g., nitinol). Shape memory can allow the shaping member 3210 and the balloon 3216 to move into a pre-selected configuration (e.g., a curved, curvilinear, helical, or serpentine configuration) in the deployed state. The configuration can be selected, for example, to allow the applicator 3208 to apply a desirable localized or overall treatment pattern. Similarly, the helical shape shown in FIG. 32A and other shapes can be selected to provide a level of occlusion at a treatment site, such as partial occlusion instead of full occlusion. Shape-memory materials can lose some or all of their shaping properties when exposed to cryogenic temperatures. Cooling assemblies 3202 configured in accordance with several embodiments of the present technology can include balloons 3216 that move into a pre-selected configuration corresponding to a shape of a shaping member 3210 before cryogenic cooling or during initial cryogenic cooling. When the cryogenic cooling causes the shaping member 3210 to lose some or all of its shaping properties, cryo-adhesion between the balloon 3216 and external material (e.g., blood and/or tissue) can cause the balloon 3216 to maintain its pre-selected configuration at least until the cryoadhesion ends.

In the embodiment illustrated in FIGS. 32A-32B, the shaping member 3210 is shown generally centered within the balloon, i.e., the balloon 3216 is generally uniformly expanded around the shaping member 3210. Alternatively, the shaping member 3210 can have a different position within the balloon 3216 when the cooling assembly 3202 is in the deployed state. For example, the shaping member 3210 can be near an inner surface of the balloon 3216. When the shaping member 3210 is spaced apart from walls of the balloon 3216, the balloon 3216 can dissipate pressure against a renal artery or renal ostium. As shown in FIG. 32A, the shaping member 3210 can extend through the distal seal 3217. Alternatively, the shaping member 3210 can be not attached to the balloon 3216 and/or terminate at a portion of the balloon 3216 proximal to the distal seal 3217. Furthermore, a distal portion of the shaping member 3210 can be configured to be spaced apart from a renal artery or renal ostium when the cooling assembly 3202 is in the deployed state. In some embodiments, the balloon 3216 is configured to generally uniformly expand around the shaping member 3210 without any internal support structures. Alternatively, the balloon 3216 can include an internal structure (e.g., webbing) extending across an inner diameter of the balloon 3216 and the shaping member 3210 can be attached to the internal structure at a position spaced apart from inner surfaces of the balloon 3216. The internal structure, for example, can be a partition between separate balloons (e.g., as discussed below with reference to FIGS. 45A-46). In some embodiments, the cooling assembly includes a structure extending along a central axis of the balloon 3216 in the deployed state. For example, the distal portion 3204 can extend along the central axis of the balloon 3216 in the deployed state and the balloon 3216 and the shaping member 3210 can connect to a lateral opening of the distal portion 3204. As another example, the distal portion 3204 can include a reduced-diameter extension extending along the central axis of the balloon 3216 and another opening separate from the reduced-diameter extension fluidly connecting the balloon 3216 to the exhaust passage. A structure extending along the central axis of the balloon 3216 can include a lumen (e.g., a lumen configured to receive a guide wire or a control wire), a protection device (e.g., a filter), and/or a monitoring device (e.g., a thermocouple or a pressure transducer).

The device 3200 can be modified for use in non-cryotherapeutic applications. For example, the supply tube 3212 can be removed and the device 3200 can be used in other applications that benefit from less than full occlusion at a treatment site. In both renal-neuromodulation applications and other applications, the balloon 3216 can be non-occlusive in the deployed state, e.g., a blood flow path can be formed along a central axis of the balloon 3216. In some non-cryotherapeutic applications, the distal portion 3204 can support a structure configured to execute a treatment (e.g., a thrombectomy) within a vessel while the balloon 3216 anchors the device 3200 to a vessel wall. In these and other embodiments, the balloon 3216 advantageously can maintain the distal portion 3204 at a central position within a vessel.

FIGS. 33A-33D illustrate a portion of a cryotherapeutic device 3300 that can have a pre-defined curved shape in a deployed configuration. The device 3300 includes a cooling assembly 3302 at a distal portion 3304 of an elongated shaft 3306 defining an exhaust passage. The distal portion 3304 can have a step 3307, and the cooling assembly 3302 can include an applicator 3308 with a balloon 3310 that can define an expansion chamber. The balloon 3310 can have a balloon proximal portion 3312, a balloon middle portion 3314, and a balloon distal portion 3316. The device 3300 further includes a supply tube 3318 extending along the shaft 3306, and the cooling assembly 3302 can have an orifice 3320 at the distal end of the supply tube 3318 and within the balloon proximal portion 3312. When the cooling assembly 3302 is in a deployed state, the balloon 3310 is curved along its length and has a generally concave first wall 3322 (shown as a lower portion of the balloon in FIG. 33A) and a generally non-concave (e.g., convex) second wall 3324 (shown as an upper portion of the balloon in FIG. 33A).

The balloon proximal portion 3312, the balloon middle portion 3314, and the balloon distal portion 3316 can be configured to contact partially circumferential portions of a renal artery or a renal ostium. For example, the balloon middle portion 3314 can be configured to contact a renal artery or a renal ostium generally along the second wall 3324 and generally not along the first wall 3322 when the cooling assembly 3302 is in a deployed state. The balloon proximal portion 3312 and the balloon distal portion 3316, for example, can be configured to contact a renal artery or a renal ostium generally along the first wall 3322 and generally not along the second wall 3324 when the cooling assembly 3302 is in the deployed state. Due to this uneven pattern of contact, the curved shape of the balloon 3310 can facilitate a desirable localized or overall treatment pattern.

As best seen in FIGS. 33B-33C, the balloon 3310 can include a reduced-elasticity portion 3326 along the first wall 3322 at the balloon middle portion 3314. In the illustrated embodiment, the reduced-elasticity portion 3326 can be a thicker portion of the balloon 3310. As shown in FIG. 33D, the balloon 3310 can be partially collapsed when the cooling assembly 3302 is in the delivery state so as to fit within a delivery sheath 3328. When the cooling assembly 3302 is in the delivery state, the reduced-elasticity portion 3326 can retain some curvature. Alternatively, the reduced-elasticity portion 3326 can be generally flat. When the cooling assembly 3302 is in a deployed state, portions of the balloon 3310 other than the reduced elasticity portion 3326, particularly portions of the balloon 3310 along the second wall 3324 at the balloon middle portion 3314 can be configured to expand (e.g., compliantly expand) to a greater degree than the reduced-elasticity portion 3326. In several embodiments, the reduced-elasticity portion 3326 is generally non-compliant and a portion of the balloon 3310 along the second wall 3324 at the balloon middle portion 3314 is generally compliant. Restriction associated with the reduced-elasticity portion 3326 can facilitate curvature of the balloon 3310 when the cooling assembly 3302 is in the deployed state. The reduced-elasticity portion 3326 can be configured to be recessed relative to a renal artery or a renal ostium when the cooling assembly 3302 is in the deployed state and, correspondingly, not encompass a heat-transfer portion having a heat-transfer rate sufficient to cause therapeutically-effective renal nerve modulation. In addition to reducing elasticity, the thickness of the reduced-elasticity portion 3326 can reduce its thermal conductivity, which can promote improve cooling efficiency and/or further facilitate a desirable localized or overall treatment pattern.

FIG. 34 illustrates a portion of a cryotherapeutic device 3400 similar to the device 3300 of FIGS. 33A-33D except having a different support configuration. The device 3400 includes a cooling assembly 3402 having an applicator 3404 with a balloon 3406 defining an expansion chamber. The cooling assembly 3402 also includes an elongated support member 3408 having a curved distal end 3410. The elongated support member 3408 and other support members described herein can help balloons move with a corresponding cooling assembly as the cooling assembly moves between a delivery state and a deployed state. For example, the elongated support member 3408 can help to prevent the balloon 3406 from becoming stuck or twisted during treatment. Optionally, elongated support members can be attached to distal portions of corresponding balloons. This can be useful, for example, to maintain a balloon in an elongated configuration.

FIGS. 35A-35B illustrate a portion of a cryotherapeutic device 3500 in which interaction with a guide member at least partially causes a complex balloon shape. In several other embodiments, a complex balloon is at least partially shaped through interaction with another cryotherapeutic-device component (e.g., a shaft or a supply tube). The device 3500 shown in FIGS. 35A-35B includes a cooling assembly 3502 at a distal portion 3504 of an elongated shaft 3506 defining an exhaust passage. The device 3500 can include an elongated guide member 3508 and a supply tube 3512, and the cooling assembly 3502 can include an orifice 3514 at the distal end of the supply tube 3512. The cooling assembly can further include an applicator 3510 with a balloon 3516 that can define an expansion chamber and can have a balloon proximal portion 3518, a proximal integral neck 3520 attached to the distal portion 3504, and a distal integral neck 3522 attached to the guide member 3508. The balloon 3516 can also have a constrained longitudinal portion 3524 (FIG. 35B) and an expandable longitudinal portion 3526 (FIG. 35B). The constrained longitudinal portion 3524 can be at least partially attached to the guide member 3508. For example, from the distal integral neck 3522 to the balloon proximal portion 3518, an internal surface of the balloon 3516 can be attached to the guide member 3508. The expandable longitudinal portion 3526 can be spaced apart from the guide member 3508 when the cooling assembly 3502 is in a deployed state. The partially-constrained shape of the balloon 3516 can be useful to facilitate a desirable localized or overall treatment pattern. Furthermore, the constrained longitudinal portion 3524 can define at least a portion of a longitudinal flow path (e.g., a blood flow path) around the balloon 3516. This can be useful, for example, to facilitate a level of occlusion at a treatment site, such as partial occlusion instead of full occlusion.

FIG. 36 illustrates a cryotherapeutic device 3600 similar to the cryotherapeutic device 3500 of FIGS. 35A-35B, except having a different pattern of attachment between a balloon and a guide member. FIG. 36 can be considered as a substitute for FIG. 35B to illustrate a separate embodiment in which all elements of the cryotherapeutic device 3500 shown in FIGS. 35A-35B are similar except for those shown differently in FIG. 36 relative to FIG. 35B. The cryotherapeutic device 3600 includes an elongated guide member 3602 and a balloon 3604 having radially spaced apart constrained longitudinal portions 3506 and radially spaced apart expanded longitudinal portions 3508. Although FIG. 36 shows two constrained longitudinal portions 3606 and two expanded longitudinal portions 3608, a greater number of constrained longitudinal portions 3606 and/or expanded longitudinal portions 3608 can be formed for example, by attaching the balloon 3604 to the guide member 3602 at a different number of radial segments of the guide member 3602. Furthermore, the distribution of constrained longitudinal portions 3606 and expanded longitudinal portions 3608 can be symmetrical or asymmetrical (e.g., along an axis parallel to the length of the guide member 3602).

Figure 37:
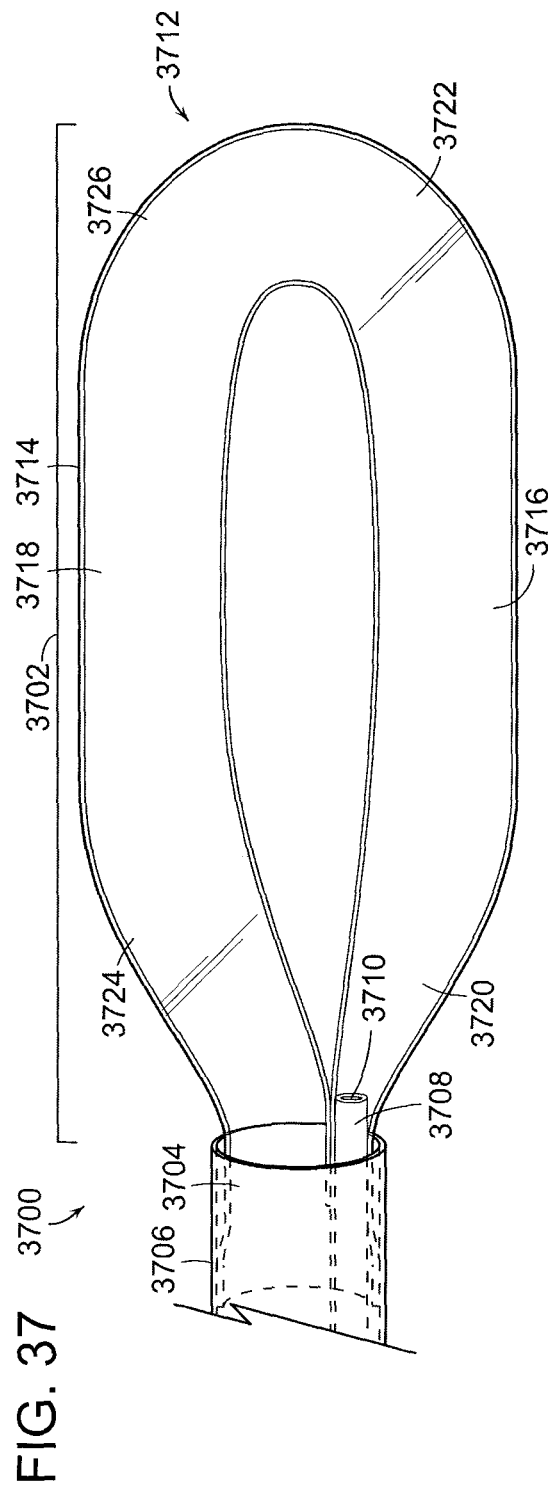
FIG. 37 is a profile view illustrating a cooling assembly having a looped balloon configured in accordance with an embodiment of the present technology.

FIG. 37 illustrates a portion of a cryotherapeutic device 3700 including a balloon having a loop shape. The device 3700 includes a cooling assembly 3702 at a distal portion 3704 of an elongated shaft 3706 defining an exhaust passage, as well as a supply tube 3708. The cooling assembly 3702 includes an orifice 3710 at the distal end of the supply tube 3708, and an applicator 3712 with a balloon 3714 having a first balloon segment 3716 and a second balloon segment 3718. The first balloon segment 3716 has a first proximal portion 3720 and a first distal portion 3722. The second balloon segment 3718 has a second proximal portion 3724 and a second distal portion 3726. The first balloon distal portion 3722 is fluidly connected to the second distal portion 3726. When the cooling assembly 3702 is in the deployed state, refrigerant can flow from the first proximal portion 3720, to the first distal portion 3722, and then to the second distal portion 3726. Upon reaching the second distal portion 3726, the refrigerant can have exhausted some, most, or all of its capacity for cryogenic cooling. Accordingly, the second balloon segment 3718 can serve primarily to exhaust refrigerant from the first distal portion 3722 and have a heat-transfer portion with a heat-transfer rate lower than a heat-transfer rate of a heat-transfer portion of the first balloon-segment 3716. In several alternative embodiments, the first balloon segment 3716 and the second balloon segment 3718 are separate balloons with a fluid connection at their distal ends. In another embodiment, the first and second balloon segments can be portions of a single balloon that is folded. Similar to non-cooling balloons discussed below, the second balloon segment 3718 can thermally insulate a portion of a renal artery or a renal ostium at a treatment site from cryogenic temperatures within the first balloon segment 3716. This can be useful, for example, to facilitate a desirable localized or overall treatment pattern.

Multiple Balloons

FIGS. 38-51 illustrate several embodiments of cryotherapeutic devices that include multiple balloons that can facilitate one or more treatment objectives related to cryogenic renal-nerve modulation, such as a desirable localized or overall treatment pattern, sizing, and full occlusion. In cryotherapeutic devices configured in accordance with several embodiments of the present technology, a primary balloon configured to generate or deliver therapeutically effective cooling for renal nerve modulation (e.g., including a primary heat-transfer portion) can be used in conjunction with a secondary balloon configured to prevent or inhibit therapeutically effective cooling temperatures at selected locations. In several embodiments, a secondary balloon includes a secondary heat-transfer portion. A secondary balloon, for example, can be warming, thermally-insulative, non-cooling, or have a low-level of cooling. Alternatively, several embodiments include multiple balloons that include primary heat-transfer portions with or without a secondary balloon.

Figure 38B:
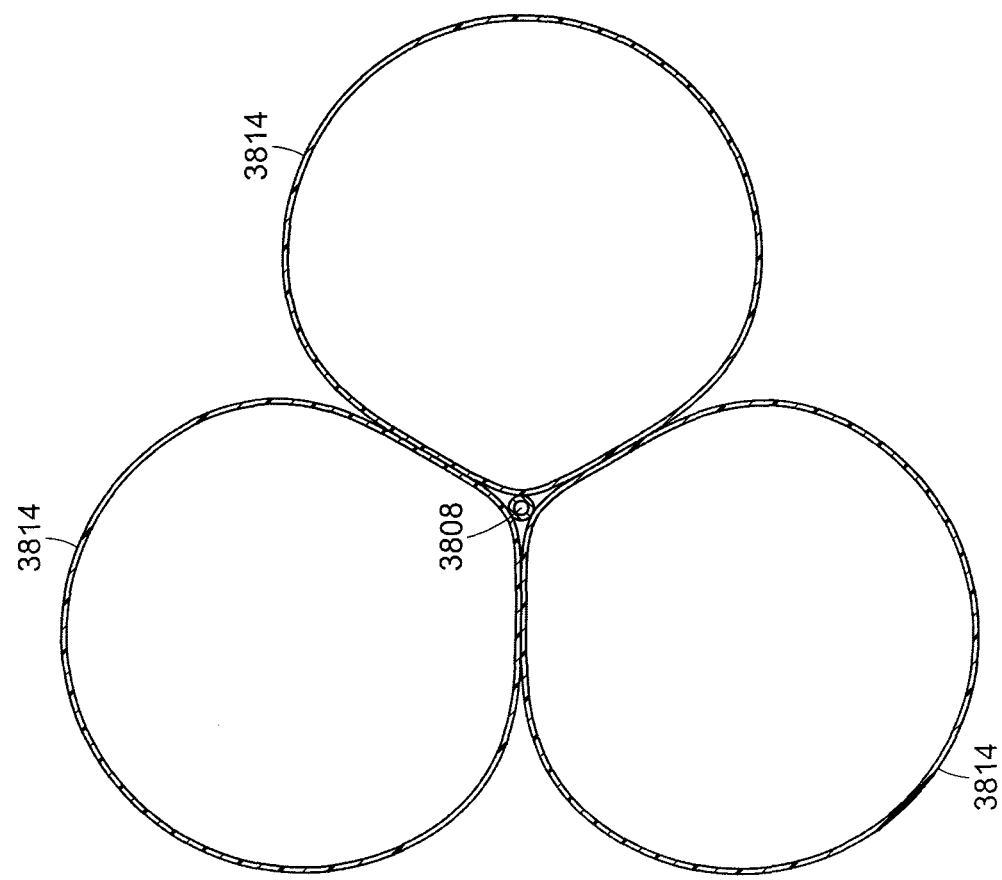
FIG. 38B is a cross-sectional view illustrating the cooling assembly of FIG. 38A.

FIGS. 38A-38B illustrate a portion of a cryotherapeutic device 3800 that can have multiple primary balloons. The device 3800 includes a cooling assembly 3802 at a distal portion 3804 of an elongated shaft 3806 defining an exhaust passage. The distal portion 3804 can have a step 3807, and the device 3800 can include an elongated guide member 3808 and a supply tube 3810. The cooling assembly 3802 can include an orifice 3811 at the distal end of the supply tube 3810 and an applicator 3812 having elongated balloons 3814 positioned generally parallel to a length of the cooling assembly 3802. The balloons 3814 have a shared proximal portion 3816 and are otherwise circumferentially distributed around the guide member 3808. The orifice 3811 is within the shared proximal portion 3816 and the balloons 3814, in conjunction with the shared proximal portion 3816, can define expansion chambers. When the cooling assembly 3802 is in a deployed state, refrigerant expanded from the supply tube 3810 can enter the shared proximal portion 3816 and circulate within the balloons 3814 to cause expansion thereof and cooling. Refrigerant can exit the balloons 3814 also through the shared proximal portion 3816 and flow proximally along the exhaust passage. The balloons 3814 can be configured to contact spaced-apart portions (e.g., spaced-apart longitudinal portions) of a renal artery or a renal ostium at a treatment site. This can be useful to facilitate a desirable localized or overall treatment pattern. Furthermore, space between the balloons 3814 can define at least a portion of a longitudinal flow path (e.g., a blood flow path) around the balloons 3814. This can be useful, for example, to facilitate a level of occlusion at a treatment site, such as partial occlusion instead of full occlusion.

Figure 39A:
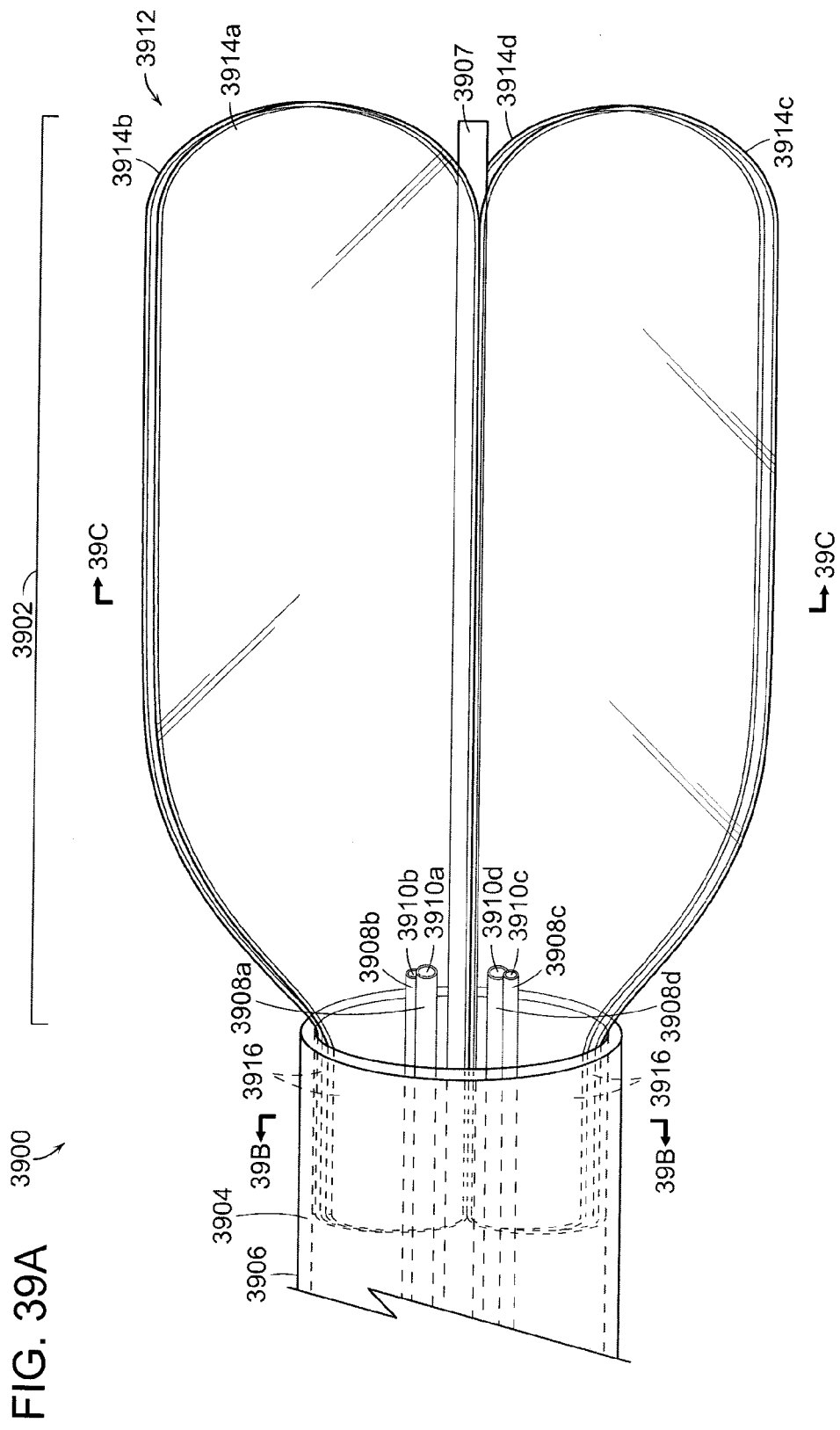
FIG. 39A is a profile view illustrating a cooling assembly having multiple elongated balloons configured in accordance with another embodiment of the present technology.
Figure 39C:
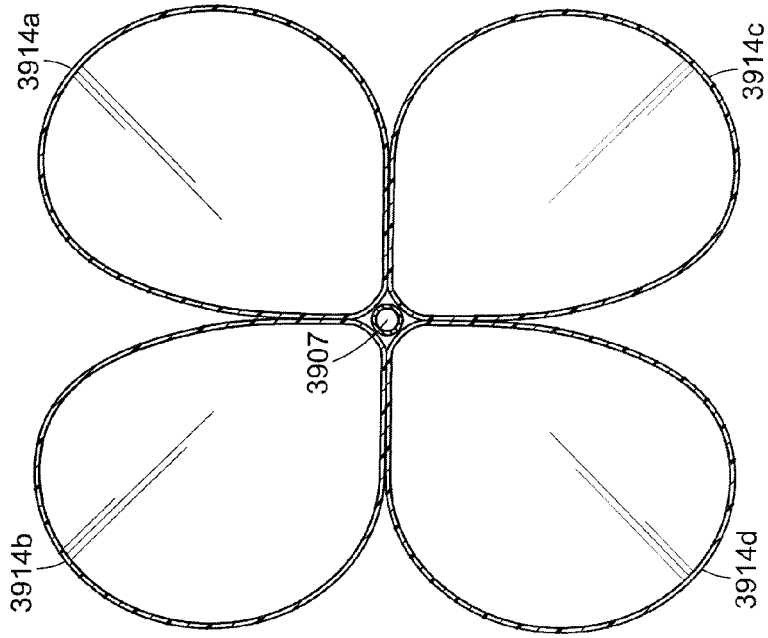
FIGS. 39B and 39C are cross-sectional views illustrating the cooling assembly of FIG. 39A.
Figure 39B:
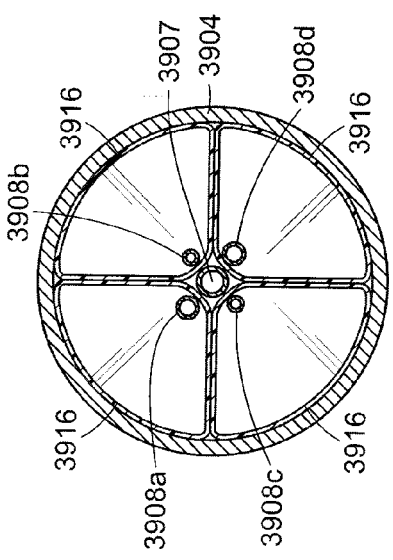

FIGS. 39A-39C illustrate a portion of a cryotherapeutic device 3900 that can have multiple balloons having different levels of cooling. The device 3900 includes a cooling assembly 3902 at a distal portion 3904 of an elongated shaft 3906, an elongated guide member 3907, and a plurality of supply tubes (individually identified as 3908a-d). The cooling assembly 3902 can include a plurality of orifices (individually identified as 3910a-d) at the distal ends of the supply tubes 3908a-d, and an applicator 3912 including a plurality of elongated balloons (individually identified as 3914a-d in FIGS. 39A and 39C). The balloons 3914a-d are circumferentially distributed around the guide member 3907 and individually include proximal necks 3916 (FIG. 39A) that can fluidly connect the balloons 3914a-d to the exhaust passage. The orifices 3910a, 3910d have larger free-passage areas than the orifices 3910b, 3910c. Similarly, the supply tubes 3908a, 3908d have smaller free-passage areas than the supply tubes 3908b, 3908d. The balloons 3914a-d are generally equal in size and have generally equal internal and external surface areas. A ratio of orifice and/or supply tube free-passage area to internal surface area can be greater for the balloons 3914a, 3914d than for the balloons 3914b, 3914c. This can cause differential cooling within the balloons 3914a, 3914d relative to the balloons 3914b, 3914c. For example, the balloons 3914a, 3914d can be configured to circulate gaseous refrigerant at a lower temperature than the balloons 3914b, 3914c. In addition or alternatively, the balloons 3914a, 3914d can be configured for generally surface-area limited cooling when the cooling assembly 3902 is in the deployed state, while the balloons 3914b, 3914c are configured for generally refrigerant-limited cooling when the cooling assembly 3902 is in the deployed state. Providing some cooling (e.g., low-level cooling, such as cooling insufficient for cryogenic renal nerve modulation) to tissue near an area targeted for therapeutically-effective renal nerve modulation can be useful, for example, to reduce heat-gain from surrounding tissue at the area targeted for therapeutically-effective renal nerve modulation. The use of multiple balloons also can facilitate a desirable localized or overall treatment pattern and/or a desired level of occlusion at a treatment site, such as partial occlusion instead of full occlusion.

Figure 40:
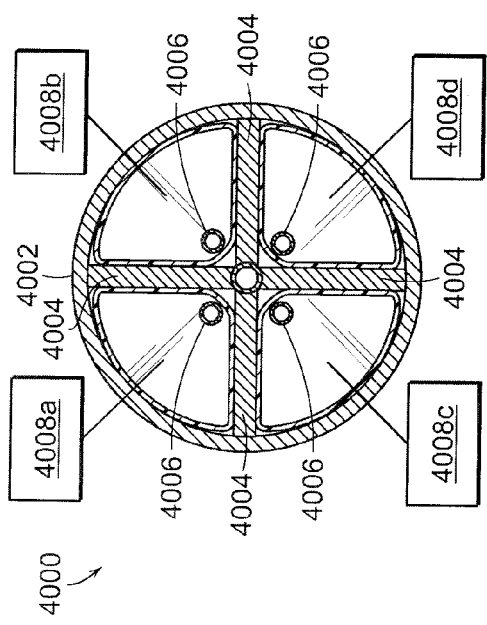
FIG. 40 is a cross-sectional view illustrating a cooling assembly having multiple elongated balloons configured in accordance with another embodiment of the present technology.

FIG. 40 illustrates a cryotherapeutic device 4000 similar to the cryotherapeutic device 3900 of FIGS. 39A-39C, except having a different mechanism for differential cooling. FIG. 40 can be considered as a substitute for FIG. 39B to illustrate a separate embodiment in which all elements of the cryotherapeutic device 3900 shown in FIGS. 39A-39C are similar except for those shown differently in FIG. 40 relative to FIG. 39B. The cryotherapeutic device 4000 includes a shaft 4002 having internal walls 4004 dividing the shaft 4002 into fluidly separate exhaust passages, and supply tubes 4006 individually within the exhaust passages. The supply tubes 4006 have generally equal sizes and can have orifices (not shown) having generally equal sizes. The cryotherapeutic device 4000 also includes a plurality of pressure regulators (individually identified as 4008a-d) in fluid communication with the exhaust passages. The pressure regulators 4008a-d can be configured to be positioned outside the vasculature. Regulating back pressures within the exhaust passages can cause temperatures within corresponding balloons (not shown) to vary. For example, the pressure regulators 4008a, 4008d can maintain a first back pressure in the corresponding exhaust passages and balloons, and the pressure regulators 4008b, 4008c can maintain a second, different back pressure in the corresponding exhaust passages and balloons. In this way, differential cooling similar to the differential cooling described above with reference to the device 3900 shown in FIGS. 39A-39C can be achieved.

FIG. 41 illustrates a portion of a cryotherapeutic device 4100 that can have multiple helical balloons. The device 4100 includes a cooling assembly 4101 at a distal portion 4102 of an elongated shaft 4103 defining an exhaust passage, a supply tube 4104, and a filler tube 4105. The cooling assembly 4101 can include a first supply orifice 4106, a second supply orifice 4107, and a filler orifice 4108 at the distal end of the filler tube 4105. The cooling assembly 4101 also includes an applicator 4109 having a plurality of helical balloons. In one embodiment, the applicator 4109 includes a first helical balloon 4110 having a first distal portion 4112 and a first proximal portion 4114, a second helical balloon 4116 (shown stippled for clarity of illustration) having a second distal portion 4118 and a second proximal portion 4120, and a third helical balloon 4122 having a third distal portion 4124 and a third proximal portion 4126. The first and second supply orifices 4106, 4107 can be fluidly connected to the first distal portion 4112 and the third distal portion 4124, respectively, and the first and third helical balloons 4110, 4122 can define expansion chambers. The second-balloon proximal portion 4120 can be sealed around the filler tube 4107 and fluidly connected to the filler orifice 4108 and the second helical balloon 4116 can define a filler chamber. When the cooling assembly 4101 is in the deployed state, the second helical balloon 4116 can be configured to be filled via the filler tube 4105. Refrigerant can expand into the first distal portion 4112 and the third distal portion 4124, and the first and third helical balloons 4110, 4122 can provide primary cooling in separate helical patterns or a combined helical pattern. The second helical balloon 4116 can thermally insulate portions of a renal artery or a renal ostium from cryogenic cooling of the first and third helical balloons 4110, 4122. This can be useful, for example, to facilitate a desirable localized or overall treatment pattern. Furthermore, the interior space between the supply tube 4004 and the first, second, and third helical balloons 4110, 4116, 4122 can define at least a portion of a longitudinal flow path (e.g., a blood flow path). This can be useful, for example, to facilitate a level of occlusion at a treatment site, such as partial occlusion instead of full occlusion.

FIG. 42 illustrates a portion of a cryotherapeutic device 4200 similar to the device 4100 shown in FIG. 41, but having modified supply and exhaust configurations in the helical balloons. The device 4200 includes a cooling assembly 4202 at a distal portion 4203 of an elongated shaft 4204 defining an exhaust passage, an elongated guide member 4205, and a supply tube 4206. The cooling assembly 4202 can include a supply orifice 4207 at the distal end of the supply tube 4206 and an applicator 4208 having a plurality of helical balloons. In one embodiment, the applicator 4208 includes a first helical balloon 4210 having a first distal portion 4212 and a first proximal portion 4214, a second helical balloon 4216 (shown stippled for clarity of illustration) having a second distal portion 4218 and a second proximal portion 4220, and a third helical balloon 4222 having a third distal portion 4224 and a third proximal portion 4226. The first distal portion 4212 and the third distal portion 4224 are fluidly connected to each other and to the second distal portion 4218. The first proximal portion 4214 and the third proximal portion 4226 are fluidly connected to the exhaust passage. When the cooling assembly 4202 is in the deployed state, refrigerant can expand into the second proximal portion 4220 and the second helical balloon 4216 can provide primary cooling in a helical pattern. The first and third helical balloons 4210, 4222 can receive refrigerant exhaust from the second distal portion 4218 and can thermally insulate portions of a renal artery or a renal ostium from cryogenic cooling within the second helical balloon 4216. Relative to the cryotherapeutic device 4200 shown in FIG. 41, the device 4100 can be useful when less cooling and/or greater spacing between areas of primary cooling is desirable. In several other embodiments, different numbers of helical balloons that are warming, thermally-insulative, non-cooling, or have a low-level of cooling are intertwined in various arrangements with helical balloons configured to provide primary cooling, such as to facilitate a desirable localized or overall treatment pattern.

Figures 43A, 43B:
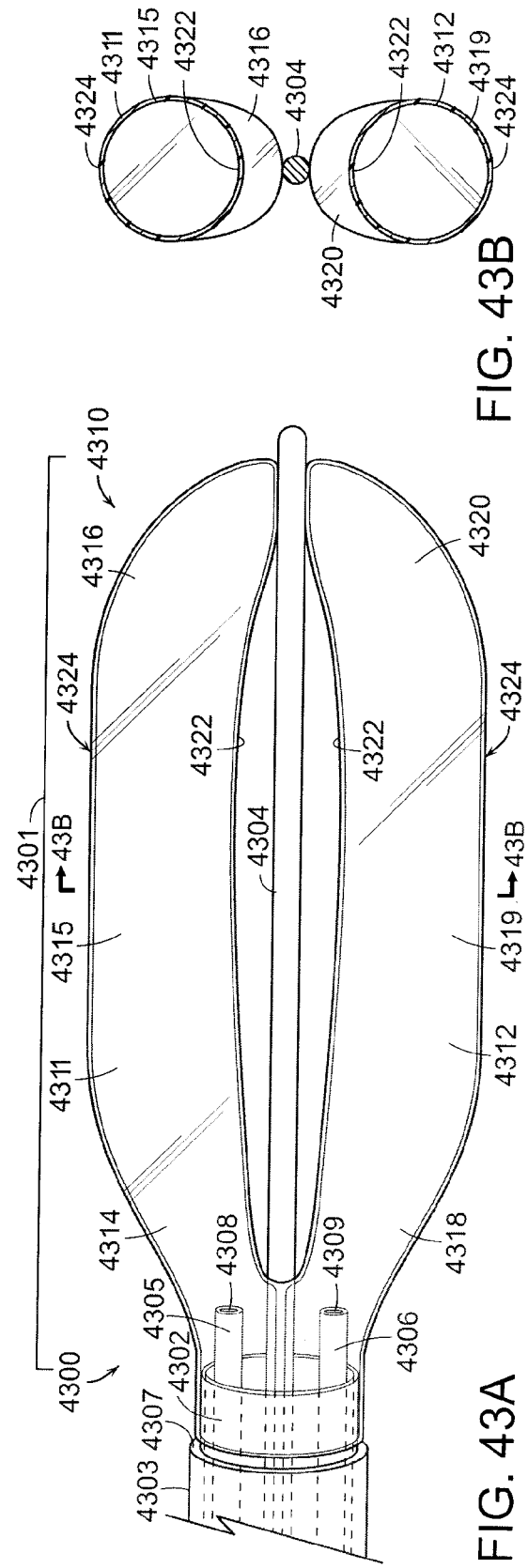
FIG. 43A is a profile view illustrating a cooling assembly having multiple elongated balloons attached to a shaping member configured in accordance with an embodiment of the present technology.
FIG. 43B is a cross-sectional view illustrating the cooling assembly of FIG. 43A.
Figure 43C:
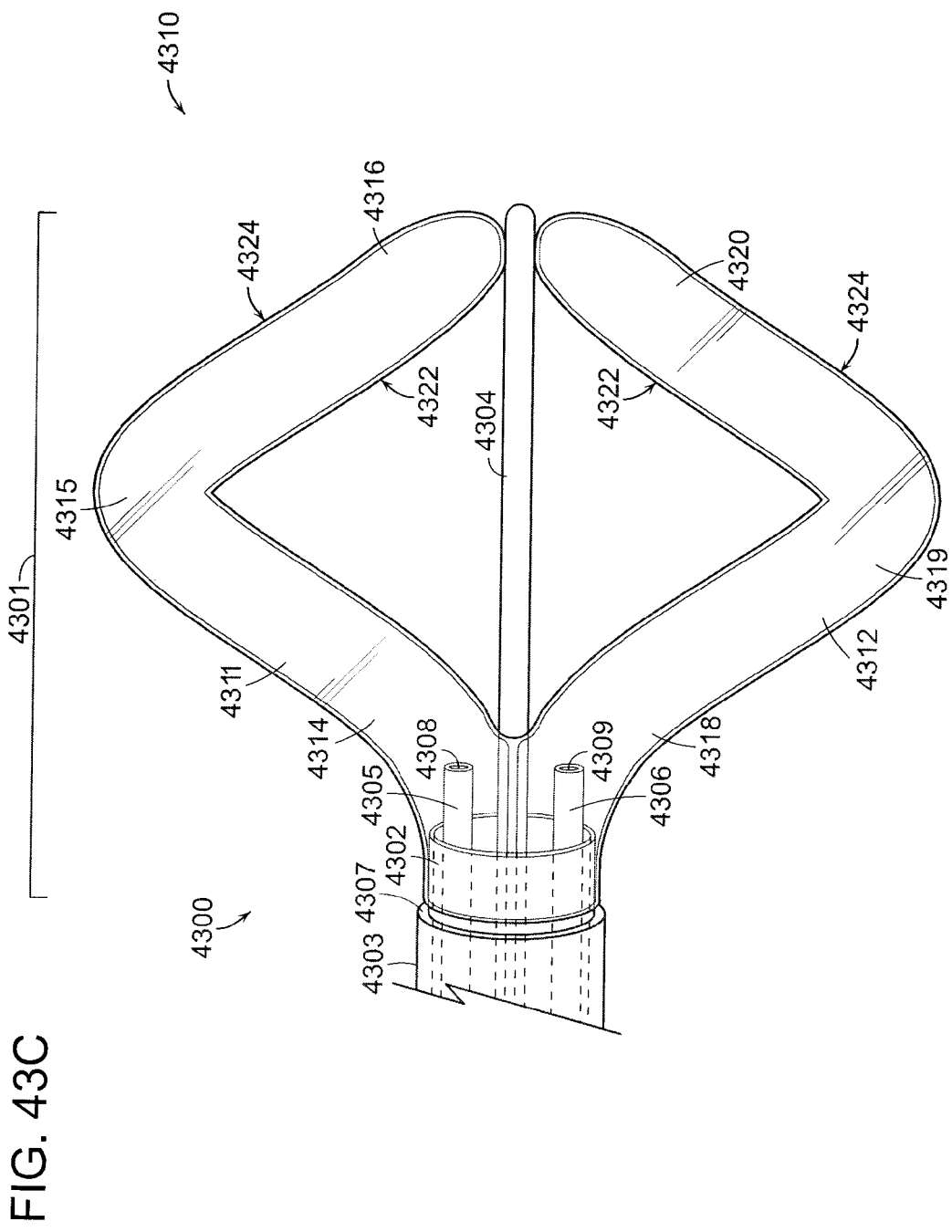
FIG. 43C is a profile view illustrating the cooling assembly of FIG. 43A with the shaping member retracted.

FIGS. 43A-43C illustrate a portion of a cryotherapeutic device 4300 that can include balloons that are movable relative to other portions of a cooling assembly. The device 4300 includes a cooling assembly 4301 at a distal portion 4302 of an elongated shaft 4303 defining an exhaust passage, as well as an elongated shaping member 4304, a first supply tube 4305, and a second supply tube 4306. The distal portion 4302 can have a step 4307, and the cooling assembly 4301 can include a first orifice 4308 at the distal end of the first supply tube 4305, and a second orifice 4309 at the distal end of the second supply tube 4306. The cooling assembly 4301 further includes an applicator 4310 with a first elongated balloon 4311 defining a first expansion chamber and a second elongated balloon 4312 defining a second expansion chamber. The first balloon 4311 has a first proximal portion 4314, a first middle portion 4315, and a first distal portion 4316. The second balloon 4312 has a second proximal portion 4318, a second middle portion 4319, and a second distal portion 4320. The first and second balloons 4311, 4312 have inner sides 4322 closest to the shaping member 4304 and outer sides 4324 opposite the inner sides 4322. The first distal portion 4316 and the second distal portion 4320 are attached to the shaping member 4304. In several embodiments, the shaping member 4304 also defines a guide lumen through which a guide wire can be threaded.

As shown in FIG. 43C, when the cooling assembly 4301 is in the deployed state, retracting the shaping member 4304 relative to the shaft 4303 can cause the first middle portion 4315 and the second middle portion 4319 to laterally move away from the shaping member 4304. A portion of the first middle portion 4315 and/or a portion of the second middle portion 4319 can be weakened (e.g., creased, heat-treated to cause weakening, and/or thinned) or otherwise configured to define a preferential bend position. As shown in FIG. 43C, after the shaping member 4304 has retracted the inner sides 4322 of the first middle portion 4315 and the second middle portion 4319 are generally concave along their lengths, while the outer sides 4324 of the first middle portion 4315 and the second middle portion 4319 are generally convex along their lengths. Controlled deflection of balloons can be particularly useful, for example, to facilitate sizing with low risk of applying excessive expansive pressure to a renal artery or a renal ostium. Controlled deflection can be particularly useful when one or more balloons of an applicator are generally non-compliant and/or achieving sizing through compliant expansion is not practical.

Figure 44C:
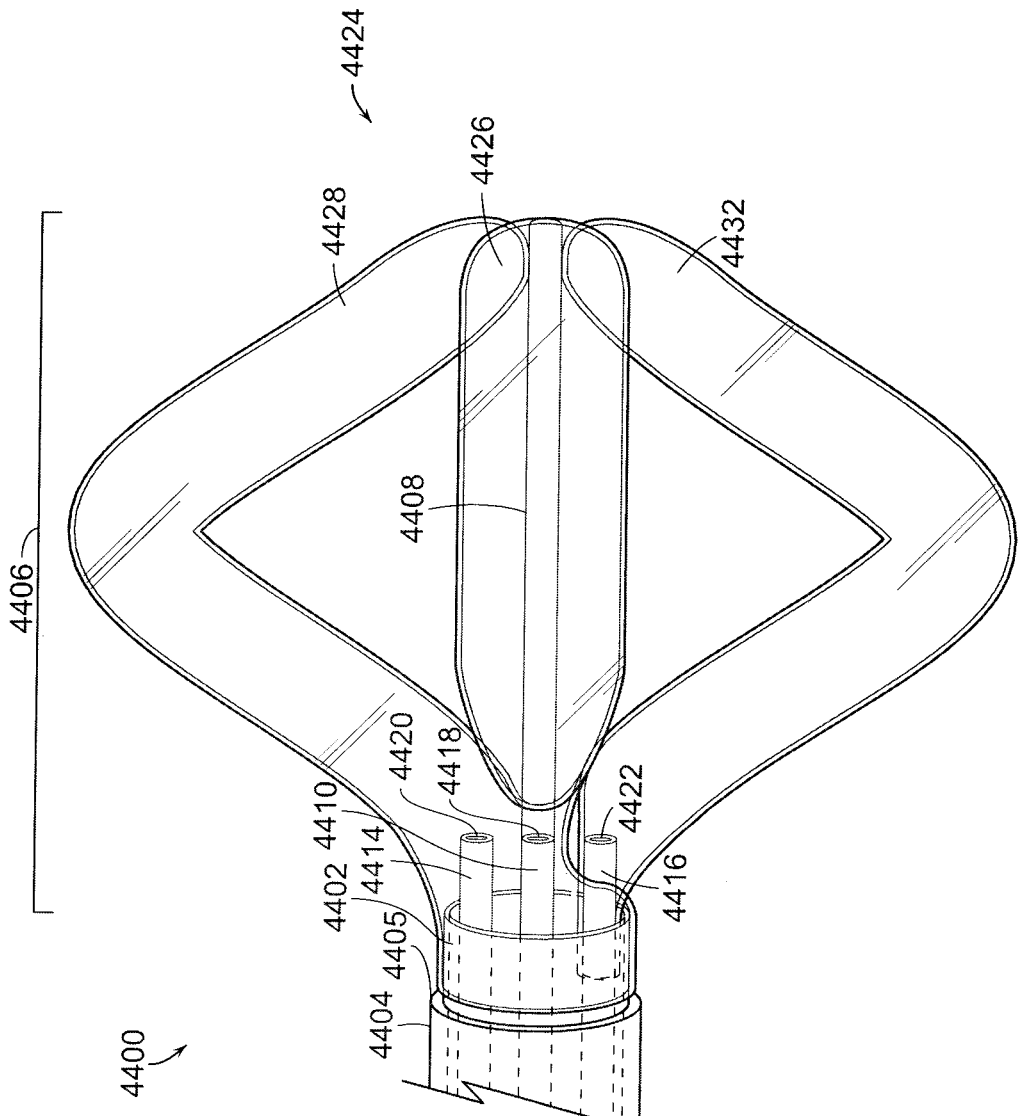
FIG. 44C is a profile view illustrating the cooling assembly of FIG. 44A with the shaping member retracted.
Figure 45A:
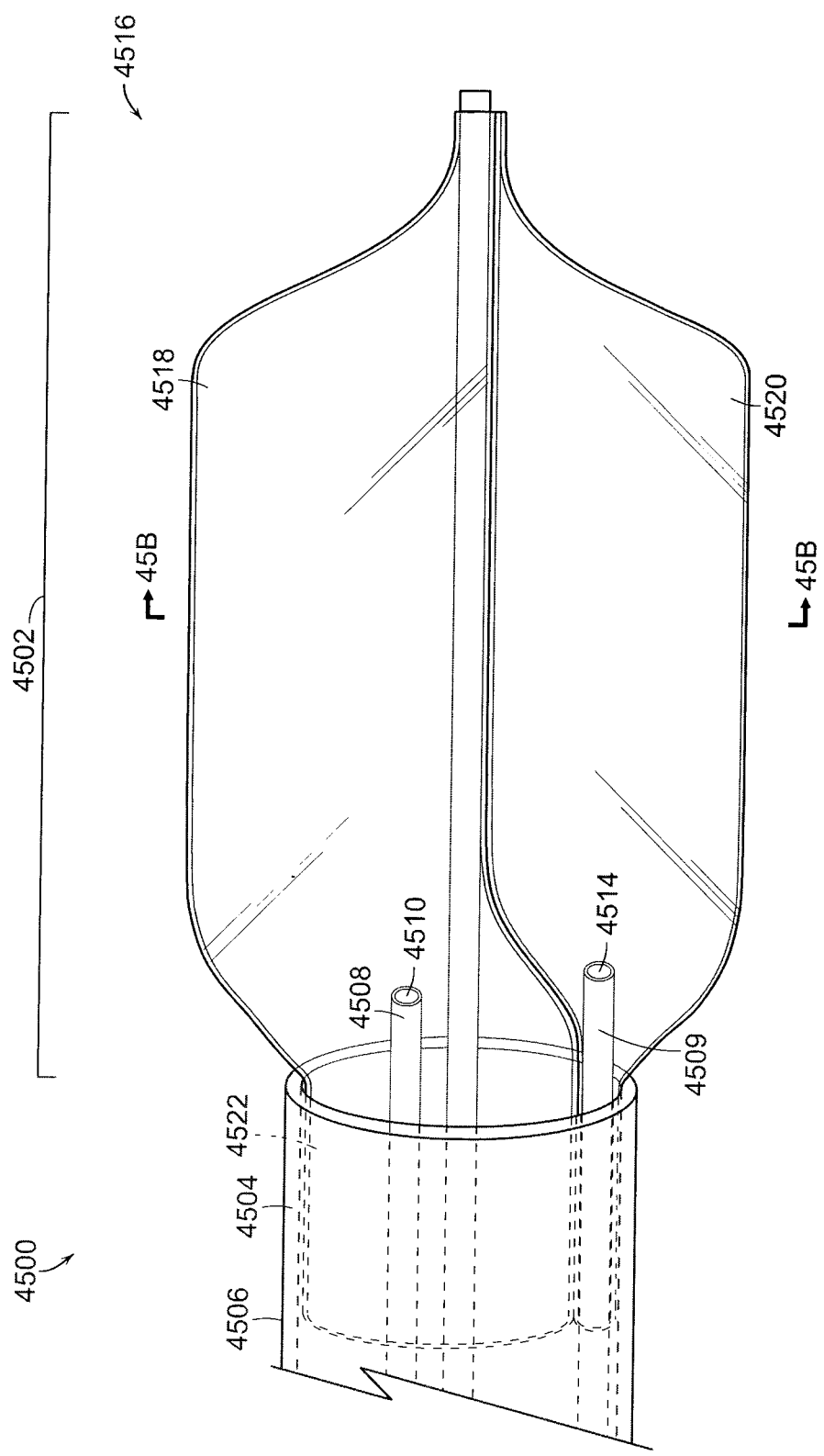
FIG. 45A is a profile view illustrating a cooling assembly having multiple elongated balloons of different composition configured in accordance with an embodiment of the present technology.

FIGS. 44A-44C illustrate a portion of a cryotherapeutic device 4400 similar to the cryotherapeutic device 4300 shown in FIGS. 43A-43B, but having a greater number of elongated balloons and including a secondary balloon. The device 4400 includes a distal portion 4402 of an elongated shaft 4404 having a step 4405 and defining an exhaust passage, a cooling assembly 4406 at the distal portion 4402, and an elongated shaping member 4408. The shaping member 4304 can be solid or can define a lumen, such as a guide lumen through which a guide wire can be threaded. The device 4400 further includes a first supply tube 4410, a second supply tube 4414, a third supply tube (not shown), and a filler tube 4416. The cooling assembly 4406 can include a first supply orifice 4418 at the distal end of the first supply tube 4410, a second supply orifice 4420 at the distal end of the second supply tube 4414, a third orifice (not shown) at the distal end of the third supply tube, and a filler orifice 4422 at the distal end of the filler tube 4416. The cooling assembly 4406 also includes an applicator 4424 with an elongated first balloon 4426 defining a first expansion chamber, an elongated second balloon 4428 defining a second expansion chamber, an elongated third balloon 4430 (FIG. 44B) defining a third expansion chamber, and an elongated fourth balloon 4432 defining a filler chamber. The first, second, and third balloons 4426, 4428, 4430 are fluidly connected to the first, second, and third supply orifices 4418, 4420. The fourth balloon is fluidly connected to the filler orifice 4422 and is sealed around the filler tube 4416. The first, second, third, and fourth balloons 4426, 4428, 4430, 4432 are attached to the shaping member 4408 such that, as shown in FIG. 44C, when the cooling assembly 4406 is in a deployed state, retracting the shaping member 4408 relative to the shaft 4404 causes the applicator 4424 to laterally expand. The first, second, and third balloons 4426, 4428, 4430 can have heat-transfer portions with heat-transfer rates sufficient to cause therapeutically-effective renal nerve modulation. The first, second, and third balloons 4426, 4428, 4430 can be configured to provide primary cooling. The fourth balloon 4432 can be a secondary balloon. In several other embodiments, a different number of primary balloons with or without secondary balloons can be included in a similar configuration to the configurations of the cryotherapeutic device 4300 shown in FIGS. 43A-43B and the cryotherapeutic device 4400 shown in FIGS. 44A-44C. In addition to sizing, these configurations can facilitate other treatment objectives, such as a desirable localized or overall treatment pattern FIGS. 45A-45B illustrate a portion of a cryotherapeutic device 4500 including a primary balloon and a secondary balloon that can have different compositions. The device 4500 includes a cooling assembly 4502 at a distal portion 4504 of an elongated shaft 4506 defining an exhaust passage, a supply tube 4508, and a filler tube 4509. The cooling assembly 4502 includes a supply orifice 4510 at the distal end of the supply tube 4508, and a filler orifice 4514 at the distal end of the filler tube 4509. The cooling assembly 4502 also includes an applicator 4516 with a first balloon 4518 that defines an expansion chamber and a second balloon 4520 that can define a filler chamber. The first balloon 4518 has a proximal neck 4522 within the distal portion 4504 fluidly connecting the first balloon 4518 to the exhaust passage. The second balloon is sealed around the filler tube 4509 and fluidly connected to the filler orifice 4514. When the cooling assembly 4502 is in a deployed state, the first balloon 4518 can be configured to deliver primary cooling and the second balloon 4520 can be a secondary balloon.

In several embodiments, the first balloon 4518 has a lower level of compliance and/or elasticity than the second balloon 4520. For example, the first balloon 4518 can be generally non-compliant and the second balloon can be generally compliant. Additionally, the first balloon 4518 can be non-compliant and the second balloon can be compliant. Non-compliant materials typically have higher strength (e.g., higher pressure ratings) than compliant materials. For this and/or other reasons, generally compliant materials can be well suited for balloons configured to receive expanded refrigerant directly from an orifice and/or to apply therapeutically effective cooling for renal nerve modulation. Generally compliant materials can be well suited for expanding to different sizes to accommodate renal arteries and renal ostiums having different cross-sectional dimensions. The device 4500 shown in FIGS. 45A-45B and several other cryotherapeutic-device components described herein can be configured to take advantage of the different properties of both non-compliant and compliant materials. FIGS. 45B and 45C are cross-sectional views of the device 4500 sized to fit within renal arteries or renal ostiums of different cross-sectional dimensions. The first balloon 4518 has generally the same size in both FIG. 45B and FIG. 45C. The second balloon 4520, however, is compliantly expanded to a greater degree in FIG. 45C than in FIG. 45B. Even with the generally non-compliant expansion of the first balloon 4518, the variable, compliant expansion of the second balloon 4520 can move the first balloon into contact with an inner surface of a renal artery or a renal ostium. Compliant expansion of the second balloon 4520 can be carefully controlled via the filler tube 4509 to prevent excessive expansive forces on the renal artery or the renal ostium.

The enlargement in FIG. 45B-1 shows a partition 4524 that includes a layer of non-compliant material 4526 and a layer of compliant material 4528. The layer of non-compliant material 4526 can be a portion of the first balloon 4518 and the layer of compliant material 4528 can be a portion of the second balloon 4520. In one embodiment, the first balloon 4518 and the second balloon 4520 can be attached together at the partition 4524, but in other embodiments the first and second balloon 4518 and 4520 are not attached to each other.

Figure 46:
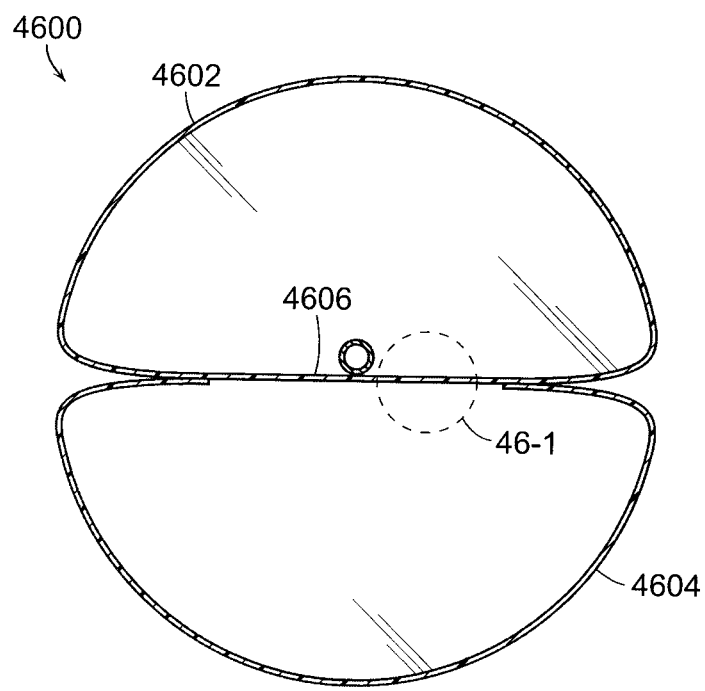
FIG. 46 is a cross-sectional view illustrating a cooling assembly having multiple elongated balloons of different composition configured in accordance with another embodiment of the present technology.
Figures 1, 46:
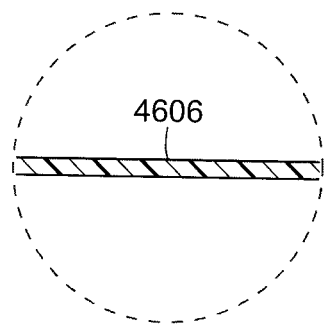

FIG. 46 illustrates a cryotherapeutic device 4600 similar to the cryotherapeutic device 4500 of FIGS. 45A-45C, except having a different partition. FIG. 46 can be considered as a substitute for FIG. 45B to illustrate a separate embodiment in which all elements of the cryotherapeutic device 4500 shown in FIGS. 45A-45C are similar except for those shown differently in FIG. 46 relative to FIG. 45B. The cryotherapeutic device 4600 includes a first balloon 4602, a second balloon 4604, and a partition 4606 between the first balloon 4602 and the second balloon 4604. As shown in the enlargement in FIG. 46-1, the partition 4606 includes a single layer, which can be a non-compliant layer of the first balloon. In another embodiment, the partition 4606 can include a single layer that is a compliant layer of the second balloon 4604. To construct the device 4600, a generally compliant balloon portion (e.g., an incomplete balloon) can be attached to a generally non-compliant balloon so as to form a generally compliant balloon having a chamber at least partially defined by a portion of the generally non-compliant balloon. In cross section, as shown in FIG. 46, the first balloon 4602 can be a generally D-shaped balloon and the second balloon 4604 can be a generally C-shaped balloon attached to a generally D-shaped balloon.

Figure 47:
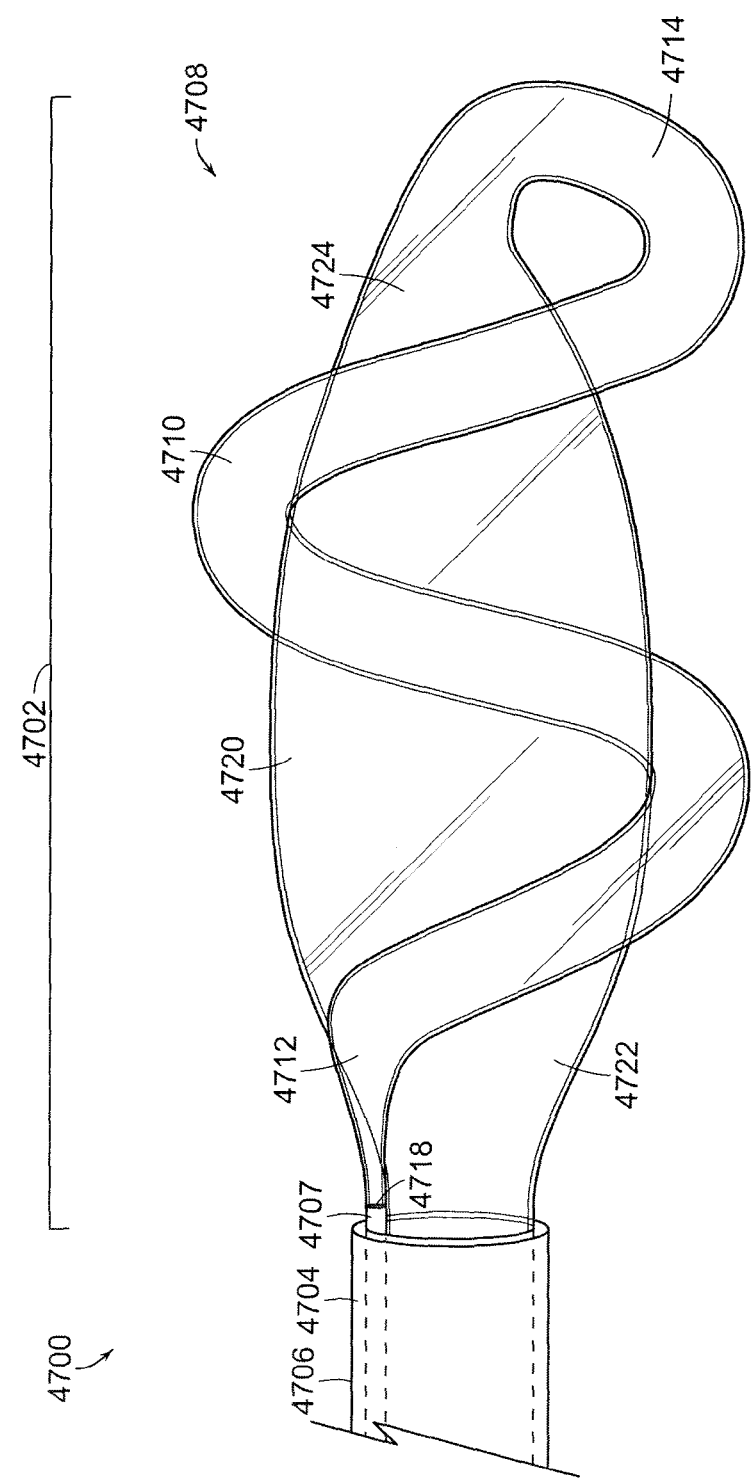
FIG. 47 is a profile view illustrating a cooling assembly having a helical primary balloon wrapped around a secondary balloon configured in accordance with an embodiment of the present technology.

Cryotherapeutic devices configured in accordance with several embodiments of the present technology can include helical primary balloons and non-helical secondary balloons. FIG. 47 illustrates a portion of a cryotherapeutic device 4700 including a cooling assembly 4702 at a distal portion 4704 of an elongated shaft 4706 defining an exhaust passage. The device 4700 also includes a supply tube 4707. The cooling assembly 4702 includes an applicator 4708 with a helical first balloon 4710 having a first proximal portion 4712 and a first distal portion 4714 and defining an expansion chamber. The supply tube 4707 can extend into the first proximal portion 4712, and the cooling assembly 4702 can have an orifice 4718 at the distal end of the supply tube 4707 within the first proximal portion 4712. The first proximal portion 4712 is sealed around the supply tube 4707. The cooling assembly 4702 can further include a second balloon 4720 having a second proximal portion 4722 and a second distal portion 4724 and defining an exhaust chamber. The second distal portion 4724 can be fluidly connected to the first distal portion 4714, and the first balloon 4710 can wrap around the second balloon 4720. The second proximal portion 4722 can be fluidly connected to the exhaust passage. When the cooling assembly 4702 is in a deployed state, refrigerant can flow from the first proximal portion 4712 to the first distal portion 4714 and then proximally through the second balloon 4720. Back pressure from the refrigerant can cause the second balloon 4720 to expand (e.g., compliantly expand), which can cause a helical diameter of the first balloon 4710 to increase. This can be useful, for example, to facilitate sizing. In addition, the helical shape of the first balloon 4710 can be useful, for example, to facilitate a desirable localized or overall treatment pattern.

FIGS. 48A-48B illustrate a portion of a cryotherapeutic device 4800 having a helical primary balloon and a non-helical secondary balloon in a different configuration. The device 4800 includes a cooling assembly 4802 at a distal portion 4804 of an elongated shaft 4806 defining an exhaust passage. The distal portion 4804 can have a step 4807, and the cooling assembly 4802 can include an applicator 4808 with a helical first balloon 4810 that defines an expansion chamber and has a first proximal portion 4812 and a first distal portion 4814. The device 4800 also can include a supply tube 4816 extending into the first proximal portion 4812, and the cooling assembly 4802 can have an orifice 4818 at the distal end of the supply tube 4816 within the first proximal portion 4812. The first proximal portion 4812 is sealed around the supply tube 4816. The cooling assembly 4802 can further include a second balloon 4820 having an integral proximal neck 4822 attached to the distal portion 4804. The second balloon 4820 can define an exhaust chamber configured to expand (e.g., compliantly expand) in response to back pressure from refrigerant exhausted from the first balloon 4810. The first balloon 4810 can be attached to an internal surface of the second balloon 4820. Expansion (e.g., compliant expansion) of the second balloon 4820 can cause a helical diameter of the first balloon 4810 to increase, such as to move a curved portion of the first balloon 4810 closer to an inner surface of a renal artery or a renal ostium. Positioning the first balloon 4810 within the second balloon 4820 can be useful, for example, to provide redundant containment of refrigerant within the vasculature.

Figure 49:
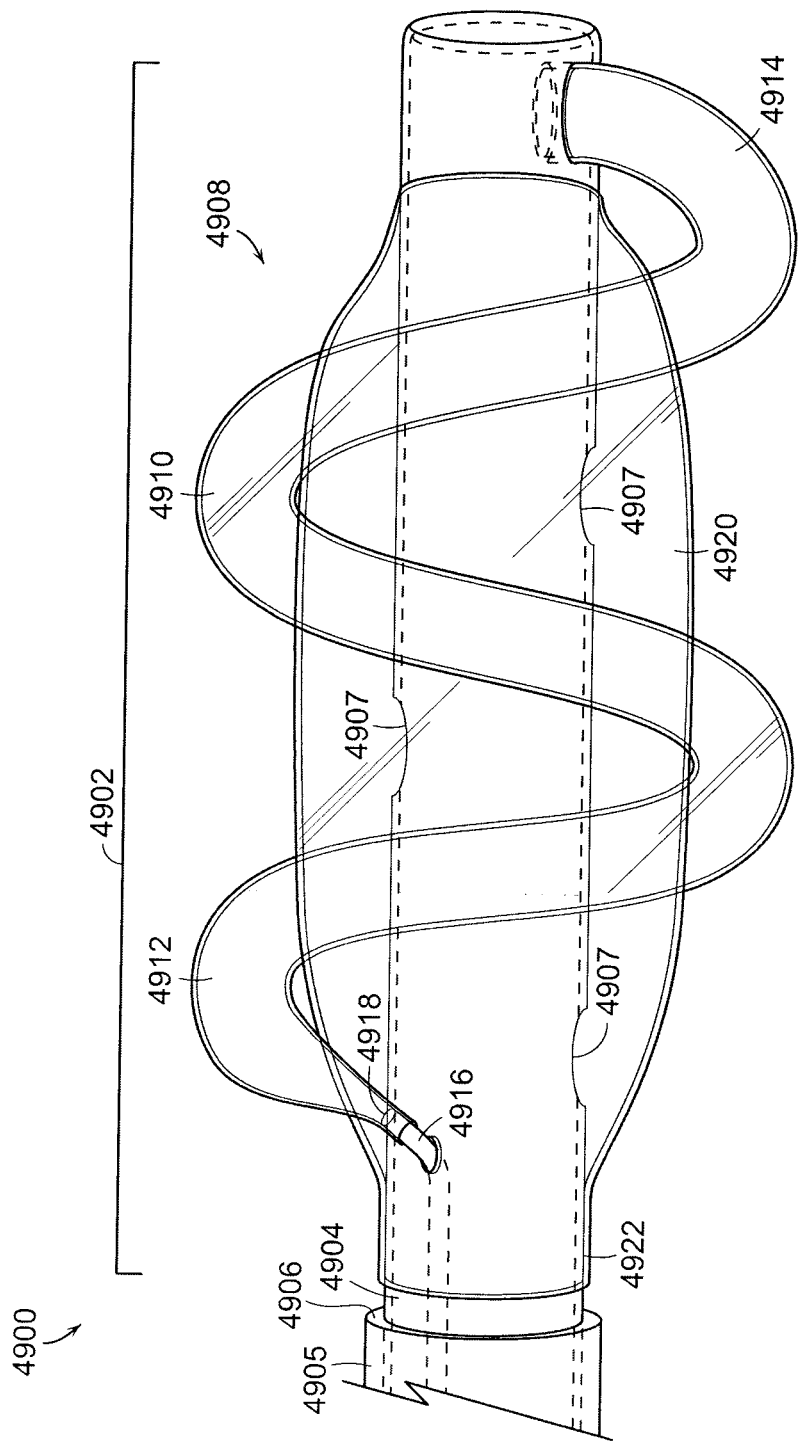
FIG. 49 is a profile view illustrating a cooling assembly having a helical primary balloon wrapped around a secondary balloon configured in accordance with another embodiment of the present technology.

FIG. 49 illustrates a portion of a cryotherapeutic device 4900 including a helical primary balloon and a non-helical secondary balloon in another configuration. The device 4900 includes a cooling assembly 4902 at a distal portion 4904 of an elongated shaft 4905 defining an exhaust passage. The distal portion 4904 can have a step 4906 and a plurality of exhaust openings 4907. The cooling assembly 4902 can include an applicator 4908 with a helical first balloon 4910 that defines an expansion chamber and has a first proximal portion 4912 and a first distal portion 4914. The device 4900 also can include a supply tube 4916 that extends into the first proximal portion 4912, and the cooling assembly 4902 can have an orifice 4918 at the distal end of the supply tube 4916. The first proximal portion 4912 can be sealed around the supply tube 4916. The cooling assembly 4902 can further include a second balloon 4920 positioned around the distal portion 4904 and having an integral proximal neck 4922 attached to the distal portion 4904. The first balloon 4910 can wrap around the second balloon 4920 and the first distal portion 4914 can be fluidly connected to the distal portion 4904 distal of the second balloon 4920. When the cooling assembly 4902 is in a deployed state, the second balloon 4920 can be configured to passively receive refrigerant from the exhaust passage through the exhaust openings 4907 and can be configured to expand (e.g., compliantly expand) in response to back pressure from refrigerant exhausted from the first balloon 4910. Expansion (e.g., compliant expansion) of the second balloon 4920 can cause a helical diameter of the first balloon 4910 to increase, which can cause a portion (e.g., a curved portion) of the first balloon 4910 to move closer to an inner surface of a renal artery or a renal ostium.

Figure 50:
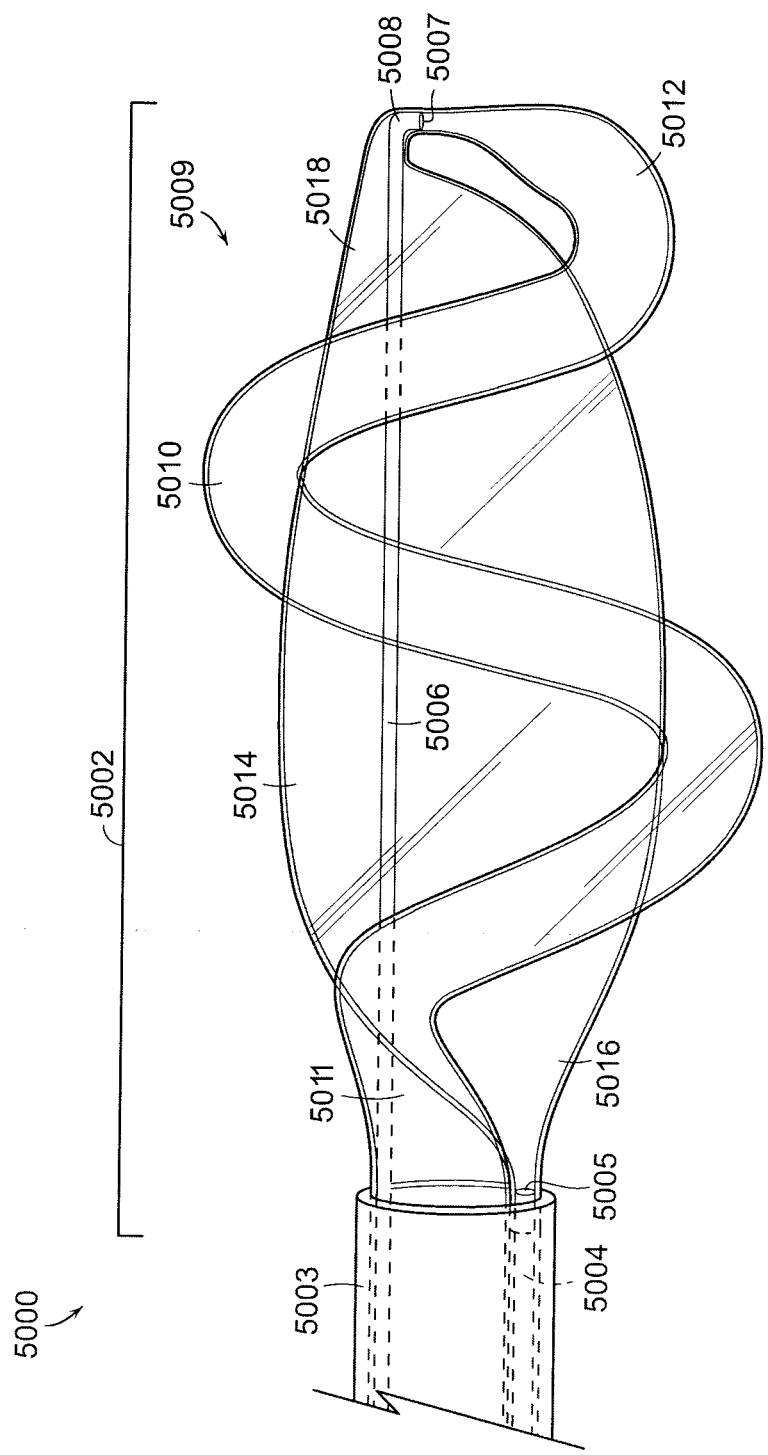
FIG. 50 is a profile view illustrating a cooling assembly having a helical primary balloon wrapped around a secondary balloon configured in accordance with another embodiment of the present technology.

FIG. 50 illustrates a portion of a cryotherapeutic device 5000 including a helical primary balloon and a non-helical secondary balloon in another configuration. The device 5000 includes a cooling assembly 5002 at a distal portion 5003 of an elongated shaft defining an exhaust passage, a filler tube 5004, a filler orifice 5005 at the distal end of the filler tube 5004, and a supply tube 5006. The cooling assembly 5002 includes a supply orifice 5007 at the distal end of the supply tube 5006. The supply tube 5006 can include a corner 5008, such as an elbow, near the supply orifice 5007. The cooling assembly 5002 further includes an applicator 5009 with a helical first balloon 5010 that defines an expansion chamber and has a first proximal portion 5011 and a first distal portion 5012. The cooling assembly 5002 can also include a second balloon 5014 having a second proximal portion 5016 and a second distal portion 5018. The second proximal portion 5016 can be fluidly connected to the filler orifice 5005 and sealed around the filler tube 5004. The second distal portion 5018 can be sealed around the supply tube 5006, but fluidly separate from the supply tube 5024 and the first balloon 5010. The first balloon 5010 can wrap around the second balloon 5014 and be configured to receive refrigerant from the supply tube 5006 and to exhaust the refrigerant through the first proximal portion 5011 into the exhaust passage. The second balloon 5014 can be configured to receive filler material from the filler tube 5004 and expand (e.g., compliantly expand) causing a helical diameter of the first balloon 5010 to increase, which can cause a portion (e.g., a curved portion) of the first balloon 5010 to move closer to an inner surface of a renal artery or a renal ostium.

Figure 51:
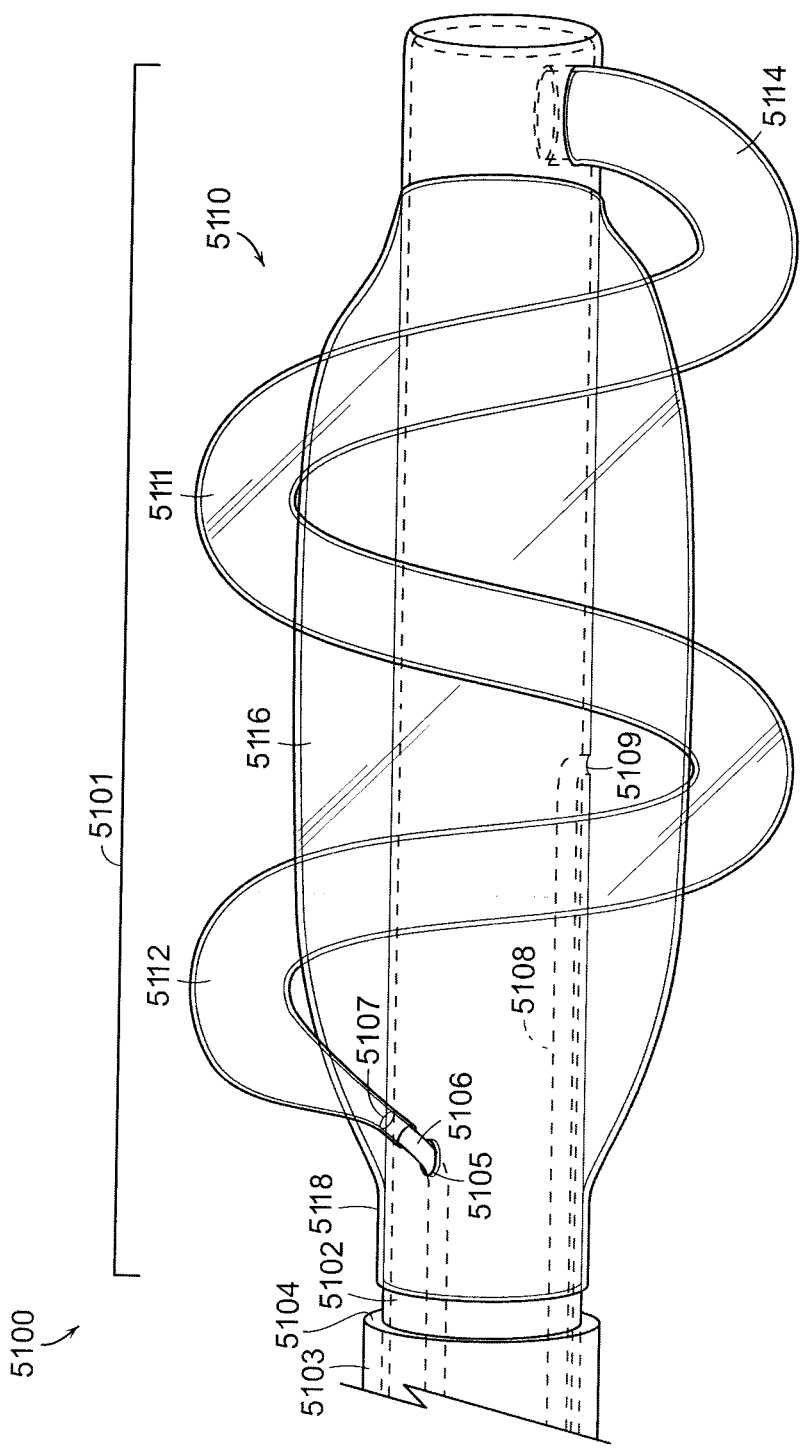
FIG. 51 is a profile view illustrating a cooling assembly having a helical primary balloon wrapped around a secondary balloon configured in accordance with another embodiment of the present technology.

FIG. 51 illustrates a portion of a cryotherapeutic device 5100 including a helical primary balloon and a non-helical secondary balloon in another configuration. The device 5100 includes a cooling assembly 5101 at a distal portion 5102 of an elongated shaft 5103 defining an exhaust passage, a supply tube 5106, and a filler tube 5108. The distal portion 5102 can have a step 5104 and an exit hole 5105. The cooling assembly 5101 can include a supply orifice 5107 at the distal end of the supply tube 5106, and a filler orifice 5109 at the distal end of the filler tube 5108. The cooling assembly 5101 can further include an applicator 5110 with a helical first balloon 5111 that defines an expansion chamber and has a first proximal portion 5112 and a first distal portion 5114. The supply tube 5106 can extend from the exit hole 5105 and extend into the first proximal portion 5112, and the first proximal portion 5112 can be sealed around the supply tube 5106. The cooling assembly 5101 can further include a second balloon 5116 around the distal portion 5102 and having an integral proximal neck 5118 attached to the distal portion 5102. The second balloon 5116 can be configured to receive filler material from the filler tube 5108 and expand (e.g., compliantly expand) causing a helical diameter of the first balloon 5111 to increase, which can cause a portion (e.g., a curved portion) of the first balloon 5111 to move closer to an inner surface of a renal artery or a renal ostium.

Proximal Secondary Balloons

Figure 52A:
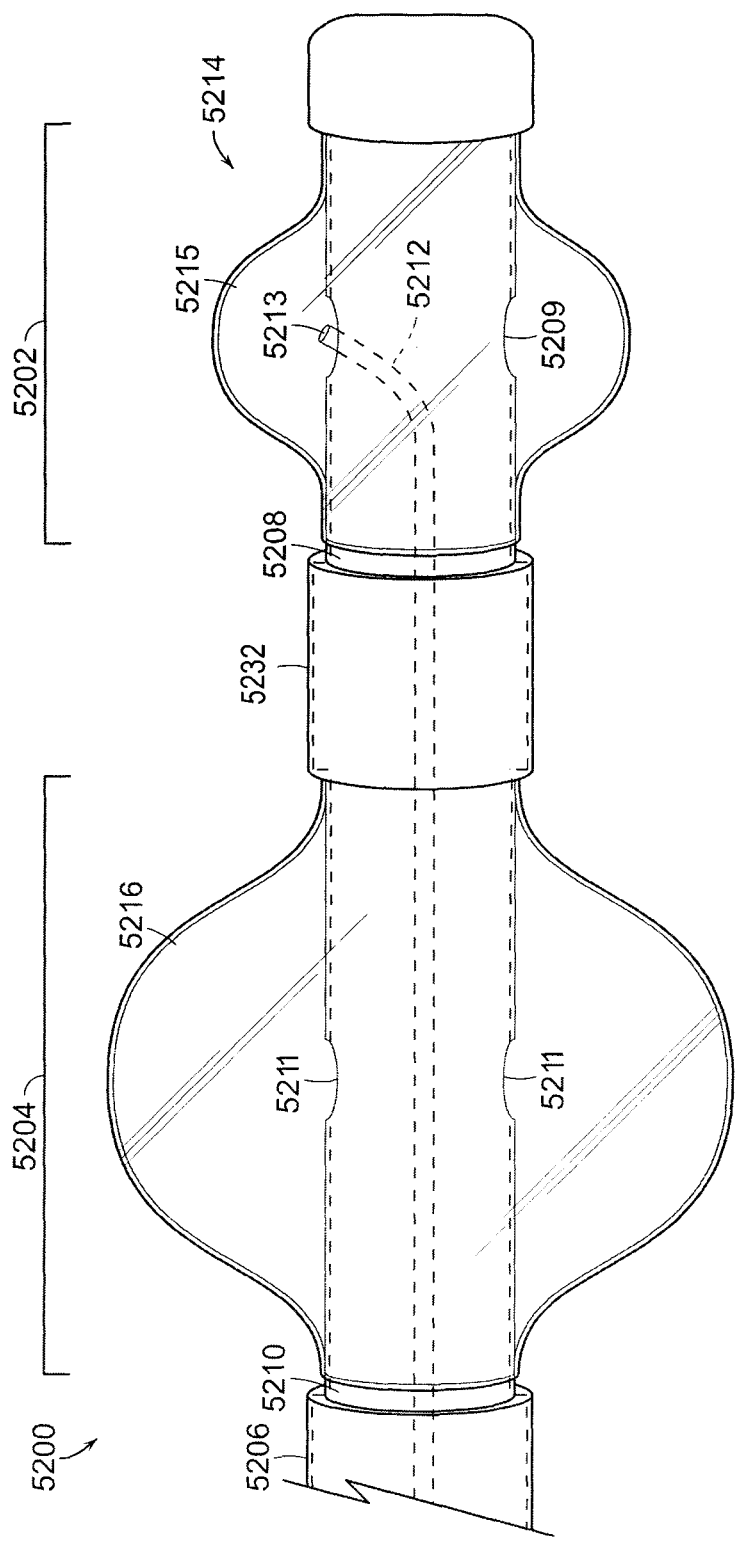
FIG. 52A is a profile view illustrating a distal portion of a cryotherapeutic device including a cooling assembly and an occlusion member configured in accordance with an embodiment of the present technology.

A primary balloon and a secondary balloon can be longitudinally spaced apart along the length of a portion of a cryotherapeutic device configured in accordance with several embodiments of the present technology. For example, a secondary balloon can be part of an occlusion member configured to fully or partially occlude a renal artery and/or a renal ostium. FIGS. 52A-53 illustrate several embodiments of cryotherapeutic devices that include proximal secondary balloons.

Figure 52B:
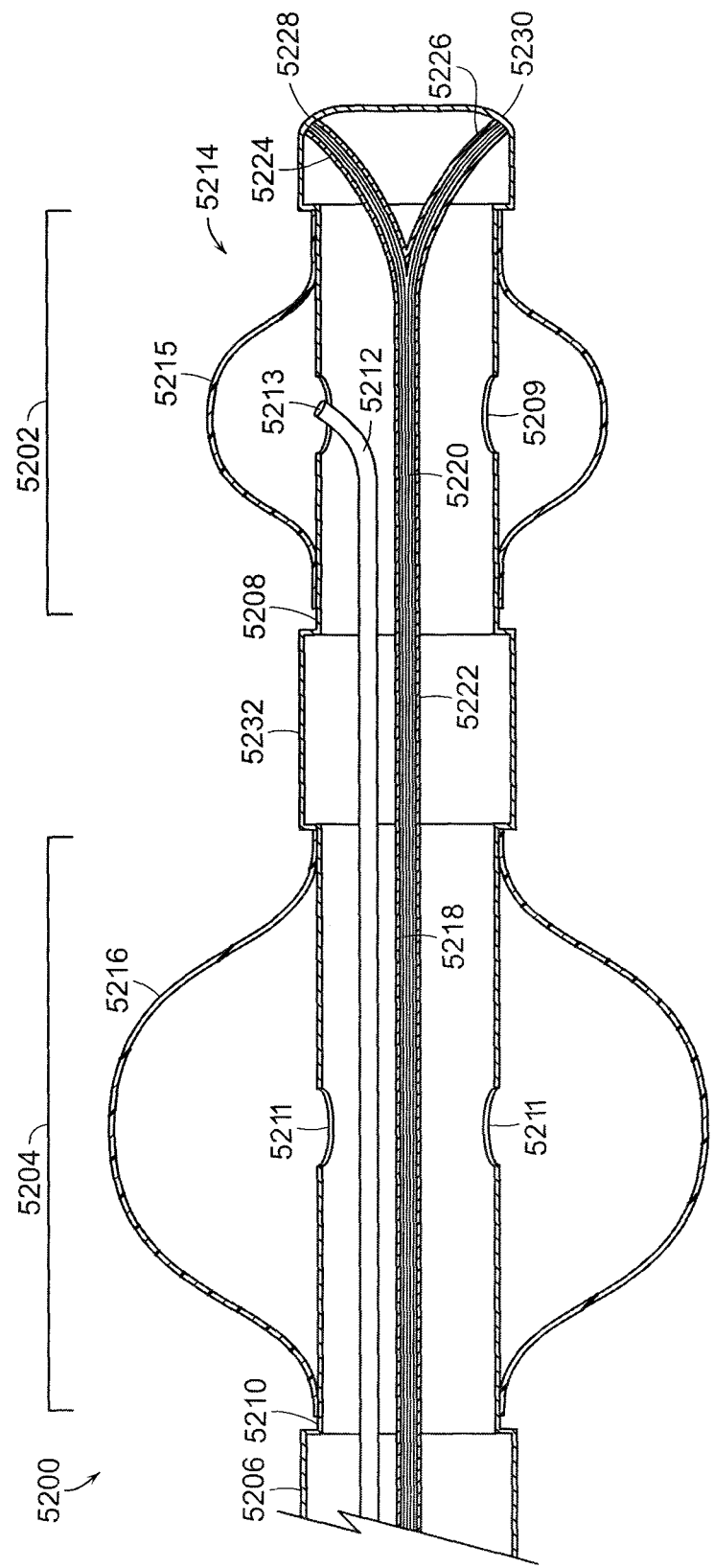
FIG. 52B is a cross-sectional view illustrating the distal portion of FIG. 52A.
Figure 53:
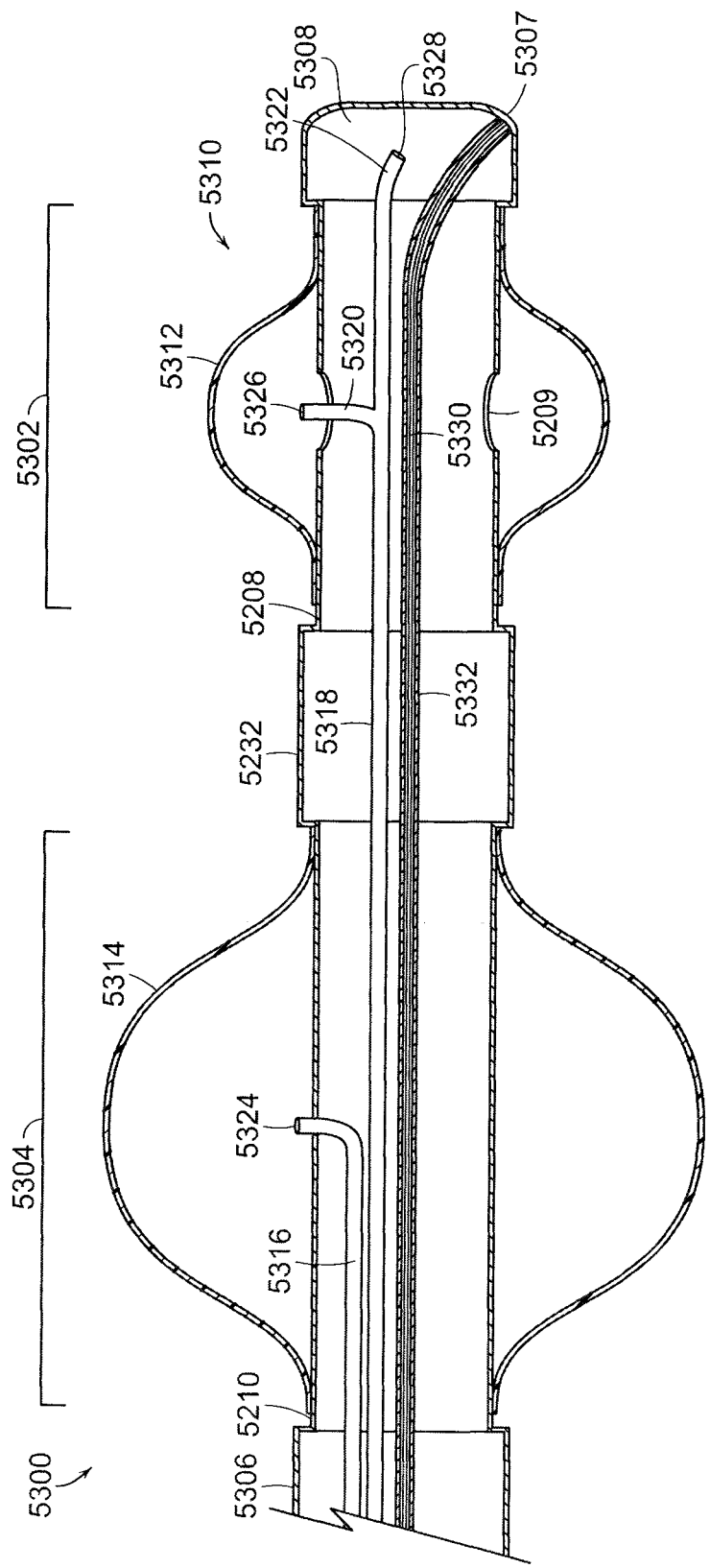
FIG. 53 is a cross-sectional view illustrating a distal portion of a cryotherapeutic device including a cooling assembly and an occlusion member configured in accordance with another embodiment of the present technology.

FIGS. 52A-52B illustrate a portion of a cryotherapeutic device 5200 including a cooling assembly 5202 and an occlusion member 5204 longitudinally spaced apart along an elongated shaft 5206 defining an exhaust passage. The shaft 5206 can have a first stepped-down portion 5208, cooling-assembly exhaust portal 5209 at the first stepped-down portion 5208, a second stepped-down portion 5210, and occlusion-member exhaust portals 5211 at the second stepped-down portion 5210. The cooling assembly 5202 and the occlusion member 5204 can be positioned at the first stepped-down portion 5208 and the second stepped-down portion 5210, respectively. The device 5200 can include a supply tube 5212, and the cooling assembly 5202 can have orifice 5213 at the distal end of the supply tube 5212. The cooling assembly 5202 also can include an applicator 5214 with a first balloon 5215 that defines an expansion chamber. The supply tube 5212 can angle out of the shaft 5206 and into the first balloon 5215. The occlusion member 5204 can include a second balloon 5216 defining an occlusion chamber. The second balloon 5216 can be configured to passively receive refrigerant from the exhaust passage through the occlusion-member exhaust portal 5211 and can be configured to expand (e.g., compliantly expand) in response to back pressure from refrigerant exhausted from the cooling assembly 5202. Both the cooling assembly 5202 and the occlusion member 5204 can be at least partially collapsible in a delivery state and are shown in FIGS. 52A-52B in an expanded state and a deployed state, respectively. In the expanded state, the occlusion member 5204 can have a cross-sectional dimension configured to fully occlude a renal artery and/or a renal ostium.

As shown in FIG. 52B, the device 5200 can further include a first elongated control member 5218, a second elongated control member 5220, and a control tube 5222 with a first distal branch 5224 and a second distal branch 5226. The shaft 5206 can further include a first distal attachment point 5228, a second distal attachment point 5230, and a flexing portion 5232 between the first stepped-down portion 5208 and the second stepped-down portion 5210. The first elongated control member 5218 can extend along the control tube 5222, along the first distal branch 5224, and attach to the first distal attachment point 5228. The second elongated control member 5220 can extend along the control tube 5222, along the second distal branch 5226, and attach to the second distal attachment point 5230. The device 5200 can be configured such that increasing or decreasing tension of the first control member 5218 and/or the second control member 5220 can control deflection of the shaft 5206. The shaft 5206 can be flexible at the flexing portion 5232 to position the first balloon against a vessel wall or ostium. In addition to or instead of fully occluding the vessel or ostium, the occlusion member 5204 can be configured in the expanded state to support the shaft 5206 within a renal artery or a renal ostium to provide controlled repositioning of the cooling assembly 5202 within the renal artery or the renal ostium. For example, the cooling assembly 5202 can be repositioned to cause therapeutically-effective, cryogenic renal-nerve modulation at different portions of a renal artery or a renal ostium.

FIG. 53 illustrates a portion of a cryotherapeutic device 5300 similar to the cryotherapeutic device 5200 shown in FIGS. 53A-53B, but the device 5300 has additional distal cooling and different supply and control configurations. The device 5300 includes a cooling assembly 5302 and an occlusion member 5304 longitudinally spaced apart along an elongated shaft 5306 defining an exhaust passage. The shaft 5306 can have a distal attachment point 5307 and a distal tip portion 5308 defining a distal expansion chamber. The cooling assembly 5302 includes an applicator 5310 having a first balloon 5312 defining an expansion chamber, and the occlusion member 5304 includes a second balloon 5314 defining an occlusion chamber fluidly separate from the exhaust passage. The device 5300 further includes a filler tube 5316 extending to the second balloon 5314 and a supply tube 5318 having a lateral branch 5320 extending to the first balloon 5312 and an angled distal portion 5322 extending to the distal tip portion 5308. The occlusion member 5304 further includes a filler orifice 5324 through which a filler material can be supplied to the second balloon 5314. The cooling assembly 5302 further includes a first supply orifice 5326 configured to direct refrigerant expansion into the first balloon 5312 and a second supply orifice 5328 configured to direct refrigerant expansion into the distal tip portion 5308.

The device 5300 further includes an elongated control member 5330 and a control tube 5332. The control member 5330 can extend along the control tube 5332 and be attached to the distal attachment point 5307. The device 5300 can be configured such that increasing or decreasing tension of the control member 5330 can control deflection of the shaft 5306. In addition to or instead of fully occluding a vessel or ostium, the occlusion member 5304 can be configured in the expanded state to support the shaft 5306 within a renal artery or a renal ostium to provide controlled repositioning of the cooling assembly 5302 within the renal artery or the renal ostium. For example, the cooling assembly 5302 can be repositioned to cause therapeutically-effective, cryogenic renal-nerve modulation at different portions of a renal artery or a renal ostium.

Alternative Cooling

Cooling assemblies configured in accordance with several embodiments of the present technology have a cooling mechanism in the deployed state that does not involve evaporation of refrigerant. For example, such embodiments can include cooling assemblies configured to circulate liquid or supercritical refrigerant at cryogenic temperatures to cause convective and conductive cooling through a primary heat-transfer portion of an applicator. In such applicators, the flow impedance of the supply can be generally equal to the flow impedance of the exhaust. For example, the cross-sectional area of a supply lumen can be generally equal to the cross-sectional area of an exhaust passage. In some embodiments, cryotherapeutic devices having cooling assemblies configured to circulate refrigerant without phase change can have features to facilitate the supply of refrigerant to the cooling assemblies and/or the exhaust of refrigerant from the cooling assemblies. For example, a first pump can be included to increase the pressure of refrigerant flowing to a cooling assembly and/or a vacuum source (e.g., a second pump) can be included to decrease the pressure of refrigerant flowing away from a cooling assembly. In addition to the first pump or alternatively, refrigerant can be supplied from a pressurized source. Based on operational considerations, e.g., refrigerant viscosity and flow impedances of supply, exhaust, and heat-transfer portions of a cryotherapeutic device, supply and exhaust pressures can be selected to cause different flow rates of refrigerant. The flow rate can be selected, for example, to correspond to a heat-transfer rate sufficient to cause therapeutically-effective cryogenic renal nerve modulation.

FIG. 54 illustrates a portion of a cryotherapeutic device 5400 that can be configured for convective heat transfer without refrigerant phase-change. The device 5400 includes a cooling assembly 5402 at a distal portion 5404 of an elongated shaft 5406 defining an exhaust passage. The cooling assembly 5402 includes an applicator 5408 with a balloon 5410 that defines a circulation chamber. The device 5400 also includes a supply tube 5412 extending along the length of the shaft 5406 and into the balloon 5410, and the cooling assembly 5402 includes an orifice 5414 at the distal end of the supply tube 5412. In several embodiments, the supply tube 5412 is relatively large and configured to transport liquid refrigerant, and the orifice 5414 is not configured to cause a pressure drop sufficient to evaporate a refrigerant. When the cooling assembly 5402 is in a deployed state, the balloon 5410 can be configured to be filled with refrigerant in at least a substantially liquid phase. The refrigerant can circulate from the supply tube 5412 to the exhaust passage. FIG. 54 includes arrows 5416 indicating a direction of refrigerant flow through the balloon 5410. The refrigerant can be a liquid having a low freezing point (e.g., ethyl alcohol) and can be transported through the supply tube 5412 at a cryogenic temperature. Convective heat transfer between the refrigerant and the balloon 5410 can cool a renal artery or a renal ostium to cause therapeutically-effective renal nerve modulation.

FIG. 55 illustrates a portion of a cryotherapeutic device 5500 that also can be configured for convective heat transfer without refrigerant phase-change. The device 5500 includes a cooling assembly 5502 at a distal portion 5504 of an elongated shaft 5506 including a shaft partition 5508 dividing the shaft into a first longitudinal portion 5510 defining supply lumen and a second longitudinal portion 5512 defining an exhaust passage. The cooling assembly 5502 includes an applicator 5514 with a balloon 5516 including a balloon partition 5518 that defines a U-shaped chamber within the balloon 5516. The balloon 5516 can be configured to circulate liquid refrigerant from the first longitudinal portion 5510, through the U-shaped chamber, and into the second longitudinal portion 5512. FIG. 55 includes an arrow 5520 indicating a direction of refrigerant flow through the balloon 5516.

In several embodiments, a cooling assembly is configured to circulate a supercritical fluid (e.g., supercritical nitrogen or water). Supercritical fluids can provide significant cooling without phase change, but typically must be maintained at relatively high pressures. Cooling assemblies configured to circulate supercritical fluids can include supply, heat-transfer, and exhaust structures having high pressure ratings. For example, such cooling assemblies can include non-expandable applicators (e.g., having metal walls). Such applicators can be moveable during a treatment to contact different portions of a renal artery or a renal ostium.

Additional Embodiments

Features of the cryotherapeutic-device components described above and illustrated in FIGS. 1-5B and 12-55 can be modified to form additional embodiments configured in accordance with the present technology. For example, the cryotherapeutic device 1700 illustrated in FIGS. 17A-17B and other cryotherapeutic devices described above and illustrated in FIGS. 1-5B and 12-55 without guide members can include guide members that extend near or through distal portions of balloons. Similarly, the cryotherapeutic devices described above and illustrated in FIGS. 1-5B and 12-55 can include control members configured to receive control wires (e.g., pull wires). A control wire can be used, for example, to control (e.g., deflect, angle, position, or steer) a cooling assembly, an applicator, or another cryotherapeutic-device component from outside the vasculature.

The cryotherapeutic-device components described above and illustrated in FIGS. 1-5B and 12-55 include balloons having a variety of features (e.g., shapes and compositions). In some cases, manufacturing considerations and other factors can cause certain features to be more or less desirable. For example, certain materials can be more compatible with extrusion processes than with molding processes or vise versa. Similarly, some balloon shapes can be more readily formed using certain manufacturing processes than using other manufacturing processes. For example, balloons having integral closed distal ends, in some cases, can be difficult to form using extrusion. The balloons and balloon features in the cryotherapeutic-device components described above and illustrated in FIGS. 1-5B and 12-55 can be modified or interchanged according to such factors. For example, distal necks (e.g., sealed distal necks) can be substituted for integral closed distal ends in the balloons described above and illustrated in FIGS. 1-5B and 12-55. This can be useful, for example, to make the balloons more compatible with extrusion manufacturing processes.

Features of the cryotherapeutic-device components described above also can be interchanged to form additional embodiments of the present technology. For example, the inner balloon 1514 of the cooling assembly 1502 illustrated in FIG. 15A can be incorporated into the cooling assembly 1902 shown in FIGS. 19A-19C. As another example, the first supply tube 1218 with the first angled distal portion 1222 of the cryotherapeutic device 1200 illustrated in FIG. 12 can be incorporated into the cooling assembly 1702 illustrated in FIGS. 17A-17B, with the first angled distal portion 1222 configured to direct expansion of refrigerant between the thermally-insulative members 1711.

Related Anatomy and Physiology

The Sympathetic Nervous System (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to physiological features as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

1. The Sympathetic Chain

Figure 56:
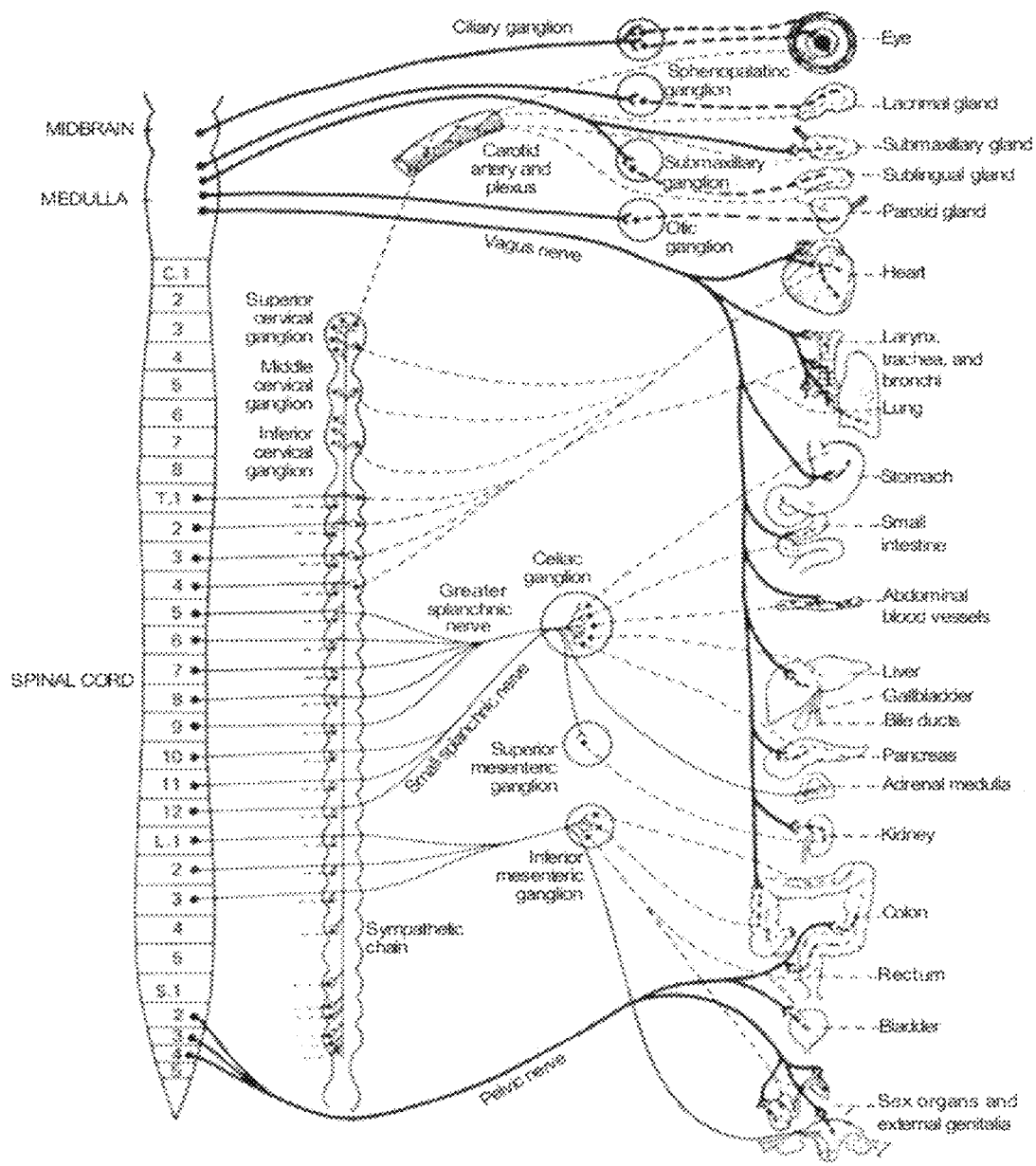
FIG. 56 is a conceptual illustration of the sympathetic nervous system (SNS) and how the brain communicates with the body via the SNS.

As shown in FIG. 56, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia, discussed above. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Innervation of the Kidneys

Figure 57:
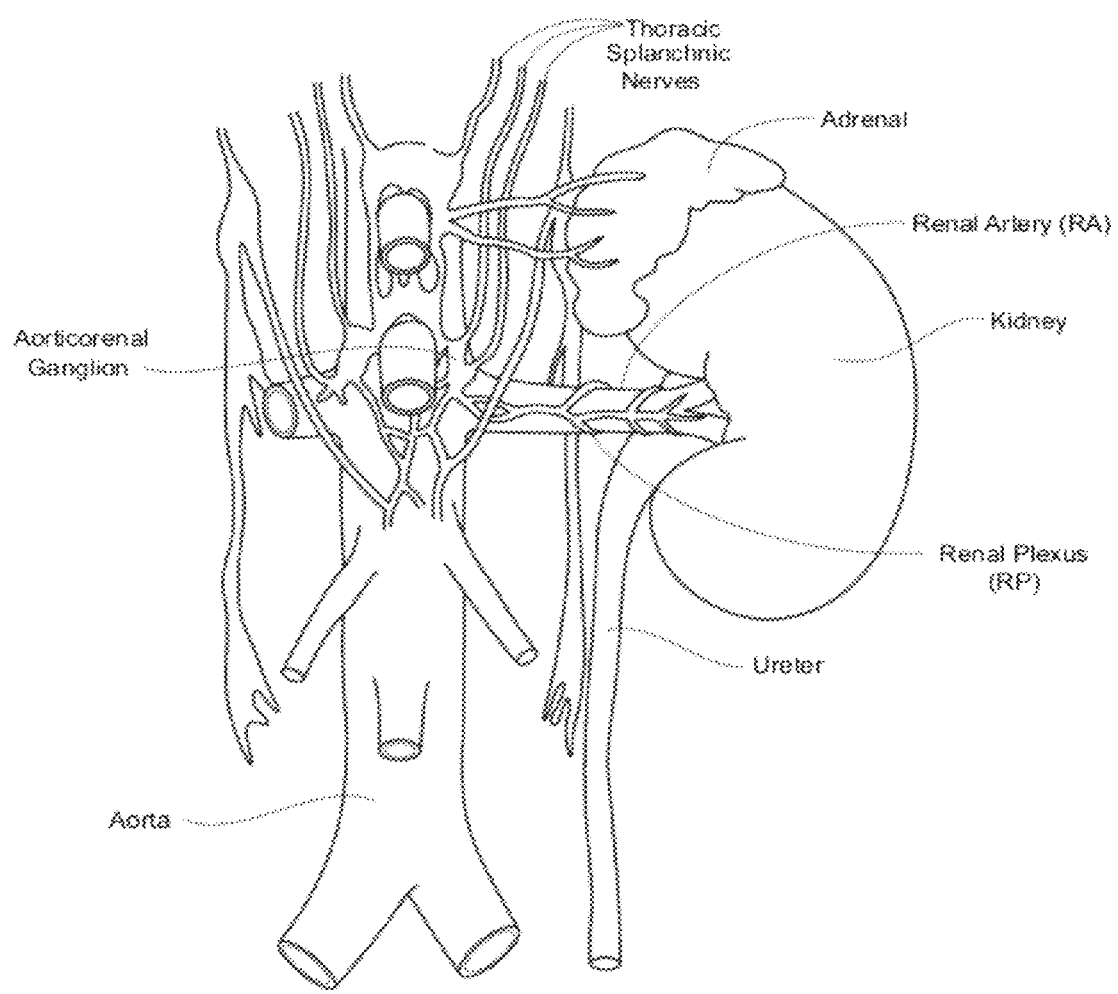
FIG. 57 is an enlarged anatomic view of nerves innervating a left kidney to form the renal plexus surrounding the left renal artery.

As FIG. 57 shows, the kidney is innervated by the renal plexus RP, which is intimately associated with the renal artery. The renal plexus RP is an autonomic plexus that surrounds the renal artery and is embedded within the adventitia of the renal artery. The renal plexus RP extends along the renal artery until it arrives at the substance of the kidney. Fibers contributing to the renal plexus RP arise from the celiac ganglion, the superior mesenteric ganglion, the aorticorenal ganglion and the aortic plexus. The renal plexus RP, also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus RP and are distributed to the renal vasculature.

3. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well known adverse consequences of chronic sympathetic over activity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium (Na+) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 58A:
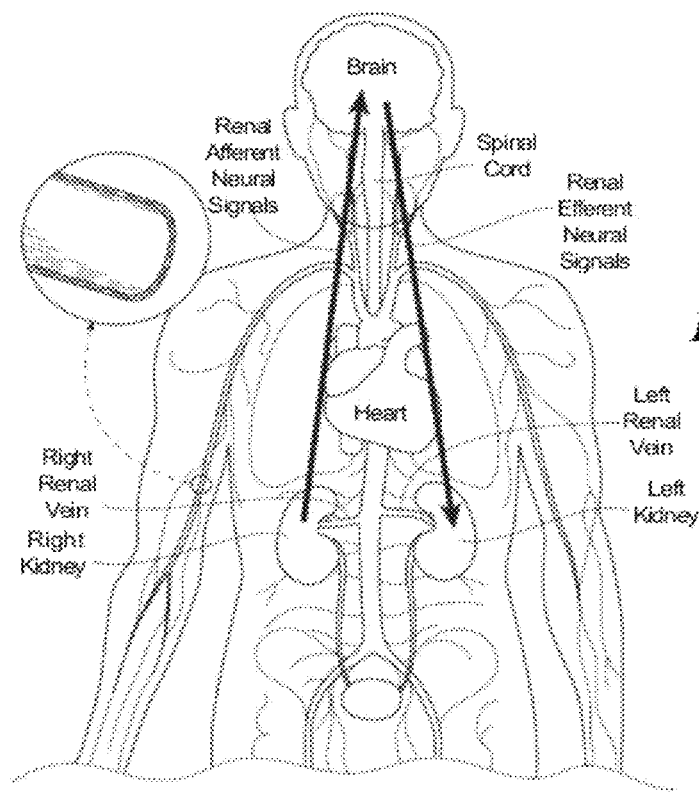
FIGS. 58A and 58B are anatomic and conceptual views, respectively, of a human body depicting neural efferent and afferent communication between the brain and kidneys.
Figure 58B:
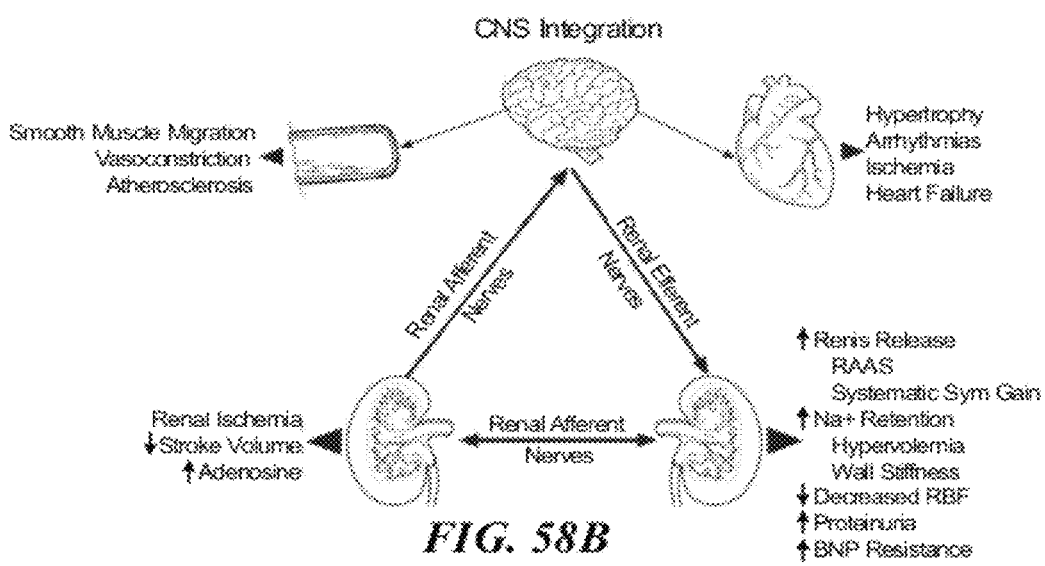

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 58A and 58B, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 56. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

C. Achieving Intravascular Access to the Renal Artery

Figure 59A:
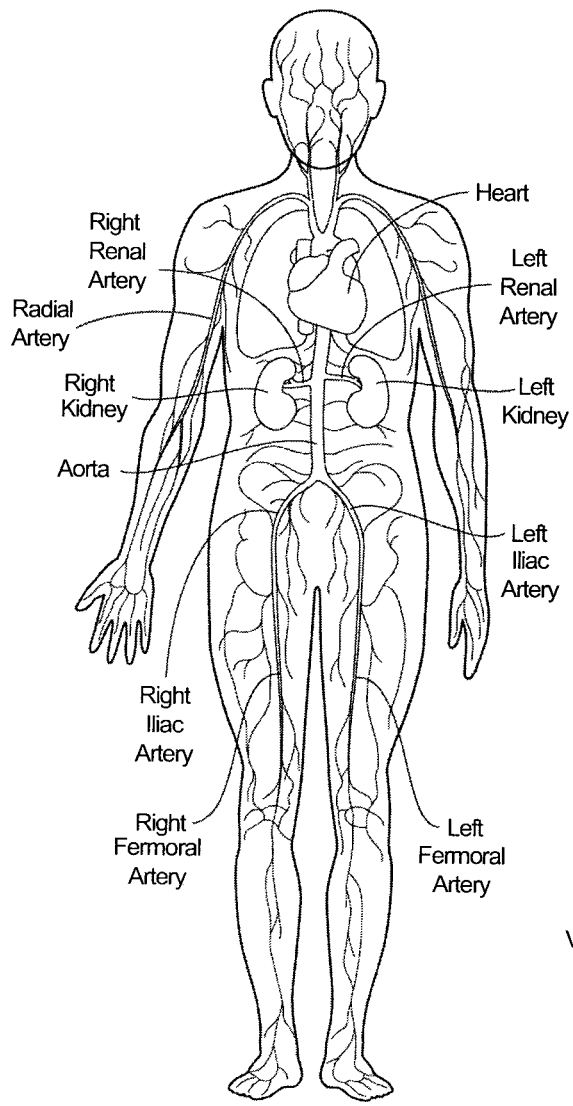
FIGS. 59A and 59B are anatomic views of the arterial vasculature and venous vasculature, respectively, of a human.

In accordance with the present technology, neuromodulation of a left and/or right renal plexus RP, which is intimately associated with a left and/or right renal artery, may be achieved through intravascular access. As FIG. 59A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

Figure 59B:
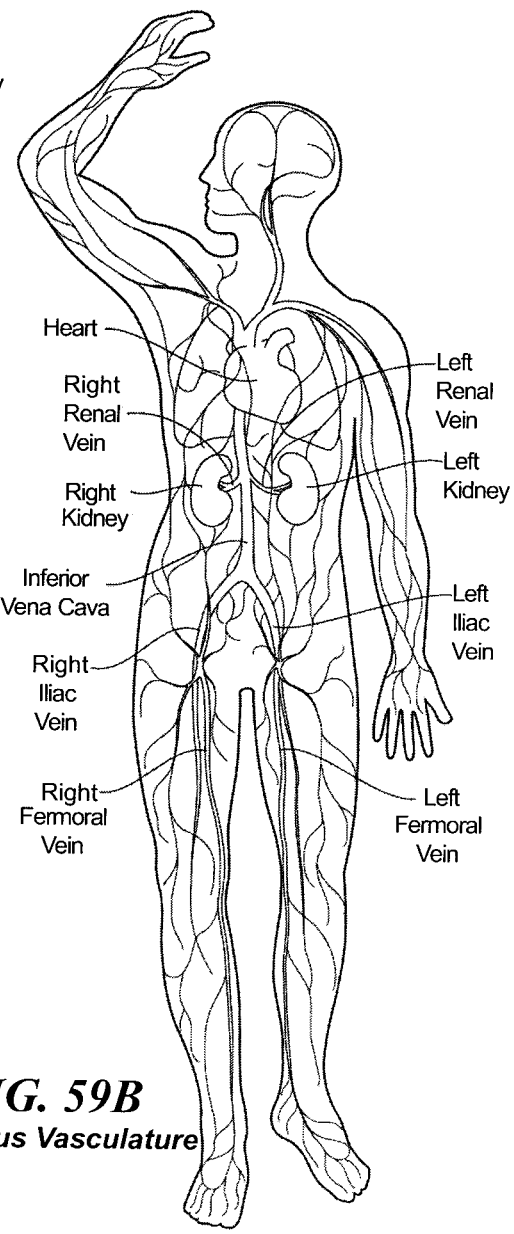

As FIG. 59B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus RP may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. When the neuromodulatory apparatus includes a cryotherapeutic device, consistent positioning, appropriate contact force applied by the cryotherapeutic device to the vessel wall, and adhesion between the cryo-applicator and the vessel wall are important for predictability. However, navigation is impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e. cause the wall of the artery to pulse).

Even after accessing a renal artery and facilitating stable contact between neuromodulatory apparatus and a luminal surface of the artery, nerves in and around the adventia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, full-circle lesion likely resulting from a continuous circumferential treatment may be potentially related to renal artery stenosis. Therefore, the formation of more complex lesions along a longitudinal dimension of the renal artery via the cryotherapeutic devices and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time should be avoided because to prevent injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility: and (f) as well as the take-off angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery should conform to the geometry of the artery. Renal artery vessel diameter, $D_{RA}$, typically is in a range of about 2-10 mm, with most of the patient population having a $D_{RA}$ of about 4 mm to about 8 mm and an average of about 6 mm. Renal artery vessel length, $L_{RA}$, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An additional property of the renal artery that may be of interest is the degree of renal motion relative to the aorta induced by respiration and/or blood flow pulsatility. A patient's kidney, which is located at the distal end of the renal artery, may move as much as 4" cranially with respiratory excursion. This may impart significant motion to the renal artery connecting the aorta and the kidney, thereby requiring from the neuromodulatory apparatus a unique balance of stiffness and flexibility to maintain contact between the cryo applicator or other thermal treatment element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

The foregoing embodiments of cryotherapeutic devices are configured to accurately position the cryo applicators in and/or near the renal artery and/or renal ostium via a femoral approach, transradial approach, or another suitable vascular approach. In any of the foregoing embodiments described above with reference to FIGS. 1-55, single balloons can be configured to be inflated to diameters of about 3 mm to about 8 mm, and multiple-balloons can collectively be configured to be inflated to diameters of about 3 mm to about 8 mm, and in several embodiments 4 mm to 8 mm. Additionally, in any of the embodiments shown and described above with reference to FIGS. 1-55, the balloons can individually and/or collectively have a length of about 8 mm to about 15 mm, and in several embodiments 10 mm. For example, several specific embodiments of the devices shown in FIGS. 1-55 can have a 10 mm long balloon that is configured to be inflated to a diameter of 4 mm to 8 mm. The shaft of the devices described above with reference to any of the embodiments shown in FIGS. 1-55 can be sized to fit within a 6 Fr sheath, such as a 4 Fr shaft size.

Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:
1. A cryotherapeutic device, comprising;
   an elongated shaft having a distal portion configured to be located intravascularly at a treatment site in a renal artery or ostium;
   a supply lumen extending along a length of the shaft, the supply lumen being configured to receive liquid refrigerant;
   a cooling assembly at the distal portion of the shaft, the cooling assembly having a delivery state and a deployed state, the cooling assembly including
      an elongated support member extending along a length of the cooling assembly,
      an orifice in fluid communication with the supply lumen, and
      an applicator configured to cause therapeutically-effective cryogenic renal-nerve modulation when the cooling assembly is in the deployed state and when the cooling assembly receives refrigerant from the supply lumen, the applicator having a balloon that defines a chamber, the balloon having
a heat-transfer portion in fluid communication with the orifice, the heat-transfer portion being non-circumferential at longitudinal segments disposed along the length of the cooling assembly and being spaced apart from the support member when the cooling assembly is in the deployed state, and
an attachment portion attached to the support member; and
an occlusion member spaced apart proximally from the applicator, the occlusion member having a collapsed state, an expanded state, and a cross-sectional dimension that fully occludes the renal artery or ostium proximal to the treatment site when the occlusion member is in the expanded state.

2. The cryotherapeutic device of claim 1, wherein:
the chamber is a first chamber;
the balloon is a first balloon; and
the occlusion member includes a second balloon defining a second chamber fluidly connected to the first chamber.

3. The cryotherapeutic device of claim 2, further comprising an exhaust passage extending along the shaft, wherein the second chamber is fluidly connected to the exhaust passage.

4. The cryotherapeutic device of claim 2, wherein:
the first chamber has a first refrigerant residence time when the cooling assembly is in deployed state;
the second chamber has a second refrigerant residence time when the occlusion member is in the expanded state; and
the first refrigerant residence time is less than the second refrigerant residence time.

5. The cryotherapeutic device of claim 1, further comprising a filler lumen extending along the shaft, wherein:
the filler lumen is fluidly connected to the occlusion member; and
the occlusion member is fluidly separate from the supply lumen.

6. The cryotherapeutic device of claim 1, wherein:
the balloon is a first balloon;
the occlusion member includes a second balloon; and
the second balloon is compliant.

7. The cryotherapeutic device of claim 1, further comprising a handle, wherein:
the shaft has a proximal portion at the handle; and
the shaft includes
a control lumen, and
an elongated control member within the control lumen and operably coupled to the distal portion of the shaft and to the handle such that increasing or decreasing tension of the control member controls deflection of the distal portion of the shaft distal to the occlusion member.

8. The cryotherapeutic device of claim 1, wherein the balloon is helical and wrapped around the support member.

9. The cryotherapeutic device of claim 1, wherein;
the ballon has a shape when the cooling assembly is in the deployed state, the shape including a plurality of recessed portions and a non-recessed area around the plurality of recessed portions, the non-recessed area at least partially defining the heat-transfer portion of the cooling assembly; and
the heat-transfer portion of the cooling assembly is non-circumferential at longitudinal segments disposing along a length of the applicator.

10. The cryotherapeutic device of claim 9, wherein the shape of the balloon when the cooling assembly in the deployed state is cylindrical.

11. The cryotherapeutic device of claim 1, wherein:
the balloon has a shape when the cooling assembly is in deployed state, the shape including a plurality of protrusions and a non-protruding area around the plurality of protrusions, the plurality of protrusions at least partially defining the heat-transfer portion of the cooling assembly; and
the heat-transfer portion of the cooling assembly is non-circumferential at longitudinal segments disposed along a length of the applicator.

12. The cryotherapeutic device of claim 1, wherein:
the balloon has a helical recessed portion and a helical non-recessed portion; and
the helical non-recessed portion at least partially defines the heat-transfer portion.

13. A cryotherapeutic device, comprising:
an elongated shaft having a distal portion configured to be located intravascularly at a treatment site in a renal artery or ostium;
a supply lumen extending along a length of the shaft, the supply lumen being configured to receive liquid refrigerant;
a cooling assembly at the distal portion of the shaft, the cooling assembly having a delivery state and a developed state, the cooling assembly including
an orifice in fluid coomunication with the supply lumen, and
an applicator configured to cause therapeutically-effective cryogenic renal-nerve modulation when the cooling assembly is in the deployed state and when the cooling assembly receives refrigerant from the supply lumen, the applicator having a heat-transfer portion in fluid communication with the orifice,
wherein
the balloon is elongated and has a proximal portion, a distal portion, and a middle portion therebetween,
the balloon has a first wall portion with a concave curvature along a length of the balloon and a second wall portion having a non-concave curvature along the length of the balloon when the cooling assembly is in the deployed state,
the middle portion of the balloon is configured to contact the renal artery or ostium along the second wall potion and not the first wall portion when the cooling assembly is in the deployed state,
the second wall portion of the balloon at the middle portion of the balloon at least partially defines the heat-transfer portion of the applicator, and
the heat-transfer portion of the applicator is non-circumferential at longitudinal segments disposed along a length of the applicator; and
an occlusion member spaced apart proximally from the applicator, the occlusion member having a collapsed state, an expanded state, and a cross-sectional dimension that fully occludes the renal artery or ostium proximal of the treatment site when the occlusion member is in the expanded state.

14. The cryotherapeutic device of claim 13, wherein:
the first wall portion has a first thickness; and
the second wall portion has a second thickness less than the first thickness.

15. A cryotherapeutic device, comprising:
an elongated shaft having a distal portion configured to be located intravascularly at a treatment site in a renal artery or ostium;

a supply lumen extending along a length of the shaft, the supply lumen being configured to receive liquid refrigerant;
a cooling assembly at the distal portion of the shaft, the cooling assembly having a delivery state and a deployed state, the cooling including
an elongated shaping member extending along a length of the cooling assembly,
a shaping member having a linear configuration when the cooling assembly is in the delivery state and a curvilinear configuration when the cooling assembly is in the deployed state,
an orifice in fluid communication with the supply lumen, and
an applicator configured to cause therapeutically-effective cryogenic renal-nerve modulation when the cooling assembly is in the deployed state and when the cooling assembly receives refrigerant from the supply lumen, the applicator having a balloon that defines a chamber, the balloon having a heat-transfer portion in fluid communication with the orifice, the balloon having a shape when the cooling assembly is in the deployed state that at least partially corresponds to the curvilinear configuration of the shaping member; and
an occlusion member spaced apart proximally from the applicator, the occlusion member having a collapsed state, an expanded state, and a cross-sectional dimension that fully occludes the renal artery or ostium proximal to the treatment site when the occlusion member is in the expanded state.

16. The cryotherapeutic device of claim 15, wherein the shape of the balloon when the cooling assembly is in the deployed state is helical.

17. The cryotherapeutic device of claim 15, wherein the shape of the balloon when the cooling assembly is in the deployed state is serpentine.

18. A cryotherapeutic device, comprising:
an elongated shaft having a distal portion configured to be located intravsacularly at a treatment site in a renal artery or ostium;
a supply lumen extending along a length of the shaft, the supply lumen being configured to receive liquid refrigerant;
an elongated shaping member longitudinally movable relative to the shaft;
a cooling assembly at the distal portion of the shaft, the cooling assembly having
a delivery state and a deployed state, the cooling assembly including
an orifice in fluid communication with the supply lumen, and
an applicator configured to cause therapeutically-effective cryogenic renal-nerve modulation when the cooling assembly is in the deployed state and when the cooling assembly receives refrigerant from the supply lumen, the applicator having
a first elongated balloon with a heat-transfer portion in fluid communication with the orifice, the first balloon having a proximal portion, a distal portion, and a middle portion therebetween,
a second elongated balloon having a proximal portion, a distal portion, and middle portion, therebetween,
wherein
the distal portion of the first and second balloons are attached to the shaping member such that retracting the shaping member relative to the shaft causes the first and second balloons to curve along a length of the cooling assembly, and the middle portions of the first and second balloons to laterally move away from the shaping member,
the middle portion of the first balloon has an outer side with a non-concave curvature along the length of the cooling assembly when the cooling assembly is in the deployed state,
the middle portion of the second balloon has an outer side with a non-concave curvature along the length of the cooling assembly when the cooling assembly is in the deployed state,
the outer sides of the middle portions of the first and second balloons at least partially define the heat-transfer portion, and
the heat-transfer portion is non-circumferential at longitudinal segments along the length of the cooling assembly; and
an occlusion member spaced apart proximally from the applicator, the occlusion member having a collapsed state, an expanded state, and a cross-sectional dimension that fully occludes the renal artery or ostium proximal to the treatment site when the occlusion member is in the expanded state.

19. The cryotherapeutic device of claim 13, wherein:
the chamber is a first chamber;
the balloon is a first balloon; and
the occlusion member includes a second balloon defining a second chamber fluidly connected to the first chamber.

20. The cryotherapeutic device of claim 19, further comprising an exhaust passage extending along the shaft, wherein the second chamber is fluidly connected to the exhaust passage.

21. The cryotherapeutic device of claim 19, wherein:
the first chamber has a first refrigerant residence time when the cooling assembly is in the deployed state;
the second chamber has a second refrigerant residence time when the occlusion member is in the expanded state; and
the first refrigerant residence time is less than the second refrigerant residence time.

22. The cryotherapeutic device of claim 13, further comprising a filler lumen extending along the shaft, wherein:
the filler lumen is fluidly connected to the occlusion member; and
the occlusion member is fluidly separate from the supply lumen.

23. The cryotherapeutic device of claim 13, wherein:
the balloon is a first balloon;
the occlusion member includes a second balloon; and
the second balloon is compliant.

24. The cryotherapeutic device of claim 15, wherein:
the chamber is a first chamber;
the balloon is a first balloon; and
the occlusion member includes a second balloon defining a second chamber fluidly connected to the first chamber.

25. The cryotherapeutic device of claim 24, further comprising an exhaust passage extending along the shaft, wherein the second chamber is fluidly connected to the exhaust passage.

26. The cryotherapeutic device of claim 24, wherein:
the first chamber has a first refrigerant residence time when the cooling assembly is in the deployed state;
the second chamber has a second refrigerant residence time when the occlusion member is in the expanded state; and
the first refrigerant residence time is less than the second refrigerant residence time.

27. The cryotherapeutic device of claim 15, further comprising a filler lumen extending along the shaft, wherein:
the filler lumen is fluidly connected to the occlusion member; and
the occlusion member is fluidly separate from the supply lumen.

28. The cryotherapeutic device of claim 15, wherein:
the balloon is a first balloon;
the occlusion member includes a second balloon; and
the second balloon is compliant.

29. The cryotherapeutic device of claim 18, wherein:
the chamber is a first chamber;
the balloon is a first balloon; and
the occlusion member includes a second balloon defining a second chamber fluidly connected to the first chamber.

30. The cryotherapeutic device of claim 29, further comprising an exhaust passage extending along the shaft, wherein the second chamber is fluidly connected to the exhaust passage.

31. The cryotherapeutic device of claim 29, wherein:
the first chamber has a first refrigerant residence time when the cooling assembly is in the deployed state;
the second chamber has a second refrigerant residence time when the occlusion member is in the expanded state; and
the first refrigerant residence time is less than the second refrigerant residence time.

32. The cryotherapeutic device of claim 18, further comprising a filler lumen extending along the shaft, wherein:
the filler lumen is fluidly connected to the occlusion member; and
the occlusion member is fluidly separate from the supply lumen.

* * * * *